US012702709B2

(12) United States Patent
Mannent et al.

(10) Patent No.: US 12,702,709 B2
(45) **Date of Patent: *Aug. 11, 2026**

(54) METHODS FOR TREATING CHRONIC RHINOSINUSITIS WITH NASAL POLYPS BY ADMINISTERING AN ANTIBODY ANTAGONIST OF IL-4R

(71) Applicants: Sanofi Biotechnology, Paris (FR); Regeneron Pharmaceuticals, Inc., Tarrytown, NY (US)

(72) Inventors: Leda Mannent, Paris (FR); Gianluca Pirozzi, Bridgewater, NJ (US); Brian Swanson, Bridgewater, NJ (US); Allen Radin, New York, NY (US); Namita A. Gandhi, New York, NY (US); Robert Evans, New York, NY (US); Jennifer Hamilton, Hopewell Junction, NY (US)

(73) Assignees: SANOFI BIOTECHNOLOGY, Gentilly (FR); REGENERON PHARMACEUTICALS, INC., Tarrytown, NY (US)

( * ) Notice: Subject to any disclaimer, the term of this patent is extended or adjusted under 35 U.S.C. 154(b) by 1178 days.

This patent is subject to a terminal disclaimer.

(21) Appl. No.: 17/534,106

(22) Filed: Nov. 23, 2021

(65) Prior Publication Data

US 2022/0204631 A1 Jun. 30, 2022

Related U.S. Application Data

(63) Continuation of application No. 16/038,925, filed on Jul. 18, 2018, now Pat. No. 11,214,621, which is a continuation of application No. 14/940,431, filed on Nov. 13, 2015, now Pat. No. 10,066,017.

(60) Provisional application No. 62/199,305, filed on Jul. 31, 2015, provisional application No. 62/158,832, filed on May 8, 2015, provisional application No. 62/083,821, filed on Nov. 24, 2014, provisional application No. 62/080,092, filed on Nov. 14, 2014.

(30) Foreign Application Priority Data

Oct. 14, 2015 (EP) .................................... 15306632

(51) Int. Cl.

| | |
|---|---|
| ***A61P 11/02*** | (2006.01) |
| ***A61K 39/395*** | (2006.01) |
| *A61K 39/00* | (2006.01) |
| *A61P 11/06* | (2006.01) |
| *C07K 14/715* | (2006.01) |
| *C07K 16/28* | (2006.01) |

(52) U.S. Cl.

CPC .......... *A61K 39/3955* (2013.01); *A61P 11/02* (2018.01); *A61K 2039/505* (2013.01); *A61K 2039/545* (2013.01); *A61P 11/06* (2018.01); *C07K 14/7155* (2013.01); *C07K 16/2866* (2013.01); *C07K 2317/21* (2013.01); *C07K 2317/76* (2013.01)

(58) Field of Classification Search

CPC ............ C07K 14/7155; C07K 16/2866; A61K 39/3955; A61P 11/02; A61P 11/06

See application file for complete search history.

(56) References Cited

U.S. PATENT DOCUMENTS

| | | | |
|---|---|---|---|
| 5,599,905 | A | 2/1997 | Mosley et al. |
| 5,714,146 | A | 2/1998 | Lewis et al. |
| 5,717,072 | A | 2/1998 | Mosley et al. |
| 5,856,296 | A | 1/1999 | Mosley et al. |
| 5,985,280 | A | 11/1999 | Ritter et al. |
| 6,156,877 | A | 12/2000 | Ritter et al. |
| 6,391,581 | B1 | 5/2002 | Mosley et al. |
| 6,548,655 | B1 | 4/2003 | Mosley et al. |
| 6,596,541 | B2 | 7/2003 | Murphy et al. |
| 6,716,587 | B2 | 4/2004 | Mosley et al. |
| 6,927,044 | B2 | 8/2005 | Stahl et al. |
| 7,141,653 | B2 | 11/2006 | Greenfeder et al. |
| 7,186,809 | B2 | 3/2007 | Armitage et al. |
| 7,317,090 | B2 | 1/2008 | Mosley et al. |
| 7,422,742 | B2 | 9/2008 | Greenfeder et al. |
| 7,465,450 | B2 | 12/2008 | Pluenneke |
| 7,531,169 | B2 | 5/2009 | Singh et al. |
| 7,582,298 | B2 | 9/2009 | Stevens et al. |
| 7,605,237 | B2 | 10/2009 | Stevens et al. |
| 7,608,693 | B2 | 10/2009 | Martin et al. |
| 7,794,717 | B2 | 9/2010 | Stevens et al. |
| 8,030,003 | B2 | 10/2011 | Rothenberg |

(Continued)

FOREIGN PATENT DOCUMENTS

| | | | |
|---|---|---|---|
| AU | 2009231482 | A1 | 10/2009 |
| CA | 2737044 | A1 | 5/2010 |

(Continued)

OTHER PUBLICATIONS

Bachert et al., "Burden of Disease on Chronic Rhinosinusitis with Nasal Polyps", Journal of Asthma and Allergy, 2021, 14: 127-134.

(Continued)

*Primary Examiner* — Zachary C Howard

(74) *Attorney, Agent, or Firm* — LATHROP GPM LLP; James H. Velema, Esq.; Judith L. Stone-Hulslander, Esq.

(57) ABSTRACT

The present invention provides methods for decreasing a nasal polyp score in a subject. The methods include administering to a subject in need thereof a therapeutic composition comprising an interleukin-4 receptor (IL-4R) antagonist such as an anti-IL-4R antibody or antigen binding fragment thereof.

30 Claims, 30 Drawing Sheets

Specification includes a Sequence Listing.

(56) References Cited

U.S. PATENT DOCUMENTS 8,075,887 B2 12/2011 Martin et al.
8,075,897 B2 12/2011 Spertini et al.
8,092,802 B2 1/2012 Stevens et al.
8,092,804 B2 1/2012 Eriksson et al.
8,178,098 B2 5/2012 Lahn et al.
8,252,284 B2 8/2012 Singh et al.
8,324,192 B2 12/2012 Dohil et al.
8,337,839 B2 12/2012 Martin et al.
8,338,135 B2 12/2012 Stevens et al.
8,497,528 B2 7/2013 Lee et al.
8,604,171 B2 12/2013 Singh et al.
8,637,239 B2 1/2014 Furuta et al.
8,735,095 B2 5/2014 Martin et al.
8,945,559 B2 2/2015 Dix et al.
9,238,692 B2 1/2016 Dix et al.
9,415,015 B2 8/2016 Jacobi et al.
9,574,004 B2 2/2017 Ardeleanu et al.
9,864,091 B2 1/2018 Chen et al.
10,059,771 B2 8/2018 Mannent et al.
10,066,017 B2 9/2018 Mannent et al.
10,137,193 B2 11/2018 Pirozzi et al.
10,392,439 B2 8/2019 Stahl et al.
10,485,844 B2 11/2019 Radin et al.
10,676,530 B2 6/2020 Stahl et al.
10,815,205 B2 10/2020 Collin-Kropelin et al.
11,034,768 B2 6/2021 Amin et al.
11,167,004 B2 11/2021 Radin et al.
11,214,621 B2 1/2022 Mannent et al.
11,292,847 B2 4/2022 Bansal et al.
11,485,788 B2 11/2022 Stahl et al.
11,771,743 B2 10/2023 Hamilton et al.
11,845,800 B2 12/2023 Ardeleanu et al.
11,866,503 B2 1/2024 Orengo et al.
11,964,016 B2 4/2024 Asrat et al.
12,090,201 B2 9/2024 Bansal et al.
12,398,212 B2 8/2025 Staudinger et al.
2002/0002132 A1 1/2002 Pluenneke et al.
2003/0103938 A1 6/2003 Jinquan et al.
2003/0113387 A1 6/2003 Tsuchida et al.
2003/0124121 A1 7/2003 Pluenneke
2005/0031609 A1 2/2005 Hultsch et al.
2005/0032164 A1 2/2005 Watson et al.
2005/0074462 A1 4/2005 Holmgren et al.
2005/0118176 A1 6/2005 Mosley et al.
2005/0255532 A1 11/2005 Ruben et al.
2005/0282181 A1 12/2005 Yan et al.
2006/0013811 A1 1/2006 Dina
2007/0041976 A1 2/2007 Pluenneke
2007/0274996 A1 11/2007 Carter et al.
2008/0054606 A1 3/2008 Mitsuo et al.
2008/0160035 A1 7/2008 Stevens et al.
2009/0062168 A1 3/2009 Timar et al.
2009/0074793 A1 3/2009 Martin et al.
2009/0098142 A1 4/2009 Kasaian et al.
2009/0264392 A1 10/2009 Warndahl et al.
2010/0021476 A1 1/2010 Stevens et al.
2010/0047254 A1 2/2010 Martin et al.
2010/0144646 A1 6/2010 Paterson
2010/0291107 A1 11/2010 Stevens et al.
2011/0195500 A1 8/2011 Rothenberg
2012/0004205 A1 1/2012 Rothenberg
2012/0047954 A1 3/2012 Coppola et al.
2012/0052072 A1 3/2012 Martin et al.
2012/0088814 A1 4/2012 Gregory
2012/0097565 A1 4/2012 Dix et al.
2012/0135010 A1 5/2012 Stevens et al.
2012/0164080 A1 6/2012 Hill et al.
2012/0207815 A1 8/2012 Benhamou et al.
2012/0240930 A1 9/2012 Kristensson et al.
2013/0052190 A1 2/2013 Pearce et al.
2013/0078675 A1 3/2013 Martin et al.
2013/0324435 A1 12/2013 Rothenberg et al.
2014/0056920 A1 2/2014 Ardeleanu et al.
2014/0072583 A1 3/2014 Ardeleanu et al.
2014/0187523 A1 7/2014 Dohil et al.
2014/0271658 A1 9/2014 Murphy et al.
2014/0271681 A1 9/2014 Martin et al.
2014/0356372 A1 12/2014 Stahl et al.
2015/0017182 A1 1/2015 Mannent et al.
2015/0185228 A1 7/2015 Reisacher
2015/0246119 A1 9/2015 Pirozzi et al.
2016/0102147 A1 4/2016 Dix et al.
2016/0152718 A1 6/2016 Kostic et al.
2016/0185866 A1 6/2016 Mannent et al.
2018/0016343 A1 1/2018 Ardeleanu et al.
2018/0155436 A1 6/2018 Orengo et al.
2019/0040146 A1 2/2019 Mannent et al.
2019/0040147 A1 2/2019 Mannent et al.
2019/0078160 A1 3/2019 Dressen et al.
2019/0125865 A1 5/2019 Pirozzi et al.
2019/0169299 A1 6/2019 Amin et al.
2019/0364622 A1 11/2019 Carlsson et al.
2019/0367622 A1 12/2019 Graham et al.
2021/0000949 A1 1/2021 Goulaouic et al.
2021/0032354 A1 2/2021 Staudinger et al.
2021/0087284 A1 3/2021 Xu et al.
2021/0322546 A1 10/2021 Pirozzi et al.
2021/0380705 A1 12/2021 Amin et al.
2022/0169739 A1 6/2022 Xu et al.
2022/0204631 A1 6/2022 Mannent et al.
2023/0146317 A1 5/2023 Stjepanovic et al.
2023/0183362 A1 6/2023 Laws
2023/0340101 A1 10/2023 Haddad et al.
2024/0199751 A1 6/2024 Ardeleanu et al.
2024/0360232 A1 10/2024 Abdulai et al.
2025/0388685 A1 12/2025 Laws et al.

FOREIGN PATENT DOCUMENTS

CN 101522716 A 9/2009
CN 102046658 A 5/2011
CN 102197052 A 9/2011
CN 105517570 A 4/2016
CN 106232140 A 12/2016
CN 107206073 A 9/2017
EP 0367566 A1 5/1990
EP 0604693 A1 7/1994
EP 1229034 B1 4/2005
EP 1113818 B1 5/2006
EP 2022507 A1 2/2009
EP 1527100 B1 7/2009
EP 1283851 B1 3/2012
EP 2888281 A1 7/2015
EP 2970460 A2 1/2016
EP 3010539 A1 4/2016
EP 3107575 A1 12/2016
EP 3218412 A1 9/2017
EP 3470432 A1 4/2019
EP 3613432 A1 2/2020
EP 3703818 A1 9/2020
EP 3962515 A1 3/2022
JP H05-246874 A 9/1993
JP 2006-131623 A 5/2006
JP 2012-507294 A 3/2012
JP 2015-527364 A 9/2015
JP 2015-528576 9/2015
JP 2016-521713 A 7/2016
JP 64-63351 B2 1/2019
RU 2162711 C2 2/2001
RU 2453303 C1 6/2012
RU 2488595 C2 7/2013
RU 2674680 C2 12/2018
TW 201029664 A 8/2010
TW 201221141 A 6/2012
WO WO 1992/019259 A1 11/1992
WO WO 1994/014975 A1 7/1994
WO WO 2000/016804 A1 3/2000
WO WO 2001/092340 A2 12/2001
WO WO 2002/007745 A1 1/2002
WO WO 2003/048083 A2 6/2003
WO WO 2003/085089 A2 10/2003
WO WO 2005/047331 A2 5/2005
WO WO 2005/085284 A1 9/2005
WO WO 2006/003407 A2 1/2006

(56) References Cited

FOREIGN PATENT DOCUMENTS

| | | |
|---|---|---|
| WO | WO 2006/072564 A1 | 7/2006 |
| WO | WO 2006/083390 A2 | 8/2006 |
| WO | WO 2007/085815 A2 | 8/2007 |
| WO | WO 2008/054606 A2 | 5/2008 |
| WO | WO 2008/116165 A2 | 9/2008 |
| WO | WO 2009/081201 A2 | 7/2009 |
| WO | WO 2009/124954 A1 | 10/2009 |
| WO | WO 2010/053751 A1 | 5/2010 |
| WO | WO 2010/065557 A2 | 6/2010 |
| WO | WO 2010/120524 A2 | 10/2010 |
| WO | WO 2011/026966 A2 | 3/2011 |
| WO | WO 2011/156000 A2 | 12/2011 |
| WO | WO 2011/159821 A1 | 12/2011 |
| WO | WO 2012/047954 A1 | 4/2012 |
| WO | WO 2012/049278 A1 | 4/2012 |
| WO | WO 2012/094643 A2 | 7/2012 |
| WO | WO 2012/177945 A2 | 12/2012 |
| WO | WO 2013/051928 A1 | 4/2013 |
| WO | WO 2013/066780 A2 | 5/2013 |
| WO | WO 2013/088109 A1 | 6/2013 |
| WO | WO 2013/155010 A1 | 10/2013 |
| WO | WO 2014/031610 A1 | 2/2014 |
| WO | WO 2014/039461 A1 | 3/2014 |
| WO | WO 2014/059178 A1 | 4/2014 |
| WO | WO 2014/164959 A2 | 10/2014 |
| WO | WO 2014/031610 A8 | 11/2014 |
| WO | WO 2014/197470 A1 | 12/2014 |
| WO | WO 2014/205365 A1 | 12/2014 |
| WO | WO 2015/006571 A1 | 1/2015 |
| WO | WO 2015/127229 A1 | 8/2015 |
| WO | WO 2016/077675 A1 | 5/2016 |
| WO | WO 2017/143270 A1 | 8/2017 |
| WO | WO 2018/045130 A1 | 3/2018 |
| WO | WO 2018/057776 A1 | 3/2018 |
| WO | WO 2018/102597 A1 | 6/2018 |
| WO | WO 2018/190990 A1 | 10/2018 |
| WO | WO 2019/089473 A1 | 5/2019 |
| WO | WO 2019/224246 A1 | 11/2019 |
| WO | WO 2020/096381 A1 | 5/2020 |
| WO | WO 2020/135710 A1 | 7/2020 |
| WO | WO 2020/223541 A1 | 11/2020 |
| WO | WO 2021/011614 A1 | 1/2021 |
| WO | WO 2021/119028 A1 | 6/2021 |

OTHER PUBLICATIONS

Brahmer, et al., "Safety and Activity of Anti-PD-L1 Antibody in Patients With Advanced Cancer", New England Journal of Medicine, vol. 366, pp. 2455-2465, Jun. 28, 2012.

Donald, et al., Unknown Publication, Current Opinion in Otolaryngology & Head and Neck Surgery, vol. 21 & 23, 2013.

Extended European Search Report for European Patent Application No. 21191120.1, mailed Mar. 2, 2022.

Extended European Search Report for European Patent Application No. 21199451.2, mailed May 9, 2022.

Hambly, et al., "Monoclonal Antibodies for the Treatment of Refractory Asthma", Current Opinion in Pulmonary Medicine, vol. 20, Issue 1, pp. 87-94, Jan. 2014.

International Search Report and Written Opinion for PCT International Patent Application No. PCT/US2018/058039, mailed Jan. 28, 2019.

International Search Report and Written Opinion for PCT International Patent Application No. PCT/US2020/030824, dated Sep. 1, 2020.

Maes, et al., "Targeting Interleukin-4 in Asthma: Lost in Translation?", American Journal of Respiratory Cell and Molecular Biology, vol. 47, pp. 261-270, 2012.

Mayo Foundation for Medical Education and Research (MFMER), "Chronic Sinusitis", Aug. 1, 2020.

Mendelsohn, et al., "Revision Rates after Endoscopic Sinus Surgery: A Recurrence Analysis", Annals of Otology, Rhinology & Laryngology, vol. 120, No. 3, pp. 162-166., 2011.

US Securities and Exchange Commission Web Site 2019, Form S-1, Dec. 21, 2018, XP055720304, Retrieved from url: <https://www.sec.gov/Archives/edgar/data/1728117/000119312518356444/d626950ds1.htm>.

Zhu et al., "Potential New Targets for Drug Development in Severe Asthma", World Allergy Organization Journal, Oct. 25, 2018, 11(30): 1-9.

Opposition against European Patent No. 3107575 (EP Application No. 15708991.3), filed on May 4, 2022, on behalf of Dr. Hans Ulrich Dörries.

U.S. Appl. No. 61/943,019, filed Feb. 21, 2014, cited in Opposition against European Patent No. 3107575 (U.S. Appl. No. 61/943,019, filed Feb. 21, 2014), filed on May 4, 2022, on behalf of Dr. Hans Ulrich Dorries.

European Patent Application No. 14306413.7 filed Sep. 15, 2014, cited in Opposition against European Patent No. 3107575 (EP Application No. 15708991.3), filed on May 4, 2022, on behalf of Dr. Hans Ulrich Dörries.

U.S. Appl. No. 62/077,669, filed Nov. 10, 2014, cited in Opposition against European Patent No. 3107575 (U.S. Appl. No. 62/077,669, filed Nov. 10, 2014), filed on May 4, 2022, on behalf of Dr. Hans Ulrich Dorries.

Barnes, "Scientific rationale for inhaled combination therapy with long-acting B2- agonists and corticosteroids", The European Respiratory Journal, Jan. 2002, 19(1): 182-191.

FDA drug label "Symbicort", revised May 2012, cited in Opposition against European Patent No. 3107575 (EP Application No. 15708991.3), filed on May 4, 2022, on behalf of Dr. Hans Ulrich Dörries.

FDA drug label "Dulera", revised Jun. 2010, cited in Opposition against European Patent No. 3107575 (EP Application No. 15708991.3), filed on May 4, 2022, on behalf of Dr. Hans Ulrich Dörries.

Bice et al., "Biologic targeted therapy in allergic asthma", Annals of Allergy, Asthma & Immunology, 2014, 112(2): 108-115, cited in Opposition against European Patent No. 3107575 (EP Application No. 15708991.3), filed on May 4, 2022, on behalf of Dr. Hans Ulrich Dörries.

Gibaldi, "Biopharmaceutics and Clinical Pharmacokinetics", 4th Edition, 1991, Lea & Febiger, pp. 12-13, cited in Opposition against European Patent No. 3107575 (EP Application No. 15708991.3), filed on May 4, 2022, on behalf of Dr. Hans Ulrich Dörries.

ClinicalTrials.gov, Information about clinical study "NCT01854047", "An Evaluation of Dupilumab in Patients With Moderate to Severe Uncontrolled Asthma", study record version of Feb. 18, 2014, retrieved from the ClinicalTrials.gov archive url: <https://clinicaltrials.ciovict2/show/record/NCT01854047?intr=Dupilumab+OR+REGN-668+OR+REGN668+OR+SAR-231893+OR+SAR231893&phase=1&draw=3&rank=13>, cited in Opposition against European Patent No. 3107575 (EP Application No. 15708991.3), filed on May 4, 2022, on behalf of Dr. Hans Ulrich Dörries.

ClinicalTrials.gov, Information about clinical study "NCT02134028", "Long-Term Safety Evaluation of Dupilumab in Patients With Asthma", study record version of Jan. 8, 2015, retrieved from the ClinicalTrials.gov archive url: <https://clinicaltrials.clovict2/show/record/NCT02134028?term=NCT02134028&draw=2&rank=1>, cited in Opposition against European Patent No. 3107575 (EP Application No. 15708991.3), filed on May 4, 2022, on behalf of Dr. Hans Ulrich Dörries.

Annex to the Notice of Opposition against European Patent No. 3107575 (EP Application No. 15708991.3), Facts and Arguments in accordance with Rule 76(2)(c) EPC, filed on May 25, 2022.

International Nonproprietary Names for Pharmaceutical Substances (INN), pp. 401, 402 and 412 of WHO Drug Information, 2012, 26(4):401-471, cited in Annex to the Notice of Opposition against European Patent No. 3107575 (EP Application No. 15708991.3), Facts and Arguments in accordance with Rule 76(2)(c) EPC, filed on May 25, 2022.

EurekAlert! press release Monoclonal antibody appears effective and safe in asthma Phase IIa trial, May 21, 2013, cited in Annex to the Notice of Opposition against European Patent No. 3107575 (EP Application No. 15708991.3), Facts and Arguments in accordance with Rule 76(2)(c) EPC, filed on May 25, 2022.

Chapter 19, "Dosage regimens", of Aulton's Pharmaceutics: The Science of Dosage Form Design, 2nd Edition, 2001, cited in Annex

(56) References Cited

OTHER PUBLICATIONS to the Notice of Opposition against European Patent No. 3107575 (EP Application No. 15708991.3), Facts and Arguments in accordance with Rule 76(2)(c) EPC, filed on May 25, 2022.
Ackerman et al., pp. 159 to 162 of Rispens and Vidarsson, Antibody Fc: Linking Adaptive and Innate Immunity, Chapter 9, "Human lgG Subclasses", pp. 159 to 162, 2013; and evidence of its publication date, cited in Annex to the Notice of Opposition against European Patent No. 3107575 (EP Application No. 15708991.3), Facts and Arguments in accordance with Rule 76(2)(c) EPC, filed on May 25, 2022.
Panaccione et al., "Optimal use of biologics in the management of Crohn's disease", Ther. Adv. Gastroenterol., 2010, 3(3):179-189, which is a review article relating to the optimal use of biologics in the inflammatory disorder, Crohn's disease, cited in Annex to the Notice of Opposition against European Patent No. 3107575 (EP Application No. 15708991.3), Facts and Arguments in accordance with Rule 76(2)(c) EPC, filed on May 25, 2022.
ClinicalTrials.gov, NCT01854047 clinical trial protocol version 22 (Feb. 3, 2014), cited in Annex to the Notice of Opposition against European Patent No. 3107575 (EP Application No. 15708991.3), Facts and Arguments in accordance with Rule 76(2)(c) EPC, filed on May 25, 2022.
Global Initiative for Asthma, pp. 29 to 31 and 58 of the Global Strategy for Asthma Management and Prevention, 2009, cited in Annex to the Notice of Opposition against European Patent No. 3107575 (EP Application No. 15708991.3), Facts and Arguments in accordance with Rule 76(2)(c) EPC, filed on May 25, 2022.
Notice of Opposition against European Patent No. 3107575 (EP Application No. 15708991.3) filed on behalf of Regina Neuefeind, dated May 25, 2022.
Applicants' letter dated Sep. 20, 2016, cited in Notice of Opposition against European Patent No. 3107575 (EP Application No. 15708991.3) filed on behalf of Regina Neuefeind, dated May 25, 2022.
Amended claims enclosed with letter dated Sep. 20, 2016, cited in Notice of Opposition against European Patent No. 3107575 (EP Application No. 15708991.3) filed on behalf of Regina Neuefeind, dated May 25, 2022.
Applicants' letter dated Jul. 25, 2019, cited in Notice of Opposition against European Patent No. 3107575 (EP Application No. 15708991.3) filed on behalf of Regina Neuefeind, dated May 25, 2022.
Amended claims enclosed with letter dated Jul. 25, 2019, cited in Notice of Opposition against European Patent No. 3107575 (EP Application No. 15708991.3) filed on behalf of Regina Neuefeind, dated May 25, 2022.
Radin et al., "Abstract 558: First-in-Human Study of REGN668/SAR231893 (IL-4Rα mAb): Safety, Tolerability and Biomarker Results of a Randomized, Double-Blind, Placebo-Controlled, Single Ascending Dose Study in Healthy Volunteers", J Allergy clin Immunol, Feb. 2013, cited in Notice of Opposition against European Patent No. 3107575 (EP Application No. 15708991.3) filed on behalf of Regina Neuefeind, dated May 25, 2022.
Swanson et al., 2014, "Poster 1023: Dupilumab suppresses Th2 inflammation in adult asthma and atopic dermatitis", World Allergy Organization Journal, Presented on Dec. 13-14, 2013, cited in Notice of Opposition against European Patent No. 3107575 (EP Application No. 15708991.3) filed on behalf of Regina Neuefeind, dated May 25, 2022.
Sanofi and Regeneron Pharmaceuticals Inc., Press Release Nov. 11, 2014, "Dupilumab Demonstrated Improvement in Lung Function, Reductions of Severe Exacerbations", cited in Notice of Opposition against European Patent No. 3107575 (EP Application No. 15708991.3) filed on behalf of Regina Neuefeind, dated May 25, 2022.
Regeneron Pharmaceuticals Inc., Press Release Jul. 9, 2014, at 5:00 PM EDT, "Regeneron and Sanofi Announce Positive Results from Phase 2B Study of Dupilumab in Patients with Moderate-to-Severe Atopic Dermatitis", cited in Notice of Opposition against European Patent No. 3107575 (EP Application No. 15708991.3) filed on behalf of Regina Neuefeind, dated May 25, 2022.
Regeneron Pharmaceuticals Inc., Mar. 2, 2013, at 9:00 AM EST, "Sanofi and Regeneron Report Positive Proof-of-Concept Data for Dupilumab, An IL-4R Alpha Antibody, in Atopic Dermatitis", cited in Notice of Opposition against European Patent No. 3107575 (EP Application No. 15708991.3) filed on behalf of Regina Neuefeind, dated May 25, 2022.
Beck et al., "Dupilumab Treatment in Adults with Moderate-to-Severe Atopic Dermatitis", N Engl J Med, Jul. 10, 2014, 371: 130-139, cited in Notice of Opposition against European Patent No. 3107575 (EP Application No. 15708991.3) filed on behalf of Regina Neuefeind, dated May 25, 2022.
Brusselle et al., "Targeting Immune Pathways for Therapy in Asthma and Chronic Obstructive Pulmonary Disease", Ann Am Thorac Soc, 2014, 11(Suppl. 5): S322-S328, cited in Notice of Opposition against European Patent No. 3107575 (EP Application No. 15708991.3) filed on behalf of Regina Neuefeind, dated May 25, 2022.
Possa et al., "Eosinophilic inflammation in allergic asthma", Frontiers in Pharmacology, 2013, 4(46): 1-9, cited in Notice of Opposition against European Patent No. 3107575 (EP Application No. 15708991.3) filed on behalf of Regina Neuefeind, dated May 25, 2022.
Liang et al., "Moderate Accuracy of Peripheral Eosinophil Count for Predicting Eosinophilic Phenotype in Steroid-Naïve Non-Atopic Adult Asthmatics", Intern Med., 2012, 51: 717-722, cited in Notice of Opposition against European Patent No. 3107575 (EP Application No. 15708991.3) filed on behalf of Regina Neuefeind, dated May 25, 2022.
Katz et al., "Blood Eosinophil Count Is a Useful Biomarker to Identify Patients with Severe Eosinophilic Asthma", Ann Am Thorac Soc., 2014, 11(4): 531-536, cited in Notice of Opposition against European Patent No. 3107575 (EP Application No. 15708991.3) filed on behalf of Regina Neuefeind, dated May 25, 2022.
NHS Health Research Authority, "Dupilumab for adult patients with moderate to severe atopic dermatitis", REC Opinion, May 30, 2014, cited in Notice of Opposition against European Patent No. 3107575 (EP Application No. 15708991.3) filed on behalf of Regina Neuefeind, dated May 25, 2022.
Notice of Opposition against European Patent No. 3470432 (Application No. 18194745.8) filed on Jul. 5, 2022, on behalf of Secerna LLP.
D1—Wenzel, Severe Asthma: from characteristics to phenotypes to endotypes (review), Clinical & Experimental Allergy, Jan. 18, 2012, 42: 650-658, cited in Notice of Opposition against European Patent No. 3470432 (Application No. 18194745.8) filed on Jul. 5, 2022, on behalf of Secerna LLP.
D2—Wenzel, Asthma phenotypes: the evolution from clinical to molecular approaches (review), Nature Medicine, May 4, 2012, 18(5): 716-725, cited in Notice of Opposition against European Patent No. 3470432 (Application No. 18194745.8) filed on Jul. 5, 2022, on behalf of Secerna LLP.
D3—GINA Report Dec. 2011, Global Strategy for Asthma Management and Prevention, GINA © 2011 & Global Initiative for Asthma, reprinted with permission, Available from www.ginasthma org, cited in Notice of Opposition against European Patent No. 3470432 (Application No. 18194745.8) filed on Jul. 5, 2022, on behalf of Secerna LLP.
D4—GINA Report Dec. 2012, Global Strategy for Asthma Management and Prevention, GINA © 2012 & Global Initiative for Asthma, reprinted with permission, Available from www.ginasthma.org, cited in Notice of Opposition against European Patent No. 3470432 (Application No. 18194745.8) filed on Jul. 5, 2022, on behalf of Secerna LLP.
D5—Wenzel et al., Dupilumab in persistent asthma with elevated eosinophil levels, N Engl J Med., May 21, 2013, 368(26): 2455-2466, cited in Notice of Opposition against European Patent No. 3470432 (Application No. 18194745.8) filed on Jul. 5, 2022, on behalf of Secerna LLP.
D6—Protocol for: Wenzel et al., Dupilumab in persistent asthma with elevated eosinophil levels, N Engl J Med., May 21, 2013, 368(26): 2455-2466, cited in Notice of Opposition against European Patent No. 3470432 (Application No. 18194745.8) filed on Jul. 5, 2022, on behalf of Secerna LLP.

(56) References Cited

OTHER PUBLICATIONS

D7—Weschler, Inhibiting interleukin-4 and interleukin-13 in difficult-to-control asthma, N Engl J Med., May 21, 2013, 368: 2511-2513, cited in Notice of Opposition against European Patent No. 3470432 (Application No. 18194745.8) filed on Jul. 5, 2022, on behalf of Secerna LLP.
D8—U.S. Pat. No. 8,075,887 B2, High Affinity Human Antibodies to Human IL-4 Receptor, issued Dec. 13, 2011, cited in Notice of Opposition against European Patent No. 3470432 (Application No. 18194745.8) filed on Jul. 5, 2022, on behalf of Secerna LLP.
D9—PCT International Publication No. WO 2010/053751 A1, High Affinity Human Antibodies to Human IL-4 Receptor, published May 14, 2010, cited in Notice of Opposition against European Patent No. 3470432 (Application No. 18194745.8) filed on Jul. 5, 2022, on behalf of Secerna LLP.
D10—Study NCT01312961 (v31), Efficacy, Safety, and Tolerability of SAR231893 (REGN668) in Patients with Persistent Moderate to Severe Eosinophilic Asthma, Aug. 20, 2012, cited in Notice of Opposition against European Patent No. 3470432 (Application No. 18194745.8) filed on Jul. 5, 2022, on behalf of Secerna LLP.
D11—Press release: Regeneron reports fourth quarter and full year 2011 financial and operating results, Feb. 13, 2012, https://investor.regeneron.com/news-releases/news-release-details/regeneron-reports-fourth-quarter-and-full-year-2011-financial, cited in Notice of Opposition against European Patent No. 3470432 (Application No. 18194745.8) filed on Jul. 5, 2022, on behalf of Secerna LLP.
D12—Otulana et al., A Phase 2b Study of Inhaled Pitrakinra, an IL-4 / IL-13 antagonist, successfully identified responder subpopulations of patients with uncontrolled asthma, American Journal of Respiratory and Critical Care Medicine, May 18, 2011, 183: A6179, cited in Notice of Opposition against European Patent No. 3470432 (Application No. 18194745.8) filed on Jul. 5, 2022, on behalf of Secerna LLP.
D13—Corren et al., A randomized, controlled, Phase 2 study of AMG 317, an IL-4Ra antagonist, in patients with asthma, Am J Respir Crit Care Med., Jan. 7, 2010, 181(8): 788-796, cited in Notice of Opposition against European Patent No. 3470432 (Application No. 18194745.8) filed on Jul. 5, 2022, on behalf of Secerna LLP.
D14—Hashimoto & Bel, Targeting IL-5 in severe asthma: a DREAM come true?, The Lancet, Aug. 8, 2012, 380(9842): 626-627, cited in Notice of Opposition against European Patent No. 3470432 (Application No. 18194745.8) filed on Jul. 5, 2022, on behalf of Secerna LLP.
D15—Pavord al., Mepolizumab for severe eosinophilic asthma (DREAM): a multicentre, double-blind, placebo-controlled trial, Lancet, Aug. 18, 2012; 380: 651-659, cited in Notice of Opposition against European Patent No. 3470432 (Application No. 18194745.8) filed on Jul. 5, 2022, on behalf of Secerna LLP.
D16—Szefler et al., Asthma Outcomes: Biomarkers, J Allergy Clin Immunol., Mar. 1, 2012, 129: S9-23, cited in Notice of Opposition against European Patent No. 3470432 (Application No. 18194745.8) filed on Jul. 5, 2022, on behalf of Secerna LLP.
D17—Spector & Tan, Is a single blood eosinophil count a reliable marker for "eosinophilic asthma?", Journal of Asthma, Aug. 20, 2012, 49.8: Early Online: 1-4, cited in Notice of Opposition against European Patent No. 3470432 (Application No. 18194745.8) filed on Jul. 5, 2022, on behalf of Secerna LLP.
D18—WHO Drug Information, vol. 26, No.4, p. 412, Dec. 9, 2012, cited in Notice of Opposition against European Patent No. 3470432 (Application No. 18194745.8) filed on Jul. 5, 2022, on behalf of Secerna LLP.
D19—Firszt & Kraft, Pharmacotherapy of Severe Asthma, Curr Opin Pharmacol., Jun. 2010, 10(3): 266-271, cited in Notice of Opposition against European Patent No. 3470432 (Application No. 18194745.8) filed on Jul. 5, 2022, on behalf of Secerna LLP.
D20—Darveax & Busse, Biologics in asthma—the next step to personalised treatment, J Allergy Clin Immunol Pract., Mar.-Apr. 2015, 3(2): 152-161, cited in Notice of Opposition against European Patent No. 3470432 (Application No. 18194745.8) filed on Jul. 5, 2022, on behalf of Secerna LLP.
D21—Eisenstein, Something new under the skin, Nature Biotechnology, Feb. 7, 2011, 29(2): 107-109, cited in Notice of Opposition against European Patent No. 3470432 (Application No. 18194745.8) filed on Jul. 5, 2022, on behalf of Secerna LLP.
D22—Chapter 19, "Dosage regimens" of Aulton's Pharmaceutics: The Science of Dosage Form Design, 2nd Edition, 2001, cited in Notice of Opposition against European Patent No. 3470432 (Application No. 18194745.8) filed on Jul. 5, 2022, on behalf of Secerna LLP.
P1—U.S. Appl. No. 61/691,625, filed Aug. 21, 2012, cited in Notice of Opposition against European Patent No. 3470432 (Application No. 18194745.8) filed on Jul. 5, 2022, on behalf of Secerna LLP.
P2—U.S. Appl. No. 61/758,097, filed Jan. 29, 2013, cited in Notice of Opposition against European Patent No. 3470432 (Application No. 18194745.8) filed on Jul. 5, 2022, on behalf of Secerna LLP.
P3—U.S. Appl. No. 61/761,279, filed Feb. 6, 2013, cited in Notice of Opposition against European Patent No. 3470432 (Application No. 18194745.8) filed on Jul. 5, 2022, on behalf of Secerna LLP.
P4—U.S. Appl. No. 61/783,796, filed Mar. 14, 2013, cited in Notice of Opposition against European Patent No. 3470432 (Application No. 18194745.8) filed on Jul. 5, 2022, on behalf of Secerna LLP.
P5—U.S. Appl. No. 61/805,797, filed Mar. 27, 2013, cited in Notice of Opposition against European Patent No. 3470432 (Application No. 18194745.8) filed on Jul. 5, 2022, on behalf of Secerna LLP.
P6—French Patent Application No. 1356994, filed Jul. 16, 2013, cited in Notice of Opposition against European Patent No. 3470432 (Application No. 18194745.8) filed on Jul. 5, 2022, on behalf of Secerna LLP.
A—Divisional Application as filed (EP 18194745.8), dated Sep. 17, 2018, cited in Notice of Opposition against European Patent No. 3470432 (Application No. 18194745.8) filed on Jul. 5, 2022, on behalf of Secerna LLP.
Notice of Opposition against European Patent No. 3470432 (Application No. 18194745.8) filed on Jul. 5, 2022, on behalf of Dr. Hans Ulrich Dorries.
P1—U.S. Appl. No. 61/691,625, filed Aug. 21, 2012, cited in Notice of Opposition against European Patent No. 3470432 (Application No. 18194745.8) filed on Jul. 5, 2022, on behalf of Dr. Hans Ulrich Dorries.
P2—U.S. Appl. No. 61/758,097, filed Jan. 29, 2013, cited in Notice of Opposition against European Patent No. 3470432 (Application No. 18194745.8) filed on Jul. 5, 2022, on behalf of Dr. Hans Ulrich Dorries.
P3—U.S. Appl. No. 61/761,279, filed Feb. 6, 2013, cited in Notice of Opposition against European Patent No. 3470432 (Application No. 18194745.8) filed on Jul. 5, 2022, on behalf of Dr. Hans Ulrich Dorries.
P4—U.S. Appl. No. 61/783,796, filed Mar. 14, 2013, cited in Notice of Opposition against European Patent No. 3470432 (Application No. 18194745.8) filed on Jul. 5, 2022, on behalf of Dr. Hans Ulrich Dorries.
P5—U.S. Appl. No. 61/805,797, filed Mar. 27, 2013, cited in Notice of Opposition against European Patent No. 3470432 (Application No. 18194745.8) filed on Jul. 5, 2022, on behalf of Dr. Hans Ulrich Dorries.
P6—French Patent Application No. 1356994, filed Jul. 16, 2013, cited in Notice of Opposition against European Patent No. 3470432 (Application No. 18194745.8) filed on Jul. 5, 2022, on behalf of Dr. Hans Ulrich Dorries.
PA—PCT International Publication No. 2014/031610 A1 published Feb. 27, 2014, cited in Notice of Opposition against European Patent No. 3470432 (Application No. 18194745.8) filed on Jul. 5, 2022, on behalf of Dr. Hans Ulrich Dorries.
OA—Divisional application as filed resulting in the opposed patent (European Patent Application No. 21199451.2, filed Sep. 28, 2021), cited in Notice of Opposition against European Patent No. 3470432 (Application No. 18194745.8) filed on Jul. 5, 2022, on behalf of Dr. Hans Ulrich Dorries.
D1—Wenzel et al., Dupilumab in persistent asthma with elevated eosinophil levels, N Engl J Med., May 21, 2013, 368(26): 2455-

(56) References Cited

OTHER PUBLICATIONS 2466, cited in Notice of Opposition against European Patent No. 3470432 (Application No. 18194745.8) filed on Jul. 5, 2022, on behalf of Dr. Hans Ulrich Dorries.
D2—WHO Drug Information, vol. 26, No.4, pp. 401-471, Proposed INN: List 108, Dec. 9, 2012, cited in Notice of Opposition against European Patent No. 3470432 (Application No. 18194745.8) filed on Jul. 5, 2022, on behalf of Dr. Hans Ulrich Dorries.
D3—O'Byrne et al., Clinical and Experimental Allergy, May 2012, 42(2): 706-711, cited in Notice of Opposition against European Patent No. 3470432 (Application No. 18194745.8) filed on Jul. 5, 2022, on behalf of Dr. Hans Ulrich Dorries.
D4—Corren et al., A randomized, controlled, Phase 2 study of AMG 317, an IL-4Ra antagonist, in patients with asthma, Am J Respir Crit Care Med., Jan. 7, 2010, 181(8): 788-796, cited in Notice of Opposition against European Patent No. 3470432 (Application No. 18194745.8) filed on Jul. 5, 2022, on behalf of Dr. Hans Ulrich Dorries.
D5—PCT International Publication No. WO 2010/053751 A1, High Affinity Human Antibodies to Human IL-4 Receptor, published May 14, 2010, cited in Notice of Opposition against European Patent No. 3470432 (Application No. 18194745.8) filed on Jul. 5, 2022, on behalf of Dr. Hans Ulrich Dorries.
D6—Gibaldi, Biopharmaceutics and Clinical Pharmakokinetics, 4th Ed., 1991, Lea & Febiger, pp. 12-13, cited in Notice of Opposition against European Patent No. 3470432 (Application No. 18194745. 8) filed on Jul. 5, 2022, on behalf of Dr. Hans Ulrich Dorries.
Notice of Opposition against European Patent No. 3470432 (Application No. 18194745.8) filed on Jul. 6, 2022, on behalf of D. Young & Co.
D1—Corren et al., A randomized, controlled, Phase 2 study of AMG 317, an IL-4Ra antagonist, in patients with asthma, Am J Respir Crit Care Med., Jan. 7, 2010, 181(8): 788-796, cited in Notice of Opposition against European Patent No. 3470432 (Application No. 18194745.8) filed on Jul. 6, 2022, on behalf of D. Young & Co.
D2—pp. 17, 28, 32, 34, 59 and 61 of the Global Initiative for Asthma: Global Strategy for Asthma Management and Prevention, 2009, cited in Notice of Opposition against European Patent No. 3470432 (Application No. 18194745.8) filed on Jul. 6, 2022, on behalf of D. Young & Co.
D3—Borish, Am J Respir Crit Care Med., 2010, 181: 769-772, cited in Notice of Opposition against European Patent No. 3470432 (Application No. 18194745.8) filed on Jul. 6, 2022, on behalf of D. Young & Co.
D4—U.S. Pat. No. 8,075,887 B2, High Affinity Human Antibodies to Human IL-4 Receptor, issued Dec. 13, 2011, cited in Notice of Opposition against European Patent No. 3470432 (Application No. 18194745.8) filed on Jul. 6, 2022, on behalf of D. Young & Co.
D5—Chapter 19, Dosage Regimens, Alton's Pharmaceutics: The Science of Dosage Form Design, 2nd Ed., 2001, cited in Notice of Opposition against European Patent No. 3470432 (Application No. 18194745.8) filed on Jul. 6, 2022, on behalf of D. Young & Co.
D6—Mould & Sweeney, Current Opinion in Drug Discovery & Development, 2007, 10(1): 84-96, cited in Notice of Opposition against European Patent No. 3470432 (Application No. 18194745. 8) filed on Jul. 6, 2022, on behalf of D. Young & Co.
D7—Panaccione and Ghosh, Ther Adv Gastroenterol., 2010, 3(3): 179-189, cited in Notice of Opposition against European Patent No. 3470432 (Application No. 18194745.8) filed on Jul. 6, 2022, on behalf of D. Young & Co.
Notice of Opposition against European Patent No. 3470432 (Application No. 18194745.8) filed on Jul. 6, 2022, on behalf of Ms. Regina Neuefeind.
A—PCT International Publication No. 2014/031610 published Feb. 27, 2014, cited in Notice of Opposition against European Patent No. 3470432 (Application No. 18194745.8) filed on Jul. 6, 2022, on behalf of Ms. Regina Neuefeind.
P1—U.S. Appl. No. 61/691,625, filed Aug. 21, 2012, cited in Notice of Opposition against European Patent No. 3470432 (Application No. 18194745.8) filed on Jul. 6, 2022, on behalf of Ms. Regina Neuefeind.
P2—U.S. Appl. No. 61/758,097, filed Jan. 29, 2013, cited in Notice of Opposition against European Patent No. 3470432 (Application No. 18194745.8) filed Jan. 29, 2013) filed on Jul. 6, 2022, on behalf of Ms. Regina Neuefeind.
P3—U.S. Appl. No. 61/761,279, filed Feb. 6, 2013, cited in Notice of Opposition against European Patent No. 3470432 (Application No. 18194745.8) filed Feb. 6, 2013) filed on Jul. 6, 2022, on behalf of Ms. Regina Neuefeind.
P4—U.S. Appl. No. 61/783,796, filed Mar. 14, 2013, cited in Notice of Opposition against European Patent No. 3470432 (Application No. 18194745.8) filed on Jul. 6, 2022, on behalf of Ms. Regina Neuefeind.
P5—U.S. Appl. No. 61/805,797, filed Mar. 27, 2013, cited in Notice of Opposition against European Patent No. 3470432 (Application No. 18194745.8) filed on Jul. 6, 2022, on behalf of Ms. Regina Neuefeind.
P6—French Patent Application No. 1356994, filed Jul. 16, 2013, cited in Notice of Opposition against European Patent No. 3470432 (Application No. 18194745.8) filed on Jul. 6, 2022, on behalf of Ms. Regina Neuefeind.
D1—Brusselle and Bracke, Ann Am Thorac Soc., 2014, 11(Suppl. 5): S322-S328, cited in Notice of Opposition against European Patent No. 3470432 (Application No. 18194745.8) filed on Jul. 6, 2022, on behalf of Ms. Regina Neuefeind.
D2—Woodruff et al., Am J Respir Crit Care Med., 2009, 180: 388-395, cited in Notice of Opposition against European Patent No. 3470432 (Application No. 18194745.8) filed on Jul. 6, 2022, on behalf of Ms. Regina Neuefeind.
D3—Liang et al., Intern Med., 2012, 51: 717-722, cited in Notice of Opposition against European Patent No. 3470432 (Application No. 18194745.8) filed on Jul. 6, 2022, on behalf of Ms. Regina Neuefeind.
D4—Gibson, Aust Prescr, 1996, 19: 44-47, cited in Notice of Opposition against European Patent No. 3470432 (Application No. 18194745.8) filed on Jul. 6, 2022, on behalf of Ms. Regina Neuefeind.
D5—WHO Drug Information, vol. 26, No.4, p. 412, 2012, cited in Notice of Opposition against European Patent No. 3470432 (Application No. 18194745.8) filed on Jul. 6, 2022, on behalf of Ms. Regina Neuefeind.
D6—Pollart et al., American Family Physician, 2009, 79(9): 761-767, cited in Notice of Opposition against European Patent No. 3470432 (Application No. 18194745.8) filed on Jul. 6, 2022, on behalf of Ms. Regina Neuefeind.
D7—Lommatzsch and Virchow, Dtsch Arztebl Int., 2014, 111: 847-855, cited in Notice of Opposition against European Patent No. 3470432 (Application No. 18194745.8) filed on Jul. 6, 2022, on behalf of Ms. Regina Neuefeind.
D8—Applicant's Submission dated Oct. 17, 2019, cited in Notice of Opposition against European Patent No. 3470432 (Application No. 18194745.8) filed on Jul. 6, 2022, on behalf of Ms. Regina Neuefeind.
D9—Wenzel et al., Dupilumab in persistent asthma with elevated eosinophil levels, N Engl J Med., May 21, 2013, 368(26): 2455-2466, cited in Notice of Opposition against European Patent No. 3470432 (Application No. 18194745.8) filed on Jul. 6, 2022, on behalf of Ms. Regina Neuefeind.
D9a—Supplementary Data of D9, cited in Notice of Opposition against European Patent No. 3470432 (Application No. 18194745. 8) filed on Jul. 6, 2022, on behalf of Ms. Regina Neuefeind.
D10—Sandeep et al., Lung India, 2010, 27(3), cited in Notice of Opposition against European Patent No. 3470432 (Application No. 18194745.8) filed on Jul. 6, 2022, on behalf of Ms. Regina Neuefeind.
D11—Shannon et al., CHEST, 2008, 133: 420-426, cited in Notice of Opposition against European Patent No. 3470432 (Application No. 18194745.8) filed on Jul. 6, 2022, on behalf of Ms. Regina Neuefeind.
D12—De Boever et al., Asthma and Lower Airway Disease, 2014, 133(4): 989-996, cited in Notice of Opposition against European Patent No. 3470432 (Application No. 18194745.8) filed on Jul. 6, 2022, on behalf of Ms. Regina Neuefeind.

(56) References Cited

OTHER PUBLICATIONS

D13—Wenzel et al., Severe asthma in adults, Am J Respir Crit Care Med., 172(2): 149-160; cited in Notice of Opposition against European Patent No. 3470432 (Application No. 18194745.8) filed on Jul. 6, 2022, on behalf of Ms. Regina Neuefeind.
D14—Al-Ramli et al., Journal of Asthma, 2008, 45(S1): 41-44, cited in Notice of Opposition against European Patent No. 3470432 (Application No. 18194745.8) filed on Jul. 6, 2022, on behalf of Ms. Regina Neuefeind.
D15—Bossley et al., J Allergy Clin Immunol., 2012, 129(4): 974-982.e13, cited in Notice of Opposition against European Patent No. 3470432 (Application No. 18194745.8) filed on Jul. 6, 2022, on behalf of Ms. Regina Neuefeind.
D16—PCT International Publication No. WO 2010/053751 A1, High Affinity Human Antibodies to Human IL-4 Receptor, published May 14, 2010, cited in Notice of Opposition against European Patent No. 3470432 (Application No. 18194745.8) filed on Jul. 6, 2022, on behalf of Ms. Regina Neuefeind.
D17—Study NCT01312961 (v31), Efficacy, Safety, and Tolerability of SAR231893 (REGN668) in Patients with Persistent Moderate to Severe Eosinophilic Asthma, Aug. 20, 2012, cited in Notice of Opposition against European Patent No. 3470432 (Application No. 18194745.8) filed on Jul. 6, 2022, on behalf of Ms. Regina Neuefeind.
D18—Birkett, 1996, Aust Preser 1996, 19: 76-78, retrieved from: https://www.nps.org.au/australian-prescriber/articles/pharmacokinetics-made-easy-11-designing-dose-regimens, cited in Notice of Opposition against European Patent No. 3470432 (Application No. 18194745. 8) filed on Jul. 6, 2022, on behalf of Ms. Regina Neuefeind.
D19—Applicant's submission dated Dec. 9, 2011, cited in Notice of Opposition against European Patent No. 3470432 (Application No. 18194745.8) filed on Jul. 6, 2022, on behalf of Ms. Regina Neuefeind.
D20—U.S. Pat. No. 8,075,887 B2, High Affinity Human Antibodies to Human IL-4 Receptor, issued Dec. 13, 2011, cited in Notice of Opposition against European Patent No. 3470432 (Application No. 18194745.8) filed on Jul. 6, 2022, on behalf of Ms. Regina D21—Neuefeind.
D21—Regeneron Science to Medicine, J.P. Morgan Healthcare Conference, Jan. 8, 2013, cited in Notice of Opposition against European Patent No. 3470432 (Application No. 18194745.8) filed on Jul. 6, 2022, on behalf of Ms. Regina Neuefeind.
D21a—Proof of publication date of D21, Jan. 8, 2013, cited in Notice of Opposition against European Patent No. 3470432 (Application No. 18194745.8) filed on Jul. 6, 2022, on behalf of Ms. Regina Neuefeind.
Annual Report 2013, Receptos Inc., 411 Pages., Apr. 1, 2013.
Chronic Sinusitis, Mayo Foundation for Medical Education and Research (MFMER), 4 Pages., Aug. 1, 2020.
DUPIXENT® (dupilumab) Injection, for Subcutaneous Use, Patient Information, Highlights of Prescribing Information, United States Food and Drug Administration, 34 Pages., Mar. 1, 2017.
Expert Panel Report 3: Guidelines for the Diagnosis and Management of Asthma, National Heart, Blood and Lung Institute, NIH, 440 Pages., Aug. 28, 2007.
Extended European Search Report received for European Application No. 19187112.8, mailed on Jan. 23, 2020.
Extended European Search Report received for European Patent Application No. 18194745.8, mailed on Jan. 16, 2019.
International Nonproprietary Names for Pharmaceutical Substances (INN), Who Drug Information records—World Health Organization, pp. 379-422, Jan. 2014.
International Search Report & Written Opinion Received for PCT Application No. PCT/US2020/042075, mailed on Nov. 16, 2020.
International Search Report and Written Opinion received for PCT Patent Application No. PCT/US2018/058039, mailed on Jan. 28, 2019.
International Search Report and Written Opinion received for PCT Patent Application No. PCT/US2019/031801, mailed on Aug. 20, 2019.
International Search Report and Written Opinion received for PCT Patent Application No. PCT/ US2013/055747, mailed on Feb. 13, 2014.
International Search Report and Written Opinion received for PCT Patent Application No. PCT/ US2015/016852, mailed on May 11, 2015.
International Search Report and Written Opinion received for PCT Patent Application No. PCT/US2014/043440, mailed on Oct. 6, 2014.
Nasal Polyps, Cleveland Clinic, Retrieved from: <<https://my.clevelandclinic.org/health/diseases/15250-nasal-polyps>>, 6 Pages., Feb. 1, 2017.
Nasal Polyps, Mayo Clinic, Retrieved from: <<https://www.mayoclinic.org/diseases-conditions/nasal-polyps/symptoms-causes/syc-20351888?p=1>>, 4 Pages., Jan. 2021.
Nasal Polyps, Healthline Website, Retrieved from: <<https://www.healthline.com/health/nasal-polyps>>, 11 Pages., Jan. 2021.
Novel Therapy Improved Disease Features in EoE, Healio Gastroenterology, Retrieved from: <<https://www.healio.com/news/gastroenterology/20191008/novel-therapy-improves-disease-features-in-eoe>>, 2 Pages., Oct. 2019.
Regeneron Annual Report, 12 Pages., Apr. 2011.
Rhinitis (Hay Fever), American Academy of Allergy, Asthma & Immunology, 1 Page., May 2016.
Section 3, The Four Components of Asthma Management, Guidelines for the Diagnosis and Management of Asthma (EPR-3), 1 Page., Aug. 2007.
WHO Drug Information, vol. 26, No. 4, Proposed INN: List 108, p. 412, Jan. 2012.
International Search Report and Written Opinion received for PCT Patent Application No. PCT/ US2015/060540, mailed on Feb. 17, 2016, 15 Pages.
Abonia, et al., High Prevalence of Eosinophilic Esophagitis in Patients with Inherited Connective Tissue Disorders, Journal of Allergy and Clinical Immunology, vol. 132, No. 2, pp. 378-386, Apr. 2013.
Aceves, et al., Relationships Between Eosinophilic Inflammation, Tissue Remodeling and Fibrosis in Eosinophilic Esophagitis, Immunology and Allergy Clinics of North America, vol. 29, No. 1, pp. 197-211, Feb. 1, 2010.
Akinlade, et al., Conjunctivitis in Dupilumab Clinical Trials, British Journal of Dermatology, XP55610279, pp. 1-5, Mar. 2019.
Akiyama, et al., A Study on Indoor Allergens Measured in Home Environments of Adult-Asthmatic Patients, Housing Research Foundation, No. 24, 11 Pages., Jan. 1997.
Al-Lazikani, et al., Standard Conformations for the Canonical Structures of Immunoglobulins, Journal of Molecular Biology, vol. 273, No. 4, pp. 927-948, Nov. 7, 1997.
Almagro, et al., Humanization of Antibodies, Frontiers in Bioscience, vol. 13, pp. 1619-1633, 2008.
Alving, et al., Increased Amount of Nitric Oxide in Exhaled Air of Asthmatics, European Respiratory Journal, vol. 6, pp. 1368-1370, Jan. 1993.
Angal, et al., A Single Amino Acid Substitution Abolishes the Heterogeneity of Chimeric Mouse/Human (IgG4) Antibody, Molecular Immunology, vol. 30, No. 1, pp. 105-108, 1993.
Arron, et al., Peripheral Biomarkers of an IL-13 Induced Bronchial Epithelial Gene Signature in Asthma, Journal of Allergy and Clinical Immunology, vol. 179, No. 2, p. S74, Feb. 2009.
Assa'ad, et al., An Antibody Against IL-5 Reduces Nos. of Esophageal Intraepithelial Eosinophils in Children with Eosinophilic Esophagitis, Gastroenterology, vol. 141, No. 5, pp. 1593-1604, Aug. 2011.
Assa'ad, Amal, What is New in the Treatment of Eosinophilic Esophagitis, Food Allergy and Anaphylaxis Meeting, Venice, Italy, 1 Page., Aug. 12, 2011.
Avdeeva, et al., Precision Medicine in Chronic Rhinosinusitis with Nasal Polyps, Current Allergy and Asthma Reports, vol. 18, No. 25, 8 Pages., Apr. 2018.
Ayars, et al., Pharmacologic Therapies in Pulmonology and Allergy, Pharmacologic Therapies in Pulmonology and Allergy, Medical Clinics, vol. 100, No. 4, pp. 851-868, Mar. 2012.

(56) References Cited

OTHER PUBLICATIONS

Bachert, et al., Efficacy and Safety of Dupilumab in Patients with Severe Chronic Rhinosinusitis with Nasal Polyps (LIBERTY NP SINUS-24 and LIBERTY NP SINUS-52): Results from Two Multicentre, Randomised, Double-Blind, Placebo-Controlled, Parallel-Group Phase 3 Trials, The Lancet, vol. 394, pp. 1638-1650, Sep. 2019.
Bachert, et al., Pharmacological Management of Nasal Polyposis, Drugs, vol. 65, No. 11, pp. 1537-1552, 2005.
Bagnasco, et al., A Critical Evaluation of Anti-IL-13 and Anti-IL-4 Strategies in Severe Asthma, International Archives of Allergy and Immunology, vol. 170, No. 2, pp. 122-131, Aug. 2016.
Balint, et al., Antibody Engineering by Parsimonious Mutagenesis, Gene, vol. 137, Issue 1, pp. 109-118, Dec. 1993.
Barnes, et al., The Cytokine Network in Asthma and Chronic Obstructive Pulmonary Disease, The Journal of Clinical Investigation, vol. 118, No. 11, pp. 3546-3556, Nov. 2008.
Barranco, et al., Dupilumab in the Management of Moderate-to-Severe Asthma: the Data so Far, Therapeutics and Clinical Risk Management, vol. 13, pp. 1139-1149, Sep. 2017.
Barthelemy, et al., Comprehensive Analysis of the Factors Contributing to the Stability and Solubility of Autonomous Human VH Domains*, Journal of Biological Chemistry, vol. 283, No. 6, pp. 3639-3654, Feb. 2008.
Bateman, et al., Can Guideline-Defined Asthma Control be Achieved? The Gaining Optimal Asthma Control Study, American Journal of Respiratory and Critical Care Medicine, vol. 170, No. 8, pp. 836-844, Jul. 2004.
Beiboer, et al., Guided Selection of a Pan Carcinoma Specific Antibody Reveals Similar Binding Characteristics yet Structural Divergence Between the Original Murine Antibody and its Human Equivalent, Journal of Molecular Biology, vol. 296, No. 3, pp. 833-849, Jan. 2000.
Belikov, B.G, Pharmaceutical Chemistry, Total Pharmaceutical Chemistry, M., Higher School, pp. 43-47, Jan. 1993.
Beyer, et al., Human Milk-Specific Mucosal Lymphocytes of the Gastrointestinal Tract Display a Th2 Cytokine Profile, Journal of Allergy and Clinical Immunology, vol. 109, Issue 4, pp. 707-713, Apr. 2002.
Bhardwaj, et al., Biomarkers for Eosinophilic Esophagitis: A Review, Annals of Allergy, Asthma & Immunology, vol. 109, Issue 3, pp. 155-159, Sep. 2012.
Bieber, et al., Atopic Dermatitis: A Candidate for Disease-Modifying Strategy, Allergy: vol. 67, pp. 969-975, Jan. 2012.
Blanchard, et al., A Striking Local Esophageal Cytokine Expression Profile in Eosinophilic Esophagitis, Journal of Allergy and Clinical Immunology, vol. 127, No. 1, pp. 208-217, Jan. 2011.
Blanchard, et al., Chemotactic Factors Associated with Eosinophilic Gastrointestinal Diseases, Immunology and allergy clinics of North America, vol. 29, No. 1, pp. 141-148, Feb. 2009.
Blanchard, et al., Coordinate Interaction Between IL-13 and Epithelial Differentiation Cluster Genes in Eosinophilic Esophagitis, The Journal of Immunology, vol. 184, No. 7, pp. 4033-4041, Apr. 2010.
Blanchard, et al., Eosinophilic Esophagitis: Pathogenesis, Genetics, and Therapy, Journal of Allergy and Clinical Immunology, vol. 118, No. 5, pp. 1054-1049, Sep. 2006.
Blanchard, Eotaxin-3 and a Uniquely Conserved Gene-Expression Profile in Eosinophilic Esophagitis, The Journal of Clinical Investigation, vol. 116, No. 2, pp. 536-547, Feb. 2005.
Blanchard, et al., IL-13 Involvement in Eosinophilic Esophagitis: Transcriptome Analysis and Reversibility with Glucocorticoids, Journal of Allergy and Clinical Immunology, vol. 120, No. 6, pp. 1292-1300, Dec. 2007.
Blanchard, et al., Inhibition of Human Interleukin-13-Induced Respiratory and Oesophageal Inflammation by Anti-Human-Interleukin-13 Antibody (CAT-354), Clinical & Experimental Allergy, vol. 35, No. 8, pp. 1096-1103, Aug. 2005.
Blankestijn, et al., Could Daratumumab be Used to Treat Severe Allergy?, Journal of Allergy and Clinical Immunology, vol. 139, No. 5, Letters to the Editor, pp. 1677-1678.e3, May 2017.
Blauvelt, et al., Dupilumab Does not Affect Correlates of Vaccine-Induced Immunity: A Randomized, Placebo-Controlled Trial in Adults with Moderate-to-Severe Atopic Dermatitis, Journal of the American Academy of Dermatology, vol. 80, Issue 1, pp. 158-167. e1, Aug. 6, 2018.
Blauvelt, et al., Long-term Management of Moderate-to-Severe Atopic Dermatitis with Dupilumab and 18 Concomitant Topical Corticosteroids {Liberty Ad Chronos): a 1-year, Randomised, Double-Blinded, Placebo-Controlled, Phase 3 Trial, The Lancet, vol. 17, pp. 140-6736, May 2016.
Borish, et al., Efficacy of Soluble IL-4 Receptor for the Treatment of Adults With Asthma, The Journal of Allergy and Clinical Immunology, vol. 107, Issue 6, pp. 963-970, Jun. 2001.
Brorson, et al., Mutational Analysis of Avidity and Fine Specificity of Anti-Levan Antibodies, The Journal of Immunology, vol. 163, No. 12, pp. 6694-6701, Dec. 1999.
Brummell, et al., Probing the Combining Site of an Anti-Carbohydrate Antibody by Saturation-Mutagenesis: Role of the Heavy-Chain CDR3 Residues, Biochemistry, vol. 32, No. 4, pp. 1180-1187, Jan. 1993.
Buddenkotte, et al., Pathophysiology and Therapy of Pruritis in Allergic and Atopic Diseases, Allergy, vol. 65, No. 7, pp. 805-821, Jan. 2010.
Burmeister-Getz, et al., Human pharmacokinetics/pharmacodynamics of an interleukin-4 and interleukin-13 dual antagonist in asthma, The Journal of Clinical Pharmacology, vol. 49, Issue 9, pp. 1025-1036, Mar. 2013.
Burton, et al., Direct Effects of IL-4 on Mast Cells Drive Their Intestinal Expansion and Increase Susceptibility to Naphylaxis in a Murine Model of Food Allergy, Mucosal Immunology, vol. 6, No. 4, pp. 740-750, Nov. 2012.
Carr, Warner W., Topical Calcineurin Inhibitors for Atopic Dermatitis: Review and Treatment Recommendations, Pediatric Drugs, vol. 15, pp. 303-310, Jan. 2013.
Carter, Paul J., Potent Antibody Therapeutics by Design, Nature Reviews Immunology, vol. 6, No. 5, pp. 343-357, May 2006.
Castro, et al., Dupilumab Efficacy and Safety in Moderate-to-Severe Uncontrolled Asthma, New England Journal of Medicine, vol. 378, No. 26, pp. 2486-2496, Jun. 28, 2018.
Castro, et al., Dupilumab Efficacy in Uncontrolled, Moderate-to-Severe Allergic Asthma in the Phase 3 Liberty Asthma Quest Study, Annals of Allergy, Asthma & Immunology, vol. 121, Issue 5, Supplement, p. S8, Nov. 1, 2018.
Chan, et al., An Update on the Classifications, Diagnosis, and Treatment of Rhinosinusitis, Current Opinion in Otolaryngology & Head and Neck Surgery, vol. 17, Issue 3, pp. 204-208, Jan. 2009.
Chan, et al., Expression of Interleukin-4 in the Epidermis of Transgenic Mice Results in a Pruritic Inflammatory Skin Disease: An Experimental Animal Model to Study Atopic Dermatitis, Journal of Investigative Dermatology, vol. 117, No. 4, pp. 977-983, Oct. 2001.
Chehade, et al., The Role of Lymphocytes in Eosinophilic Gastrointestinal Disorders, Immunology and Allergy Clinics of North America, vol. 29, Issue 1, pp. 149-158, Feb. 2009.
Chin, et al., Nasal Polyposis: An Inflammatory Condition Requiring Effective Anti- Inflammatory Treatment, Current Opinion in Otolaryngology & Head and Neck Surgery, vol. 21, No. 1, pp. 23-30, Feb. 2013.
Cho, et al., Spontaneous Eosinophilic NasalInflammation in a Genetically-Mutant Mouse Comparative Study with an Allergic Inftammation Model, PLoS One, vol. 7, No. 4, pp. 1-8, Apr. 2012.
Choi, et al., Predicting Antibody Complementarity Determining Region Structures Without Classification, Molecular BioSystems, vol. 7, pp. 3327-3334, Oct. 2011.
Clackson, et al., Making Antibody Fragments Using Phage Display Libraries, Nature, vol. 352, No. 6336, pp. 624-628, Aug. 15, 1991.
Colice, et al., Categorizing Asthma Severity: An Overview of National Guidelines, Clinical Medicine & Research, vol. 2, No. 3, pp. 155-163, Aug. 2004.

(56) References Cited

OTHER PUBLICATIONS

Collins, et al., Baseline Characteristics and Correlation Between Dysphagia and Disease Activity in Patients with Eosinophilic Esophagitis in a Randomized, Placebo-Controlled, Phase 2 Dupilumab Trial, Sa115 Abstract, AGA Abstract, p. S259.
Colman, P M., Effects of Amino Acid Sequence Changes on Antibody-Antigen Interactions, Research in Immunology, vol. 145, No. 1, pp. 33-36, Jan. 1994.
Cork, et al., 605 Efficacy and Safety of Dupilumab in Adolescent Patients with Moderate-to-Severe Atopic Dermatitis, XP002793331, 3 Pages., May 1, 2019.
Cork, et al., An Open-Label Phase IIa Trial Assessing the Pharmacokinetics, Safety and Efficacy of Dupilumab in a Paediatric Population With Moderate-to-Severe Atopic Dermatitis, British Association of Dermatologists, vol. 177, Supplement 1, P94, pp. 25-77, Jul. 1, 2017.
Corren, et al., A Randomized, Controlled, Phase 2 Study of AMG 317, An IL-4Rα Antagonist, in Patients with Asthma, American Journal of Respiratory and Critical Care Medicine, vol. 181, No. 8, pp. 788-796, Jan. 7, 2010.
Corren, et al., D201 Dupilumab Efficacy In Patients With Uncontrolled, Moderate-to-Severe Asthma And Serologic Evidence of Allergic Bronchopulmonary Aspergillosis, Annals of Allergy, Asthma & immunology, Elsevier, vol. 123, No. 5, Nov. 1, 2019.
Corren, et al., Effects of Combined Treatment with Allergen Immunotherapy and Dupilumab on Nasal Allergen Challenge and Tolerability in Immunotherapy, Allergy, p. 78, Jun. 6, 2020.
Cortes, et al., Proton Pump Inhibitors Inhibit IL-4 and IL-13 Signaling Stat6 Activation, Journal of Immunology, vol. 39, p. S204, Sep. 13, 2009.
Darsow, et al., Pruritus and Atopic Dermatitis, Clinical Reviews in Allergy & Immunology, vol. 41, pp. 237-244, Jan. 2011.
Darveaux, et al., Biologics in Asthma—The Next Step Towards Personalized Treatment, Journal of Allergy and Clinical Immunology, vol. 3, No. 2, pp. 152-161, Jan. 2015.
Davies, et al., Affinity Improvement of Single Antibody VH Domains: Residues in all Three Hypervariable Regions Affect Antigen Binding, Immunotechnology, vol. 2, Issue 3, pp. 169-179, Sep. 1996.
Davis, et al., The Evolutionary and Structural ‘Logic’ of Antigen Receptor Diversity, Seminars in Immunology, vol. 16, Issue 4, pp. 239-243, Aug. 2004.
De Genst, et al., Antibody Repertoire Development in Camelids, Developmental and Comparative Immunology, vol. 30, pp. 187-198, Jan. 2006.
Dellon, Evan S., 19—A Randomized, Double-Blind, Placebo-Controlled Trail of a Novel Recombinant, Humanized, Anti-Interleukin-13 Monoclonal Antibody (RPC4046) in Patients with Active Eosinophilic Esophagitis: Results of the HEROES Study, ACG 2016 Annual Scientific Meeting and PostGraduate Course, The Venetian Las Vegas NV, 3 Pages.
Dellon, Evan S., The Pathogenesis of Eosinophilic Esophagitis: Beyond the Eosinophil, Digestive Diseases and Sciences, vol. 58, pp. 1445-1448, Apr. 2013.
Desreumaux, et al., Interleukin 3, Granulocyte-Macrophage Colony-Stimulating Factor, and Interleukin 5 in Eosinophilic Gastroenteritis, Gastroenterology, vol. 110, No. 3, pp. 768-774, Mar. 1996.
Djukanovic, et al., Standardised Methodology of Sputum Induction and Processing, European Respiratory Journal, pp. 1S-2S, Jan. 2002.
Durham, et al., Targeted Anti-Inflammatory Therapeutics in Asthma and Chronic Obstructive Lung Disease, Transnational Research, vol. 167, No. 1, pp. 192-203, Jan. 2016.
Figueiredo, et al., Inflammatory Genes in Nasal Polyposis, Current Opinion in Otolaryngology & Head and Neck Surgery, vol. 16, pp. 18-21, Feb. 2008.
Fillon, et al., Epithelial Function In Eosinophilic Gastrointestinal Diseases, Immunology and Allergy Clinics of North America, vol. 29, No. 1, pp. 171-178, Jan. 2009.
Foroughi, et al., Anti-IgE Treatment of Eosinophil-Associated Gastrointestinal Disorders, Journal of Allergy and Clinical Immunology, vol. 120, Issue 3, pp. 594-601, Sep. 2007.
Franciosi, et al., Eosinophilic Esophagitis, Immunology and Allergy Clinics of North America, vol. 29, Issue 1, pp. 19-27, Feb. 2009.
Frieri, Marianne, Asthma Linked with Rhinosinusitis: An Extensive Review, Allergy & Rhinology (Providence), vol. 5, No. 1, pp. e41-e49, Mar. 2014.
Frois, et al., Inhaled Corticosteroids or Long-Acting Beta-Agonists Alone or in Fixed- dose Combinations in Asthma Treatment: a Systematic Review of Ftuticasone/Budesonide and Formoterol/ Salmeterol, Clinical Therapeutics, vol. 31, No. 12, pp. 2779-2802, Dec. 2009.
Gavett, et al., Interleukin-4 Receptor Blockade Prevents Airway Responses Induced by Antigen Challenge in Mice, American Journal of Physiology-Lung Cellular and Molecular Physiology, vol. 16, No. 2, pp. 253-261, Jan. 1997.
Gevaert, et al., Mepolizumab, A Humanized Anti-IL-5 mAb, as a Treatment Option for Severe Nasal Polyposis, Journal of Allergy and Clinical Immunology, vol. 128, No. 5, pp. 989-995, Nov. 2011.
Gevaert, et al., Nasal IL-5 Levels Determine the Response to Anti-IL-5 Treatment in Patients with Nasal Polyps, Journal of Allergy and Clinical Immunology, vol. 118, No. 5, pp. 1133-1141, 2006.
Giembycz, et al., A Holy Grail of Asthma Management: Toward Understanding How Long-Acting Beta (2)-24 Adrenoceptor Agonists Enhance the Clinical Efficacy of Inhaled Corticosteroids, British Journal of Pharmacology, vol. 153, pp. 1090-1104, Jan. 2008.
Glare, et al., Asthmatic Airway Biopsy Specimens are More Likely to Express the IL-4 Alternative Splice Variant L-452, Journal of Allergy and Clinical Immunology, vol. 104, pp. 978-982, Nov. 1999.
Goodson, J. Max., Dental Applications, Medical Applications of Controlled Release, vol. 2, pp. 115-138, Jan. 1, 1984.
Green, et al., Molecular Cloning: A Laboratmy Manual, Cold Spring Harbor Laboratory Press, Fourth Edition, 34 Pages., Jan. 2012.
Griffiths, et al., Human Anti-Self Antibodies With High Specificity From Phage Display Libraries, The EMBO Journal, vol. 12, No. 2, pp. 725-734, Feb. 1993.
Groves, et al., Inhibition of IL-4 and IL-13 With An IL-4 Mutein (Aeroderm) Protects Against Flares in Atopic Eczema, AERODERM in AD. Poster at St. John’s Institute of Dermatology, 1 Page., Jan. 2007.
Grunewald, et al., An Antagonistic IL-4 Mutant Prevents Type I Allergy in the Mouse: Inhibition of the IL-4/IL-13 Receptor System completely Abrogates Humoral Immune Response to Allergen and Development of Allergic Symptoms in Vivo, The Journal of Immunology, vol. 160, No. 8, pp. 4004-4009, Jan. 1998.
Gu, et al., Expression and Role of Acidic Mammalian Chitinase and Eotaxin-3 in Chronic Rhinosinusitis with Nasal Polyps, Journal of Otolaryngology-Head and Neck Surgery, vol. 40, No. 1, pp. 64-69, Feb. 1, 2011.
Hamilton, et al., Drug Evaluation Review: Dupilumab in Atopic Dermatitis, Immunotherapy, vol. 7, No. 10, 16 Pages., Jan. 2015.
Hijnen, et al., Serum Thymus and Activation-Regulated Chemokine (TARC) and Cutaneous T Cell-Attracting Chemokine (CTACK) Levels in Allergic Diseases, Journal of Allergy and Clinical Immunology, vol. 113, No. 2, pp. 334-340, Feb. 2004.
Hirano, et al., Correlation Between Esophageal Distensibility and Objectivity Measures of Disease in Patients with Active Eosinophilic Esopagitis a Post Hoc Analysis of a Randomized, Placebo-Controlled, Phase 2 Dupilumab Trial, Sa1113 Asbtract, AGA Abstract, p. S-244, May 1, 2018.
Hirano, et al., Dupilumab Efficacy and Safety in Adult Patients With Active Eosinophilic Espophagitis: A Randomized Double-Blind Placebo-Controlled Phase 2 Trial, World Congress of Gastroenterology ACG, Orlando Florida, 20 Pages.
Hirano, et al., Efficacy of Dupilumab in a Phase 2 Randomized Trial of Adults with Active Eosinophilic Esophagitis, Gastroenterology, vol. 158, pp. 111-122, Jan. 2020.
Holt, et al., Domain Antibodies: Proteins for therapy, Trends in Biotechnology, vol. 21, Issue 11, pp. 484-490, Nov. 2003.

(56) References Cited

OTHER PUBLICATIONS

Hong, et al., Management of Itch in Atopic Dermatitis, Seminars in Cutaneous Medicine and Surgery, vol. 30, No. 2, pp. 71-86, Jun. 2011.
Hopkins, et al., Psychometric Validity of The 22-Item Sinonasal Outcome Test, Clinical Otolaryngology, vol. 34, No. 5, pp. 447-454, Sep. 24, 2009.
Hopkins, et al., The Lund-Mackay staging system for chronic rhinosinusitis: How is it used and what does it predict?, Otolaryngology—Head and Neck Surgery, vol. 137, No. 4, pp. 555-561, Oct. 1, 2007.
Huang, et al., Severe Atopic Dermatitis in Children, Current Allergy and Asthma Reports, Current Science, vol. 18, No. 6, XP036511794, pp. 1-8, May 2018.
Ivashkin, et al., Eosinophilic Esophagitis: A Review of the Literature and a Description of its Own Observation, FUGHC, vol. 22, No. 1, Available at: RZHGGK online—www.gastro-j.ru, pp. 71-81, Jan. 2012.
Ivashkin, et al., Eosinophilic Esophagitis: A Training Manual for Doctors, Moscow, Russia, pp. 13-21,57-62, Jan. 2013.
Jahnz-Rozyk, et al., Serum Thymus and Activation-Regulated Chemokine, Macrophage-Derived Chemokine and Eotaxin as Markers of Severity of Atopic Dermatitis, Allergy, vol. 60, No. 5, pp. 685-688, Apr. 2005.
Jakubke, et al., Amino Acids, Peptides and Proteins: An Introduction, The Macmillan Press Ltd., doi 10.1007/978-1-349-02503, 349 Pages., Jan. 1977.
Jakubke, et al., Amino Acids, Peptides, Proteins, M: Mir, pp. 92-94, 1985.
Jia, et al., Periostin is a Systemic Biomarker of Eosinophilic Airway Inflammation in Asthmatic Patients, The Journal of Allergy and Clinical Immunology, vol. 130, No. 3, pp. 647-654, Sep. 2012.
Junttila, et al., Tuning Sensitivity to IL-4 and IL-13: Differential Expression of IL-4Ra, IL-13Rα1, and Yc Egulates Relative Cytokine Sensitivity, Journal of Experimental Medicine, vol. 205, No. 11, pp. 2595-2608, Jan. 2008.
Jyonouchi, et al., Invariant Natural Killer T cells in children with Eosinophilic Esophagitis, Basic Mechanisms in Allergic Disease, Clinical & Experimental Allergy, vol. 44, No. 1, pp. 58-68, Jan. 2013.
Kagami, et al., Significant Elevation of Serum Levels of Eotaxin-3/CCL26, but not of Eotaxin-2/CCL24, in Patients with Atopic Dermatitis: Serum Eotaxin-3/CCL26 Levels Reflect the Disease Activity of Atopic Dermatitis, Clinical & Experimental Immunology, vol. 134, No. 2, pp. 309-313, Jan. 2003.
Kakinuma, et al., Serum Macrophage-Derived Chemokine (MDC) Levels are Closely Related With the Disease Activity of Atopic Dermatitis, Clinical & Experimental Immunology, vol. 127, No. 2, pp. 270-273, Jan. 2002.
Kakinuma, et al., Thymus and Activation-Regulated Chemokine in Atopic Dermatitis: Serum Thymus and Activation-Regulated Chemokine Level is Closely Related with Disease Activity, Journal of Allergy and Clinical Immunology, vol. 107, No. 3, pp. 535-541, Mar. 2001.
Kakkar, et al., Population PK and IgE Pharmacodynamic Analysis of a Fully Human Monoclonal Antibody Against IL4 Receptor, Pharmaceutical Research, vol. 28, No. 10, pp. 2530-2542, Jan. 2011.
Kanehisa Laboratories, KEGG: Kyoto Encyclopedia of Genes and Genomes, KEGG Drug Entry No. D10354, Retrieved from: <<http://www.genomajp/dbget-bin/www_bget?dr:D10354>>, 2 Pages., Jan. 2016.
Katial, Rohit, Biomarkers for Nononcologic Gastrointestinal Diseases, Immunology and Allergy Clinics of North America, vol. 29, Issue 1, pp. 119-127, Feb. 2009.
Kim, et al., Rebound Eosinophilia after Treatment of Hypereosinophilic Syndrome and Eosinophilic Gastroenteritis with Monoclonal Anti-IL-5 Antibody SCH55700, Journal of Allergy and Clinical Immunology, vol. 114, No. 6, pp. 1449-1455, Dec. 1, 2004.
Kimura, et al., Increased Expression And Role of Thymic Stromal-lymphopoietin in Nasal Polyposis, Annals of Allergy, Asthma & Immunology, vol. 3, No. 3, pp. 186-193, Jul. 1, 2011.
Klementina, et al., Precision Medicine in Chronic Rhinosinusitis with Nasal Polyps, Allergy and Asthma Reports, vol. 18, No. 4, 8 Pages., Mar. 24, 2018.
Klimka, et al., Human Anti-CD30 Recombinant Antibodies by Guided Phage Antibody Selection Using Cell Panning, British Journal of Cancer, vol. 83, No. 2, pp. 252-260, Mar. 10, 2000.
Knappik, et al., Fully Synthetic Human Combinatorial Antibody Libraries (HuCAL) Based on Modular Consensus Frameworks and CDRs Randomized with Trinucleotides, Journal of Molecular Biology, vol. 296, No. 1, pp. 57-86, Jan. 1, 2000.
Kobayashi, et al., Tryptophan H33 Plays an Important Role in Pyrimidine (6-4) Pyrimidone Photoproduct Binding by a High-Affinity Antibody, Protein Engineering, Design and Selection, vol. 12, No. 10, pp. 879-884, Oct. 1, 1999.
Konikoff, et al., A Randomized, Double-Blind, Placebo-Controlled Trial of Fluticasone Propionate for Pediatric Eosinophilic Esophagitis, Gastroenterology, vol. 131, No. 5, pp. 1381-1391, Nov. 1, 2006.
Kopf, et al., Disruption of the Murine IL-4 Gene Blocks Th2 Cytokine Responses, Nature, vol. 362, No. 6417, pp. 245-248, Mar. 18, 1993.
Kopp, et al., Combination of Omalizumab and Specific Immunotherapy is Superior to Immunotherapy in Patients With Seasonal Allergic Rhinoconjunctivitis and Co-Morbid Seasonal Allergic Asthma, Clinical & Experimental Allergy, vol. 39, Issue 2, pp. 271-279, Jan. 22, 2009.
Kostic, et al., A Fully Human IL4Rα Antibody for Inhibition of IL-4/IL-13-driven TH2 Responses in Allergic Disease, Clinical Immunology, vol. 135, pp. S105-S106, Jan. 2010.
Kottyan, et al., Genome-Wide Association Analysis of Eosinophilic Esophagitis Provides Insight into the Tissue Specificity of this Allergic Disease, Nature Genetics, vol. 46, No. 8, pp. 895-900, Aug. 2014.
Kroegel, et al., Global Initiative for Asthma (GINA) guidelines: 15 Years of Application, Expert Review of Clinical Immunology, vol. 5, No. 3, pp. 239-249, May 2009.
Kulis, et al., Single-Tree Nut Immunotherapy Attenuates Allergic Reactions in Mice with Hypersensitivity to Multiple Tree Nuts, Journal of Allergy and Clinical Immunology, vol. 127, No. 1, pp. 81-88, Nov. 2010.
Lange, et al., The Sino-Nasal Outcome Test 22 validated for Danish patients, Danish Medical Bulletin, vol. 58, No. 2, pp. 1-6, Feb. 2011.
Langer, Robert, New Methods Of Drug Delivery, Science, vol. 249, Issue 4976, pp. 1527-1533, Sep. 28, 1990.
Leung, et al., Effect of Anti-IgE Therapy in Patients with Peanut Allergy, New England Journal of Medicine, vol. 348, No. 11, pp. 986-993, Mar. 2003.
Leung, et al., New Insights into Atopic Dermatitis, The Journal of Clinical Investigation, vol. 113, No. 5, pp. 651-657, Apr. 2004.
Lezcano-Meza, et al., Interleukin (IL)-4 and To a Lesser Extent Either IL-13 or Interferon-Gamma Regulate the Reduction of Eotaxin-2/CCL24 in Nasal Polyps, Allergy, vol. 58, No. 10, pp. 1011-1017, Sep. 19, 2003.
Liacouras, et al., Eosinophilic Esophagitis: Updated Consensus Recommendations for Children and Adults, Journal of Allergy and Clinical Immunology, vol. 128, No. 1, pp. 3-20, Apr. 2011.
Lilly, et al., Elevated Plasma Eotaxin Levels in Patients with Acute Asthma, The Journal of Allergy and Clinical Immunology, vol. 104, No. 4, Point 1, pp. 786-790, Oct. 1999.
Liu, et al., Hydrodynamics-Based Transfection in Animals by Systemic Administration of Plasmid DNA, Gene Therapy, vol. 6, No. 7, pp. 1258-1266, Aug. 1999.
Lommatzsch, et al., Severe Asthma: Definition, Diagnosis and Treatment, Deutsches Ärzteblatt International, vol. 111, No. 50, pp. 847-855, Dec. 12, 2014.
Lucendo, et al., Adult Versus Pediatric Eosinophilic Esophagitis: Important Differences and Similarities for the Clinician to Understand, Expert Review of Clinical Immunology, vol. 8, No. 8, pp. 733-745, Nov. 2012.
Ludmila, et al., Poster 1013: IL-4R Alpha Antibody Inhibits IgE Production and Airway Remodeling in the Mouse Model of House

(56) References Cited

OTHER PUBLICATIONS

Dust Mite-Induced Eosinophilic Asthma, World Allergy Organization Journal, vol. 7, No. 1, 1 Page., Feb. 2014.
Lwin, et al., Eosinophilic Gastritis: Histopathological Characterization and Quantification of the Normal Gastric Eosinophil Content, Modern Pathology, vol. 24, No. 4, pp. 556-563, Apr. 2011.
Maliszewski, et al., In Vivo Biological Effects of Recombinant Soluble Interleukin-4 Receptor, Experimental Biology and Medicine, vol. 206, No. 3, pp. 233-237, Jul. 1994.
Mannon, et al., Interleukin 13 and its Role in Gut Defence and Inflammation, Gut, vol. 61, No. 12, pp. 1765-1773, Jan. 2012.
Marone, et al., The Intriguing Role of Interleukin 13 in the Pathophysiology of Asthma, Frontiers in Pharmacology, vol. 10, pp. 1-13, Dec. 2013.
Martel, et al., Translational Animal Models of Atopic Dermatitis for Preclinical Studies, Yale Journal of Biology and Medicine, vol. 90, 14 Pages., Sep. 2017.
Martin, et al., Modeling Antibody Hypervariable Loops: A Combined Algorithm, Proceedings of the National Academy of Sciences, vol. 86, No. 23, pp. 9268-9272, Dec. 1989.
Mashkovsky, et al., Unknown Publication, Medicines, 14th edition, Moscow, pp. 8-9, Jan. 2001.
Masterson, et al., Update on Clinical and Immunological Features of Eosinophilic Gastrointestinal Diseases, Current Opinion in Gastroenterology, vol. 27, No. 6, pp. 515-522, Oct. 2011.
Mathias, et al., IgE-Mediated Systemic Anaphylaxis and Impaired Tolerance to Food Antigens in Mice with Enhanced IL-4 Receptor Signaling, Journal of Allergy and Clinical Immunology, vol. 127, No. 3, pp. 795-805, Dec. 2010.
Mendelsohn, et al., Revision Rates after Endoscopic Sinus Surgery: A Recurrence Analysis, Annals of Otology, Rhinology & Laryngology, vol. 120, No. 3, pp. 162-166, Jan. 2011.
Meteran, et al., Novel Monoclonal Treatments in Severe Asthma, Journal of Asthma, vol. 54, No. 10, pp. 991-1011, Mar. 2017.
Mishra, et al., An Etiological Role for Aeroallergens and Eosinophils in Experimental Esophagitis, The Journal of Clinical Investigation, vol. 107, No. 1, pp. 83-90, Jan. 2001.
Mishra, et al., IL-5 Promotes Eosinophil Trafficking to the Esophagus, The Journal of Immunology, vol. 168, No. 5, pp. 2464-2469, Mar. 2002.
Mishra, et al., Intratracheal IL-13 Induces Eosinophilic Esophagitis by an IL-5, Eotaxin-1, and STAT6-Dependent Mechanism, Gastroenterology, vol. 125, No. 5, pp. 1419-1427, Nov. 2003.
Molfino, et al., Molecular and Clinical Rationale for Therapeutic Targeting of Interleukin-5 and its Receptor, Clinical and Experimental Allergy, vol. 42, No. 5, pp. 712-737, Sep. 23, 2011.
Mordenti, et al., Interspecies Scaling of Clearance and vol. of Distribution Data for Five Therapeutic Proteins, Pharmaceutical Research, vol. 8, pp. 1351-1359, Nov. 1991.
Morioka, et al., IL-4/IL-13 Antagonist DNA Vaccination Successfully Suppresses Th2 Type Chronic Dermatitis, British Journal of Dermatology, vol. 160, No. 6, pp. 1172-1179, Jun. 2009.
Mueller, et al., Structure, Binding, and Antagonists in the IL-4/IL-13 Receptor System, Biochimica et Biophysica Acta, pp. 237-250, Jan. 2002.
Naclerio, et al., Dupilumab Improves Sense of Smell and Reduces Anosmia Among Patients with Nasal Polyposis and Chronic Sinusitis: Results from a Phase 2a Trial, Journal of Allergy and Clinical Immunology, vol. 139, No. 2, AB90, 1 Page, Feb. 1, 2017.
Nadeau, et al., Oral Immunotherapy and Anti-IgE Antibody-Adjunctive Treatment for Food Allergy, Immunology and Allergy Clinics of North America, vol. 32, No. 1, pp. 111-133, Feb. 1, 2012.
Nadeu, et al., Rapid Oral Desensitization in Combination with Omalizumab Therapy in Patients with Cow's Milk Allergy, The Journal of Allergy and Clinical Immunology, vol. 127, No. 6, pp. 1622-1624, Jun. 1, 2011.
Nagaraju, et al., Bortezomib Treatment Diminishes Hazelnut-Induced Intestinal Anaphylaxis in Mice: Immunomodulation, European Journal of Immunology, vol. 46, No. 07, pp. 1727-1736, May 11, 2016.
NCBI, Alignment Heavy Chain Dupilumab with SEQ ID No. 9, Basic Local Alignment Search Tool, XP055240680, 2 Pages., Jan. 12, 2016.
NCBI, Alignment of Light Chain of Dupilumab With SEQ ID No. 10, XP055240683, 2 Pages., Jan. 12, 2016.
Newton, et al., A Review of Nasal Polyposis, Therapeutics and Clinical Risk Management, vol. 4, No. 2, pp. 507-512, Apr. 1, 2008.
Nguyen, et al., Immune Modulation for Treatment of Allergic Disease, Immunological Reviews, vol. 242, No. 1, pp. 258-271, Jul. 1, 2011.
NHLBI, Quick Reference Charts for the Classification and Step wise Treatment of Asthma, Adapted from 2007 National Heart, Lung and Blood Institute Guidelines for the Diagnosis and Treatment of Asthma Expert Panel Report 3, 2 Pages., Jan. 2007.
Nicodeme, et al., Esophageal Distensibility as a Measure of Disease Severity in Patients with Eosinophilic Esophagitis, Clinical Gastroenterology and Hepatology, vol. 11, No. 9, pp. 1101-1107, Sep. 2013.
Niederberger, Verena, Allergen Specific Immunotherapy, Immunology Letters, vol. 122, Issue 2, pp. 131-133, Feb. 2009.
Niranjan, et al., Pathogenesis of Allergen-Induced Eosinophilic Esophagitis is Independent of Interleukin (IL)-13, Immunology and Cell Biology, vol. 91, No. 6, pp. 408-415, Jul. 2013.
Noel, et al., Eosinophilic Esophagitis, The New England Journal of Medicine, vol. 351, pp. 940-941, Aug. 2006.
Novartis Pharmaceuticals, A Double Blinded, Randomized, Placebo-Controlled Trial of Intravenous QAX576 in the treatment of Eosinophilic Esophagitis, QAX576, Jan. 2013.
Oetjen, et al., Sensory Neurons Co-opt Classical Immune Signaling Pathways to Mediate Chronic Itch, Cell, vol. 171, Issue 1, pp. 217-228, Sep. 2017.
Oh, et al., Investigational Therapeutics Targeting the IL-4/1 L-13/STAT-6 Pathway for the Treatment of Asthma, European Respiratory Review, vol. 19, No. 115, pp. 46-54, Jan. 2010.
Ohno, et al., Antigen-Binding Specificities of Antibodies are Primarily Determined by Seven Residues of VH, Proceedings of the National Academy of Sciences, vol. 82, No. 9, pp. 2945-2949, May 1985.
Ong, Peck Y., Editorial Update on Emerging Treatments of Atopic Dermatitis, Expert Opinion on Emerging Drugs, vol. 17, No. 2, pp. 129-133, Jan. 2012.
Otani, et al., Anti-IL-5 Therapy Reduces Mast Cell and IL-9 Cell Numbers in Pediatric Patients with Eosinophilic Esophagitis, Journal of Allergy and Clinical Immunology, vol. 131, No. 6, pp. 1576-1582, Apr. 2013.
Otulana, et al., A Phase 2b Study of Inhaled Pitrakinra, An IL-4R/IL-13 Antagonist, Successfully Identified 8 Responder Subpopulations of Patients with Uncontrolled Asthma, Abstract A6179, American Journal of Respiratory and Critical Care Medicine, vol. 183, 1 Page., Jan. 2011.
Oyoshi, et al., Cellular and Molecular Mechanisms in Atopic Dermatitis, Advances in Immunology, vol. 102, pp. 135-226, Jan. 2009.
Paller, et al., 621 Dupilumab in Adolescents with Moderate-to-Severe Atopic Dermatitis and a History of Inadequate Response, or Intolerance to Cyclosporine: Subgroup Analysis from a Pivotal 16-Week Trial, XP002793332, 2 Pages., Jan. 2019.
Paller, et al., Early and Sustained, Clinically Meaningful Responses with Dupilumab Treatment in a Phase 3 Trial in Adolescents with Moderate-to-Severe Atopic Dermatitis, Pediatric Dermatology, vol. 36, Supplemennt 1, XP55610351, p. S4, Apr. 29, 2019.
Paton, D M., Dupilumab: Human Monoclonal Antibody Against IL-4Ralpha for Moderate to Servere Atopic Dermatitis, Drugs Today, vol. 53, No. 9, pp. 477-487, Sep. 1, 2017.
Pesek, et al., Emerging Drugs for Eosinophilic Esophagitis, Expert Opinion on Emerging Drugs, vol. 23, No. 2, pp. 173-183, Jun. 8, 2018.
Peserico, et al., Reduction of Relapses of Atopic Dermatitis with Methylprednisolone Aceptonate Cream Twice Weekly in Addition to Maintenance Treatment with Enrollment: A Multicentre, Randomized, Double-Blind, Controlled Study, British Journal of Dermatology, vol. 158, No. 04, pp. 801-807, Jan. 2008.

(56) References Cited

OTHER PUBLICATIONS

Phan, et al., Assessment of Pruritus Intensity: Prospective Study on Validity and Reliability of the Visual Analogue Scale, Numerical Rating Scale and Verbal Rating Scale in 471 Patients with Chronic Pruritus, Acta Dermato-Venereologica, vol. 92, pp. 449-581, Jan. 2012.

Portolano, et al., Lack of Promiscuity in Autoantigen-Specific H and L Chain Combinations as Revealed by Human H and L Chain "Roulette", Journal of Immunology, vol. 150, No. 3, pp. 880-887, Feb. 1993.

Powell, et al., Compendium of Excipients for Parenteral Formulations, PDA Journal of Pharmaceutical Science and Technology, vol. 52, No. 5, pp. 238-311, Sep. 1, 1998.

Prieto, et al., Eosinophilic Esophagitis in Adults: an Update on Medical Management, Current Gastroenterology Reports, vol. 15, No. 324, pp. 1-9, May 2013.

Prussin, et al., Eosinophilic Gastrointestinal Disease and Peanut Allergy are Alternatively Associated with IL-51 and IL-5-TH2 Responses, Journal of Allergy and Clinical Immunology, vol. 124, No. 6, pp. 1326-1332, Dec. 2009.

Pubchem, CAS Registry No. 1190264-60-8, PubChem SID No. 172232447. National Center for Biotechnology Information, Retrieved From: <<http://pubchem.ncbi.nlm.nih.gov/substance/172232447#section=Top>>, XP055240678, 5 Pages., Mar. 2016.

Rafi, et al., Effects of Omalizumab in Patients with Food Allergy, in Allergy & Asthma Proceedings, vol. 31, No. 1, pp. 76-83, Jan. 2010.

Rayapudi, Indoor insect Allergens are Potent Inducers of Experimental Eosinophilic Esophagitis in Mice, Journal of Leukocyte Biology, vol. 88, No. 2, pp. 337-346, Aug. 2010.

Regeneron Phamaceuticals, Highlights of Prescribing Information, XP055534130, Retrieved From URL <<https://www.regeneron.com/sites/defaulllfiles/Dupixent_FPI.pdf>>, 4 Pages., Apr. 2017.

Regeneron Pharmaceuticals, A Study to Determine the Safety and Tolerability of Dupilumab (REGN668/SAR231893) in Patients Aged ≥6 to ≥18 Years With Atopic Dermatitis (Eczema), ClinicalTrials.gov Identifier: NCT02407756, Retrieved From: <<https://clinicaltrials.gov/ct2/show/NCT02407756>>, 9 Pages.

Regeneron Pharmaceuticals, Dupilumab as an Adjunct for Subcutaneous Grass Immunotherapy, History of Changes for Study: NCT03558997, Retrieved From: <<https://clinicaltrials.gov/ct2/history/NCT03558997?V_5=View#StudyPageTop>>, 46 Pages., May 2020.

Regeneron Pharmaceuticals, Dupixent: Highlights of Prescribing Information, "XP55610296, Retrieved From URL: <<https://d1egnxy4x1q3f.cloudfront.net/ Regeneron/Dupixent_FPI.pdf>>", pp. 1-8, Mar. 2019.

Regeneron Pharmaceuticals, Regeneron and Sanofi Announce Positive Phase 2 Study Results for Dupilumab in Patients Active Moderate-to-severe Eosinophilic Esophagitis, Acquire Media, 4 Pages., Oct. 2017.

Regeneron Pharmaceuticals, Regeneron and Sanofi Announce Positive Phase 2 Top-line Dupilumab Results in Patients with Chronic Sinusitis with Nasal Polyps, Acquire Media, XP055240175, 3 Pages., Sep. 30, 2014.

Regeneron Pharmaceuticals, Sanofi and Regeneron Report Positive Proof- of-Concept Data for Dupilumab, and IL-4R alpha Antibody, in Atopic Dermatitis, Presented at the 71st Annual Meeting of the American Academy of Dermatology, Mar. 2013.

Regeneron Pharmaceuticals Inc., Highlights of Prescribing Information (Dupixent), Dupixent Food and Drug Administration Label, 4 Pages., Mar. 2017.

Regeneron Pharmaceuticals Inc., Sanofi and Regeneron Announce Publication of Positive 5 Phase 2a Results of Dupilumab in Asthma in the New England Journal of Medicine, Press Release, Acquire Media, 3 Pages., May 2013.

Regeneron Pharmaceuticals, Inc., Sanofi and Regeneron report positive results with Sarilumab in first phase 3 rheumatoid arthritis registration trial, Press Release, Acquire Media, 6 Pages., Nov. 2013.

Ring, et al., Guidelines for Treatment of Atopic Eczema Part I, Journal of the European Academy of Dermatology and Venereology, vol. 26, pp. 1045-1060, Jan. 2012.

Rizk, Habib, Role of Aspirin Desensitization in the Management of Chronic Rhinosinusitis, Current Opinion in Otolaryngology & Head and Neck Surgery, vol. 19, Issue 3, pp. 210-217, Jan. 2011.

Roitt, et al., Immunology—Sixth Edition, Mosby—Harcourt Publishers Limited, pp. 110-111, Jan. 2001.

Roll, et al., Safety of Specific Immunotherapy using a Four-Hour Ultra-Rush Induction Scheme in Bee and Wasp Allergy, Journal of Investigational Allergology and Clinical Immunology, vol. 16, No. 2, pp. 79-85, Jan. 2006.

Romaniuk, L I., Allergan-Specific Immunotherapy Mechanisms Methods and Efficacy, Clinical Immunology, Allergology and Infectology, Special Issue, pp. 44-47, Jan. 2012.

Rothenberg, Marc E., Eosinophilic Esophagitis: Biology to Therapy, Gastroenterology, vol. 137, No. 4, pp. 1238-1249, Oct. 2009.

Rothenberg, Marc E., Eosinophilic Gastrointestinal Disorders (EGID), Journal of Allergy and Clinical Immunology, vol. 113, No. 1, pp. 11-28, Jan. 2004.

Rothenberg, et al., Intravenous Anti-IL-13 mAb QAX576 for the Treatment of Eosinophilic Esophagitis, The Journal of Allergy and Clinical Immunology, vol. 135, No. 2, pp. 500-507, Feb. 2015.

Saeki, et al., Guidelines for Management of Atopic Dermatitis, Advances in Medicine, Special Issue, vol. 228, No. 1, pp. 75-79, Jan. 2009.

Sampson, et al., A Phase II, Randomized, Double-Blind, Parallel-Group, PlaceboOcontrolled Oral Food Challenge Trial of Xolair (Omalizumab) in Peanut Allergy, The Journal of Allergy and Clinical Immunology, vol. 127, No. 5, pp. 1309-1310.e1, May 2011.

Sanofi, A Controlled Clinical Study of Dupilumab in Patients With Bilateral Nasal Polyps (SINUS-24), ClinicalTrials.gov Identifier: NCT02912468, 18 Pages., Jul. 2019.

Sanofi, An Evaluation of Dupilumab in Patients with Nasal Polyposis and Chronic Symptoms of Sinusitis, Clinical Trials: NCT01920893, 4 Pages., Jun. 2014.

Sanofi, Controlled Clinical Study of Dupilumab in Patients With Nasal Polyps (SINUS-52), ClinicalTrials.gov Identifier: NCT02898454, 18 Pages., Oct. 2019.

Sanofi, Efficacy, Safety, and Tolerability of Dupilumab in Patients With Persistent Moderate to Severe Eosinophilic Asthma, Clinical trials, Archive History for NCT01312961, 9 Pages., Nov. 2019.

Sanofi, Evaluation of Dupilumab in Patients With Severe Steroid Dependent Asthma (VENTURE), Archive History for NCT02528214, Retrieved at URL: <<https://clinicaltrials.gov/ct2/history/NCT02528214?V_38=View#StudyPageTop>>, 15 Pages., Oct. 2018.

Sanofi, Evaluation of SAR440340 and as Combination Therapy With Dupilumab in Moderate-to-Severe Asthma Participants, Clinical Trials Accession No. NCT03387852, Retrieved from: <<https://clinicaltrials.gov/ct2/show/NCT03387852>>, 10 Pages., May 2020.

Sanofi, History of Changes for Study: NCT01259323 Sequential Ascending Dose Study to Assess the Safety and Tolerability of REGN668 (SAR231893) in Patients With Atopic Dermatitis, ClinicalTrials.gov Identifier: NCT01259323, Retrieved from: <<https://clinicaltrials.gov/ct2/histo[Y/NCT01259323?V5= View#StudyPageTop>>, 6 Pages., Oct. 2012.

Sanofi, History of Changes for Study: NCT01548404 Study of Dupilumab in Adult Patients With Extrinsic Moderate to Severe Atopic Dermatitis, ClinicalTrials.gov Identifier: NCT01548404, Retrieved from: <<https://clinicaltrials.gov/ct2/histo[Y/NCT01548404?V2=view#StudyPageToQ>>, 7 Pages., Nov. 2017.

Sato, et al., Recombinant Soluble Murine IL-4 Receptor can Inhibit or Enhance IgE Responses in Vivo, The Journal of Immunology, vol. 150, No. 7, pp. 2717-2723, Apr. 1993.

Scavuzzo, et al., Inflammatory Mediators and Eosinophilia in Atopic and Non-Atopic Patients with Nasal Polyposis, Biomedicine and Pharmacotherapy, vol. 59, No. 6, pp. 323-329, 2005.

Schmid, et al., Basophil Sensitivity Decreases During the Updosing of SCIT in Subjects Allergic to Grass Pollen, Journal of Allergy and Clinical Immunology, vol. 127, No. S2, p. AB203, Jan. 2011.

Schmidt, J J., DNA Cloning: A Practical Approach vols. I and II, Edited by D M Glover, IRL Press Oxford, 1 Page., Jan. 1985.

(56) References Cited

OTHER PUBLICATIONS

Schmitt, et al., What are the Best Outcome Measurements for Atopic Eczema? A Systematic Review, Journal of Allergy and Clinical Immunology, vol. 120, No. 6, pp. 1389-1398, Dec. 2007.
Schneider, et al., A Pilot Study of Omalizumab to Facilitate Rapid Oral Desensitization in High-Risk Peanut-Allergic Patients, Journal of Allergy and Clinical Immunology, vol. 132, No. 6, pp. 1368-1374, Dec. 2002.
Schubert, et al., Evaluation and Treatment of Allergic Fungal Sinusitis. I. Demographics and Diagnosis, The Journal of Allergy and Clinical Immunology, vol. 102, No. 3, pp. 387-394, Sep. 1998.
Schubert, et al., Evaluation and Treatment of Allergic Fungal Sinusitis. II. Treatment and Follow-up, The Journal of Allergy and Clinical Immunology, vol. 102, No. 3, pp. 395-402, Sep. 1998.
Sefton, Michael V., Implantable Pumps, Critical Reviews in Biomedical Engineering, vol. 14, No. 3, pp. 201-240, Jan. 1987.
Sekiya, et al., Increased Levels of a TH2-type CC Chemokine Thymus and Activation-Regulated Chemokine TARC) in Serum and Induced Sputum of Asthmatics, Allergy, vol. 57, No. 02, pp. 173-177, Jan. 2002.
Shannon, et al., Differences in Airway Cytokine Profile in Severe Asthma Compared to Moderate Asthma, CHEST, vol. 133, No. 2, pp. 420-426, Feb. 2008.
Sheahan, et al., Local IgE Production in Nonatopic Nasal Polyposis, Journal of Otolaryngology—Head and Neck Surgery, vol. 39, No. 1, pp. 45-51, Feb. 2010.
Siegfried, et al., Use of Dupilimab in Pediatric Atopic Dermatitis: Access, dosing, and Implications for Managing Severe Atopic Dermatitis, Pediatric Dermatology, vol. 36, No. 01, pp. 172-176, Jan. 2019.
Silverberg, et al., Dupilumab Treatment Induces Rapid Clinical Improvement of Itch in Patients With Moderate-to-Severe Atopic Dermatitis, 76th American Academy of Dermatology Annual Meeting, San Diego, USA, p. 1.
Silverberg, et al., Dupilumab Treatment Rapidly Improves Itch in Patients With Moderate to-Severe Atopic Dermatitis, 75th Annual Scientific Meeting of the American College of Asthma, p. 1.
Simpson, et al., Dupilumab Therapy Provides Clinically Meaningful Improvement in Patient-Reported 45 Outcomes (PROs): A Phase Llb, Randomized, Placebo-Controlled, Clinical Trial in Adult Patients with Moderate to Severe Topic Dermatitis (AD), Journal of the American Academy of Dermatology, vol. 75, No. 3, pp. 506-515, Jun. 4, 2016.
Simpson, et al., Patient Burden of Moderate to Severe Atopic Dermatitis (AD): Insights From a Phase b Clinical Trial of Dupilumab in Adults, Journal of the American Academy of Dermatology, vol. 74, No. 3, pp. 491-498, Jan. 14, 2016.
Simpson, et al., Two Phase 3 Trials of Dupilumab Versus Placebo in Atopic Dermatitis, The New England Journal of Medicine, vol. 375, No. 24, pp. 2335-2348, Sep. 30, 2016.
Slager, et al., IL-4 Receptor Polymorphisms Predict Reduction in Asthma Exacerbations During Response to an Anti-IL-4 Receptor Alpha Antagonist, vol. 130, No. 2, pp. 516-522, Apr. 26, 2012.
Small, et al., Efficacy and Safety of Mometasone Furoate Nasal Spray in Nasal Polyposis, The Journal of Allergy and Clinical Immunology, vol. 116, Issue 6, pp. 1275-1281, Sep. 27, 2005.
Sriaroon, et al., Biological Modulators in Eosinophilic Diseases, Clinical Reviews in Allergy & Immunology, vol. 50, No. 2, pp. 252-272, Aug. 17, 2014.
Stein, et al., Anti-IL-5 (Mepolizumab) Therapy for Eosinophilic Esophagitis, Journal of Allergy and Clinical Immunology, vol. 118, No. 6, pp. 1312-1319, Dec. 1, 2006.
Stone, et al., Immunomodulatory Therapy of Eosinophil-Associated Gastrointestinal Diseases, Clinical & Experimental Allergy, vol. 38, No. 12, pp. 1858-1865, Dec. 1, 2008.
Straumann, et al., Anti-Interleukin-5 Antibody Treatment (Mepolizumab) in Active Eosinophilic Oesophagitis: A Randomised, Placebo-Controlled, Double-Blind Trial, Gut, vol. 59, No. 1, pp. 21-30, Jan. 2010.
Straumann, Alex, Clinical Evaluation of the Adult who has Eosinophilic Esophagitis, Immunology and Allergy Clinics of North America, vol. 29, No. 1, pp. 11-18, Feb. 2009.
Straumann, et al., Eosinophilic Esophagitis: Escalating Epidemiology?, Journal of Allergy and Clinical Immunology, vol. 115, 2, pp. 418-419, Feb. 2005.
Straumann, et al., Idiopathic Eosinophilic Esophagitis is Associated with a TH2-Type Allergic Inflammatory Response, Journal of Allergy and Clinical Immunology, vol. 108, No. 6, pp. 954-961, Dec. 2001.
Straumman, et al., Anti-TNF-[Alpha](Infliximab) Therapy for Severe Adult Eosinophilic Esophagitis, Journal of Allergy and Clinical Immunology, vol. 122, No. 2, pp. 425-427, Aug. 2008.
Tang, et al., YKL-40 in Asthmatic Patients, and its Correlations with Exacerbation, Eosinophils and Immunoglobulin E, European Respiratory Society, vol. 35, pp. 757-760, Jan. 2010.
Taylor, et al., A Transgenic Mouse That Expresses a Diversity of Human Sequence Heavy and Light Chain Immunoglobulins, Nucleic Acids Research, vol. 20, No. 23, pp. 6287-6295, Dec. 11, 1992.
Tazawa, et al., Relative Importance of IL-4 and IL-13 in Lesional Skin of Atopic Dermatitis, Archives of Dermatological Research Springer, vol. 295, pp. 459-464, Mar. 2004.
Terui, et al., Learning from Fungus Allergy in Atopic Dermatitis Patients, Japanese Journal of Medical Mycology, vol. 41, No. 3, pp. 157-160, Jan. 2000.
Thaci, et al., Efficacy and Safety of Dupilumab in Adults with Moderate-to-Severe Atopic Dermatitis 47 Inadequately Controlled by Topical Treatments: A Randomised, Placebo-Controlled, Dose-Ranging Phase 2b Trial, Lancet, vol. 387, No. 10013, pp. 40-52, Oct. 2015.
Tomkinson, et al., A Murine IL-4 Receptor Antagonist that Inhibits IL-4- and IL-13-Induced Responses Prevents Antigen-Induced Airway Eosinophilia and Airway Hyperresponsiveness, The Journal of Immunology, vol. 166, No. 9, pp. 5792-5800, Jan. 2001.
Trangsrud, et al., Intranasal Corticosteroids for Allergic Rhinitis, Pharmacotherapy, vol. 22, No. 11, pp. 1458-1467, Jan. 2002.
Tsianakas, et al., Dupilumab: A Milestone in the Treatment of Atopic Dermatitis, Lancet, vol. 387, No. 10013, pp. 4-5, Oct. 2015.
Tsubouchi, et al., Successful Treatment with Mepolizumab in a Case of Allergic Bronchopulmonary Aspergillosis Complicated with Nontuberculous Mycobacterial Infection, Respiratory Medicine Case Reports, vol. 28, 100875, 5 Pages., Jan. 1, 2019.
Ul-Haq, et al., Interleukin-4 Receptor Signaling and its Binding Mechanism: A therapeutic insight from Inhibitors Tool Box, Cytokine and Growth Factor Reviews, vol. 32, pp. 3-15, Jan. 2016.
Vakharia, et al., Monoclonal Antibodies for Atopic Dermatitis: Progress and Potential, BioDrugs, vol. 31, No. 5, pp. 409-422, Oct. 2017.
Van Zele, et al., Differentiation of Chronic Sinus Diseases by Measurement of Inflammatory Mediators, Allergy, vol. 61, No. 11, pp. 1280-1289, Jan. 2006.
Van Zele, et al., Oral Steroids and Doxycycline: Two Different Approaches to Treat Nasal Polyps, Journal of Allergy and Clinical Immunology, vol. 125, No. 5, pp. 1069-1076, Jan. 2010.
Veerappan, et al., Prevalence of Eosinophilic Esophagitis in an Adult Population Undergoing Upper Endoscopy: A Prospective Study, Clinical Gastroenterology and Hepatology, vol. 7, No. 4, pp. 420-426, Apr. 2009.
Vestergaard, et al., A Th2 Chemokine, TARC, Produced by Keratinocytes May Recruit CLA+CCR4+ Lymphocytes into Lesional Atopic Dermatitis Skin, Journal of Investigative Dermatology, vol. 115, No. 4, pp. 640-646, Oct. 2000.
Virchow, et al., Cellular and Immunological Markers of Allergic and Intrinsic Bronchial Asthma, Lung, vol. 172, No. 6, pp. 313-334, Jan. 1994.
Vlaminck, et al., The Importance of Local Eosinophilia in the Surgical Outcome of Chronic Rhinosinusitis: A 3-Year Prospective Observational Study, American Journal of Rhinology & Allergy, vol. 28, No. 3, pp. 260-264.
Walker, et al., Atopic Dermatitis: Correlation of Peripheral Blood T Cell Activation, Eosinophilia and Serum Actors with Clinical Severity, Clinical and Experimental Allergy, vol. 23, pp. 143-153, Jan. 1993.

(56) References Cited

OTHER PUBLICATIONS

Walker, et al., Use of Biologics as Immunotherapy in Asthma and Related Diseases, Expert Review of Clinical Immunology, vol. 4, No. 6, pp. 743-756, Jan. 2008.
Wang, et al., Peanut-Induced Intestinal Allergy is Mediated Through a Mast Cell-IgE-FcepsilonRI-IL-13 Pathway, Journal of Allergy and Clinical Immunology, vol. 126, No. 2, pp. 306-316, Jul. 2010.
Wang, et al., The IIL-17 Cytokine Family and their Role in Allergic Inflammation, Current Opinion in Immunology, vol. 20 Number, pp. 697-702, Dec. 2008.
Ward, et al., Binding Activities of a Repertoire of Single Immunoglobulin Variable Domains Secreted From *Escherichia coli,* Nature, vol. 341, No. 6242, pp. 544-546, Oct. 1989.
Wark, et al., Latest Technologies for the Enhancement of Antibody Affinity, Advanced Drug Delivery Reviews, vol. 58, No. 5-6, pp. 657-670, Aug. 2006.
Weber, et al., Anti-IL-4 as a New Strategy in Allergy, Chemical immunology and Allergy, vol. 96, pp. 120-125, Mar. 2012.
Wegmann, et al., Targeting Cytokines in Asthma Therapy: Could IL-37 be a Solution?, Expert Review of Respiratory Medicine, vol. 11, No. 9, pp. 675-677, Jan. 2017.
Weihrauch, et al., Elevated Serum Levels of CC Thymus and Activation-Related Chemokine (Tarc) in Primary Hodgkin's Disease: Potential for a Prognostic Factor, Cancer Research, vol. 65, No. 13, pp. 5516-5519, Jul. 2005.
Weinbrand-Goichberg, et al., Eosinophilic Esophagitis: An Immune-Mediated Esophageal Disease, Immunologic Research, vol. 56, No. 2-3, pp. 249-260, Jul. 2013.
Wenzel, et al., Dupilumab efficacy and safety in adults with uncontrolled persistent asthma despite use of medium-to-high-dose inhaled corticosteroids plus a long-acting B2 agonist: a randomised double-blind placebo-controlled pivotal phase 2b dose-ranging trial, Lancet, vol. 388, No. 10039, pp. 31-44, Jul. 2016.
Wenzel, et al., Dupilumab in Persistent Asthma with Elevated Eosinophil Levels, The New England, Journal of Medicine, vol. 368, No. 26, pp. 2455-2466, May 21, 2013.
Wenzel, et al., Effect of An Interleukin-4 Variant on Late Phase Asthmatic Response to Allergen Challenge in Asthmatic Patients: Results of Two Phase 2a Studies, The Lancet, vol. 370, No. 9596, pp. 1422-1431, Jan. 2007.
Wenzel, et al., Late Breaking Abstract: Inhaled Pitrakinra, an IL-4/IL-13 Antagonist, Reduced Exacerbations in Patients with Eosinophilic Asthma, ERS—Programme, European Respiratory Society, Annual Congress, p. 3980, Sep. 21, 2010.
Wershil, Barry K., Exploring the Role of Mast Cells in Eosinophilic Esophagitis, Immunology and Allergy Clinics of North America, vol. 29, No. 1, pp. 189-195, Feb. 2009.
Whalley, et al., A New Instrument for Assessing Quality of Life in Atopic Dermatitis: International Development of the Quality of Life Index for Atopic Dermatitis (Qoliad), British Journal of Dermatology, vol. 150, pp. 274-283, Feb. 2004.
WHO, International Nonproprietary Names for Pharmaceutical Substances (INN), World Health Organization, Drug Information, vol. 26, No. 4, XP055084074, pp. 401-471, Jan. 2012.
Wilhelm, et al., Innate Lymphoid Cells and Type 2 (Th2) Mediated Immune Responses—Pathogenic or Beneficial?, Frontiers in Immunology, vol. 2, Article 68, pp. 1-4, Nov. 2011.
Wills-Karp, et al., Untangling the Complex Web of IL-4 and IL-13 Mediated Signaling Pathways, Science Signaling, vol. 1, No. 51, pp. 1-5, Dec. 2008.
Winter, et al., Pathogenic Long-Lived Plasma Cells and Their Survival Niches in Autoimmunity, Malignancy, and Allergy, The Journal of Immunology, vol. 189, No. 11, pp. 5105-5111, Nov. 2012.
Wong, et al., Guidelines for the Management of Atopic Dermatitis (eczema) for Pharmacists, Canadian Pharmacists Journal, vol. 150, No. 5, pp. 285-297, Sep. 2017.
Woodruff, et al., T-Helper Type 2-Driven Inflammation Defines Major Subphenotypes of Asthma, American Journal of Respiratory and Critical Care Medicine, vol. 180, No. 5, pp. 388-395, May 2009.
Wu, et al., Receptor-mediated in Vitro Gene Transformation by a Soluble DNA Carrier System, The Journal of Biological Chemistry, vol. 262, No. 10, pp. 4429-4432, Apr. 1987.
Yamanaka, et al., The Role of Cytokines/Chemokines in the Pathogenesis of Atopic Dermatitis, Current Problems in Dermatology, vol. 41, pp. 80-92, Jan. 2011.
Yang, et al., Anti-IL-4 Receptor mAb Attenuates Allergic Airway Hyperresponsiveness (AHR) and Inflammation in Allergic Mice, Journal of Allergy and Clinical Immunology, Poster 168, Abstracts S69, vol. 109, No. 1, 1 Page., Jan. 2002.
Yasuhara, et al., Fundamentals of Clinical Pharmacokinetics, Clinical Pharmacology, vol. 41, Issue 4, pp. 155-158, Jul. 2010.
Zuo, et al., IL-13 Induced Esophageal Remodeling and Gene Expression by an Eosinophil-Independent, L-13R {alpha}2-Inhibited Pathway, Journal of Immunology, vol. 185, pp. 660-669, Jan. 2010.
Zurawski, et al., The Primary Binding Subunit of the Human Interleukin-4 Receptor is Also a Component of the Interleukin-13 Receptor, Journal of Biological Chemistry, vol. 270, No. 23, pp. 13869-13878, Jan. 1995.
"Clinical Protocol for diagnosing and treating bronchial asthma", Republic of Belarus, Oct. 25, 2006, No. 807, pp. 196-204 [in Russian], obtained from url: https://web.archive.org/web/20170517155846/https://www.bsmu.by/downloads/kafedri/k_p oli_ter/stud/5.pdf.
Abe, Yasuhiko, et al., "Advances in the Diagnosis and Treatment of Eosinophilic Esophagitis", (English abstract), Gastroenterological Endoscopy, 2014, vol. 56, Issue 9, pp. 3378-3393.
Alobid et al., "Role of Medical Therapy on the Management of Nasal Polyps", Curr Allergy Asthma Rep., 2012, 12: 144-153.
Bacharier et al., "Dupilumab in Children with Uncontrolled Moderate-to-Severe Asthma", NEJM, Dec. 9, 2021, vol. 385, No. 24, pp. 2230-2240, Retrieved from url: https://www.nejm.org/doi/pdf/10.1056/NEJMoa2106567?articleTools=true.
Bachert et al., "ICON: Chronic Rhinosinusitis", World Allergy Organization, 2014, 7(25): 1-28.
Baiardini, et al., A New Tool to Evaluate the Impact of Chronic Urticaria on Quality of Life: Chronic Urticaria Quality of Life Questionnaire (CU-Q2oL), European Academy of Allergy and Clinical Immunology, vol. 60, No. 8, pp. 1073-1078, 2005.
Baturin et al., Micogenic sensibilization in patients having a controlled bronchial asthma, Scientific notes of Orel State University, No. 6, (56), pp. 187-191, 2013.
Beck et al., "Dupilumab Treatment for Generalized Prurigo Nodularis", JAMA Dermatol., Jan. 2019, 155(1): 118-120.
Bergmann, M.M. et al., "Evaluation of Food Allergy in Patients with Atopic Dermatitis", J Allergy Clin Immunol, 1, pp. 22-28, Jan. 1, 2013.
Besnard et al., "IL-33-activated dendritic cells are critical for allergic airway inflammation", Eur Journal of Immunology, Jun. 2011, 41(6): 1675-1686.
Bhatt et al., "Dupilumab for COPD with Type 2 Inflammation Indicated by Eosinophil Counts", NEJM, May 21, 2023, 389(3): 205-214.
Blakely, Kim et al., "Dupilumab, a monoclonal antibody for atopic dermatitis: a review of current literature", Skin Therapy Letter, March-Apr. 2016,vol. 21, No. 2, Dupilumab Clinical Trials in AD, 13 pages.
Bloomstein et al., "Simultaneous treatment of Samter triad and prurigo nodularis with dupilumab", JAAD Case Reports, Dec. 1, 2021, vol. 18, p. 20-22, Retrieved from the Internet: url: https://www.jaadcasereports.org/article/S2352-5126(21)00725-6/pdf.
Boguniewicz, Mark et al., "Recent insights into atopic dermatitis and implications for management of infectious complications", Journal of Allergy and Clinical Immunology, Jan. 2010, 125(1):4-13.
Brandt et al., "Th2 Cytokines and Atopic Dermatitis", J Clin Cell Immunol., Aug. 10, 2011, 2(3): 110.
Bruton, Kelly et al., "Interrupting reactivation of immunologic memory diverts the allergic response and prevents anaphylaxis", Journal of Allergy and Clinical Immunology, vol. 147, No. 4, Dec. 15, 2020, pp. 1381-1392.

(56) References Cited

OTHER PUBLICATIONS

Calugareanu et al., "Dramatic improvement of generalized prurigo nodularis with dupilumab", J Eur Acad Dermatol Venereol, Aug. 2019, 33(8): e303-e304.
Canonica, et al., The EAACI/GA2LEN/EDF/WAO Guideline for the Definition, Classification, Diagnosis, and Management of Urticaria: The 2013 Revision and Update, European Academy of Allergy and Clinical Immunology, vol. 69, No. 7, pp. 868-887, 2014.
Casale, et al., Similar Efficacy with Omalizumab in Chronic Idiopathic/Spontaneous Urticaria Despite Different Background Therapy, The Journal of Allergy and Clinical Immunology: In Practice, vol. 3, No. 5, pp. 743-750.e1, 2015.
Caswell-Smith et al., "Day-time variation of serum periostin in asthmatic adults treated with ICS/LABA and adults without asthma", Allergy Asthma Clin Immunol., 2017, 13: 8, Epublished Feb. 8, 2007.
Celakovska, J. et al., "Sensitization to aeroallergens in atopic dermatitis patients: association with concomitant allergic diseases", JEADV 2015; 29, 1500-1505.
Chaker, Adam et al., "Short-term subcutaneous grass pollen immunotherapy under the umbrella of anti-IL-4: A randomized controlled trial", Journal of Allergy and Clinical Immunology, vol. 137, No. 2, Oct. 31, 2015, 19 pages.
Chen, Ching, et al., "Enhancement and destruction of antibody function by somatic mutation: unequal occurrence is controlled by V gene combinatorial associations", The EMBO Journal vol. 15, No. 12, pp. 2784-2794, 1995.
Chen, et al., Different Expression Patterns of Plasma Th1-, Th2-, Th17- and Th22-related Cytokines Correlate With Serum Autoreactivity and Allergen Sensitivity in Chronic Spontaneous Urticaria, Journal of the European Academy of Dermatology & Venereology, vol. 32, No. 3, pp. 441-448, Mar. 2018.
Clinical Trials, Study NCT00436670, "Phase II Study to Evaluate the Efficacy of AMG 317", first posted Feb. 19, 2007, Amgen actual study completion date—Feb. 2009, 7 pages.
Clinical Trials, Study NCT01859988, phase 2b, "Study of Dupilumab Administered to Adult Patients With Moderate-to-Severe Atopic Dermatitis", study completion date—Sep. 2014, 10 pages.
Clinical Trials, Study NCT03682770—"Study in Pediatric Subjects With Peanut Allergy to Evaluate Efficacy and Safety of Dupilumab as Adjunct to AR10 Immunotherapy" Aug. 20, 2020, located at: URL:https://clinicaltrials.gov/ct2/history/NCT03682770?V_8=View#StudyPageTop, (retrieved on Mar. 10, 2022), 7 pages.
ClinicalTrials.gov Identifier NCT02528214, Oct. 24, 2017, Evaluation of Dupilumab in Patients with Severe Steroid Dependent Asthma (VENTURE).
ClinicalTrials.gov Identifier: NCT02948959, Oct. 27, 2016, Evaluation of Dupilumab in Children With Uncontrolled Asthma (VOYAGE).
ClinicalTrials.gov, "An Evaluation of Dupilumab in Patients With Moderate to Severe Uncontrolled Asthma", Clinical Trial Protocol Version 22, Feb. 3, 2014, ClinicalTrials.gov ID: NCT01854047.
Confino-Cohen et al., Low Stimulated Il-4 Secretion in Pbmc From Patients With Chronic Idiopathic Urticaria, Cytokine, vol. 27, No. 2-3, pp. 74-80, 2004.
Corren, Jonathan et al., "Short-term subcutaneous allergy immunotherapy and dupilumab are well-tolerated in allergic rhinitis: A randomized trial", Journal of Asthma and Allergy, vol. 14, Aug. 16, 2021, pp. 1045-1063.
D'erme, Angelo et al., "Spotlight on dupilumab in the treatment of atopic dermatitis: design, development, and potential place in therapy", Drug Des Devel Ther, 2017, vol. 11, p. 1473-1480, DOI:10.2147/DDDT.S113192, Abstract, c. 1475-1478, 8 pages.
Degirmenci et al., Analysis of the Association of Chronic Spontaneous Urticaria With Interlekin-4, -10, Transforming Growth Factor-β1, Interferon-γ, Interleukin-17a and -23 by Autologous Serum Skin Test, Advances in Dermatology and Allergology/Postpy Dermatologii i Alergologii, vol. 34, No. 1, pp. 70-76, 2017.
drugs.com, "Asthma Medications", 2014, obtained from url: <http://web.archive.org/web/20140131041952/http://www.drugs.com/asthma.html>.
Endo et al., "The Interleukin-33-p38 Kinase Axis Confers Memory T Helper 2 Cell Pathogenicity in the Airway", Immunity, Feb. 17, 2015, 42(2): 294-308.
Errichetti et al., "Recalcitrant chronic urticaria treated with dupilumab: Report of two instances refractory to H1-antihistamines, omalizumab and cyclosporine and brief literature review", Dermatologic Therapy, Mar./Apr. 2021, 34(2): e14821.
Extended European Search Report for European Application No. 23206862.7, dated Apr. 24, 2024.
Extended European Search Report for European Application No. 23202532.0, dated Mar. 27, 2024.
Extended European Search Report for European Application No. 24150594.0, dated Jul. 5, 2024.
FDA "Highlights of Prescribing Information", Sep. 29, 2022, Retrieved from url: https://www.accessdata.fda.gov/drugsatfda_docs/label/2022/761055s044lbl.pdf.
Finkelman, Fred, et al., "Regulation of murine in vivo IgG and IgE responses by a monoclonal anti-IL-4 receptor antibody", Jun. 1991;3(6); 599-607.
Garraud, Olivier, et al., "Regulation of immunoglobulin production in hyper-IgE (Job's) syndrome", J. Allergy Clin. Immunol., Feb. 1999. (2 Pt. 1): 333-340.
Gimenez-Arnau, et al., The Pathogenesis of Chronic Spontaneous Urticaria: The Role of Infiltrating Cells, The Journal of Allergy and Clinical Immunology: In Practice, vol. 9, No. 6, pp. 2195-2208, Jun. 2021.
Gong, J.Q et al., "Skin Colonization by *Staphylococcus aureus* in patients with eczema and atopic dermatitis and relevant combined topical therapy: a double-blind multicentre randomized controlled trial", British Journal of Dermatology, No. 155, pp. 680-687 (2006), Mar. 28, 2006.
Gonnet, et al., Exhaustive Matching of the Entire Protein Sequence Database, Science, vol. 256, No. 5062, pp. 1443-1445, Jun. 5, 1992.
Goryachkina et al., Allergic bronchopulmonary aspergillosis, Allergiology, n.2, 2008, pp. 11-14.
Grob, et al., Comparative Study of the Impact of Chronic Urticaria, Psoriasis and Atopic Dermatitis on the Quality of Life, British Journal of Dermatology, vol. 152, No. 2, pp. 289-295, 2005.
Hamilton et al., "Dupilumab normalizes the eosinophilic esophagitis disease transcriptome in adult patients with eosinophilic esophagitis", Gastroenterology, 2020, 158:Suppl 1:S-835-S-835. abstract.
Harris, Jeffrey et al., "A randomized trial of the efficacy and safety of quilizumab in adults with inadequately controlled allergic asthma", Respiratory Research (2016) 17:29, 11 pages.
Hawro, et al., The Urticaria Activity Score—Validity, Reliability, and Responsiveness, The Journal of Allergy and Clinical Immunology: In Practice, vol. 6, No. 4, pp. 1185-1190.e1, 2018.
Hendricks et al., "Dupilumab use in dermatologic conditions beyond atopic dermatitis—a systematic review", Journal of Dermatological Treatment, 2023, 23(1): 19-28.
Herdman, et al., Development and Preliminary Testing of the New Five-level Version of EQ-5D (EQ-5D-5L), Quality of Life Research, vol. 20, No. 10, pp. 1727-1736, Apr. 9, 2011.
Hollis, et al., Comparison of Urticaria Activity Score Over 7 Days (UAS7) Values Obtained from Once-Daily and Twice-Daily Versions: Results from the ASSURE-CSU Study, American Journal of Clinical Dermatology, vol. 19, No. 2, pp. 267-274, Jan. 24, 2018.
Igelman, Sean et al., "Off-label use of dupilumab for pediatric patients with atopic dermatitis: A multicenter retrospective review", Journal of the American Academy of Dermatology, Mosby, Inc., US, vol. 82, No. 2, Oct. 10, 2019, pp. 407-411.
Inoue et al., "Periostin as a biomarker for the diagnosis of pediatric asthma", Pediatr Allergy Asthma, Aug. 2016, 27(5): 521-526, Epublished Apr. 7, 2016.
International Search Report with Written Opinion for PCT International Patent Application No. PCT/US2020/066559, mailed May 31, 2021.
International Search Report with Written Opinion for PCT International Patent Application No. PCT/US2021/053328, mailed Feb. 23, 2022.

(56) References Cited

OTHER PUBLICATIONS

International Search Report with Written Opinion for PCT International Patent Application No. PCT/US2022/038185, mailed Jan. 10, 2023.
International Search Report with Written Opinion for PCT International Patent Application No. PCT/US2022/078341 mailed Mar. 7, 2023.
International Search Report with Written Opinion for PCT International Patent Application No. PCT/US2024/020860 mailed Aug. 26, 2024, 2023.
Kharkevich, "Pharmacology", 10th Ed., GEOTAR-Media, 2010, 908 pages, p. 42. [Russian w/ English translation].
Kharkevich, "Pharmacology", 9th Ed., Revised, added and corrected, GEOTAR-Media, 2006, pp. 66-67. [Russian language only].
Kim et al., "Engineering of anti-human interleukin-4 receptor alpha antibodies with potent antagonistic activity", Scientific Reports, 2019, vol. 9, Article No. 7772, pp. 1-12.
Krylov and Bobyrev, "Pharmacology", Moscow, 1999, "Routes of administration". [Russian language only].
Kussie, Paul, et al., "A Single Engineered Amino Acid Substitution Changes Antibody Fine Specificity", Journal of Immunology: 152, pp. 146-152, 1994.
Kwiatek, Monika et al., "Mechanical properties of the esophagus in eosinophilic esophagitis" Gastroenterology, 2011, vol. 140, No. 1, pp. 82-90.
Langley, R.G., et al., "Secukinumab in plaque psoriasis—results of two phase 3 trials", New England Journal of Medicine, Jul. 24, 2014, 371:4, pp. 326-338.
Lee et al., "Blockade of IL-33/ST2 ameliorates airway inflammation in a murine model of allergic asthma", Exp Lung Res., Mar. 2014, 40(2): 66-76.
Lee et al., "Dupilumab as a novel therapy for difficult to treat chronic spontaneous urticaria", Clinical Communicatinos, May 2019, 7(5): P1659-1661.E1.
Lee et al., "Inhibition of Murine Allergic Response by Monoclonal Interleukin-4 Receptor Antibody", J Rhinol., 2000, 7(2): 149-153.
Lee et al., "Targeting eosinophils in respiratory diseases: Biological axis, emerging therapeutics and treatment modalities", Life Sciences, 2018, 267: 118973.
Liew et al., "Interleukin-33 in health and disease", Nat Rev immunology, Nov. 2016, 16(11): 676-689.
Linden, Carey et al., "Analysis of allergen specific IgE cut points to cat and dog in the Childhood Allergy Study", Annals of Allergy, Asthma & Immunology, 2011, 106.2: 153-158. e2.
Liu et al., "Anti-IL-33 antibody treatment inhibits airway inflammation in a murine model of allergic asthma", Biochemical and Biophysical Research Communications, Aug. 14, 2009, 386(1): 181-185.
Lucae, S. et al., "IgE responses to exogenous and endogenous allergens in atopic dermatitis patients under long-term systemic cyclosporine A treatment", Allergy 71 (2016); 115-118.
Macharadze, Modern Clinical Aspects of total and Specific IGE evaluation, Pediatrics, 2017, vol. 96, No. 2, pp. 121-127.
Mathias, et al., Evaluating the Minimally Important Difference of the Urticaria Activity Score and Other Measures of Disease Activity in Patients With Chronic Idiopathic Urticaria, Annals of Allergy, Asthma & Immunology, vol. 108, No. 1, pp. 20-24, Jan. 2012.
Maurer, et al., Omalizumab for the Treatment of Chronic Idiopathic or Spontaneous Urticaria, The New England Journal of Medicine, vol. 368, No. 10, pp. 924-935, Feb. 24, 2013.
Maurer, et al., Unmet Clinical Needs in Chronic Spontaneous Urticaria. A GA2LEN Task Force Report†, Allergy, vol. 66, No. 3, pp. 317-330, 2011.
Mcgregor et al., "Role of Biologics in Asthma", Am J Respir Crit Care Med., Feb. 15, 2019, 1999(4): 433-445.
Mlynek, et al., How to Assess Disease Activity in Patients With Chronic Urticaria?, European Academy of Allergy and Clinical Immunology, vol. 63, No. 6, pp. 777-780, 2008.
Moestrup et al., "Patient-reported outcomes (PROs) in chronic urticaria", Int'l Journal opf Dermatology, Dec. 2017, 56(12): 1342-1348.
Mollanazar et al., "Reduced Itch Associated with Dupilumab Treatment in 4 Patients with Prurigo Nodularis", JAMA Dermatology, Jan. 2019, 155(1): 121-122.
Mulder, DJ et al., "Understanding eosinophilic esophagitis: the cellular and molecular mechanisms of an emerging disease", Mucosal Immunology, Mar. 2011, vol. 4, No. 2, pp. 139-147.
Na et al., "IL-33 enhances Siglec-8 mediated apoptosis of human eosinophils", Cytokine, Oct. 17, 2011, 57(1): 169-174.
Navarini, A., et al., "Interrupting IL-6-receptor signaling improves atopic dermatitis but associates with bacterial superinfection", Nov. 2011 J Allergy Clin Immunol, Letters to the Editor, pp. 1128-1130.
Paller et al., "Efficacy and safety of dupilumab with concomitant topical corticosteroids in children 6 to 11 years old with severe atopic dermatitis: A randomized, double-blinded, placebo-controlled phase 3 trial", J Am Acad Dermatol., Nov. 2020, vol. 83, No. 5, pp. 1282-1293, Epub Jun. 20, 2020.
Peters et al., "Uncontrolled asthma: a review of the prevalence, disease burden and options for treatment", Respir Med., Jul. 2006, 100(7): 1139-1151.
Radin et al., "First-in-Human Study of REGN668/SAR231893 (IL-4Rα mAb): Safety, Tolerability and Biomarker Results of a Randomized, Double-Blind, Placebo- Controlled, Single Ascending Dose Study in Healthy Volunteers", J. Allergy Clin. Immunol., 2013, vol. 131(2), Suppl., p. AB158, (made available on Jan. 26, 2013), 2 pgs.
Ramonell et al., Dupilumab treatment for allergic bronchopulmonary aspergillosis: A case series, J Clin Innunol Pract., Feb. 2020, 8(2): 742-743.
Reed, Craig, et al., "Patient-reported outcomes in esophageal diseases", Clinical Gastroenterology and Hepatology, Elsevier, Amsterdam, NL, vol. 16. No. 3, pp. 305-310.
Regeneron Pharmaceuticals, Inc., Center for Drug Evaluation and Research, Approval Package for Application No. 761055Orig1s014, Dupixent Solution for Injection, Jun. 26, 2019.
Sandeep et al., Evaluation of serum immunoglobulin E levels in bronchial asthma, Lung India, Jul.-Sep. 2010, 27(3).
Sanofi (Dec. 22, 2017) "Evaluation of SAR440340 and as Combination Therapy with Dupilumab in Moderate-to-Severe Asthma Participants", Clinical Trials Accession No. A327NCT03387852, Retrieved from: <<https://clinicaltrials.gov/ct2/show/NCT03387852>>.
Sanofi, "Dupixent (dupilumab) significantly reduced severe asthma attacks in children and is the only biologic to demonstrate improvement in children's lung function in a randomized Phase 3 trial", Oct. 13, 2020, pp. 1-6, retieved from url: https://ml-eu.globenewswire.com/Resource/Download/326080b9-593f-4d56-8035-48827a7b5bf4.
Sanofi, clinicaltrials.gov (Aug. 20, 2012) "Efficacy, Safety, and Tolerability of Dupilumab in Patients With Persisten Moderate to Severe Eosinophilic Asthma," [accessible on the internet at: https://clinicaltrials.gov/ct2/show/NCT01312961].
Semprini et al., Change in biomarkers of type-2 inflammation following severe exacerbations of asthma, Thorax, 2019, 74: 95-98.
Shikiar, et al., Minimal Important Difference (MID) of the Dermatology Life Quality Index (DLQI): Results From Patients With Chronic Idiopathic Urticaria, Health and Quality of Life Outcomes, vol. 3, No. 36, pp. 1-5, May 20, 2005.
Staubach et al., "Severe chronic spontaneous urticaria in children—treatment options according to the guidelines and beyond—a 10 years review", Journal of Dermatological Treatment, 2022, 33(2): 1119-1122.
Stull et al., "Analysis of disease activity categories in chronic spontaneous/idiopathic urticaria", British Journal of Dermatology, Oct. 1, 2017, 177(4): 1093-1101.
Tanis et al., "Dupilumab treatment for prurigo nodularis", J Drugs Dermatol., Sep. 1, 2019, 18(9): 940-942, Retrieved from url: https://pubmed.ncbi.nlm.nih.gov/31524352/.
Ulashchik, "The targeted transport of the medicinal substances and the therapeutic physical factors", Voprosy kurortologii, fizioterapii, i lechebnoi fizicheskoi kultury 2014, 91(6): 52-61 [in Russian].

(56) References Cited

OTHER PUBLICATIONS

Vincent, M. et al., "Single-Dose, First-in-Human Study of AMG 317: Pharmacokinetics and Safety in Healthy and Asthmatic Adults", the Journal of Allergy and Clinical Immunology, vol. 121, Issue 2, Supplement 1, S10, Abstract, Feb. 1, 2008, 1 page.

Waccholz et al., "Detection of Allergen-Specific IgE Antibody Responses", 2005, Journal of Immunotoxicology, 1:3-4, 189-199.

Wambre, ER, "Baseline characteristics of peanut-allergic individuals during the dupilumab as adjunct to AR101 clinical trial", Abstract, retrieved at: https://onlinelibrary.wiley.com/doi/10.1111/all.14506, Sep. 7, 2020, 1 page.

Weller, Development and Validation of the Urticaria Control Test: a Patient-reported Outcome Instrument for Assessing Urticaria Control, Journal of Allergy and Clinical Immunology, vol. 133, No. 5, pp. 1365-1372.e6, 2014.

Weller, et al., Development, Validation, and Initial Results of the Angioedema Activity Score, European Academy of Allergy and Clinical Immunology, vol. 68, No. 9, pp. 1185-1192, 2013.

Wille, et al., Development of the EQ-5D-Y: a Child-friendly Version of the EQ-5D, Quality of Life Research, vol. 19, No. 6, pp. 875-886, Apr. 20, 2010.

Yamashita, Shuya et al., "Flavones suppress type I IL-4 receptor signaling by down-regulating the expression of common gamma chain", FEBS Letters, 2010, vol. 584, issue 4, p. 775-779, Abstract, Introduction, located at: https://febs.onlinelibrary.wiley.com/doi/full/10.1016/j.febslet.2009.12.044, 13 pages.

Zuberbier, et al., Epidemiology of Urticaria: a Representative Cross-sectional Population Survey, Clinical and Experimental Dermatology, vol. 35, No. 8, pp. 869-873, 2010.

Zuberbier, et al., The EAACI/GA²LEN/EDF/WAO Guideline for the Definition, Classification, Diagnosis and Management of Urticaria, European Academy of Allergy and Clinical Immunology, vol. 73, No. 7, pp. 1393-1414, 2018.

Third Party Observation dated Aug. 1, 2023 for European Publication No. 4011915 (Application No. 21199451.2).

D1—GINA Report Dec. 2011, Global Strategy for Asthma Management and Prevention, GINA © 2011 & Global Initiative for Asthma, reprinted with permission, Available from www.ginasthma org, cited in Third Party Observation dated Aug. 1, 2023, for European Publication No. 4011915 (Application No. 21199451.2).

D2—Wenzel, Severe Asthma: from characteristics to phenotypes to endotypes (review), Clinical & Experimental Allergy, Jan. 18, 2012, 42: 650-658, cited in Third Party Observation dated Aug. 1, 2023, for European Publication No. 4011915 (Application No. 21199451.2).

D3—Wenzel, Asthma phenotypes: the evolution from clinical to molecular approaches (review), Nature Medicine, May 4, 2012, 18(5): 716-725, cited in Third Party Observation dated Aug. 1, 2023, for European Publication No. 4011915 (Application No. 21199451.2).

D4—U.S. Pat. No. 8,075,887 B2, High Affinity Human Antibodies to Human IL-4 Receptor, issued Dec. 13, 2011, cited in Third Party Observation dated Aug. 1, 2023, for European Publication No. 4011915 (Application No. 21199451.2).

Notice of Opposition against European Patent No. 3973987 (Application No. 21191120.1) filed on Oct. 1, 2024, on behalf of Dr. H. Ulrich Dörries.

P1—U.S. Appl. No. 61/943,019, filed Feb. 21, 2014, cited in Notice of Opposition against European Patent No. 3973987 (Application No. 21191120.1) filed on Oct. 1, 2024, on behalf of Dr. H. Ulrich Dörries.

P2—EP 14306413.7 (Sep. 15, 2014), cited in Notice of Opposition against European Patent No. 3973987 (Application No. 21191120.1) filed on Oct. 1, 2024, on behalf of Dr. H. Ulrich Dörries.

P3—U.S. Appl. No. 62/077,669, filed Nov. 10, 2014, cited in Notice of Opposition against European Patent No. 3973987 (Application No. 21191120.1) filed on Oct. 1, 2024, on behalf of Dr. H. Ulrich Dörries.

WO—WO 2015/127229, parent application as filed, cited in Notice of Opposition against European Patent No. 3973987 (Application No. 21191120.1) filed on Oct. 1, 2024, on behalf of Dr. H. Ulrich Dörries.

D1—Wenzel et al., The New England Journal of Medicine, 368(26):2455-66, published online on May 21, 2013, cited in Notice of Opposition against European Patent No. 3973987 (Application No. 21191120.1) filed on Oct. 1, 2024, on behalf of Dr. H. Ulrich Dörries.

D1a—Supplementary Appendix to D1, published together with D1, cited in Notice of Opposition against European Patent No. 3973987 (Application No. 21191120.1) filed on Oct. 1, 2024, on behalf of Dr. H. Ulrich Dörries.

D2—Gibaldi M., "Biopharmaceutics and Clinical Pharmacokinetics", 4th Edition, 1991, Lea & Febiger, pp. 12-13, cited in Notice of Opposition against European Patent No. 3973987 (Application No. 21191120.1) filed on Oct. 1, 2024, on behalf of Dr. H. Ulrich Dörries.

D3—NCT01312961 clinical trial protocol, version 36, Jan. 13, 2014, cited in Notice of Opposition against European Patent No. 3973987 (Application No. 21191120.1) filed on Oct. 1, 2024, on behalf of Dr. H. Ulrich Dörries.

D4—NCT01854047 clinical trial protocol, version 23, Feb. 18, 2014, cited in Notice of Opposition against European Patent No. 3973987 (Application No. 21191120.1) filed on Oct. 1, 2024, on behalf of Dr. H. Ulrich Dörries.

D5—WO 2014/031610 A1, published on Feb. 27, 2014, cited in Notice of Opposition against European Patent No. 3973987 (Application No. 21191120.1) filed on Oct. 1, 2024, on behalf of Dr. H. Ulrich Dörries.

D6—Wenzel S. et al., Lancet, 388:31-44, published online on Apr. 26, 2016, cited in Notice of Opposition against European Patent No. 3973987 (Application No. 21191120.1) filed on Oct. 1, 2024, on behalf of Dr. H. Ulrich Dörries.

D7—pp. 401, 402 and 412 of WHO Drug Information, vol. 26, No. 4, 2012, cited in Notice of Opposition against European Patent No. 3973987 (Application No. 21191120.1) filed on Oct. 1, 2024, on behalf of Dr. H. Ulrich Dörries.

D8—EurekAlert!, press release; "Monoclonal antibody appears effective and safe in, cited in Notice of Opposition against European Patent No. 3973987 (Application No. 21191120.1) filed on Oct. 1, 2024, on behalf of Dr. H. Ulrich Dörries. asthma Phase IIa trial", May 21, 2013.

D9—Chapter 19, "Dosage regimens", of Aulton's Pharmaceutics: The Science of Dosage Form Design, 2nd Edition, 2001, cited in Notice of Opposition against European Patent No. 3973987 (Application No. 21191120.1) filed on Oct. 1, 2024, on behalf of Dr. H. Ulrich Dörries.

D10—Panaccione R. and Ghosh S., Therapeutic Advances in Gastroenterology, 3(3):179-189, published on May 2010, cited in Notice of Opposition against European Patent No. 3973987 (Application No. 21191120.1) filed on Oct. 1, 2024, on behalf of Dr. H. Ulrich Dörries.

D11—Press release from Regeneron Pharmaceuticals Inc., Mar. 2, 2013, cited in Notice of Opposition against European Patent No. 3973987 (Application No. 21191120.1) filed on Oct. 1, 2024, on behalf of Dr. H. Ulrich Dörries.

D12—Global Initiative for Asthma (GINA) Guidelines 2012, updated in 2012, cited in Notice of Opposition against European Patent No. 3973987 (Application No. 21191120.1) filed on Oct. 1, 2024, on behalf of Dr. H. Ulrich Dörries.

D13—Jin et al., Therapeutics and Clinical Risk Management, 4(1): 269-286, 2008, cited in Notice of Opposition against European Patent No. 3973987 (Application No. 21191120.1) filed on Oct. 1, 2024, on behalf of Dr. H. Ulrich Dörries.

D14—NCT01015027 clinical trial protocol, version 7, Jun. 13, 2013, cited in Notice of Opposition against European Patent No. 3973987 (Application No. 21191120.1) filed on Oct. 1, 2024, on behalf of Dr. H. Ulrich Dörries.

D15—NCT01484600 clinical trial protocol, version 2, Mar. 12, 2012, cited in Notice of Opposition against European Patent No. 3973987 (Application No. 21191120.1) filed on Oct. 1, 2024, on behalf of Dr. H. Ulrich Dörries.

(56) References Cited

OTHER PUBLICATIONS

D16—NCT01537653 clinical trial protocol, version 7, Dec. 5, 2013, cited in Notice of Opposition against European Patent No. 3973987 (Application No. 21191120.1) filed on Oct. 1, 2024, on behalf of Dr. H. Ulrich Dörries.
D17—NCT01537640 clinical trial protocol, version 6, Dec. 5, 2013, cited in Notice of Opposition against European Patent No. 3973987 (Application No. 21191120.1) filed on Oct. 1, 2024, on behalf of Dr. H. Ulrich Dörries.
D18—NCT01259323 clinical trial protocol, version 6, Oct. 2, 2012, cited in Notice of Opposition against European Patent No. 3973987 (Application No. 21191120.1) filed on Oct. 1, 2024, on behalf of Dr. H. Ulrich Dörries.
D19—NCT01385657 clinical trial protocol, version 4, Sep. 27, 2013, cited in Notice of Opposition against European Patent No. 3973987 (Application No. 21191120.1) filed on Oct. 1, 2024, on behalf of Dr. H. Ulrich Dörries.
Notice of Opposition against European Patent No. 3973987 (Application No. 21191120.1) filed on Oct. 9, 2024, on behalf of Secerna LLP.
D1—WHO Drug Information, vol. 26, No. 4, p. 412, Dec. 9, 2012, cited in Notice of Opposition against European Patent No. 3973987 (Application No. 21191120.1) filed on Oct. 9, 2024, on behalf of Secerna LLP.
D2—Wenzel et al., Dupilumab in persistent asthma with elevated eosinophil levels. N Engl J Med. 2013; 368(26):2455-66, May 21, 2013, cited in Notice of Opposition against European Patent No. 3973987 (Application No. 21191120.1) filed on Oct. 9, 2024, on behalf of Secerna LLP.
D3—Protocol for: Wenzel et al. Dupilumab in persistent asthma with elevated eosinophil levels. N Engl J Med 2013; 368:2455-66, May 21, 2013, cited in Notice of Opposition against European Patent No. 3973987 (Application No. 21191120.1) filed on Oct. 9, 2024, on behalf of Secerna LLP.
D4—Study NCT01854047, An Evaluation of Dupilumab in Patients with Moderate to Severe Uncontrolled Asthma, Feb. 18, 2014, cited in Notice of Opposition against European Patent No. 3973987 (Application No. 21191120.1) filed on Oct. 9, 2024, on behalf of Secerna LLP.
D5—Press release: Sanofi and Regeneron Announce Positive Results from Phase 2b Study of Dupilumab in Patients with Moderate-to-Severe Asthma, https://investor.regeneron.com/news-releases/news-release-details/regeneron-and-sanofi-announce-positive-results-phase-2b-study-0, Nov. 11, 2014, cited in Notice of Opposition against European Patent No. 3973987 (Application No. 21191120.1) filed on Oct. 9, 2024, on behalf of Secerna LLP.
D6—WO 2014/031610 A1 published Feb. 27, 2014, cited in Notice of Opposition against European Patent No. 3973987 (Application No. 21191120.1) filed on Oct. 9, 2024, on behalf of Secerna LLP.
D7—Aulton. Pharmaceutics The Science of Dosage Form Design 2nd Edition. Chapter 19, 275-288, Oct. 2001, cited in Notice of Opposition against European Patent No. 3973987 (Application No. 21191120.1) filed on Oct. 9, 2024, on behalf of Secerna LLP.
D8—Panaccione & Ghosh. Optimal use of biologics in the management of Crohn's disease. Therapeutic Advances in Gastroenterology 2010, 3(3), 179-189, May 2010, cited in Notice of Opposition against European Patent No. 3973987 (Application No. 21191120.1) filed on Oct. 9, 2024, on behalf of Secerna LLP.
D9—Mould & Green, Pharmacokinetics and Pharmacodynamics of Monoclonal Antibodies. Concepts and Lessons for Drug Development, 2010, 24(1), 23-39, Feb. 1, 2010, cited in Notice of Opposition against European Patent No. 3973987 (Application No. 21191120.1) filed on Oct. 9, 2024, on behalf of Secerna LLP.
D10—Eisenstein. Something new under the skin. Nature Biotechnology 2011 29(2), 107-109, Feb. 7, 2011, cited in Notice of Opposition against European Patent No. 3973987 (Application No. 21191120.1) filed on Oct. 9, 2024, on behalf of Secerna LLP.
D11—Costantino et al., Intranasal delivery: Physicochemical and therapeutic, aspects, International Journal of Pharmaceutics, 2007, 337(1-2), Abstract, cited in Notice of Opposition against European Patent No. 3973987 (Application No. 21191120.1) filed on Oct. 9, 2024, on behalf of Secerna LLP.
D12—Gibaldi. Biopharmaceutics and clinical pharmacokinetics. Fourth Edition 1991. 12-13, cited in Notice of Opposition against European Patent No. 3973987 (Application No. 21191120.1) filed on Oct. 9, 2024, on behalf of Secerna LLP.
D13—Press Release: Sanofi and Regeneron Report Positive Proof-of-Concept Data for Dupilumab, an IL-4R alpha Antibody, in Atopic Dermatitis. https://investor.regeneron.com/news-releases/news-release-details/sanofi-and-regeneron-report-positive-proof-concept-data, Mar. 2, 2013, cited in Notice of Opposition against European Patent No. 3973987 (Application No. 21191120.1) filed on Oct. 9, 2024, on behalf of Secerna LLP.
D14—WO 2022/076289 A1 (pp. 1 to 4), published Apr. 14, 2022, cited in Notice of Opposition against European Patent No. 3973987 (Application No. 21191120.1) filed on Oct. 9, 2024, on behalf of Secerna LLP.
D15—Shannon et al. Differences in Airway Cytokine Profile in Severe Asthma Compared to Moderate Asthma, Chest 2007, 133(2), 420-6, Dec. 10, 2007., cited in Notice of Opposition against European Patent No. 3973987 (Application No. 21191120.1) filed on Oct. 9, 2024, on behalf of Secerna LLP.
D16—Bossley et al. Paediatric severe asthma is characterized by eosinophilia and remodelling without TH2 cytokines. J Allergy Clin Immunol. 2012, 129(4), 974-982, Apr. 2012, cited in Notice of Opposition against European Patent No. 3973987 (Application No. 21191120.1) filed on Oct. 9, 2024, on behalf of Secerna LLP.
D17—EMEA. Annex I Summary of product characteristics for dupilumab, Sept. 2, 2022, cited in Notice of Opposition against European Patent No. 3973987 (Application No. 21191120.1) filed on Oct. 9, 2024, on behalf of Secerna LLP.
D18—Wenzel. Severe Asthma: from characteristics to phenotypes to endotypes. Clinical & Experimental Allergy 2012, 42, 650-658, Jan. 18, 2012, cited in Notice of Opposition against European Patent No. 3973987 (Application No. 21191120.1) filed on Oct. 9, 2024, on behalf of Secerna LLP.
D19—Wenzel. Severe Asthma in Adults. Am J Respir Crit Care Med. 2005 172(2) 149-160, cited in Notice of Opposition against European Patent No. 3973987 (Application No. 21191120.1) filed on Oct. 9, 2024, on behalf of Secerna LLP.
D20—Nakawah et al. Asthma, Chronic Obstructive Pulmonary Disease (COPD), and the Overlap Syndrome. 2013 J Am Board Fam Med 2013 26:4 470-477, Jul. 2013, cited in Notice of Opposition against European Patent No. 3973987 (Application No. 21191120.1) filed on Oct. 9, 2024, on behalf of Secerna LLP.
D21—Firszt & Kraft, Pharmacotherapy of severe asthma. Curr Opin Pharmacol. 2010. 10(3), 266-271, Jun. 2010, cited in Notice of Opposition against European Patent No. 3973987 (Application No. 21191120.1) filed on Oct. 9, 2024, on behalf of Secerna LLP.
D22—Al-Ramli et al. Th-17 cell-related cytokines' potential role in the pathogenesis of severe asthma. J Asthma. 2008 45, Suppl 1: 41-44, Jul. 2, 2009, cited in Notice of Opposition against European Patent No. 3973987 (Application No. 21191120.1) filed on Oct. 9, 2024, on behalf of Secerna LLP.
D23—Jennifer D Hamilton et al. Biomarkers elevated in atopic dermatitis (AD) are reduced by therapeutic blockade of IL-4 receptor alpha signalling with patients with moderate-to-severe AD. Abstract 1042, International Investigative Dermatology, XP055566280,, cited in Notice of Opposition against European Patent No. 3973987 (Application No. 21191120.1) filed on Oct. 9, 2024, on behalf of Secerna LLP. Edinburgh, May 8, 2013.
D24—EMEA Guideline for Industry—dose-response information to support drug registration ICH-E4, Nov. 1994, cited in Notice of Opposition against European Patent No. 3973987 (Application No. 21191120.1) filed on Oct. 9, 2024, on behalf of Secerna LLP.
D25—Dirks & Meibohm. Population Pharmacokinetics of Therapeutic Monoclonal Antibodies. Clin. Pharmacokinet. 2010; 49 (10) 633-659, cited in Notice of Opposition against European Patent No. 3973987 (Application No. 21191120.1) filed on Oct. 9, 2024, on behalf of Secerna LLP.
D26—Bai et al. A guide to rational dosing of monoclonal antibodies. Clin. Pharmacokinet. 2012, 52(2)119-135, cited in Notice of

(56) References Cited

OTHER PUBLICATIONS

Opposition against European Patent No. 3973987 (Application No. 21191120.1) filed on Oct. 9, 2024, on behalf of Secerna LLP.
P1—U.S. Appl. No. 61/943,019, filed Feb. 21, 2014, cited in Notice of Opposition against European Patent No. 3973987 (Application No. 21191120.1) filed on Oct. 9, 2024, on behalf of Secerna LLP.
P2—EP 14306413.7, filed on Sep. 15, 2014, cited in Notice of Opposition against European Patent No. 3973987 (Application No. 21191120.1) filed on Oct. 9, 2024, on behalf of Secerna LLP.
P3—U.S. Appl. No. 62/077,669, filed Nov. 10, 2014, cited in Notice of Opposition against European Patent No. 3973987 (Application No. 21191120.1) filed on Oct. 9, 2024, on behalf of Secerna LLP.
A—Divisional application as filed, Apr. 30, 2022, cited in Notice of Opposition against European Patent No. 3973987 (Application No. 21191120.1) filed on Oct. 9, 2024, on behalf of Secerna LLP.
Notice of Opposition against European Patent No. 3973987 (Application No. 21191120.1) filed on Oct. 10, 2024, on behalf of Dr. Luigi Rumi.
TM1—WO 2015/127229 A1, published Aug. 27, 2015, cited in Notice of Opposition against European Patent No. 3973987 (Application No. 21191120.1) filed on Oct. 10, 2024, on behalf of Dr. Luigi Rumi.
TM2—U.S. Appl. No. 61/943,019, filed Feb. 21, 2014, cited in Notice of Opposition against European Patent No. 3973987 (Application No. 21191120.1) filed on Oct. 10, 2024, on behalf of Dr. Luigi Rumi.
TM3—EP 14306413, filed on Sep. 15, 2014, cited in Notice of Opposition against European Patent No. 3973987 (Application No. 21191120.1) filed on Oct. 10, 2024, on behalf of Dr. Luigi Rumi.
TM4—U.S. Appl. No. 62/077,669, filed Nov. 10, 2014, cited in Notice of Opposition against European Patent No. 3973987 (Application No. 21191120.1) filed on Oct. 10, 2024, on behalf of Dr. Luigi Rumi.
TM6—WHO Drug Information vol. 26(4), 412, Dec. 9, 2012, cited in Notice of Opposition against European Patent No. 3973987 (Application No. 21191120.1) filed on Oct. 10, 2024, on behalf of Dr. Luigi Rumi.
TM7—Regeneron press release, "Sanofi and Regeneron report positive proof-of-concept data for dupilumab, an IL-4R alpha antibody in atopic dermatitis", Mar. 2, 2013, cited in Notice of Opposition against European Patent No. 3973987 (Application No. 21191120.1) filed on Oct. 10, 2024, on behalf of Dr. Luigi Rumi.
TM8—Pollart S.M. and Elward K.S. Overview of changes to asthma guidelines: diagnosis and screening. Am Fam Physician. May 1, 2009;79(9):761-7, cited in Notice of Opposition against European Patent No. 3973987 (Application No. 21191120.1) filed on Oct. 10, 2024, on behalf of Dr. Luigi Rumi.
TM9—"Global Strategy for Asthma Management and Prevention", Global Initiative for Asthma (GINA), 2011, cited in Notice of Opposition against European Patent No. 3973987 (Application No. 21191120.1) filed on Oct. 10, 2024, on behalf of Dr. Luigi Rumi.
TM10—Wenzel S et al. Dupilumab in persistent asthma with elevated eosinophil levels. N Engl J Med. Jun. 27, 2013;368(26):2455-66. doi: 10.1056/NEJMoa1304048. Epub May 21, 2013, cited in Notice of Opposition against European Patent No. 3973987 (Application No. 21191120.1) filed on Oct. 10, 2024, on behalf of Dr. Luigi Rumi.
TM11—Mutschler Arzneimittelwirkungen—Lehrbuch der Pharmakologie and Toxikologie, p. 83, 3.3.1 Dosierung, "Initialdosis, Erhaltungsdosis", cited in Notice of Opposition against European Patent No. 3973987 (Application No. 21191120.1) filed on Oct. 10, 2024, on behalf of Dr. Luigi Rumi.
TM12—NCT01854047, Feb. 18, 2014 (v23) , cited in Notice of Opposition against European Patent No. 3973987 (Application No. 21191120.1) filed on Oct. 10, 2024, on behalf of Dr. Luigi Rumi.
TM13—WO 2014/031610 A1, published Feb. 27, 2014, cited in Notice of Opposition against European Patent No. 3973987 (Application No. 21191120.1) filed on Oct. 10, 2024, on behalf of Dr. Luigi Rumi.
Notice of Opposition against European Patent No. 3973987 (Application No. 21191120.1) filed on Oct. 10, 2024, on behalf of Boult Wade Tennant LLP.
WO229—WO 2015/127229, published Aug. 27, 2015—PCT publication of the parent application, cited in Notice of Opposition against European Patent No. 3973987 (Application No. 21191120.1) filed on Oct. 10, 2024, on behalf of Boult Wade Tennant LLP.
D1—Wenzel et al., "Dupilumab in Persistent Asthma with Elevated Eosinophil Levels" New England Journal of Medicine, vol. 368 No. 26: 2455-2466, Jun. 27, 2013, cited in Notice of Opposition against European Patent No. 3973987 (Application No. 21191120.1) filed on Oct. 10, 2024, on behalf of Boult Wade Tennant LLP.
D2—Supplementary Appendix of Wenzel, 2013 (D1) , cited in Notice of Opposition against European Patent No. 3973987 (Application No. 21191120.1) filed on Oct. 10, 2024, on behalf of Boult Wade Tennant LLP.
D3—NCT01854047 "An evaluation of dupilumab in subjects with moderate to severe uncontrolled asthma", Clinical trial study record, Version 23, Feb. 18, 2014, cited in Notice of Opposition against European Patent No. 3973987 (Application No. 21191120.1) filed on Oct. 10, 2024, on behalf of Boult Wade Tennant LLP.
D4—U.S. Pat. No. 8,075,887 B2, issued Dec. 13, 2011, cited in Notice of Opposition against European Patent No. 3973987 (Application No. 21191120.1) filed on Oct. 10, 2024, on behalf of Boult Wade Tennant LLP.
D5—GINA Guidelines, 2009, cited in Notice of Opposition against European Patent No. 3973987 (Application No. 21191120.1) filed on Oct. 10, 2024, on behalf of Boult Wade Tennant LLP.
D6—WHO Drug Information, vol. 26, No.4, pp. 401-402 and 412, extract from "Proposed INN: List 108", published on Dec. 9, 2012, cited in Notice of Opposition against European Patent No. 3973987 (Application No. 21191120.1) filed on Oct. 10, 2024, on behalf of Boult Wade Tennant LLP.
D7—Radin, et al., Abstract 558, J Clin Immunol., Feb. 2013, cited in Notice of Opposition against European Patent No. 3973987 (Application No. 21191120.1) filed on Oct. 10, 2024, on behalf of Boult Wade Tennant LLP.
D8—Hashimoto and Bel, "Current treatment of severe asthma", Clinical & Experimental Allergy, vol. 42, pp. 693-705, 2012, cited in Notice of Opposition against European Patent No. 3973987 (Application No. 21191120.1) filed on Oct. 10, 2024, on behalf of Boult Wade Tennant LLP.
D9—Regeneron Press Release, May 21, 2013, cited in Notice of Opposition against European Patent No. 3973987 (Application No. 21191120.1) filed on Oct. 10, 2024, on behalf of Boult Wade Tennant LLP.
D10—Eurekalert! Press Release, "Monoclonal antibody appears effective and safe in asthma Phase IIa trial", May 21, 2013, cited in Notice of Opposition against European Patent No. 3973987 (Application No. 21191120.1) filed on Oct. 10, 2024, on behalf of Boult Wade Tennant LLP.
D11—Mould and Green, "Pharmacokinetics and Pharmacodynamics of Monoclonal Antibodies", Biodrugs, vol. 24(1), pp. 23-39, 2010, cited in Notice of Opposition against European Patent No. 3973987 (Application No. 21191120.1) filed on Oct. 10, 2024, on behalf of Boult Wade Tennant LLP.
D12—Galli et al., "Atopic Dermatitis and Asthma", Allergy Asthma Proc., vol. 28, pp. 540-543, 2007, cited in Notice of Opposition against European Patent No. 3973987 (Application No. 21191120.1) filed on Oct. 10, 2024, on behalf of Boult Wade Tennant LLP.
D13—NCT01312961 clinical trial study record, Version 36, Jan. 13, 2014, cited in Notice of Opposition against European Patent No. 3973987 (Application No. 21191120.1) filed on Oct. 10, 2024, on behalf of Boult Wade Tennant LLP.
D14—NCT01015027 clinical trial study record, Version 7, Jun. 13, 2013, cited in Notice of Opposition against European Patent No. 3973987 (Application No. 21191120.1) filed on Oct. 10, 2024, on behalf of Boult Wade Tennant LLP.
D15—NCT01484600 clinical trial study record, Version 2, Mar. 12, 2012, cited in Notice of Opposition against European Patent No. 3973987 (Application No. 21191120.1) filed on Oct. 10, 2024, on behalf of Boult Wade Tennant LLP.

(56) References Cited

OTHER PUBLICATIONS

D16—NCT01537653 clinical trial study record, Version 7, Dec. 5, 2013, cited in Notice of Opposition against European Patent No. 3973987 (Application No. 21191120.1) filed on Oct. 10, 2024, on behalf of Boult Wade Tennant LLP.
D17—NCT01537640 clinical trial study record, Version 6, Dec. 5, 2013, cited in Notice of Opposition against European Patent No. 3973987 (Application No. 21191120.1) filed on Oct. 10, 2024, on behalf of Boult Wade Tennant LLP.
D18—NCT01259323 clinical trial study record, Version 6, Oct. 2, 2012, cited in Notice of Opposition against European Patent No. 3973987 (Application No. 21191120.1) filed on Oct. 10, 2024, on behalf of Boult Wade Tennant LLP.
D19—NCT01385657 clinical trial study record, Version 4, Sep. 27, 2013, cited in Notice of Opposition against European Patent No. 3973987 (Application No. 21191120.1) filed on Oct. 10, 2024, on behalf of Boult Wade Tennant LLP.
P1—U.S. Appl. No. 61/943,019, filed Feb. 21, 2014, cited in Notice of Opposition against European Patent No. 3973987 (Application No. 21191120.1) filed on Oct. 10, 2024, on behalf of Boult Wade Tennant LLP.
P2—EP 14306413.7, filed on Sep. 15, 2014, cited in Notice of Opposition against European Patent No. 3973987 (Application No. 21191120.1) filed on Oct. 10, 2024, on behalf of Boult Wade Tennant LLP.
P3—U.S. Appl. No. 62/077,669, filed Nov. 10, 2014, cited in Notice of Opposition against European Patent No. 3973987 (Application No. 21191120.1) filed on Oct. 10, 2024, on behalf of Boult Wade Tennant LLP.
Notice of Opposition against European Patent No. 3973987 (Application No. 21191120.1) filed on Oct. 10, 2024, on behalf of Michaelski Hüttermann & Partner Patentanwalte mbD.
D1—Wenzel et al., 2013, cited in Notice of Opposition against European Patent No. 3973987 (Application No. 21191120.1) filed on Oct. 10, 2024, on behalf of Michaelski Hüttermann & Partner Patentanwalte mbD.
D2—Steinke et Borish, 2002, cited in Notice of Opposition against European Patent No. 3973987 (Application No. 21191120.1) filed on Oct. 10, 2024, on behalf of Michaelski Hüttermann & Partner Patentanwalte mbD.
D3—Wenzel et al., 2007, cited in Notice of Opposition against European Patent No. 3973987 (Application No. 21191120.1) filed on Oct. 10, 2024, on behalf of Michaelski Hüttermann & Partner Patentanwalte mbD.
D4—Corren et al., 2010, cited in Notice of Opposition against European Patent No. 3973987 (Application No. 21191120.1) filed on Oct. 10, 2024, on behalf of Michaelski Hüttermann & Partner Patentanwalte mbD.
D5—US 2003185821, cited in Notice of Opposition against European Patent No. 3973987 (Application No. 21191120.1) filed on Oct. 10, 2024, on behalf of Michaelski Hüttermann & Partner Patentanwalte mbD.
D6—Pollart et al., 2009, cited in Notice of Opposition against European Patent No. 3973987 (Application No. 21191120.1) filed on Oct. 10, 2024, on behalf of Michaelski Hüttermann & Partner Patentanwalte mbD.
D7—Wenzel et al., 2005, cited in Notice of Opposition against European Patent No. 3973987 (Application No. 21191120.1) filed on Oct. 10, 2024, on behalf of Michaelski Huttermann & Partner Patentanwalte mbD.
D8—Study Record Version 22 of clinical trial NCT01854047, Feb. 3, 2014, cited in Notice of Opposition against European Patent No. 3973987 (Application No. 21191120.1) filed on Oct. 10, 2024, on behalf of Michaelski Hüttermann & Partner Patentanwalte mbD.
D9—Ramli et al., 2008, cited in Notice of Opposition against European Patent No. 3973987 (Application No. 21191120.1) filed on Oct. 10, 2024, on behalf of Michaelski Hüttermann & Partner Patentanwalte mbD.
D10—EP 3470432 A1, published Mar. 30, 2022, cited in Notice of Opposition against European Patent No. 3973987 (Application No. 21191120.1) filed on Oct. 10, 2024, on behalf of Michaelski Hüttermann & Partner Patentanwalte mbD.
D11—Chames et al. 2009, cited in Notice of Opposition against European Patent No. 3973987 (Application No. 21191120.1) filed on Oct. 10, 2024, on behalf of Michaelski Hüttermann & Partner Patentanwalte mbD.
D12—Bumbacea et al., 2004, cited in Notice of Opposition against European Patent No. 3973987 (Application No. 21191120.1) filed on Oct. 10, 2024, on behalf of Michaelski Hüttermann & Partner Patentanwalte mbD.
D13—Jenkins et al., 2003, cited in Notice of Opposition against European Patent No. 3973987 (Application No. 21191120.1) filed on Oct. 10, 2024, on behalf of Michaelski Hüttermann & Partner Patentanwalte mbD.
D14—Reasons for the decision in the parent patent (EP 15708991. 3); dated Mar. 7, 2024, cited in Notice of Opposition against European Patent No. 3973987 (Application No. 21191120.1) filed on Oct. 10, 2024, on behalf of Michaelski Huttermann & Partner Patentanwalte mbD.
D15—Greulich et al., 2010, cited in Notice of Opposition against European Patent No. 3973987 (Application No. 21191120.1) filed on Oct. 10, 2024, on behalf of Michaelski Hüttermann & Partner Patentanwalte mbD.
D16—Birkett et al., 1996, cited in Notice of Opposition against European Patent No. 3973987 (Application No. 21191120.1) filed on Oct. 10, 2024, on behalf of Michaelski Hüttermann & Partner Patentanwalte mbD.
D17—Pavord et al., 2012, cited in Notice of Opposition against European Patent No. 3973987 (Application No. 21191120.1) filed on Oct. 10, 2024, on behalf of Michaelski Hüttermann & Partner Patentanwalte mbD.
D18—Bousquet et al., 1990, cited in Notice of Opposition against European Patent No. 3973987 (Application No. 21191120.1) filed on Oct. 10, 2024, on behalf of Michaelski Hüttermann & Partner Patentanwalte mbD.
D19—Haldar et al., 2009, cited in Notice of Opposition against European Patent No. 3973987 (Application No. 21191120.1) filed on Oct. 10, 2024, on behalf of Michaelski Hüttermann & Partner Patentanwalte mbD.
D20—List of approved antibodies until 2014, cited in Notice of Opposition against European Patent No. 3973987 (Application No. 21191120.1) filed on Oct. 10, 2024, on behalf of Michaelski Hüttermann & Partner Patentanwalte mbD.
D21—Convolutum of clinical trial protolcols completed before the priority date, cited in Notice of Opposition against European Patent No. 3973987 (Application No. 21191120.1) filed on Oct. 10, 2024, on behalf of Michaelski Hüttermann & Partner Patentanwalte mbD.
D22—Tan et al., 2006, cited in Notice of Opposition against European Patent No. 3973987 (Application No. 21191120.1) filed on Oct. 10, 2024, on behalf of Michaelski Hüttermann & Partner Patentanwalte mbD.
D23—Onrust et al., 1999, cited in Notice of Opposition against European Patent No. 3973987 (Application No. 21191120.1) filed on Oct. 10, 2024, on behalf of Michaelski Hüttermann & Partner Patentanwalte mbD.
D24—Spratlin et al., 2010, cited in Notice of Opposition against European Patent No. 3973987 (Application No. 21191120.1) filed on Oct. 10, 2024, on behalf of Michaelski Hüttermann & Partner Patentanwalte mbD.
D25—Chmielowski, 2013, cited in Notice of Opposition against European Patent No. 3973987 (Application No. 21191120.1) filed on Oct. 10, 2024, on behalf of Michaelski Hüttermann & Partner Patentanwalte mbD.
D26—Cohenuram and Saif, 2007, cited in Notice of Opposition against European Patent No. 3973987 (Application No. 21191120. 1) filed on Oct. 10, 2024, on behalf of Michaelski Hüttermann & Partner Patentanwalte mbD.
D27—Rau, 2002, cited in Notice of Opposition against European Patent No. 3973987 (Application No. 21191120.1) filed on Oct. 10, 2024, on behalf of Michaelski Hüttermann & Partner Patentanwalte mbD.

(56) References Cited

OTHER PUBLICATIONS

D28—Metzger-Filho, 2013, cited in Notice of Opposition against European Patent No. 3973987 (Application No. 21191120.1) filed on Oct. 10, 2024, on behalf of Michaelski Hüttermann & Partner Patentanwalte mbD.
D29—Frampton, 2013, cited in Notice of Opposition against European Patent No. 3973987 (Application No. 21191120.1) filed on Oct. 10, 2024, on behalf of Michaelski Hüttermann & Partner Patentanwalte mbD.
D30—Leyland-Jones, 2003, cited in Notice of Opposition against European Patent No. 3973987 (Application No. 21191120.1) filed on Oct. 10, 2024, on behalf of Michaelski Huttermann & Partner Patentanwalte mbD.
D31—Washburn et al., 2006, cited in Notice of Opposition against European Patent No. 3973987 (Application No. 21191120.1) filed on Oct. 10, 2024, on behalf of Michaelski Hüttermann & Partner Patentanwalte mbD.
D32—WO 2014/031610 A1, published on Feb. 27, 2014, cited in Notice of Opposition against European Patent No. 3973987 (Application No. 21191120.1) filed on Oct. 10, 2024, on behalf of Michaelski Huttermann & Partner Patentanwalte mbD.
D33—Wang et al., 2008, cited in Notice of Opposition against European Patent No. 3973987 (Application No. 21191120.1) filed on Oct. 10, 2024, on behalf of Michaelski Hüttermann & Partner Patentanwalte mbD.
D34—Mould and Sweeney 2007, cited in Notice of Opposition against European Patent No. 3973987 (Application No. 21191120.1) filed on Oct. 10, 2024, on behalf of Michaelski Huttermann & Partner Patentanwalte mbD.
Notice of Opposition against European Patent No. 3973987 (Application No. 21191120.1) filed on Oct. 10, 2024, on behalf of Hampton Knowles Limited.
D1—Wenzel et al., N. Engl. J. Med., 2013, 368(26):2455-2466, cited in Notice of Opposition against European Patent No. 3973987 (Application No. 21191120.1) filed on Oct. 10, 2024, on behalf of Hampton Knowles Limited.
D5—WO 2014/031610 A1, published Feb. 27, 2014, cited in Notice of Opposition against European Patent No. 3973987 (Application No. 21191120.1) filed on Oct. 10, 2024, on behalf of Hampton Knowles Limited.
D7—pp. 401, 402 and 412 of WHO Drug Information, 2012, 26(4):401-471, cited in Notice of Opposition against European Patent No. 3973987 (Application No. 21191120.1) filed on Oct. 10, 2024, on behalf of Hampton Knowles Limited.
D8—EurekAlert! press release "Monoclonal antibody appears effective and safe in asthma Phase IIa trial", May 21, 2013, cited in Notice of Opposition against European Patent No. 3973987 (Application No. 21191120.1) filed on Oct. 10, 2024, on behalf of Hampton Knowles Limited.
D9—Chapter 19, "Dosage regimens", of Aulton's Pharmaceutics: The Science of Dosage Form Design, 2nd Edition, 2001, cited in Notice of Opposition against European Patent No. 3973987 (Application No. 21191120.1) filed on Oct. 10, 2024, on behalf of Hampton Knowles Limited.
D10—Panaccione and Ghosh, Ther. Adv. Gastroenterol., 2010, 3(3):179-189, which is a review article relating to the optimal use of biologics in the inflammatory disorder, Crohn's disease, cited in Notice of Opposition against European Patent No. 3973987 (Application No. 21191120.1) filed on Oct. 10, 2024, on behalf of Hampton Knowles Limited.
D11—Regeneron press release "Sanofi and Regeneron report positive proof- of- concept data for dupilumab, an IL-4R alpha antibody, in atopic dermatitis", dated Mar. 2, 2013, cited in Notice of Opposition against European Patent No. 3973987 (Application No. 21191120.1) filed on Oct. 10, 2024, on behalf of Hampton Knowles Limited.
DYC01—pp. 159 to 162 of Rispens and Vidarsson, Antibody Fc: Linking Adaptive and Innate Immunity, Chapter 9, "Human IgG Subclasses", pp. 159 to 162, 2013; and evidence of its publication date, cited in Notice of Opposition against European Patent No. 3973987 (Application No. 21191120.1) filed on Oct. 10, 2024, on behalf of Hampton Knowles Limited.
DYC02—Interlocutory decision in Opposition proceedings for EP3107575B, dated Mar. 7, 2024, cited in Notice of Opposition against European Patent No. 3973987 (Application No. 21191120.1) filed on Oct. 10, 2024, on behalf of Hampton Knowles Limited.
DYC03—NCT01854047 clinical trial protocol version 22 (Feb. 3, 2014) , cited in Notice of Opposition against European Patent No. 3973987 (Application No. 21191120.1) filed on Oct. 10, 2024, on behalf of Hampton Knowles Limited.
DYC04—Regeneron press release "Sanofi and Regeneron announce publication of positive Phase 2A results of dupilumab in asthma in the New England Journal of Medicine", May 21, 2013, cited in Notice of Opposition against European Patent No. 3973987 (Application No. 21191120.1) filed on Oct. 10, 2024, on behalf of Hampton Knowles Limited.
DYC05—Swanson et al., World Allergy Organization Journal, 2014, 7(Suppl 1):P13, poster abstract 1023, cited in Notice of Opposition against European Patent No. 3973987 (Application No. 21191120.1) filed on Oct. 10, 2024, on behalf of Hampton Knowles Limited.
DYC06—Radin et al., J Allergy Clin Immunol, 2013, 131(2_ Suppl):AB158, abstract 558, cited in Notice of Opposition against European Patent No. 3973987 (Application No. 21191120.1) filed on Oct. 10, 2024, on behalf of Hampton Knowles Limited.
DYC07—Mould and Sweeney, Current Opinion in Drug Discovery & Development, 2007, 10(1):84-96, cited in Notice of Opposition against European Patent No. 3973987 (Application No. 21191120.1) filed on Oct. 10, 2024, on behalf of Hampton Knowles Limited.
DYC08—Wang et al., Clinical Pharmacology & Therapeutics, 2008, 84(5):548-558, cited in Notice of Opposition against European Patent No. 3973987 (Application No. 21191120.1) filed on Oct. 10, 2024, on behalf of Hampton Knowles Limited.
DYC09—Fracasso et al., Clin Cancer Res, 2007, 13(3):986- 993, cited in Notice of Opposition against European Patent No. 3973987 (Application No. 21191120.1) filed on Oct. 10, 2024, on behalf of Hampton Knowles Limited.
DYC10—Mould et al., Br J Clin Pharmacol, 2007, 64(3):278-291, cited in Notice of Opposition against European Patent No. 3973987 (Application No. 21191120.1) filed on Oct. 10, 2024, on behalf of Hampton Knowles Limited.
DYC11—Sohn et al., Br J Clin Pharmacol, 2014, 78(3):477-487, cited in Notice of Opposition against European Patent No. 3973987 (Application No. 21191120.1) filed on Oct. 10, 2024, on behalf of Hampton Knowles Limited.
DYC12—Dostalek et al., Clin Pharmacokinet, 2013, 52:83-124, cited in Notice of Opposition against European Patent No. 3973987 (Application No. 21191120.1) filed on Oct. 10, 2024, on behalf of Hampton Knowles Limited.
DYC13—Corren et al., Am. J. Respir. Crit. Care Med., 2010, 181:788-796, cited in Notice of Opposition against European Patent No. 3973987 (Application No. 21191120.1) filed on Oct. 10, 2024, on behalf of Hampton Knowles Limited.
DYC14—Borish, Am. J. Respir. Crit. Care Med., 2010, 181:769-772, cited in Notice of Opposition against European Patent No. 3973987 (Application No. 21191120.1) filed on Oct. 10, 2024, on behalf of Hampton Knowles Limited.
DYC15—Wenzel, Clinical & Experimental Allergy, 2012, 42:650-658, cited in Notice of Opposition against European Patent No. 3973987 (Application No. 21191120.1) filed on Oct. 10, 2024, on behalf of Hampton Knowles Limited.
DYC16—Hashimoto, The Lancet, 2012, 380:626-627, cited in Notice of Opposition against European Patent No. 3973987 (Application No. 21191120.1) filed on Oct. 10, 2024, on behalf of Hampton Knowles Limited.
DYC17—Szefler et al., J Allergy Clin Immunol, 2012, 129:S9-23, cited in Notice of Opposition against European Patent No. 3973987 (Application No. 21191120.1) filed on Oct. 10, 2024, on behalf of Hampton Knowles Limited.
U.S. Appl. No. 13/971,334 2014/0056920 U.S. Pat. No. 9,574,004, filed Aug. 20, 2013 Feb. 27, 2014 Feb. 21, 2017, Marius Ardeleanu.
U.S. Appl. No. 15/400,076, filed Jan. 6, 2017, Marius Ardeleanu.

(56) References Cited

OTHER PUBLICATIONS

U.S. Appl. No. 15/627,669 2018/0016343, filed Jun. 20, 2017 Jan. 17, 2018, Marius Ardeleanu.
U.S. Appl. No. 14/627,728 2015/0246119 U.S. Pat. No. 10,137,193, filed Feb. 20, 2015 Sep. 3, 2015 Nov. 27, 2018, Gianluca Pirozzi.
U.S. Appl. No. 16/157,708 2019/0125865, filed Oct. 11, 2018 May 2, 2019, Gianluca Pirozzi.
U.S. Appl. No. 17/215,604 2021/0322546, filed Mar. 29, 2021 Oct. 21, 2021, Gianluca Pirozzi.
U.S. Appl. No. 14/310,419 2015/0017182 U.S. Pat. No. 10,059,771, filed Jun. 20, 2014 Jan. 15, 2015 Aug. 28, 2018, Leda Mannent.
U.S. Appl. No. 16/038,816 2019/0040146, filed Jul. 18, 2018 Feb. 7, 2019, Leda Mannent.
U.S. Appl. No. 14/940,431 2016/0185866 U.S. Pat. No. 10,066,017, filed Nov. 13, 2015 Jun. 30, 2016 Sep. 4, 2018, Leda Mannent.
U.S. Appl. No. 16/038,925 2019/0040147 U.S. Pat. No. 11,214,621, filed Jul. 18, 2018 Feb. 7, 2019 Jan. 4, 2022, Leda Mannent.
U.S. Appl. No. 16/173,848 2019/0169299 U.S. Pat. No. 11,034,768, filed Oct. 29, 2018 Jun. 6, 2019 Jun. 15, 2021, Nikhil Amin.
U.S. Appl. No. 17/314,251 2021/0380705, filed May 7, 2021 Dec. 9, 2021, Nikhil Amin.
U.S. Appl. No. 16/863,800 2021/0000949, filed Apr. 30, 2020 Jan. 7, 2021, Helene Goulaouic.
U.S. Appl. No. 16/929,624 2021/0032354, filed Jul. 15, 2020 Feb. 4, 2021, Heribert Staudinger.
Aldington, S. et al., "Asthma exacerbations .5: Assessment and management of severe asthma in adults in hospital", Thorax, May 1, 2007, 62(5): 447-458.
Alotaibi et al., "Dupilumab as a treatment for allergic fungal rhinosinusitis: a case series", Rhinology Online, Aug. 11, 2023, 6(18): 18-24.
clinicaltrials.gov, (Dec. 18, 2020) "Dupilumab for the Treatment of Chronic Inducible Cold Urticaria in Patients Who Remain Symptomatic Despite the Use of H1-antihistamine (LIBERTY-CINDU CUrIADS)", Study History, ClinicalTrials.gov Identifier: NCT04681729, https://clinicaltrials.gov/study/NCT04681729?term=NCT04681729&rank=1&tab=history.
clinicaltrials.gov, (Aug. 31, 2022) "A Study to Investigate the Pharmacokinetics and Safety of Dupilumab in Participants ≥2 Years to <12 Years of Age With Uncontrolled Chronic Spontaneous Urticaria (CSU) (LIBERTY-CSU CUPIDKids)", Study History, ClinicalTrials.gov Identifier: NCT05526521, https://clinicaltrials.gov/study/NCT05526521?term=nct05526521&rank=1&tab=history.
Ferrucci et al., "Rapid disappearance of both severe atopic dermatitis and cold urticaria following dupilumab treatment", Clin. Exp. Dermatol., Apr. 2020, 45(3):345-346. Epub Sep. 12, 2019.
International Search Report and Written Opinion of PCT International Patent Application No. PCT/EP2023/973630, mailed Feb. 15, 2024.
Kolkhir et al., "New Treatments for Chronic Urticaria", Ann. Allergy Asthma Immunol., Jan. 2020, 124(1): 2-12. Epub Aug. 23, 2019.
Maltseva et al., "Cold urticaria—What we know and what we do not know", Allergy, Apr. 2021, 76(4): 1077-1094. Epub Dec. 24, 2020.
Matsumoto, "Serum periostin: a novel biomarker for asthma management", Allergol Int., Jun. 2014, 63(2): 153-160, Epub Apr. 25, 2014. doi: 10.2332/allergolint.13-RAI-0678.
U.S. Appl. No. 13/971,334 2014/0056920 U.S. Pat. No. 9,574,004, filed Aug. 20, 2013 Feb. 27, 2014 Feb. 21, 2017, Marius Ardeleanu, Methods for Treating or Preventing Asthma by Administering an IL-4R Antagonist.
U.S. Appl. No. 15/400,076, filed Jan. 6, 2017, Marius Ardeleanu, Methods for Treating or Preventing Asthma by Administering an IL-4R Antagonist.
U.S. Appl. No. 15/627,669 2018/0016343 U.S. Pat. No. 11,845,800, filed Jun. 20, 2017 Jan. 18, 2018 Dec. 19, 2023, Methods for Treating or Preventing Asthma by Administering an IL-4R Antagonist.
U.S. Appl. No. 18/495,182 2024/0199751, filed Oct. 26, 2023 Jun. 20, 2024, Marius Ardeleanu, Methods for Treating or Preventing Asthma by Administering an IL-4R Anatagonist.
U.S. Appl. No. 14/627,728 2015/0246119 U.S. Pat. No. 10,137,193, filed Feb. 20, 2015 Sep. 3, 2015 Nov. 27, 2018, Gianluca Pirozzi, Methods for Treating or Preventing Asthma by Administering an IL-4R Antagonist.
U.S. Appl. No. 16/157,708 2019/0125865, filed Oct. 11, 2018 May 2, 2019, Gianluca Pirozzi, Methods for Treating or Preventing Asthma by Administering an IL-4R Anatagonist.
U.S. Appl. No. 17/215,604 2021/0322546, filed Mar. 29, 2021 Oct. 21, 2021, Gianluca Pirozzi, Methods for Treating or Preventing Asthma by Administering an IL-4R Antagonist.
U.S. Appl. No. 14/310,419 2015/0017182 U.S. Pat. No. 10,059,771, filed Jun. 20, 2014 Jan. 15, 2015 Aug. 28, 2018, Leda Mannent, Methods for Treating Nasal Polyposis by Administering an IL-4R Anatagonist.
U.S. Appl. No. 16/038,816 2019/0040146, filed Jul. 18, 2018 Feb. 7, 2019, Leda Mannent, Methods for Treating Nasal Polyosis by Administering an IL-4R Antagonist.
U.S. Appl. No. 14/940,431 2016/0185866 U.S. Pat. No. 10,066,017, filed Nov. 13, 2015 Jun. 30, 2016 Sep. 4, 2018, Leda Mannent, Methods for Treating Chronic Sinusitis with Nasal Polyps by Administering an IL-4R Anatagonist.
U.S. Appl. No. 16/038,925 2019/0040147 U.S. Pat. No. 11,214,621, filed Jul. 18, 2018 Feb. 7, 2019 Jan. 4, 2022, Leda Mannent, Methods for Treating Chronic Sinusitis with Nasal Polyps by Administering an IL-4R Antagonist.
U.S. Appl. No. 16/173,848 2019/0169299 U.S. Pat. No. 11,034,768, filed Oct. 29, 2018 Jun. 6, 2019 Jun. 15, 2021, Nikhil Amin, Methods for Treating or Preventing Asthma by Administering an IL-4R Antagonist.
U.S. Appl. No. 17/314,251 2021/0380705, filed May 7, 2021 Dec. 9, 2021, Nikhil Amin, Methods for Treating or Preventing Asthma by Administering an IL-4R Antagonist.
U.S. Appl. No. 16/863,800 2021/0000949, filed Apr. 30, 2020 Jan. 7, 2021, Helene Goulaouic, Methods for Treating or Preventing Asthma by Administering an IL-33 Antagonist.
U.S. Appl. No. 16/929,624 2021/0032354, filed Jul. 15, 2020 Feb. 4, 2021, Heribert Staudinger, Methods for Treating or Preventing Asthma by Administering an IL-4R Antagonist.
U.S. Appl. No. 17/872,225 2023/0146317, filed Jul. 25, 2022 May 11, 2023, Aleksandra Stjepanovic, Methods for Treating Chronic Spontaneous Urticaria by Administering an IL-4R Antagonist.
U.S. Appl. No. 17/786,226 2023/0340101, filed Jun. 16, 2022 Oct. 26, 2023, El-Bdaoui Haddad, Methods for Treating or Preventing Allergic Asthma by Administering an IL-33 Antagonist and/or an IL-4R Antagonist.
U.S. Appl. No. 17/493,101 2022/0169739, filed Oct. 4, 2021 Jun. 2, 2022, Christine Xu, Methods for Treating Asthma in Pediatric Subjects by Administering an IL-4R Antagonist.
U.S. Appl. No. 17/969,033 2023/0183362, filed Oct. 19, 2022 Jun. 15, 2023, Ashish Bansal, Methods for Treating Prurigo Nodularis by Administering an IL-4R Antagonist.
U.S. Appl. No. 19/104,869, filed Aug. 29, 2023, Elizabeth Laws, Methods for Treating Chronic Inducible Cold Uticaria by Administering an IL-4R Antagonist.
U.S. Appl. No. 18/612,039, filed Mar. 21, 2024, Raolat Abdulai, Methods for Treating Chronic Obstructive Pulmonary Disease (COPD) by Administering an IL-4R Antagonist.
Anonymous, "A Phase 2B, Randomized, Double-Blind, Placebo-Controlled, Parallel-Group, Dose-Ranging Study Investigating the Efficacy, Safety, and Pharmacokinetic Profiles of REGN3500 Administered to Adult Patients With Moderate-to-Severe Atopic Dermatitis", Mar. 12, 2019.
Chong et al., "Biologics for chronic rhinosinusitis", Cochrane Database Syst. Rev., Feb. 27, 2020, 2(2): CD013513.
Diamant et al., "Biomarkers in asthma and allergic rhinitis", Pulmonary Pharmacology & Therapeutics, Dec. 2010, 23(6): 468-481, Epublished Jun. 30, 2010.
Extended European Search Report for European Patent Application No. 25192276.1, mailed Mar. 6, 2026.

(56) References Cited

OTHER PUBLICATIONS

Hox et al., "Benefits and harm of systemic steroids for short- and long-term use in rhinitis and rhinosinusitis: an EAACI position paper", Clin. Transl. Allergy, Sep. 28, 2020, 10: 38.
International Search Report and Written Opinion of PCT International Patent Application No. PCT/EP2025/024486, mailed Jul. 24, 2025.
Le Floch et al., "Dual blockade of IL-4 and IL-13 with dupilumab, an IL-4Rα antibody, is required to broadly inhibit type 2 inflammation", Allergy, May 2020, 75(5)(: 1188-1204, Epublished Jan. 3, 2020.
Lee et al., "237: A Study of Dupilumab in Adults with CRSsNP: Results from the Liberty ORION study", J. Allergy and Clin. Immunol., Feb. 2025, 155(2 Suppl.): AB76.
Oka et al., "A case of intractable chronic rhinosinusitis without nasal polyps leading remission after treatment switching from anti-IL-5 to anti-IL-4Rα monoclonal antibody", Otolaryngology Case Reports, Jun. 2023, 27: 100512.
Reagan-Shaw et al., "Dose translation from animal to human studies revisited", The FASEB Journal, Oct. 17, 2007, 22(3): 659-661.
Notice of Opposition against European Patent No. 4011915 (Application No. 21199451.2) dated Oct. 16, 2023, filed on behalf of Dr. Luigi Rumi.
Letter from the Opponent regarding the Opposition against European Patent No. 4011915 (Application No. 21199451.2), dated Jul. 14, 2025, filed on behalf of Dr. Luigi Rumi.
TM1—WO 2014/031610, grandparent application as filed, cited in Letter from the Opponent dated Jul. 14, 2025, regarding the Notice of Opposition against European Patent No. 4011915 (Application No. 21199451.2) filed Oct. 16, 2023, on behalf of Dr. Luigi Rumi.
TM9—WHO Drug Information, vol. 26, No. 4, pp. 401-471, "Proposed INN: List 108", published on Dec. 9, 2012 (as evidenced by the Annex appended to the document retrieved from https://www.who.int/publications/m/item/inn-pl-108), cited in Letter from the Opponent dated Jul. 14, 2025, regarding the Notice of Opposition against European Patent No. 4011915 (Application No. 21199451.2) filed Oct. 16, 2023, on behalf of Dr. Luigi Rumi.
TM11—Pollart SM, et al. Am Fam Physician. May 1, 2009;79(9): 761-7. 2009, cited in Letter from the Opponent dated Jul. 14, 2025, regarding the Notice of Opposition against European Patent No. 4011915 (Application No. 21199451.2) filed Oct. 16, 2023, on behalf of Dr. Luigi Rumi.
TM12—Wenzel S., Clinical and Experimental Allergy, 42(5): 650-8, published on Jan. 18, 2012 (as evidenced by the Annex appended to the document), cited in Letter from the Opponent dated Jul. 14, 2025, regarding the Notice of Opposition against European Patent No. 4011915 (Application No. 21199451.2) filed Oct. 16, 2023, on behalf of Dr. Luigi Rumi.
TM13—Wenzel S.E., Nature Medicine, 18(5): 716-25, May 4, 2012, cited in Letter from the Opponent dated Jul. 14, 2025, regarding the Notice of Opposition against European Patent No. 4011915 (Application No. 21199451.2) filed Oct. 16, 2023, on behalf of Dr. Luigi Rumi.
TM14—Wenzel S. Am J Respir Crit Care Med. Jul. 15, 2005;172(2):149-60. 2005, cited in Letter from the Opponent dated Jul. 14, 2025, regarding the Notice of Opposition against European Patent No. 4011915 (Application No. 21199451.2) filed Oct. 16, 2023, on behalf of Dr. Luigi Rumi.
TM15—Global Initiative for Asthma (GINA) Guidelines 2012; updated until Jun. 30, 2012, cited in Letter from the Opponent dated Jul. 14, 2025, regarding the Notice of Opposition against European Patent No. 4011915 (Application No. 21199451.2) filed Oct. 16, 2023, on behalf of Dr. Luigi Rumi.
TM16—Taylor D.R. et al., "A new perspective on concepts of asthma severity and control", Eur Respir J. Sep. 2008;32(3):545-54, cited in Letter from the Opponent dated Jul. 14, 2025, regarding the Notice of Opposition against European Patent No. 4011915 (Application No. 21199451.2) filed Oct. 16, 2023, on behalf of Dr. Luigi Rumi.
TM17—Woodruff P.G. et al., "T-helper type 2-driven inflammation defines major subphenotypes of asthma", Am J Respir Crit Care Med. Sep. 1, 2009;180(5):388-95, cited in Letter from the Opponent dated Jul. 14, 2025, regarding the Notice of Opposition against European Patent No. 4011915 (Application No. 21199451.2) filed Oct. 16, 2023, on behalf of Dr. Luigi Rumi.
TM18—Liang Z. et al., "Moderate accuracy of peripheral eosinophil count for predicting eosinophilic phenotype in steroid-nai've non-atopic adult asthmatics", Intern Med. 2012;51(7):717-22, cited in Letter from the Opponent dated Jul. 14, 2025, regarding the Notice of Opposition against European Patent No. 4011915 (Application No. 21199451.2) filed Oct. 16, 2023, on behalf of Dr. Luigi Rumi.
TM19—Haldar P. et al., "Cluster analysis and clinical asthma phenotypes", Am J Respir Crit Care Med. Aug. 1, 2008;178(3):218-224, cited in Letter from the Opponent dated Jul. 14, 2025, regarding the Notice of Opposition against European Patent No. 4011915 (Application No. 21199451.2) filed Oct. 16, 2023, on behalf of Dr. Luigi Rumi.
TM20—Miskoff J.A. et al., "Fractional Exhaled Nitric Oxide Testing: Diagnostic Utility in Asthma, Chronic Obstructive Pulmonary Disease, or Asthma-chronic Obstructive Pulmonary Disease Overlap Syndrome", Cureus. Jun. 10, 2019;11(6):e4864, cited in Letter from the Opponent dated Jul. 14, 2025, regarding the Notice of Opposition against European Patent No. 4011915 (Application No. 21199451.2) filed Oct. 16, 2023, on behalf of Dr. Luigi Rumi.
TM21—Dweik Read A. et al., Official clinical practice guideline of the American Thoracic Society; May 2011, cited in Letter from the Opponent dated Jul. 14, 2025, regarding the Notice of Opposition against European Patent No. 4011915 (Application No. 21199451.2) filed Oct. 16, 2023, on behalf of Dr. Luigi Rumi.
TM22—Wenzel S. et al., The New England Journal of Medicine, 368(26): 2455-66, published online on May 21, 2013, cited in Letter from the Opponent dated Jul. 14, 2025, regarding the Notice of Opposition against European Patent No. 4011915 (Application No. 21199451.2) filed Oct. 16, 2023, on behalf of Dr. Luigi Rumi.
TM22a—Supplementary Appendix of D2, cited in Letter from the Opponent dated Jul. 14, 2025, regarding the Notice of Opposition against European Patent No. 4011915 (Application No. 21199451.2) filed Oct. 16, 2023, on behalf of Dr. Luigi Rumi.
TM23—Corren J, et al. Am J Respir Crit Care Med. Apr. 15, 2010;181(8):788-96. 2010, cited in Letter from the Opponent dated Jul. 14, 2025, regarding the Notice of Opposition against European Patent No. 4011915 (Application No. 21199451.2) filed Oct. 16, 2023, on behalf of Dr. Luigi Rumi.
TM24—WO 2010/053751 A1, cited in Letter from the Opponent dated Jul. 14, 2025, regarding the Notice of Opposition against European Patent No. 4011915 (Application No. 21199451.2) filed Oct. 16, 2023, on behalf of Dr. Luigi Rumi.
TM25—Study record for NCT01312961 accessed from ClinicalTrials.gov, Version 31 dated Aug. 20, 2012, cited in Letter from the Opponent dated Jul. 14, 2025, regarding the Notice of Opposition against European Patent No. 4011915 (Application No. 21199451.2) filed Oct. 16, 2023, on behalf of Dr. Luigi Rumi.
Notice of Opposition against European Patent No. 4011915 (Application No. 21199451.2) dated Jul. 8, 2024, filed on behalf of Dr. Hans Ulrich Dorries.
WO—WO 2014/031610, grandparent application as filed, cited in Notice of Opposition against European Patent No. 4011915 (Application No. 21199451.2) filed on Jul. 8, 2024, on behalf of Dr. Hans Ulrich Dorries.
D1—WHO Drug Information, vol. 26, No. 4, pp. 401-471, "Proposed INN: List 108", published on Dec. 9, 2012 (as evidenced by the Annex appended to the document retrieved from https://www.who.int/publications/m/item/inn-pl-108), cited in Notice of Opposition against European Patent No. 4011915 (Application No. 21199451.2) filed on Jul. 8, 2024, on behalf of Dr. Hans Ulrich Dorries.
D2—Wenzel S. et al., The New England Journal of Medicine, 368(26): 2455-66, published online on May 21, 2013, cited in Notice of Opposition against European Patent No. 4011915 (Application No. 21199451.2) filed on Jul. 8, 2024, on behalf of Dr. Hans Ulrich Dorries.

(56) References Cited

OTHER PUBLICATIONS

D3—WO 2010/053751 A1, cited in Notice of Opposition against European Patent No. 4011915 (Application No. 21199451.2) filed on Jul. 8, 2024, on behalf of Dr. Hans Ulrich Dorries.
D4—Otulana et al., American Journal of Respiratory and Critical Care Medicine, 183: A6179, American Thoracic Society 2011 International Conference Abstract, May 18, 2011, cited in Notice of Opposition against European Patent No. 4011915 (Application No. 21199451.2) filed on Jul. 8, 2024, on behalf of Dr. Hans Ulrich Dorries.
D5—Wenzel S.E., Nature Medicine, 18(5): 716-25, May 4, 2012, cited in Notice of Opposition against European Patent No. 4011915 (Application No. 21199451.2) filed on Jul. 8, 2024, on behalf of Dr. Hans Ulrich Dorries.
D6—Global Initiative for Asthma (GINA) Guidelines 2012; updated until Jun. 30, 2012, cited in Notice of Opposition against European Patent No. 4011915 (Application No. 21199451.2) filed on Jul. 8, 2024, on behalf of Dr. Hans Ulrich Dorries.
D7—WO 2011/156000 A2, cited in Notice of Opposition against European Patent No. 4011915 (Application No. 21199451.2) filed on Jul. 8, 2024, on behalf of Dr. Hans Ulrich Dorries.
D8—News provided by Aerovance Inc., "Phase 2b Clinical Trial Results Show Aerovance's AerovantTM is Effective in Patients with Eosinophilic Asthma", Jun. 8, 2010, cited in Notice of Opposition against European Patent No. 4011915 (Application No. 21199451. 2) filed on Jul. 8, 2024, on behalf of Dr. Hans Ulrich Dorries.
D9—Wenzel S.E. et al., Late Breaking Abstract: Inhaled pitrakinra, an IL-antagonist, reduced exacerbations in patients with eosinophilic asthma; European Respiratory Journal 2010; 36: Suppl. 54, P3980, Sep. 21, 2010, cited in Notice of Opposition against European Patent No. 4011915 (Application No. 21199451.2) filed on Jul. 8, 2024, on behalf of Dr. Hans Ulrich Dorries.
D10—Wenzel S., Clinical and Experimental Allergy, 42(5): 650-8, published on Jan. 18, 2012 (as evidenced by the Annex appended to the document), cited in Notice of Opposition against European Patent No. 4011915 (Application No. 21199451.2) filed on Jul. 8, 2024, on behalf of Dr. Hans Ulrich Dorries.
D11—Dweik Read A. et al., Official clinical practice guideline of the American Thoracic Society; May 2011, cited in Notice of Opposition against European Patent No. 4011915 (Application No. 21199451.2) filed on Jul. 8, 2024, on behalf of Dr. Hans Ulrich Dorries.
D12—Stewart L., Katial R.K., Immunology and allergy clinics of North America, 32(3): 347-62, available online on Jul. 5, 2012 (as evidenced by the Annex appended to the document), cited in Notice of Opposition against European Patent No. 4011915 (Application No. 21199451.2) filed on Jul. 8, 2024, on behalf of Dr. Hans Ulrich Dorries.
D13—Press release from Regeneron, "Regeneron Reports Fourth Quarter and Full Year 2011 Financial and Operating Results", Feb. 13, 2012, cited in Notice of Opposition against European Patent No. 4011915 (Application No. 21199451.2) filed on Jul. 8, 2024, on behalf of Dr. Hans Ulrich Dorries.
Notice of Opposition against European Patent No. 4011915 (Application No. 21199451.2) dated Jul. 12, 2024, filed on behalf of Michalski Hüttermann & Partner.
D1—Wenzel S.E., Nature Medicine, 18(5): 716-725, May 4, 2012, cited in Notice of Opposition against European Patent No. 4011915 (Application No. 21199451.2) filed on Jul. 12, 2024, on behalf of Michalski Hüttermann & Partner.
D2—Bumbacea D et al. Eur Respir J. Jul. 2004;24(1):122-128, cited in Notice of Opposition against European Patent No. 4011915 (Application No. 21199451.2) filed on Jul. 12, 2024, on behalf of Michalski Hüttermann & Partner.
D3—Jenkins HA, et al. Chest. Oct. 2003; 124(4):1318-1324, cited in Notice of Opposition against European Patent No. 4011915 (Application No. 21199451.2) filed on Jul. 12, 2024, on behalf of Michalski Hüttermann & Partner.
D4—ten Brinke A, et al. Am J Respir Crit Care Med. Sep. 1, 2001;164(5):744-748, cited in Notice of Opposition against European Patent No. 4011915 (Application No. 21199451.2) filed on Jul. 12, 2024, on behalf of Michalski Hüttermann & Partner.
D5—Steinke JW, Borish L.. Respir Res. 2001;2(2):66-70, cited in Notice of Opposition against European Patent No. 4011915 (Application No. 21199451.2) filed on Jul. 12, 2024, on behalf of Michalski Hüttermann & Partner.
D6—WO 2010/053751 A1, cited in Notice of Opposition against European Patent No. 4011915 (Application No. 21199451.2) filed on Jul. 12, 2024, on behalf of Michalski Hüttermann & Partner.
D7—T. Greulich, et al.Eur Respir J 2010; 36: Suppl. 54, 5492, cited in Notice of Opposition against European Patent No. 4011915 (Application No. 21199451.2) filed on Jul. 12, 2024, on behalf of Michalski Hüttermann & Partner.
D8—Bartoli ML et al Respir Med. Feb. 2004;98(2):184-93, cited in Notice of Opposition against European Patent No. 4011915 (Application No. 21199451.2) filed on Jul. 12, 2024, on behalf of Michalski Hüttermann & Partner.
D9—Fleming L, et al. Thorax. Mar. 2012;67(3):193-8, cited in Notice of Opposition against European Patent No. 4011915 (Application No. 21199451.2) filed on Jul. 12, 2024, on behalf of Michalski Hüttermann & Partner.
D10—Bousquet J, et al. N Engl J Med. Oct. 11, 1990;323(15):1033-1039, cited in Notice of Opposition against European Patent No. 4011915 (Application No. 21199451.2) filed on Jul. 12, 2024, on behalf of Michalski Hüttermann & Partner.
D11—Wardlaw AJ, et al. Br Med Bull. 2000;56(4):985-1003, cited in Notice of Opposition against European Patent No. 4011915 (Application No. 21199451.2) filed on Jul. 12, 2024, on behalf of Michalski Hüttermann & Partner.
D12—Haldar P, et al. N Engl J Med. Mar. 5, 2009;360(10):973-84, cited in Notice of Opposition against European Patent No. 4011915 (Application No. 21199451.2) filed on Jul. 12, 2024, on behalf of Michalski Hüttermann & Partner.
D13—Pavord ID, et al., Lancet. Aug. 18, 2012;380(9842):651-659, cited in Notice of Opposition against European Patent No. 4011915 (Application No. 21199451.2) filed on Jul. 12, 2024, on behalf of Michalski Hüttermann & Partner.
D14—excerpt from clinicaltrials.gov NCT01312961, cited in Notice of Opposition against European Patent No. 4011915 (Application No. 21199451.2) filed on Jul. 12, 2024, on behalf of Michalski Hüttermann & Partner.
D15—Wenzel S et al., The New England Journal of Medicine, 368(26): 2455-66, published online on May 21, 2013, cited in Notice of Opposition against European Patent No. 4011915 (Application No. 21199451.2) filed on Jul. 12, 2024, on behalf of Michalski Hüttermann & Partner.
D16—Sandeep T et al., Lung India. Jul. 2010;27(3):138-40, cited in Notice of Opposition against European Patent No. 4011915 (Application No. 21199451.2) filed on Jul. 12, 2024, on behalf of Michalski Hüttermann & Partner.
D17—European Search Opinion in parent case EP3470432, cited in Notice of Opposition against European Patent No. 4011915 (Application No. 21199451.2) filed on Jul. 12, 2024, on behalf of Michalski Hüttermann & Partner.
D18—European Search Opinion of the present case, cited in Notice of Opposition against European Patent No. 4011915 (Application No. 21199451.2) filed on Jul. 12, 2024, on behalf of Michalski Hüttermann & Partner.
D19—Kharitonov S, et al., The European Respiratory Society Task Force. Eur Respir J. Jul. 1997; 10(7):1683-1693, cited in Notice of Opposition against European Patent No. 4011915 (Application No. 21199451.2) filed on Jul. 12, 2024, on behalf of Michalski Hüttermann & Partner.
D20—Wenzel S, et al.. Lancet. Oct. 2, 20070;370(9596):1422-1431, cited in Notice of Opposition against European Patent No. 4011915 (Application No. 21199451.2) filed on Jul. 12, 2024, on behalf of Michalski Hüttermann & Partner.
D21—Corren J, et al. Am J Respir Crit Care Med. Apr. 15, 2010;181(8):788-796, cited in Notice of Opposition against European Patent No. 4011915 (Application No. 21199451.2) filed on Jul. 12, 2024, on behalf of Michalski Hüttermann & Partner.

(56) References Cited

OTHER PUBLICATIONS

D22—US 2003/0185821 A1, cited in Notice of Opposition against European Patent No. 4011915 (Application No. 21199451.2) filed on Jul. 12, 2024, on behalf of Michalski Hüttermann & Partner.
D23—Annex 1: Sequence alignments, cited in Notice of Opposition against European Patent No. 4011915 (Application No. 21199451.2) filed on Jul. 12, 2024, on behalf of Michalski Hüttermann & Partner.
D24—Annex 2: excerpts from the patent with all passages mentioning the term "FEV1", cited in Notice of Opposition against European Patent No. 4011915 (Application No. 21199451.2) filed on Jul. 12, 2024, on behalf of Michalski Hüttermann & Partner.
D25—GINA Report 2009, cited in Notice of Opposition against European Patent No. 4011915 (Application No. 21199451.2) filed on Jul. 12, 2024, on behalf of Michalski Hüttermann & Partner.
D26—Pollart SM, et al. Am Fam Physician. May 1, 2009;79(9):761-767, cited in Notice of Opposition against European Patent No. 4011915 (Application No. 21199451.2) filed on Jul. 12, 2024, on behalf of Michalski Hüttermann & Partner.
D27—Wenzel S. Am J Respir Crit Care Med. Jul. 15, 2005;172(2):149-160, cited in Notice of Opposition against European Patent No. 4011915 (Application No. 21199451.2) filed on Jul. 12, 2024, on behalf of Michalski Hüttermann & Partner.
D28—Al-Ramli W et al.J Asthma. 2008;45 Suppl 1:41-44, cited in Notice of Opposition against European Patent No. 4011915 (Application No. 21199451.2) filed on Jul. 12, 2024, on behalf of Michalski Hüttermann & Partner.
D29—Annex 3: Disclosure of the string "severe asthma" in the application as filed on Aug. 20, 2013, and p. 1-p. 6, cited in Notice of Opposition against European Patent No. 4011915 (Application No. 21199451.2) filed on Jul. 12, 2024, on behalf of Michalski Hüttermann & Partner.
Notice of Opposition against European Patent No. 4011915 (Application No. 21199451.2) dated Jul. 16, 2024, filed on behalf of Boult Wade Tennant LLP.
D1—Text of EP21199451.2—divisional application as originally filed on Aug. 20, 2013, cited in Notice of Opposition against European Patent No. 4011915 (Application No. 21199451.2) filed on Jul. 16, 2024, on behalf of Boult Wade Tennant LLP.
D2—WO 2014/031610, grandparent application as filed on Aug. 20, 2013, cited in Notice of Opposition against European Patent No. 4011915 (Application No. 21199451.2) filed on Jul. 16, 2024, on behalf of Boult Wade Tennant LLP.
D3—U.S. Pat. No. 8,075,887 B2, cited in Notice of Opposition against European Patent No. 4011915 (Application No. 21199451.2) filed on Jul. 16, 2024, on behalf of Boult Wade Tennant LLP.
D4—Munakata, Exhaled Nitric Oxide (FeNO) as a Non-invasive Marker of Airway Inflammation, Allergology International, vol. 61: 365-372, 2012, cited in Notice of Opposition against European Patent No. 4011915 (Application No. 21199451.2) filed on Jul. 16, 2024, on behalf of Boult Wade Tennant LLP.
D5—GINA Report 2009, cited in Notice of Opposition against European Patent No. 4011915 (Application No. 21199451.2) filed on Jul. 16, 2024, on behalf of Boult Wade Tennant LLP.
D6—Pavord ID, et al., Lancet. Aug. 18, 2012;380(9842):651-9, cited in Notice of Opposition against European Patent No. 4011915 (Application No. 21199451.2) filed on Jul. 16, 2024, on behalf of Boult Wade Tennant LLP.
D7—Study record for NCT01312961 accessed from ClinicalTrials.gov, Version 31 dated Aug. 20, 2012, cited in Notice of Opposition against European Patent No. 4011915 (Application No. 21199451.2) filed on Jul. 16, 2024, on behalf of Boult Wade Tennant LLP.
D8—Press release from Regeneron, "Regeneron Reports Fourth Quarter and Full Year 2011 Financial and Operating Results", Feb. 13, 2012, cited in Notice of Opposition against European Patent No. 4011915 (Application No. 21199451.2) filed on Jul. 16, 2024, on behalf of Boult Wade Tennant LLP.
D9—Otulana et al., American Journal of Respiratory and Critical Care Medicine, 183: A6179, American Thoracic Society 2011 International Conference Abstract, May 18, 2011, cited in Notice of Opposition against European Patent No. 4011915 (Application No. 21199451.2) filed on Jul. 16, 2024, on behalf of Boult Wade Tennant LLP.
D10—Hashimoto and Bel., Current treatment of severe asthma, Clin. Exp. Allergy., vol. 42(5): 693-705, May 2012, cited in Notice of Opposition against European Patent No. 4011915 (Application No. 21199451.2) filed on Jul. 16, 2024, on behalf of Boult Wade Tennant LLP.
D11—Alving et al., Increased amount of nitric oxide in exhaled air of asthmatics, Eur Respir J., vol. 6: 1366-1370, 1993, cited in Notice of Opposition against European Patent No. 4011915 (Application No. 21199451.2) filed on Jul. 16, 2024, on behalf of Boult Wade Tennant LLP.
D12—Wenzel S. et al., The New England Journal of Medicine, 368(26): 2455-66, published online on May 21, 2013, cited in Notice of Opposition against European Patent No. 4011915 (Application No. 21199451.2) filed on Jul. 16, 2024, on behalf of Boult Wade Tennant LLP.
D13—Supplementary Appendix of Wenzel, 2013, cited in Notice of Opposition against European Patent No. 4011915 (Application No. 21199451.2) filed on Jul. 16, 2024, on behalf of Boult Wade Tennant LLP.
D14—WHO Drug Information, vol. 26, No. 4, pp. 401-471, "Proposed INN: List 108", published on Dec. 9, 2012 (as evidenced by the Annex appended to the document retrieved from https://www.who.int/publications/m/item/inn-pl-108), cited in Notice of Opposition against European Patent No. 4011915 (Application No. 21199451.2) filed on Jul. 16, 2024, on behalf of Boult Wade Tennant LLP.
D15—Proprietors letter of Oct. 17, 2019 on EP3470432, cited in Notice of Opposition against European Patent No. 4011915 (Application No. 21199451.2) filed on Jul. 16, 2024, on behalf of Boult Wade Tennant LLP.
D16—Brusselle and Bracke, Targeting Immune Pathways for Therapy in Asthma and Chronic Obstructive Pulmonary Disease, Ann Am Throrac Soc, vol. 11, Supplement 5, S322-S328, Dec. 2014, cited in Notice of Opposition against European Patent No. 4011915 (Application No. 21199451.2) filed on Jul. 16, 2024, on behalf of Boult Wade Tennant LLP.
D17—Wechsler, Inhibiting Interleukin-4 and Interleukin-13 in Difficult-to-Control Asthma, New England Journal of Medicine, vol. 368;26: 2511-2513, Jun. 27, 2013, cited in Notice of Opposition against European Patent No. 4011915 (Application No. 21199451.2) filed on Jul. 16, 2024, on behalf of Boult Wade Tennant LLP.
Notice of Opposition against European Patent No. 4011915 (Application No. 21199451.2) dated Jul. 17, 2024, filed on behalf of Secerna LLP.
D1—Wenzel S., Clinical and Experimental Allergy, 42(5): 650-8, published on Jan. 18, 2012 (as evidenced by the Annex appended to the document), cited in Notice of Opposition against European Patent No. 4011915 (Application No. 21199451.2) filed on Jul. 17, 2024, on behalf of Secerna LLP.
D2—Firszt & Kraft, Pharmacotherapy of Severe Asthma. Curr Opin Pharmacol. (2010); 10(3): 266-271, cited in Notice of Opposition against European Patent No. 4011915 (Application No. 21199451.2) filed on Jul. 17, 2024, on behalf of Secerna LLP.
D3—Pollart SM, et al. Am Fam Physician. May 1, 2009;79(9):761-7, cited in Notice of Opposition against European Patent No. 4011915 (Application No. 21199451.2) filed on Jul. 17, 2024, on behalf of Secerna LLP.
D4—Wenzel S et al., The New England Journal of Medicine, 368(26): 2455-66, published online on May 21, 2013, cited in Notice of Opposition against European Patent No. 4011915 (Application No. 21199451.2) filed on Jul. 17, 2024, on behalf of Secerna LLP.
D5—Protocol for: Wenzel et al. Dupilumab in persistent asthma with elevated eosinophil levels. N Engl J Med 2013; 368:2455-66, cited in Notice of Opposition against European Patent No. 4011915 (Application No. 21199451.2) filed on Jul. 17, 2024, on behalf of Secerna LLP.
D6—Wechsler, Inhibiting Interleukin-4 and Interleukin-13 in Difficult-to-Control Asthma, New England Journal of Medicine, vol. 368;26: 2511- 2513, Jun. 27, 2013, cited in Notice of Opposition against

(56) References Cited

OTHER PUBLICATIONS

European Patent No. 4011915 (Application No. 21199451.2) filed on Jul. 17, 2024, on behalf of Secerna LLP.
D7—U.S. Pat. No. 8,075,887 B2, cited in Notice of Opposition against European Patent No. 4011915 (Application No. 21199451.2) filed on Jul. 17, 2024, on behalf of Secerna LLP.
D8—WO 2010/053751 A1, cited in Notice of Opposition against European Patent No. 4011915 (Application No. 21199451.2) filed on Jul. 17, 2024, on behalf of Secerna LLP.
D9—Study record for NCT01312961 accessed from ClinicalTrials.gov, Version 31 dated Aug. 20, 2012, cited in Notice of Opposition against European Patent No. 4011915 (Application No. 21199451.2) filed on Jul. 17, 2024, on behalf of Secerna LLP.
D10—Regeneron Science to Medicine, J.P. Morgan Healthcare Conference, Jan. 2013, cited in Notice of Opposition against European Patent No. 4011915 (Application No. 21199451.2) filed on Jul. 17, 2024, on behalf of Secerna LLP.
D11—Press release from Regeneron, "Regeneron Reports Fourth Quarter and Full Year 2011 Financial and Operating Results", Feb. 13, 2012, cited in Notice of Opposition against European Patent No. 4011915 (Application No. 21199451.2) filed on Jul. 17, 2024, on behalf of Secerna LLP.
D12—Otulana et al., American Journal of Respiratory and Critical Care Medicine, 183: A6179, American Thoracic Society 2011 International Conference Abstract, May 18, 2011, cited in Notice of Opposition against European Patent No. 4011915 (Application No. 21199451.2) filed on Jul. 17, 2024, on behalf of Secerna LLP.
D13—Wenzel S.E. et al., Late Breaking Abstract: Inhaled pitrakinra, an IL-antagonist, reduced exacerbations in patients with eosinophilic asthma; European Respiratory Journal 2010; 36: Suppl. 54, p. 3980, Sep. 21, 2010, cited in Notice of Opposition against European Patent No. 4011915 (Application No. 21199451.2) filed on Jul. 17, 2024, on behalf of Secerna LLP.
D14—Corren J, et al. Am J Respir Crit Care Med. Apr. 1, 20105;181(8):788-96, cited in Notice of Opposition against European Patent No. 4011915 (Application No. 21199451.2) filed on Jul. 17, 2024, on behalf of Secerna LLP.
D15—Editorial commentary on Corren et al. Borish—Am J Respir Crit Care Med;181(8):769-772. Jan. 7, 2010, cited in Notice of Opposition against European Patent No. 4011915 (Application No. 21199451.2) filed on Jul. 17, 2024, on behalf of Secerna LLP.
D16—Hashimoto and Bel., Current treatment of severe asthma, Clin. Exp. Allergy., vol. 42(5): 693-705, May 2012, cited in Notice of Opposition against European Patent No. 4011915 (Application No. 21199451.2) filed on Jul. 17, 2024, on behalf of Secerna LLP.
D17—Pavord ID, et al., Lancet. Aug. 18, 2012;380(9842):651-659, cited in Notice of Opposition against European Patent No. 4011915 (Application No. 21199451.2) filed on Jul. 17, 2024, on behalf of Secerna LLP.
D18—Nancy M. Abdelaty, Patient characteristics that can predict response to omalizumab an (Anti-IgE Antibody) for achieving better control of asthmatic patients, Egyptian Journal of Chest Diseases and Tuberculosis, vol. 61, Issue 3, pp. 15-22, Jul. 2012, cited in Notice of Opposition against European Patent No. 4011915 (Application No. 21199451.2) filed on Jul. 17, 2024, on behalf of Secerna LLP.
D19—Szefler et al. Asthma Outcomes: Biomarkers. J Allergy Clin Immunol. 2012 129: S9-23. Mar. 1, 2012, cited in Notice of Opposition against European Patent No. 4011915 (Application No. 21199451.2) filed on Jul. 17, 2024, on behalf of Secerna LLP.
D20—Spector & Tan. Is a single blood eosinophil count a reliable marker for "eosinophilic asthma?". Journal of Asthma 49.8 (2012): Early Online: 1-4. Aug. 20, 2012, cited in Notice of Opposition against European Patent No. 4011915 (Application No. 21199451.2) filed on Jul. 17, 2024, on behalf of Secerna LLP.
D21—WHO Drug Information, vol. 26, No. 4, pp. 401-471, "Proposed INN: List 108", published on Dec. 9, 2012 (as evidenced by the Annex appended to the document retrieved from https://www.who.int/publications/m/item/inn-pl-108) , cited in Notice of Opposition against European Patent No. 4011915 (Application No. 21199451.2) filed on Jul. 17, 2024, on behalf of Secerna LLP.
D22—Darveaux & Busse. Biologics in asthma—the next step to personalised treatment. J Allergy Clin Immunol Pract. Mar.-Apr. 2015; 3(2): 152-161. Mar. 2015, cited in Notice of Opposition against European Patent No. 4011915 (Application No. 21199451.2) filed on Jul. 17, 2024, on behalf of Secerna LLP.
D23—Eisenstein. Something new under the skin. Nature Biotechnology 29(2), 107-109 (2011). Feb. 7, 2011, cited in Notice of Opposition against European Patent No. 4011915 (Application No. 21199451.2) filed on Jul. 17, 2024, on behalf of Secerna LLP.
D24—Chapter 19, "Dosage regimens" of Aulton's Pharmaceutics: The Science of Dosage Form Design, 2nd Edition, 2001, cited in Notice of Opposition against European Patent No. 4011915 (Application No. 21199451.2) filed on Jul. 17, 2024, on behalf of Secerna LLP.
D25—Djukanovic et al.2002, Eur. Respire. J. 37: 1S-2S), cited in Notice of Opposition against European Patent No. 4011915 (Application No. 21199451.2) filed on Jul. 17, 2024, on behalf of Secerna LLP.
D26—Alving et al., Increased amount of nitric oxide in exhaled air of asthmatics, Eur Respir J., vol. 6: 1366-1370, 1993, cited in Notice of Opposition against European Patent No. 4011915 (Application No. 21199451.2) filed on Jul. 17, 2024, on behalf of Secerna LLP.
D27—Appeal Brief filed by Proprietor during prosecution of U.S. Appl. No. 13/971,334, Mar. 24, 2016, cited in Notice of Opposition against European Patent No. 4011915 (Application No. 21199451.2) filed on Jul. 17, 2024, on behalf of Secerna LLP.
D28—Handlogten et al "Prevention of Fab-arm exchange and antibody reduction via stabilization of the IgG4 hinge region" MAbs. 12(1): 1779974. 2020, cited in Notice of Opposition against European Patent No. 4011915 (Application No. 21199451.2) filed on Jul. 17, 2024, on behalf of Secerna LLP.
D29—Silva et al. The S228P Mutation Prevents in Vivo and in Vitro IgG4 Fab-arm Exchange as demonstrated using a Combination of Novel Quantitative Immunoassays and Physiological Matrix Preparation, J Biol Chem. Jan. 8, 2015;290(9):5462-5469, cited in Notice of Opposition against European Patent No. 4011915 (Application No. 21199451.2) filed on Jul. 17, 2024, on behalf of Secerna LLP.
D30—Dumet et al "Insights into the IgG heavy chain engineering patent landscape as applied to lgG4 antibody development" MABS. 11(8) 1341-1350, 2019, cited in Notice of Opposition against European Patent No. 4011915 (Application No. 21199451.2) filed on Jul. 17, 2024, on behalf of Secerna LLP.
D31—Center for Drug Evaluation and Research "Clinical Review, Brenda Carr, MD, BLA 761055, Dupixent (dupilumab)" Application Number: 761055Orig1s000 Reference ID: 4075125, Apr. 9, 2015, cited in Notice of Opposition against European Patent No. 4011915 (Application No. 21199451.2) filed on Jul. 17, 2024, on behalf of Secerna LLP.
D32—Shannon et al."Differences in airway cytokine profile in severe asthma compared to moderate asthma" Chest. 133(2):420-6. Feb. 2008, cited in Notice of Opposition against European Patent No. 4011915 (Application No. 21199451.2) filed on Jul. 17, 2024, on behalf of Secerna LLP.
D33—Bossley et al "Pediatric severe asthma is characterized by eosinophilia and remodeling without TH2 cytokines" J Allergy Clin Immunol. 129(4): 974-82.e13. Apr. 2012, cited in Notice of Opposition against European Patent No. 4011915 (Application No. 21199451.2) filed on Jul. 17, 2024, on behalf of Secerna LLP.
D34—Wenzel "Severe Asthma in Adults" Am J Respir Crit Care Med. 172(2) 149-160, 2005, cited in Notice of Opposition against European Patent No. 4011915 (Application No. 21199451.2) filed on Jul. 17, 2024, on behalf of Secerna LLP.
D35—Al-Ramli W et al.J Asthma. 2008;45 Suppl 1:41-4, cited in Notice of Opposition against European Patent No. 4011915 (Application No. 21199451.2) filed on Jul. 17, 2024, on behalf of Secerna LLP.
D36—Lommatzsch et al."Severe Asthma: Definition, Diagnosis and Treatment", Dtsch Arztebl Int., 111(50): 847-855. Dec. 2014, cited in Notice of Opposition against European Patent No. 4011915 (Application No. 21199451.2) filed on Jul. 17, 2024, on behalf of Secerna LLP.

(56) References Cited

OTHER PUBLICATIONS

D37—Costantino et al."Intranasal delivery: Physicochemical and therapeutic aspects" International Journal of Pharmaceutics. 337(1-2), 1-24, 2007, cited in Notice of Opposition against European Patent No. 4011915 (Application No. 21199451.2) filed on Jul. 17, 2024, on behalf of Secerna LLP.
D38—Thomson et al."Omalizumab: Clinical Use for the Management of Asthma" Clin Med Insights Circ Respir Pulm Med. 6: 27-40, 2012, cited in Notice of Opposition against European Patent No. 4011915 (Application No. 21199451.2) filed on Jul. 17, 2024, on behalf of Secerna LLP.
D39—Kelly et al."Nedocromil sodium versus sodium cromoglycate for preventing exercise-induced bronchoconstriction" Cochrane Database Syst Rev. 2000(3): CD002731. Jul. 24, 2000, cited in Notice of Opposition against European Patent No. 4011915 (Application No. 21199451.2) filed on Jul. 17, 2024, on behalf of Secerna LLP.
D40—Gore "The utility of antifungal agents for asthma" Curr Opin Pulm Med. 16(1):36-41. Jan. 2010, cited in Notice of Opposition against European Patent No. 4011915 (Application No. 21199451.2) filed on Jul. 17, 2024, on behalf of Secerna LLP.
Notice of Opposition against European Patent No. 4011915 (Application No. 21199451.2) dated Jul. 17, 2024, filed on behalf of Hampton Knowles Limited.
D2—Wenzel S. et al., The New England Journal of Medicine, 368(26): 2455-66, published online on May 21, 2013, cited in Notice of Opposition against European Patent No. 4011915 (Application No. 21199451.2) filed on Jul. 17, 2024, on behalf of Hampton Knowles Limited.
D4—Otulana et al., American Journal of Respiratory and Critical Care Medicine, 183: A6179, American Thoracic Society 2011 International Conference Abstract, May 18, 2011, cited in Notice of Opposition against European Patent No. 4011915 (Application No. 21199451.2) filed on Jul. 17, 2024, on behalf of Hampton Knowles Limited.
D7—WO 2011/156000 A2, cited in Notice of Opposition against European Patent No. 4011915 (Application No. 21199451.2) filed on Jul. 17, 2024, on behalf of Hampton Knowles Limited.
D9—Wenzel S.E et al., Late Breaking Abstract: Inhaled pitrakinra, an IL-antagonist, reduced exacerbations in patients with eosinophilic asthma; European Respiratory Journal 2010; 36: Suppl. 54, p. 3980, Sep. 21, 2010, cited in Notice of Opposition against European Patent No. 4011915 (Application No. 21199451.2) filed on Jul. 17, 2024, on behalf of Hampton Knowles Limited.
D10—Wenzel S., Clinical and Experimental Allergy, 42(5): 650-8, published on Jan. 18, 2012 (as evidenced by the Annex appended to the document), cited in Notice of Opposition against European Patent No. 4011915 (Application No. 21199451.2) filed on Jul. 17, 2024, on behalf of Hampton Knowles Limited.
D31—Corren J, et al. Am J Respir Crit Care Med. Apr. 15, 2010;181(8):788- 96, cited in Notice of Opposition against European Patent No. 4011915 (Application No. 21199451.2) filed on Jul. 17, 2024, on behalf of Hampton Knowles Limited.
DYC01—Woodruff P.G et al., "T-helper type 2-driven inflammation defines major subphenotypes of asthma", Am J Respir Crit Care Med. Sep. 1, 2009;180(5):388-95, cited in Notice of Opposition against European Patent No. 4011915 (Application No. 21199451.2) filed on Jul. 17, 2024, on behalf of Hampton Knowles Limited.
DYC02—Szefler et al. Asthma Outcomes: Biomarkers. J Allergy Clin Immunol.,129: S9-23. Mar. 1, 2012, cited in Notice of Opposition against European Patent No. 4011915 (Application No. 21199451.2) filed on Jul. 17, 2024, on behalf of Hampton Knowles Limited.
DYC03—Shannon et al "Differences in airway cytokine profile in severe asthma compared to moderate asthma" Chest. 133(2):420-6. Feb. 2008, cited in Notice of Opposition against European Patent No. 4011915 (Application No. 21199451.2) filed on Jul. 17, 2024, on behalf of Hampton Knowles Limited.
DYC04—Editorial commentary on Corren et al. Borish—Am J Respir Crit Care Med; 181(8):769-772; Jul. 1, 2010, cited in Notice of Opposition against European Patent No. 4011915 (Application No. 21199451.2) filed on Jul. 17, 2024, on behalf of Hampton Knowles Limited.
DYC05—Hashimoto and Bel., Current treatment of severe asthma, Clin. Exp. Allergy., vol. 42(5): 693-705, May 2012, cited in Notice of Opposition against European Patent No. 4011915 (Application No. 21199451.2) filed on Jul. 17, 2024, on behalf of Hampton Knowles Limited.
DYC06—U.S. Pat. No. 8,075,887 B2, cited in Notice of Opposition against European Patent No. 4011915 (Application No. 21199451.2) filed on Jul. 17, 2024, on behalf of Hampton Knowles Limited.
DYC07—Kostic et al., Clinical Immunology, 2010, 135:S105-S106, cited in Notice of Opposition against European Patent No. 4011915 (Application No. 21199451.2) filed on Jul. 17, 2024, on behalf of Hampton Knowles Limited.
DYC08—excerpt from clinicaltrials.gov NCT01312961, cited in Notice of Opposition against European Patent No. 4011915 (Application No. 21199451.2) filed on Jul. 17, 2024, on behalf of Hampton Knowles Limited.
DYC09—Global Initiative for Asthma, "Global Strategy for Asthma Management and Prevention", 2011, chapters 2 and 3, cited in Notice of Opposition against European Patent No. 4011915 (Application No. 21199451.2) filed on Jul. 17, 2024, on behalf of Hampton Knowles Limited.
Reply of the Patent Proprietor to the Notice of Opposition against European Patent No. 4011915 (Application No. 21199451.2) dated Jan. 27, 2025, filed on behalf of Sanofi Biotechnology.
D80—Wenzel et al. (2016), Lancet, 388: 31-14, cited in Reply of the Patent Proprietor dated Jan. 27, 2005, filed on behalf of Sanofi Biotechnology, in response to the Notices of Opposition against European Patent No. 4011915 (Application No. 21199451.2).
D81—Wang et al. (2007), N Engl J Med, 357; 21:2189-2194, cited in Reply of the Patent Proprietor dated Jan. 27, 2005, filed on behalf of Sanofi Biotechnology, in response to the Notices of Opposition against European Patent No. 4011915 (Application No. 21199451.2).
D82—Lagakos et al. (2006), N Engl J Med 354;16:1667-1669, cited in Reply of the Patent Proprietor dated Jan. 27, 2005, filed on behalf of Sanofi Biotechnology, in response to the Notices of Opposition against European Patent No. 4011915 (Application No. 21199451.2).
Reply of the Patent Proprietor to the Communication of Notices of Opposition against European Patent No. 3470432 (Application No. 18194745.8), dated Jul. 20, 2022, on behalf of Sanofi Biotechnology.
European Patent Office Decision Revoking European Patent No. 3470432 (Application No. 18194745.8), dated Feb. 2, 2023.
Reply of the Patent Proprietor to the Notice of Opposition against European Patent No. 3973987 (Application No. 21191120.1), filed Apr. 24, 2025, on behalf of Sanofi Biotechnology.
D87—Wenzel et al., Dupilumab efficacy and safety in adults with uncontrolled persistent asthma despite use of medium-to-high-dose inhaled corticosteroids plus a long-acting B2 agonist: a randomised double-blind placebo-controlled pivotal phase 2b dose-ranging trial, Lancet, Apr. 27, 2016, 388:31-44, cited in Reply of the Patent Proprietor to the Notice of Opposition against European Patent No. 3973987 (Application No. 21191120.1), filed Apr. 24, 2025, on behalf of Sanofi Biotechnology.
D88—Castro et al., "Dupilumab Efficacy and Safety in Moderate-to-Severe Uncontrolled Asthma", NEJM, Jun. 28, 2018, vol. 378, No. 26, pp. 2486-2496, cited in Reply of the Patent Proprietor to the Notice of Opposition against European Patent No. 3973987 (Application No. 21191120.1), filed Apr. 24, 2025, on behalf of Sanofi Biotechnology.
D89—EMA Guidance on FIH Trials, Committee for Medicinal Products for Human Use (CHMP), Jul. 19, 2007, cited in Reply of the Patent Proprietor to the Notice of Opposition against European Patent No. 3973987 (Application No. 21191120.1), filed Apr. 24, 2025, on behalf of Sanofi Biotechnology.
D90—Kips et al., New anti-asthma therapies: suppression of the effect of interleukin (IL)-4 and IL-5, European Respiratory Journal, 2001, 17(3): 499-506, cited in Reply of the Patent Proprietor to the

(56) References Cited

OTHER PUBLICATIONS

Notice of Opposition against European Patent No. 3973987 (Application No. 21191120.1), filed Apr. 24, 2025, on behalf of Sanofi Biotechnology.
D91—Oldhoff et al., Anti-IL-5 recombinant humanized monoclonal antibody (mepolizumab) for the treatment of atopic dermatitis, Allergy, May 2005, 60(5): 693-696, cited in Reply of the Patent Proprietor to the Notice of Opposition against European Patent No. 3973987 (Application No. 21191120.1), filed Apr. 24, 2025, on behalf of Sanofi Biotechnology.
D92—Schujis et al., Cytokine targets in airway inflammation, Curr Opin Pharmacol, Jun. 2013, 13(3): 351-361, cited in Reply of the Patent Proprietor to the Notice of Opposition against European Patent No. 3973987 (Application No. 21191120.1), filed Apr. 24, 2025, on behalf of Sanofi Biotechnology.
D93—Bice et al., "Biologic targeted therapy in allergic asthma", Annals of Allergy, Asthma & Immunology, 2014, 112(2): 108-115, cited in Reply of the Patent Proprietor to the Notice of Opposition against European Patent No. 3973987 (Application No. 21191120.1), filed Apr. 24, 2025, on behalf of Sanofi Biotechnology.
D94—Hay et al., Clinical development success rates for investigational drugs, Nature Biotechnology, Jan. 9, 2014, 32: 40-51, cited in Reply of the Patent Proprietor to the Notice of Opposition against European Patent No. 3973987 (Application No. 21191120.1), filed Apr. 24, 2025, on behalf of Sanofi Biotechnology.
D95—Rabe et al., Efficacy and Safety of Dupilumab in Glucocorticoid-Dependent Severe Asthma, NEJM, May 21, 2018, 378: 2475-2485, cited in Reply of the Patent Proprietor to the Notice of Opposition against European Patent No. 3973987 (Application No. 21191120.1), filed Apr. 24, 2025, on behalf of Sanofi Biotechnology.
D96—Declaration of Prof. Ian Pavord dated Apr. 24, 2025, cited in Reply of the Patent Proprietor to the Notice of Opposition against European Patent No. 3973987 (Application No. 21191120.1), filed Apr. 24, 2025, on behalf of Sanofi Biotechnology.
D96a—List of Publications by Prof. Ian Pavord, cited in Reply of the Patent Proprietor to the Notice of Opposition against European Patent No. 3973987 (Application No. 21191120.1), filed Apr. 24, 2025, on behalf of Sanofi Biotechnology.
Reply of the Patent Proprietor to the Communication of Notices of Opposition against European Patent No. 3107575 (Application No. 15708991.3), dated Jan. 2, 2023, on behalf of Sanofi Biotechnology.
D41—GINA Report Dec. 2012, Global Strategy for Asthma Management and Prevention, GINA © 2012 & Global Initiative for Asthma, reprinted with permission, Available from www.ginasthma.org, cited in Reply of the Patent Proprietor to the Communication of Notices of Opposition against European Patent No. 3107575 (Application No. 15708991.3), dated Jan. 2, 2023, on behalf of Sanofi Biotechnology.
D42—Rabe et al., Efficacy and Safety of Dupilumab in Glucocorticoid-Dependent Severe Asthma, NEJM, May 21, 2018, 378: 2475-2485, cited in Reply of the Patent Proprietor to the Communication of Notices of Opposition against European Patent No. 3107575 (Application No. 15708991.3), dated Jan. 2, 2023, on behalf of Sanofi Biotechnology.
D43—EMA Guidance, Committee for Medicinal Products for HUman Use (CHMP), Jul. 19, 2007, cited in Reply of the Patent Proprietor to the Communication of Notices of Opposition against European Patent No. 3107575 (Application No. 15708991.3), dated Jan. 2, 2023, on behalf of Sanofi Biotechnology.
D44—Corren et al., A randomized, controlled, Phase 2 study of AMG 317, an IL-4Ra antagonist, in patients with asthma, Am J Respir Crit Care Med., Jan. 7, 2010, 181(8): 788-796, cited in Reply of the Patent Proprietor to the Communication of Notices of Opposition against European Patent No. 3107575 (Application No. 15708991.3), dated Jan. 2, 2023, on behalf of Sanofi Biotechnology.
D45—Schujis et al., Cytokine targets in airway inflammation, Curr Opin Pharmacol, Jun. 2013, 13(3): 351-361, Epulished May 2, 2013, cited in Reply of the Patent Proprietor to the Communication of Notices of Opposition against European Patent No. 3107575 (Application No. 15708991.3), dated Jan. 2, 2023, on behalf of Sanofi Biotechnology.
D46—Hay et al., Clinical development success rates for investigational drugs, Nature Biotechnology, Jan. 9, 2014, 32: 40-51, cited in Reply of the Patent Proprietor to the Communication of Notices of Opposition against European Patent No. 3107575 (Application No. 15708991.3), dated Jan. 2, 2023, on behalf of Sanofi Biotechnology.
D47—Wang et al., Monoclonal antibody pharmacokinetics and pharmacodynamics, Clinical Pharmacology & Therapeutics, 2008, 84(5):548-558, cited in Reply of the Patent Proprietor to the Communication of Notices of Opposition against European Patent No. 3107575 (Application No. 15708991.3), dated Jan. 2, 2023, on behalf of Sanofi Biotechnology.
D48—Mould et al., Current Opinion in Drug Discovery & Development, 2007, 10(1): 84-96, cited in Reply of the Patent Proprietor to the Communication of Notices of Opposition against European Patent No. 3107575 (Application No. 15708991.3), dated Jan. 2, 2023, on behalf of Sanofi Biotechnology.
D49—Kips et al., New anti-asthma therapies: suppression of the effect of interleukin (IL)-4 and IL-5, European Respiratory Journal, 2001, 17(3): 499-506, cited in Reply of the Patent Proprietor to the Communication of Notices of Opposition against European Patent No. 3107575 (Application No. 15708991.3), dated Jan. 2, 2023, on behalf of Sanofi Biotechnology.
D50—Pavord et al., Mepolizumab for severe eosinophilic asthma (DREAM): a multicentre, double-blind, placebo-controlled trial, Lancet, Aug. 18, 2012; 380: 651-659, cited in Reply of the Patent Proprietor to the Communication of Notices of Opposition against European Patent No. 3107575 (Application No. 15708991.3), dated Jan. 2, 2023, on behalf of Sanofi Biotechnology.
D51—Oldhoff et al., Anti-IL-5 recombinant humanized monoclonal antibody (mepolizumab) for the treatment of atopic dermatitis, Allergy, May 2005, 60(5): 693-696, cited in Reply of the Patent Proprietor to the Communication of Notices of Opposition against European Patent No. 3107575 (Application No. 15708991.3), dated Jan. 2, 2023, on behalf of Sanofi Biotechnology.
D52—REC Standard Operating Procedures, cited in Reply of the Patent Proprietor to the Communication of Notices of Opposition against European Patent No. 3107575 (Application No. 15708991.3), dated Jan. 2, 2023, on behalf of Sanofi Biotechnology.
D53—REC Annual Report, cited in Reply of the Patent Proprietor to the Communication of Notices of Opposition against European Patent No. 3107575 (Application No. 15708991.3), dated Jan. 2, 2023, on behalf of Sanofi Biotechnology.
D57—NHS Health Research Authority, "Dupilumab for adult patients with moderate to severe atopic dermatitis", REC Opinion, May 30, 2014, cited in Reply to Patent Proprietor's Response to Notices of Opposition against European Patent No. 3107575 (EP Application No. 15708991.3) filed on behalf of Regina Neuefeind, dated Apr. 20, 2023.
Reply to Patent Proprietor's Response to Notices of Opposition against European Patent No. 3107575 (EP Application No. 15708991.3) filed on behalf of Dr. Regina Neuefeind, dated Apr. 20, 2023.
D54—Chain A, Dupilumab Fab heavy chain, Accession No. 6WGB_A, Dec. 1, 2020, cited in Reply to Patent Proprietor's Response to Notices of Opposition against European Patent No. 3107575 (EP Application No. 15708991.3) filed on behalf of Regina Neuefeind, dated Apr. 20, 2023.
D55—Chain B, Dupilumab Fab light chain, Accession No. 6WGB_B, Dec. 1, 2020, cited in Reply to Patent Proprietor's Response to Notices of Opposition against European Patent No. 3107575 (EP Application No. 15708991.3) filed on behalf of Regina Neuefeind, dated Apr. 20, 2023.
D56—Preliminary Opinion T0829/19, cited in Reply to Patent Proprietor's Response to Notices of Opposition against European Patent No. 3107575 (EP Application No. 15708991.3) filed on behalf of Regina Neuefeind, dated Apr. 20, 2023.
Response to Summons to Attend Oral Proceedings regarding Opposition against European Patent No. 3107575 (EP Application No. 15708991.3), filed on behalf of Dr. Regina Neuefeind, dated Nov. 15, 2023.

(56) References Cited

OTHER PUBLICATIONS

Response to Summons to Attend Oral Proceedings regarding Opposition against European Patent No. 3107575 (EP Application No. 15708991.3), filed on behalf of Dr. Hans Ulrich Dorries, dated Nov. 15, 2023.
Response to Summons to Attend Oral Proceedings regarding Opposition against European Patent No. 3107575 (EP Application No. 15708991.3), filed on behalf of D. Young & Co., dated Nov. 15, 2023.
Submission Under Rule 116 EPC by Patent Proprietor regarding Opposition against European Patent No. 3107575 (EP Application No. 15708991.3), filed on behalf of Sanofi Biotechnology, dated Nov. 15, 2023.
Norwegian Publicaiton No. NO983141L dated Jan. 10, 2000, cited in Submission Under Rule 116 EPC by Patent Proprietor regarding Opposition against European Patent No. 3107575 (EP Application No. 15708991.3), filed on behalf of Sanofi Biotechnology, dated Nov. 15, 2023.
Appeal No. T0563/24-3.3.04 Following Opposition against European Patent No. 3107575 (EP Application No. 15708991.3) filed on behalf of D Young & Co. LLP, dated May 7, 2024.
Grounds for Appeal regarding Appeal Number T0563/24-3.3.04 Following Opposition against European Patent No. 3107575 (EP Application No. 15708991.3) filed on behalf of D Young & Co. LLP, dated Jul. 8, 2024.
Fracasso et al., A Phase 1 Escalating Single-Dose and Weekly Fixed-Dose Study of Cetuximab: Pharmacokinetic and Pharmacodynamic Rationale for Dosing, Clin Cancer Res, 2007, 13(3):986-993, cited in Grounds for Appeal regarding Appeal Number T0563/24-3.3.04 Following Opposition against European Patent No. 3107575 (EP Application No. 15708991.3) filed on behalf of D Young & Co. LLP, dated Jul. 8, 2024.
Mould et al., Population pharmacokinetics-pharmacodynamics of alemtuzumab (Campath®) in patients with chronic lymphocytic leukaemia and its link to treatment response, Br J Clin Pharmacol, 2007, 64(3):278-291, cited in Grounds for Appeal regarding Appeal No. T0563/24-3.3.04 Following Opposition against European Patent No. 3107575 (EP Application No. 15708991.3) filed on behalf of D Young & Co. LLP, dated Jul. 8, 2024.
Sohn et al., The pharmacokinetics and pharmacodynamics of denosumab in patients with advanced solid tumours and bone metastases: a systematic review, Br J Clin Pharmacol, 2014, 78(3):477-487, cited in Grounds for Appeal regarding Appeal Number T0563/24-3.3.04 Following Opposition against European Patent No. 3107575 (EP Application No. 15708991.3) filed on behalf of D Young & Co. LLP, dated Jul. 8, 2024.
Dostalek et al., Pharmacokinetics, pharmacodynamics and physiologically-based pharmacokinetic modelling of monoclonal antibodies, Clin Pharmacokinet, 2013, 52: 83-124, cited in Grounds for Appeal regarding Appeal No. T0563/24-3.3.04 Following Opposition against European Patent No. 3107575 (EP Application No. 15708991.3) filed on behalf of D Young & Co. LLP, dated Jul. 8, 2024.
Patentee's Reply to Grounds for Appeal regarding Appeal Number T0563/24-3.3.04 Following Opposition against European Patent No. 3107575 (EP Application No. 15708991.3), filed on behalf of Sanofi Biotechnology, dated Nov. 11, 2024.
Comments in Preparation of the Oral Proceedings regarding Pantentee's Reply to Grounds for Appeal regarding Appeal No. T0563/24-3.3.04 Following Opposition against European Patent No. 3107575 (EP Application No. 15708991.3), filed on behalf of Sanofi Biotechnology, dated Jun. 12, 2025.
Letter of the Patent Proprietor regarding Appeal Number T0563/24-3.3.04 Following Opposition against European Patent No. 3107575 (EP Application No. 15708991.3), filed on behalf of Sanofi Biotechnology, dated Nov. 12, 2025.
Written Submission Under Rule 116 EPC regarding European Patent No. 3703818 (EP Application No. 18799655.8), filed on behalf of Hampton Knowles Limited, dated Dec. 18, 2025.
Written Submission Under Rule 116 EPC regarding European Patent No. 3703818 (EP Application No. 18799655.8), filed on behalf of Dr. Hans Ulrich Dorries, dated Dec. 19, 2025.
Written Submission Under Rule 116 EPC regarding European Patent No. 3703818 (EP Application No. 18799655.8), filed by Boehmert & Boehmert, dated Dec. 22, 2025.
Written Submission Under Rule 116 EPC regarding European Patent No. 3703818 (EP Application No. 18799655.8), filed on behalf of Lanyon Oppositions Limited (O2), dated Dec. 22, 2025.
Written Submission Under Rule 116 EPC regarding European Patent No. 3703818 (EP Application No. 18799655.8), filed on behalf of Dr. Luigi Rumi, dated Dec. 23, 2025.
Written Submission Under Rule 116 EPC regarding European Patent No. 3703818 (EP Application No. 18799655.8), filed on behalf of Boult Wade Tennant LLP, dated Dec. 23, 2025.
Written Submission Under Rule 116 EPC regarding European Patent No. 3703818 (EP Application No. 18799655.8), filed on behalf of Michaelski Hüttermann & Partner Patentanwalte mbD, dated Dec. 23, 2025.
Patentee's Submission Under Rule 116 EPC regarding European Patent No. 3703818 (EP Application No. 18799655.8), filed on behalf of Sanofi Biotechnology, dated Dec. 23, 2025.
List of Consolidated References for Written Submissions and Patentee's Submission regarding European Patent No. 3703818 (EP Application No. 18799655.8), dated Jan. 27, 2026.
D1 - Clinicaltrials.gov, "Evaluation of Dupilumab in Patients With Severe Steroid Dependent Asthma (VENTURE)," online archive of < https://clinicaltrials.gov/study/NCT02528214?intr=REGN668&cond=Asthma&rank=9 > ("NCT02528214") Version 38, Oct. 24, 2017.
D2 - Wenzel S et al., "Dupilumab efficacy and safety in adults with uncontrolled persistent asthma despite use of medium-to-high dose inhaled corticosteroids plus a long-acting [32 agonist; a randomised double-blind placebo-controlled pivotal phase 2b dose-ranging trial," The Lancet (2016) 388(10039): 31-44.
D2a - Supplementary Appendix to D2.
D3 - Regeneron Press Release dated Oct. 31, 2017.
D4—Clinical trials.gov, "Evaluation of Dupilumab in Patients With Persistent Asthma (Liberty Asthma Quest)," online archive of <https://clinicaltrials.gov/study/NCT02414854> ("NCT02414854") Sep. 11, 2017.
D5—Regeneron Press Release, "Regeneron and Sanofi announce positive Dupilumab topline results from phase 3 trial in uncontrolled persistent asthma" Available from <https://investor.regeneron.com/news-releases/news-release-details/regeneron-andsanofi-announce-positive-dupilumab-topline-0> Sep. 11, 2017.
D6—Clinical trials.gov, "Dupilumab Compassionate Use Study" online archive of https://clinicaltrials.gov/study/NCT03020810 ("NCT03020810") Jan. 13, 2017.
D7—Chung KF., "Dupilumab: a potential new treatment for severe asthma", Lancet (2016) 2;388(10039):3-4.
D8 / D55—Bel EH et al., "Oral glucocorticoid-sparing effect of mepolizumab in eosinophilic asthma," N Engl J Med (2014) 371(13):1189-97.
D8a—Supplementary Appendix to D8.
D9—Nair P et al., "Oral Glucocorticoid-Sparing Effect of Benralizumab in Severe Asthma," N Engl J Med (2017) 376(25):2448-2458.
D9a—Supplementary Appendix to D9.
D10—Global Initiative for Asthma, "Global Strategy for Asthma Management and Prevention," Vancouver, GINA 2014. Available from.
D11—Fahy JV. "Type 2 inflammation in asthma—present in most, absent in many," Nat Rev Immunol (2015) (1):57-65.
D12—Donohue JF and Jain N, "Exhaled nitric oxide to predict corticosteroid responsiveness and reduce asthma exacerbation rates," Respir Med. (2012) D13—107(7):943-52.
D13—Hashimoto S and Bel EH, "Current treatment of severe asthma," Clin Exp Allergy (2012) 42(5):693-705.
D14—Clinicaltrials.gov, "Evaluation of Dupilumab in Patients With Severe Steroid Dependent Asthma (VENTURE)," Clinical Trial Protocol for NCT02528214.

(56) References Cited

OTHER PUBLICATIONS

D15-Brusselle G and Bracke K, "Targeting immune pathways for therapy in asthma and chronic obstructive pulmonary disease," Ann Am Thorac Soc. (2014) 11 Suppl 5:S322-8.
D16 / D67—WO 2015/127229 (Sanofi and Regeneron).
D17—Barranco et al., "Dupilumab in the management of moderate-to-severe asthma: the data so far", Therapeutics and Clinical Risk Management, Sep. 1, 2017, 13, 1139-1149.
D18—Brodlie et al., "The oral corticosteroid-sparing effect of omalizumab in children with severe asthma", Archives of Disease in Childhood, Jun. 9, 2012, 97, 604-609.
D19—Molimard et al., "Omalizumab reduces oral corticosteroid use in patients with severe allergic asthma: Real-life data", Jul. 5, 2010, 104, 1381-1385.
D20—EP 3 703 818 B1 (granted patent/"patent in suit").
D21—WO 2019/089473 (application as originally filed).
D22—Braunstahl et al. "Reduction in oral corticosteroid use in patients receiving omalizumab for allergic asthma in the real-world setting"; BioMed Central, Allergy, Asthma & Clinical Immunology 2013, 9:47; http://www.aacijoumal.com/content/9/1/47.
D23—Wenzel et al.; "Dupilumab in Persistent Asthma with Elevated Eosinophil Levels"; The New England Journal of Medicine 2013; 368; 26.
D24—WO 2014/031610 AI.
D25—GINA "Pocket Guide for Asthma Management and Prevention"; Global Initiative for Asthma, 2016.
D26—Mash et al., 2001 "Inhaled versus oral steroids for adults with chronic asthma"; Cochrane Database of Systematic Reviews 2001, Issue 1. Art. No. CD002160. DOI: 10.1002/14651858.CD002160.
D27—Schellenberg et al., 2007 "Oral corticosteroids in asthma: A review of benefits and risks"; Can Respir J 2007;14 (Suppl C):1C-7C.
D28—Luskin et al., 2016; "Health care resource use and costs associated with possible side effects of high oral corticosteroid use in asthma: a claims-based analysis"; ClinicoEconomics and Outcomes Research 2016:8 641-648.
D29—Lin et al., 2016; "A review of omalizumab for the management of severe asthma"; Drug Design, Development and Therapy 2016:10 2369-2378.
D30—Barnes et al., 2003; "How do corticosteroids work in asthma? ", Ann. Intern. Med ; 2003 ; 139 : 359-37.
D31—Dupixent Label 2017.
D32—Austin et al. "Blood Eosinophil dose response to oral corticosteroids in a population of patients with severe asthma", European Respiratory Journal, 2016, 48: PA1100.
D33—Ray A et al. J Clin Invest. 2016;126(7):2394-2403.
D34—pp. 401, 402 and 412 of WHO Drug Information, 2012, 26(4):401-471.
D35—Shirley, Dupilumab: First Global Approval, Drugs, 2017, 77: 1115-1121.
D36 / D65—Santini G. et al., Expert Opinion on Investigational Drugs, 26(3):357-366, published online on Feb. 7, 2017.
D37—Pollart et al., 2009.
D38—Wenzel, "Severe Asthma in Adults", Am J Respir Crit Care Med., 2005, 172: 149-160.
D39—Al-Ramli et al., 2008.
D40—ESR EP3470432 2018.
D41—Gina Report 2016.
D42—Pavord et al., 2012.
D43—Bumbacea et al., 2004.
D44—Kharitonov et al., Exhaled and Nasal Nitric Oxide Measurements: Reccomendations, Eur. Respir J., 1997, 10: 1683-1693.
D45—Normansell et al., 2016.
D46—ClinicalTrials.gov, Trial protocol of Sep. 28, 2017 for ClinicalTrials.gov ID NCT01000506.
D47—U.S. Appl. No. 62/579,120, filed Oct. 30, 2017 (also referred to as "Prio 1").
D48—U.S. Appl. No. 62/710,381, filed Feb. 16, 2018 (also referred to as "Prio 2").
D49—U.S. Appl. No. 62/647,368, filed Mar. 23, 2018 (also referred to as "Prio 3").
D50—EP 18305566.4, filed on May 4, 2018 (also referred to as "Prio 4").
D51—U.S. Appl. No. 62/742,736, filed Oct. 8, 2018 (also referred to as "Prio 5").
D52—Rabe K.F. et al., "Efficacy and Safety of Dupilumab in Glucocorticoid- Dependent Severe Asthma", N Engl J Med. Jun. 28, 2018; 378(26):2475-2485. doi: 10.1056/NEJMoal804093. Epub May 21, 2018.
D52a—Supplementary Appendix of TM7 (Rabe et al.).
D52b—Clinical trial protocol of the study of D1, published together with D1 on May 21, 2018.
D53—WHO Drug Information vol. 26(4), 412, Dec. 9, 2012.
D54—Nguyen V.Q. and Ulrik C.S., "Measures to reduce maintenance therapy with oral corticosteroid in adults with severe asthma", Allergy Asthma Proc. Nov. 2016; 37(6): 125-139.
D56—Siergiejko Z. et al., "Oral corticosteroid sparing with omalizumab in severe allergic IgE-mediated) asthma patients", Curr Med Res Opin. Nov. 2011; 27(11):2223-8. doi: 10.1185/03007995.201 1.620950. Epub Sep. 21, 2011.
D57—Woodruff P.G et al., "T-helper type 2-driven inflammation defines major subphenotypes of asthma", Am J Respir Crit Care Med. Sep. 1, 2009;180(5):388-95. doi: 10.1164/rccm.200903-0392OC. Epub May 29, 2009. Erratum in: Am J Respir Crit Care Med. Oct. 15, 2009;180(8): 796. PMID: 19483109; PMCID: PMC2742757.
D58—Wenzel SE, "Asthma phenotypes: the evolution from clinical to molecular approaches", Nat Med. May 4, 2012;18(5):716-25. doi: 10.1038/nm.2678. PMID: 22561835 (also referred to as "Wenzel, 2012").
D59—Haldar P. et al., "Cluster analysis and clinical asthma phenotypes", Am J Respir Crit Care Med. Aug. 1, 2008,178(3):218-224. doi: 10.1164/rccm.200711-1754OC. Epub May 14, 2008. PMID: 18480428; PMCID: PMC3992366.
D60—Miskoff J.A et al., "Fractional Exhaled Nitric Oxide Testing: Diagnostic Utility in Asthma, Chronic Obstructive Pulmonary Disease, or Asthma-chronic Obstructive Pulmonary Disease Overlap Syndrome", Cureus. Jun. 1, 2019 O; 11(6):e4864. doi: 10.7759/cureus.4864. PMID: 31417809; PM CID: PMC6690504.
D61—Dweik R.A et al., "An official ATS clinical practice guideline: interpretation of exhaled nitric oxide levels (FENO) for clinical applications", Am J Respir Crit Care Med. 2011, 184:602-15. 10.1164/rccm.9120-IIST.
D62—"Global Strategy for Asthma Management and Prevention", Global Initiative for Asthma (GINA), 2009.
D63—Bleecker E.R. et al. Efficacy and safety of benralizumab for patients with severe asthma uncontrolled with high-dosage inhaled corticosteroids and long-acting E2-agonists (SIROCCO): a randomised, multicentre, placebo-controlled phase 3 trial. Lancet. Oct. 29, 2016,388(10056):2115-2127. doi: 10.1016/S0140-6736(16)31324-1. Epub Sep. 5, 2016. PMID: 27609408.
D64—Ortega I-LG et al. Mepolizumab treatment in patients with severe eosinophilic asthma. N Engl J Med. Sep. 25, 2014;371(13):1198-207. doi: 10.1056/NEJMoa1403290. Epub Sep. 8, 2014. Erratum in: N Engl J Med. Apr. 30, 2015;372(18):1777. doi: 10.1056/NEJMxl 50017. PMID: 25199059.
D66—Pelaia C et al., "Dupilumab for the treatment of asthma", Expert Opinion on Biological Therapy, Dec. 2017, 17(12): 1565-1572, Epublished Oct. 8, 2017.
D67 / D16—WO 2015/127229 A1, published Aug. 27, 2015.
D68—Bernstein et al., "Effect of fixed-dose subcutaneous reslizumab on asthma exacerbations in patients with severe uncontrolled asthma and corticosteroid sparing in patients with oral corticosteroid-dependent asthma: results from two phase 3, randomised, double-blind, placebo-controlled trials", Lancet Respir Med., May 2020, 8(5): 461-474, Epublished Feb. 14, 2020.
D69—Wechsler et al., "Evaluation of the oral corticosteroid-sparing effect of tezepelumab in adults with oral corticosteroid-dependent asthma (SOURCE): a randomised, placebo-controlled, phase 3 study", Lancet Respir Med., Jul. 2022, 10(7): 650-660, Epublished Mar. 29, 2022.

(56) References Cited

OTHER PUBLICATIONS

D70—Busse et al., "Tralokinumab did not demonstrate oral corticosteroid-sparing effects in severe asthma", Eur Respir J, Jan. 31, 2019, 53(2): 1800948.
D71—Agache et al., "Efficacy and safety of treatment with biologicals (benralizumab, dupilumab, mepolizumab, omalizumab and reslizumab) for severe eosinophilic asthma. A systematic review for the EAACI Guidelines—recommendations on the use of biologicals in severe asthma", Allergy, May 2020, 75(5):1023-1042.
D72—Sweeney et al., "Comorbidity in severe asthma requiring systemic corticosteroid therapy: cross-sectional data from the Optimum Patient Care Research Database and the British Thoracic Difficult Asthma Registry", Thorax, Apr. 2016, 71(4): 339-346, Epublished Jan. 27, 2016.
D73—Choo et al., "Morbidity associated with oral corticosteroids in opatients with severe asthma", Thorax, Apr. 2016, 71(4): 302-304, Epublished Feb. 22, 2016.
D74—Pollart et al., "Overview of changes to asthma guidelines: diagnosis and screening", American Family Physician, May 1, 2009, 79(9): 761-767.
D75—Altman et al., "Absence of evidence is not evidence of absence", BMLJ, Aug. 19, 1995, 311: 485.
D76—Declaration of Prof. lan Pavord, Dec. 17, 2025.
D76a—List of Publications by Prof. Ian Pavord.
D77—Hanania et al., "Omazumilab in Severe Allergic Asthma ladequately Controlled with Standard Therapy", Annals of Internal Medicine, May 3, 2011, 154(9): 573-582 & W-200-W-202.
D78—Normansell et al., Omazumilab for asthma in adults and children (review), Cochrane Library, 2014.
D79—Shiner et al., "Randomised, double-blind, placebo-controlled trial of Methotrexate in steroid-dependent asthma", The Lancet, 1990, 336: 137-140.
D80—Fajt et al., "Development of New Therapies for Severe Asthma", Allergy Asthma Immunol Res., Jan. 2017, 9(1): 3-14.
D81—Holgate et al., "Effects of omalizumab on markers of inflammation in patients with allergic asthma", Allergy, Dec. 2009, 64(12): 1728-1736.
D82—Busse et al., "Omalizumab, anti-IgE recombinant humanized monoclonal antibody, for the treatment of severe allergic asthma", J. Allergy Clin Immunol., 108(2): 184-190.
D83—Annex I—Declaration and CV of Prof. M.D. Ph.D. Dsc Felix JF Herth, dated Dec. 11, 2025.
Taylor et al., 2008; "A new perspective on concepts of asthma severity and control", European Respiratory Journal, vol. 32, pp. 545-554.
Reddel et al., 2009; "An official American Thoracic Society/European Respiratory Society statement: asthma control and exacerbations: standardizing endpoints for clinical asthma trials and clinical practice", Am. J. Respir. Crit. Care Med; 180; pp. 59-99.
Shaw et al., 2015, "Clinical and inflammatory characteristics of the European U-BIOPRED adult severe asthma cohort", Eur. Respir. J.; 46; pp. 1308-1321.
Hekking et al., 2015; "The prevalence of severe refractory asthma", Journal of Allergy and Clinical Immunology, 135(4), pp. 896-902.
Han et al., 2017; "Efficacy and safety of dupilumab for the treatment of adult atopic dermatitis: A meta-analysis of randomized clinical trials", J. Allergy Clin. Immunol. 888-891.
Patentee's Response to opponents' submissions under Rule 116 EPC regarding European Patent No. 3703818 (EP Application No. 18799655.8), filed on behalf of Sanofi Biotechnology, dated Feb. 9, 2026.
D84—Second Declaration of Prof. lan Pavord, Feb. 9, 2026.
D85—Chung et al., 2014; International ERS/ATS Guidelines on Definition, Evaluation and Treatment of Severe Asthma, Eur. Respir. J.; 43; pp. 343-373.
D86—Broerson et al., "Adrenal insufficiency in corticosteroids use: systematic review and meta-analysis", The Journal of Clinical Endocrinology & Metabolism, Jun. 1, 2015, 100(6): 2171-2180.
D87—Daley-Yates, "Inhaled corticosteroids: potency, dose equivalence and therapeutic index", British Journal of Pharmacology, Mar. 14, 2015, 80(3): 372-380.
D88—Joseph et al., "Systemic glucocorticoid therapy and adrenal insufficiency in adults: a systematic review", Seminars in Arthritis and Rheumatism, Aug. 2016, 46(1): 133-141.
D23a—Protocol for: Wenzel et al., Dupilumab in persistent asthma with elevated eosinophil levels, N Engl J Med., May 21, 2013, 368(26): 2455-2466.
Response to Patentee's submission under Rule 116 EPC dated Dec. 23, 2025, regarding European Patent No. 3703818 (EP Application No. 18799655.8), filed on behalf of Dr. Luigi Rumi, dated Feb. 13, 2026.
D89—Second Declaration and CV of Prof. M.D. Ph.D. Dsc Felix JF Herth, dated Feb. 19, 2026.
List of Consolidated References for Written Submissions and Patentee's Submission regarding European Patent No. 4011915 (EP Application No. 21199451.2), dated Mar. 2, 2026.
D89—Excerpt from ClinicalTrials.gov Study NCT01312961 (v30), Efficacy, Safety, and Tolerability of SAR231893 (REGN668) in Patients with Persistent Moderate to Severe Eosinophilic Asthma, Jul. 25, 2012.
D90—Al-Ramli et al., Journal of Asthma, 2008, 45(S1): 41-44, cited in Notice of Opposition against European Patent No. 3470432 (Application No. 18194745.8) filed on Jul. 6, 2022, on behalf of Ms. Regina Neuefeind.
Summons to Attend Oral Proceedings regarding European Patent Application No. 15804646.6, dated Feb. 3, 2026.

| # subjects | | | | | |
|---|---|---|---|---|---|
| Placebo | 30 | 30 | 28 | 28 | 26 |
| Dupilumab | 30 | 30 | 30 | 30 | 30 |

subjects

| | | | | | |
|---|---|---|---|---|---|
| FEV1 % Predicted: | | | | | |
| PLACEBO | 17 | 19 | 19 | 17 | 15 |
| DUPILUMAB | 16 | 16 | 15 | 15 | 15 |
| FEV1 Liter: | | | | | |
| PLACEBO | 17 | 19 | 19 | 17 | 15 |
| DUPILUMAB | 16 | 16 | 15 | 15 | 15 |

Figure 23A
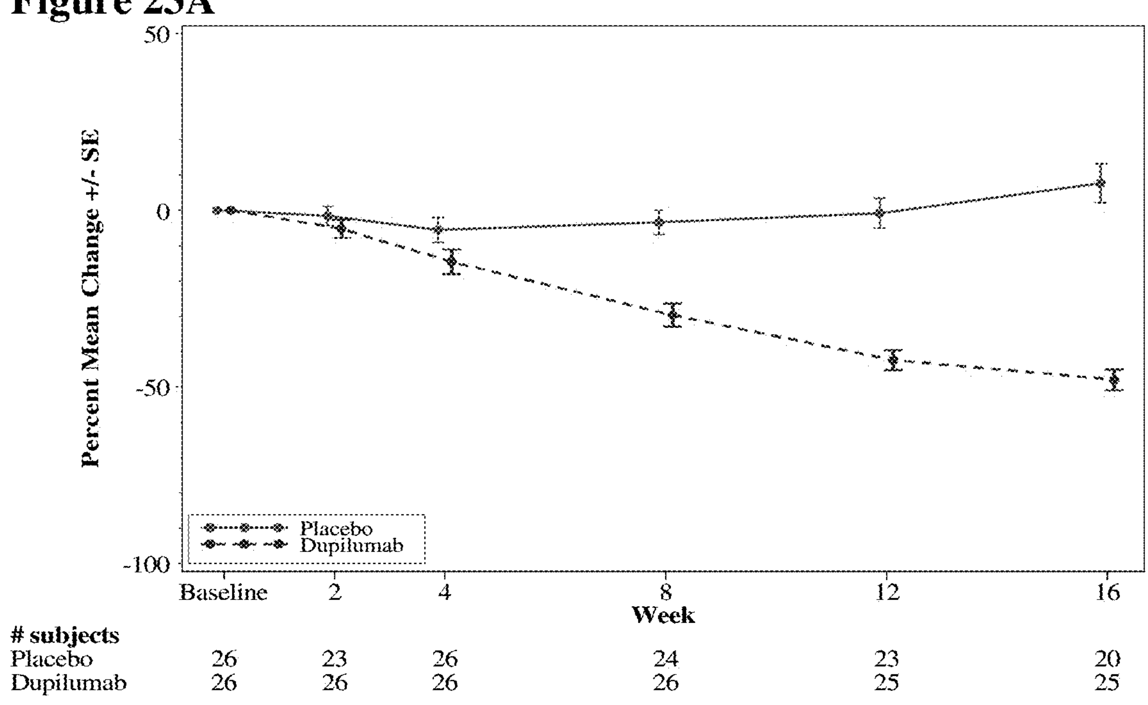
Figure 23B
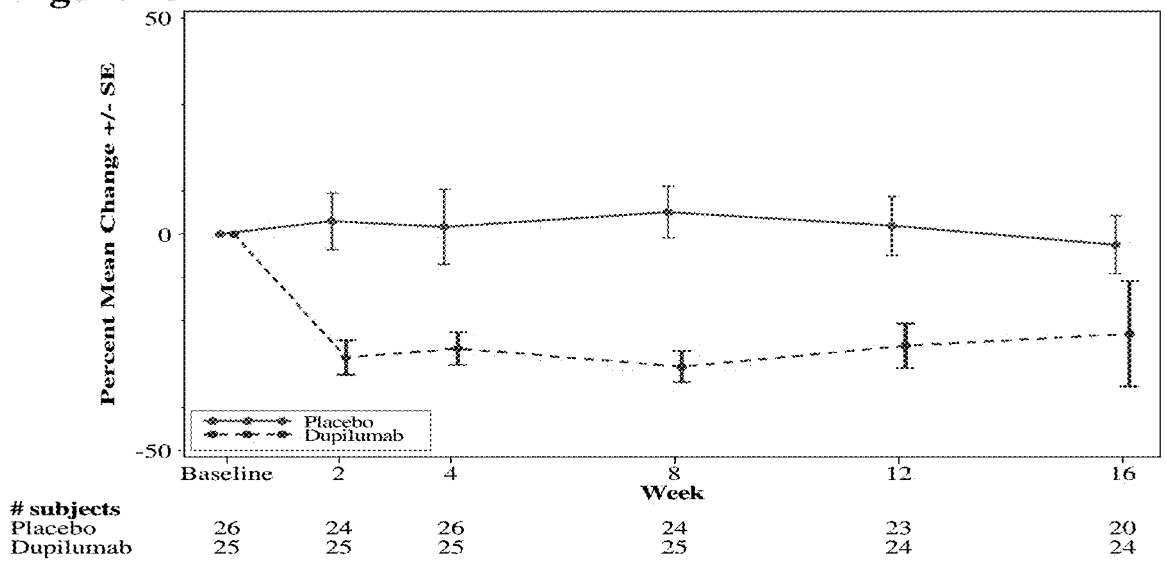

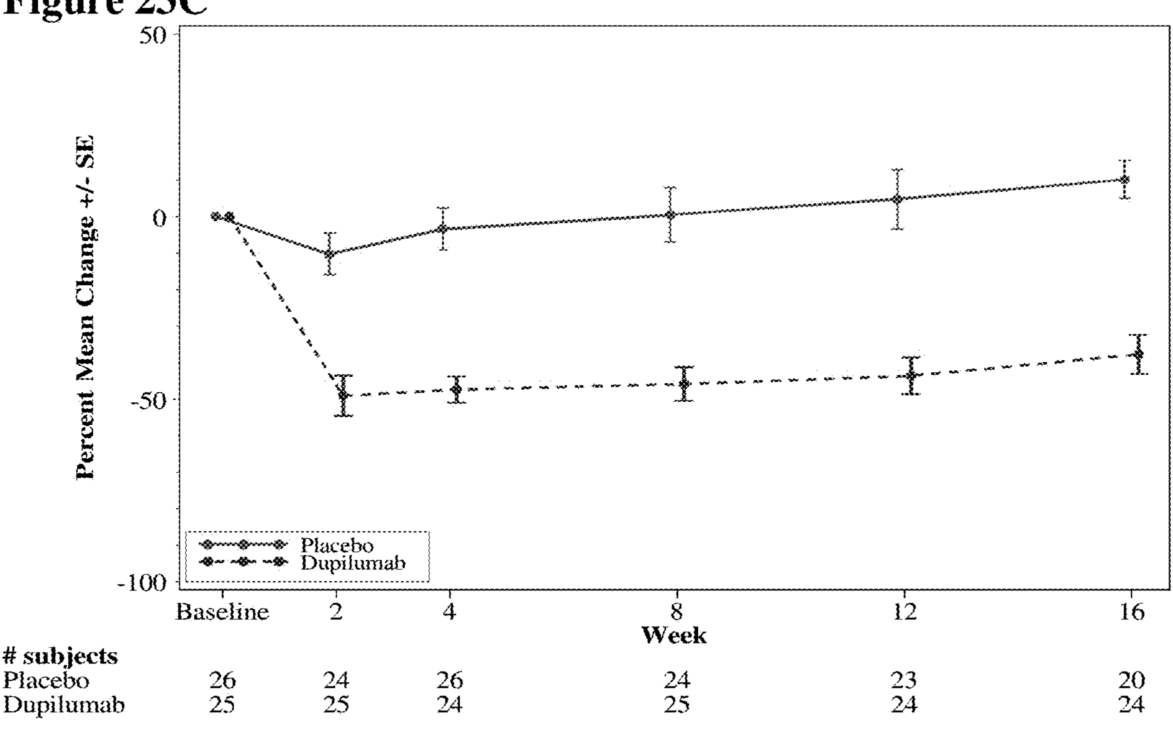
Figure 23D
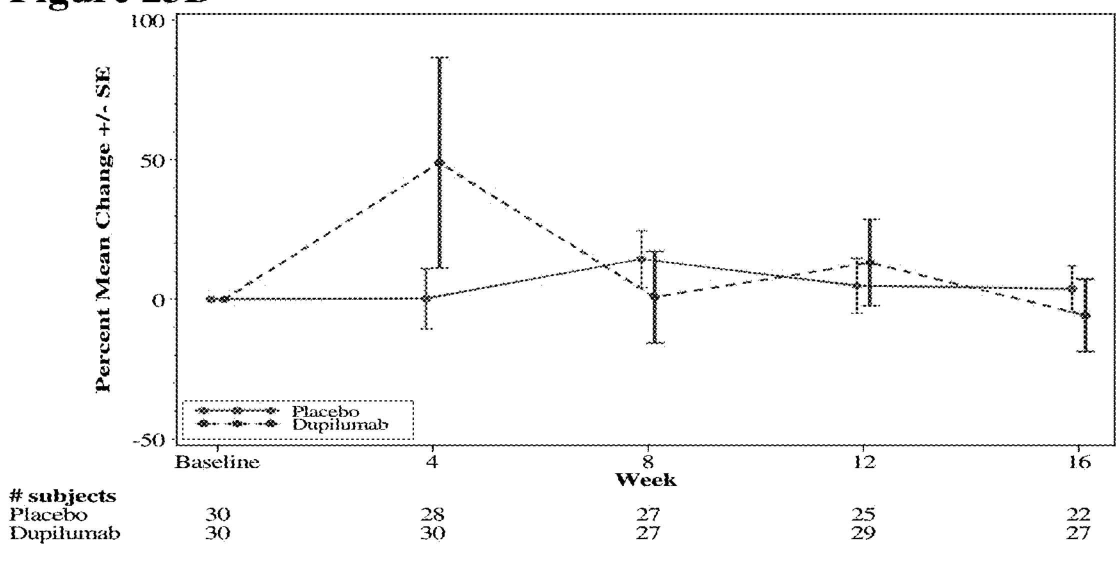

METHODS FOR TREATING CHRONIC RHINOSINUSITIS WITH NASAL POLYPS BY ADMINISTERING AN ANTIBODY ANTAGONIST OF IL-4R

RELATED APPLICATIONS

This application is a continuation of U.S. patent application Ser. No. 16/038,925, filed Jul. 18, 2018, which is a continuation of U.S. patent application Ser. No. 14/940,431, filed Nov. 13, 2015, now U.S. Pat. No. 10,066,017, which claims the benefit of U.S. Provisional Patent Application Ser. No. 62/080,092, filed Nov. 14, 2014, 62/083,821, filed Nov. 24, 2014, 62/158,832, filed May 8, 2015, and 62/199,305, filed Jul. 31, 2015, and European Patent Application No. 15306632.9, filed Oct. 14, 2015, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Nov. 23, 2021, is named 724604_SA9-162CIPCON2_SL.txt and is 10,479 bytes in size.

FIELD OF THE INVENTION

The present invention relates to the field of therapeutic treatments of inflammatory conditions. More specifically, the invention relates to the administration of interleukin-4 receptor (IL-4R) antagonists to decrease nasal polyp score and to treat associated conditions.

BACKGROUND

Chronic sinusitis (CS), an inflammatory condition of the sinuses, is a common syndrome, with estimates of prevalence as high as 13% in Western populations. This condition is characterized by any combination of specific symptoms including nasal congestion, decreased or lost sense of smell, anterior and/or posterior nasal discharge, facial pain, and/or headache and consequences thereof, often for a period of years. CS can be clinically divided into CS with or without nasal polyps.

Nasal polyposis (NP) is a clinical condition characterized by the presence of multiple polyps in the upper nasal cavity, originating from the osteomeatal complex. NP is a T helper cell-2 (Th-2) driven inflammatory process affecting the mucosa of the nose and paranasal sinuses. Eosinophils and their products are thought to be a hallmark of nasal polyp-associated inflammation as elevated levels of interleukin-5 (IL-5; promotes eosinophil survival and differentiation), eosinophil cationic protein (ECP), and eotaxin (eosinophil chemoattractant), factors that attract and activate eosinophils, are typically found in nasal polyps. Eosinophils are the predominant inflammatory cell found in the sinuses and nasal polyps, and nasal polyps are also associated with elevated levels of IgE. NP is characterized by long-term symptoms of nasal obstruction and congestion, reduction in or loss of sense of smell, anterior and posterior rhinorrhea, and facial pain. Current treatment options range from local or systemic corticosteroids to functional endoscopic sinus surgery.

Current medical management of chronic sinusitis with nasal polyps/nasal polyposis (CSwNP) primarily focuses on controlling inflammation, which involves administration of topical and systemic corticosteroids with a goal of reducing polyp mass and number. In case of failure, surgical excision is indicated. However, disease recurrence is reported to be frequent after surgery, with rates of recurrence approaching 50% in patients with tissue eosinophilia.

BRIEF SUMMARY OF THE INVENTION

In one aspect, the invention provides a method for decreasing a nasal polyp score (NPS) of a subject in need thereof comprising determining the NPS of the subject and administering to the subject a pharmaceutical composition comprising an antibody or antigen binding fragment thereof that specifically binds an interleukin-4 receptor (IL-4R), wherein the antibody or antigen binding fragment thereof comprises heavy chain and light chain CDR sequences from the heavy chain variably region (HCVR) and light chain variable region (LCVR) sequence pair of SEQ ID NOs:1 and 2, such that the NPS of the subject is decreased (e.g., by about 10% to about 50%, by about 20% to about 40%, or by about 25% to about 30%). For example, in one embodiment, the antibody or antigen binding fragment thereof comprises heavy chain CDR sequences of SEQ ID NOs:3, 4 and 5, and light chain CDR sequences of SEQ ID NOs:6, 7 and 8. For example, in one embodiment, the antibody or antigen-binding fragment thereof comprises an HCVR having the amino acid sequence of SEQ ID NO:1 and an LCVR having the amino acid sequence of SEQ ID NO:2. The antibody can have, for example, a heavy chain sequence of SEQ ID NO:9, and a light chain sequence of SEQ ID NO:10.

In one embodiment, the IL-4R antagonist is dupilumab or an antigen-binding fragment thereof. Other exemplary anti-IL-4R antibodies or antigen-binding fragments thereof are described, for example, in U.S. Pat. Nos. 7,605,237 and 7,608,693.

A subject suitable for treatment with an IL-4R antagonist may have a total of at least 5 nasal polyps, with two or more nasal polyps present in each nostril prior to the administering step and/or may suffer from one or more conditions selected from the group consisting of sinusitis, rhinitis, asthma, aspirin hypersensitivity, Non-Steroidal Anti-Inflammatory Drug (NSAID) hypersensitivity, and Samter's triad (defined by presence of nasal polyps, asthma, and aspirin and NSAID sensitivity), and/or may have undergone surgery for one or both of nasal polyps and chronic rhinosinusitis. In certain embodiments, a subject suitable for treatment has one or more conditions selected from the group consisting of chronic sinusitis with nasal polyps (CSwNP), chronic sinusitis with bilateral nasal polyps, and chronic rhinosinusitis with nasal polyps (CRSwNP) (e.g., with or without asthma). The subject suitable for treatment may or may not have asthma. In some embodiments, for a subject suitable for treatment, a first functional endoscopy sinus surgery (FESS) is indicated, a revised surgery is indicated, or surgery is contraindicated.

In some embodiments, the IL-4R antagonist is indicated for the long-term treatment of adults with chronic sinusitis with bilateral nasal polyposis, who have persistent signs and symptoms despite treatment with intranasal corticosteroids (INCS), or is indicated for the long-term treatment of adults with bilateral nasal polyposis with associated chronic sinusitis who have persistent signs and symptoms despite treatment with INCS, or is indicated for the treatment of adults with bilateral nasal polyposis with persistent signs and symptoms despite treatment with intranasal or oral corticosteroids, or intolerance to oral corticosteroids.

In some embodiments, the IL-4R antagonist is administered at a dose of between about 100 mg and about 600 mg. In some embodiments, the IL-4R antagonist is administered in an initial dose of between about 400 mg and about 600 mg, and in one or more subsequent doses of between about 200 mg and about 400 mg each. In some embodiments, the IL-4R antagonist is administered in an initial dose of about 600 mg, and in one or more subsequent doses of about 300 mg each. In other embodiments, the IL-4R antagonist is administered once every seven days (QW). In certain embodiments, the pharmaceutical composition is administered to the subject systemically or locally. For example, the pharmaceutical composition may be administered subcutaneously, intravenously, or intranasally. In one embodiment, the pharmaceutical composition is administered to the subject subcutaneously at a dose of 300 mg or a dose of 600 mg.

In some embodiments, the administering step is followed by an improvement in one or more nasal polyposis-associated parameters selected from the group consisting of loss of smell, runny nose, post nasal drip, and nasal peak inspiratory flow (NPIF). In some embodiments, the improvement in one or more of loss of smell, runny nose, post nasal drip and nasal peak inspiratory flow occurs in the day (AM), at night (PM) or both in the AM and in the PM. In some embodiments, the administering step is followed by a decrease in one or more of serum IgE levels, plasma eotaxin-3 levels and serum thymus and activation-regulated chemokine (TARC) levels. In some embodiments, the administering step is followed by a decrease in one or more of total IgE levels, eotaxin-3 levels, and ECP levels in nasal secretions of the subject.

In another aspect, the invention provides a method for decreasing an NPS of a subject in need thereof comprising determining the NPS of the subject, administering to the subject a loading dose of about 400 to about 600 mg of an antibody or antigen binding fragment thereof that specifically binds an IL-4R, wherein the antibody or antigen binding fragment thereof comprises heavy chain and light chain CDR sequences from the HCVR and LCVR sequence pair of SEQ ID NOs:1 and 2 and administering to the subject one or more maintenance doses of about 200 to about 300 mg each of the antibody or antigen binding fragment thereof, such that the NPS of the subject is decreased (e.g., by about 10% to about 50%, by about 20% to about 40%, or by about 25% to about 30%). For example, in one embodiment, the antibody or antigen binding fragment thereof comprises heavy chain CDR sequences of SEQ ID NOs:3, 4 and 5, and light chain CDR sequences of SEQ ID NOs:6, 7 and 8. For example, in one embodiment, the antibody or antigen-binding fragment thereof comprises an HCVR having the amino acid sequence of SEQ ID NO:1 and an LCVR having the amino acid sequence of SEQ ID NO:2. The antibody can have, for example, a heavy chain sequence of SEQ ID NO:9, and a light chain sequence of SEQ ID NO:10. In one embodiment, the IL-4R antagonist is dupilumab or an antigen binding fragment thereof.

In some embodiments, the loading dose of an IL-4R antagonist is about 600 mg and the one or more maintenance doses of an IL-4R antagonist are about 300 mg each. In other embodiments, the IL-4R antagonist is administered once every seven days (QW). In certain embodiments, the pharmaceutical composition is administered to the subject systemically or locally. For example, the pharmaceutical composition may be administered subcutaneously, intravenously, or intranasally. In one embodiment, the pharmaceutical composition is administered to the subject subcutaneously at a dose of 300 mg or a dose of 600 mg.

A subject suitable for treatment with an IL-4R antagonist may have a total of at least 5 nasal polyps, with two or more nasal polyps present in each nostril prior to the administering step and/or may suffer from one or more conditions selected from the group consisting of sinusitis, rhinitis, asthma, aspirin hypersensitivity, NSAID hypersensitivity, and Samter's triad, and/or may have undergone surgery for one or both of nasal polyps and chronic rhinosinusitis. In certain embodiments, a subject suitable for treatment has one or more conditions selected from the group consisting of CSwNP, chronic sinusitis with bilateral nasal polyps, and CRSwNP (e.g., with or without asthma). The subject suitable for treatment may or may not have asthma. In some embodiments, for a subject suitable for treatment, a FESS is indicated, a revised surgery is indicated, or surgery is contraindicated.

In some embodiments, the administering steps are followed by an improvement in one or more nasal polyposis-associated parameters selected from the group consisting of loss of smell, runny nose, post nasal drip, and NPIF. In some embodiments, the improvement in one or more of loss of smell, runny nose, post nasal drip and nasal peak inspiratory flow occurs in the AM, in the PM or both in the AM and in the PM. In some embodiments, the administering steps are followed by a decrease in one or more of serum IgE levels, plasma eotaxin-3 levels and serum TARC levels. In some embodiments, the administering step is followed by a decrease in one or more of total IgE levels, eotaxin-3 levels, and ECP levels in nasal secretions of the subject.

In another aspect, the invention provides a method for decreasing an NPS of a subject in need thereof comprising determining the NPS of the subject, administering to the subject one or more maintenance doses of an ICS, administering to the subject a loading dose of about 400 to about 600 mg of an antibody or antigen binding fragment thereof that specifically binds an IL-4R, wherein the antibody or antigen binding fragment thereof comprises heavy chain and light chain CDR sequences from the HCVR and LCVR sequence pair of SEQ ID NOs:1 and 2, and administering to the subject one or more maintenance doses of about 200 to about 300 mg each of the antibody or antigen binding fragment thereof, wherein the ICS is administered for the duration of administration of the antibody or antigen binding fragment thereof, such that the NPS of the subject is decreased (e.g., by about 10% to about 50%, by about 20% to about 40%, or by about 25% to about 30%). For example, in one embodiment, the antibody or antigen binding fragment thereof comprises heavy chain CDR sequences of SEQ ID NOs:3, 4 and 5, and light chain CDR sequences of SEQ ID NOs:6, 7 and 8. For example, in one embodiment, the antibody or antigen-binding fragment thereof comprises an HCVR having the amino acid sequence of SEQ ID NO:1 and an LCVR having the amino acid sequence of SEQ ID NO:2. The antibody can have, for example, a heavy chain sequence of SEQ ID NO:9, and a light chain sequence of SEQ ID NO:10. In one embodiment, the IL-4R antagonist is dupilumab or an antigen binding fragment thereof.

In some embodiments, the loading dose of an IL-4R antagonist is about 600 mg and the one or more maintenance doses of an IL-4R antagonist are about 300 mg each. In other embodiments, the IL-4R antagonist is administered once every seven days (QW). In certain embodiments, the pharmaceutical composition is administered to the subject systemically or locally. For example, the pharmaceutical composition may be administered subcutaneously, intravenously, or intranasally. In one embodiment, the pharmaceutical composition is administered to the subject subcutaneously at a dose of 300 mg or a dose of 600 mg. In some embodiments, the ICS is mometasone furoate nasal spray (MFNS). In some embodiments, about 100 mg MFNS is administered to each nostril of the subject once or twice a day.

A subject suitable for treatment with an IL-4R antagonist may have a total of at least 5 nasal polyps, with two or more nasal polyps present in each nostril prior to the administering step and/or may suffer from one or more conditions selected from the group consisting of sinusitis, rhinitis, asthma, aspirin hypersensitivity, NSAID hypersensitivity, and Samter's triad, and/or may have undergone surgery for one or both of nasal polyps and chronic rhinosinusitis. In certain embodiments, a subject suitable for treatment has one or more conditions selected from the group consisting of CSwNP, chronic sinusitis with bilateral nasal polyps, and CRSwNP (e.g., with or without asthma). The subject suitable for treatment may or may not have asthma. In some embodiments, for a subject suitable for treatment, a FESS is indicated, a revised surgery is indicated, or surgery is contraindicated.

In some embodiments, the administering steps are followed by an improvement in one or more nasal polyposis-associated parameters selected from the group consisting of loss of smell, runny nose, post nasal drip, and NPIF. In some embodiments, the improvement in one or more of loss of smell, runny nose, post nasal drip and nasal peak inspiratory flow occurs in the AM, in the PM or both in the AM and in the PM. In some embodiments, the administering steps are followed by a decrease in one or more of serum IgE levels, plasma eotaxin-3 levels and serum TARC levels. In some embodiments, the administering step is followed by a decrease in one or more of total IgE levels, eotaxin-3 levels, and ECP levels in nasal secretions of the subject.

In another aspect, the invention provides a method for decreasing an NPS and improving one or more additional nasal polyposis-associated parameters of a subject in need thereof comprising determining the NPS of the subject, determining levels of one or more additional nasal polyposis-associated parameters of the subject, administering to the subject one or more maintenance doses of an ICS, administering to the subject a loading dose of about 400 to about 600 mg of an antibody or antigen binding fragment thereof that specifically binds an IL-4R, wherein the antibody or antigen binding fragment thereof comprises heavy chain and light chain CDR sequences from the HCVR and LCVR sequence pair of SEQ ID NOs:1 and 2, and administering to the subject one or more maintenance doses of about 200 to about 300 mg each of the antibody or antigen binding fragment thereof, wherein the ICS is administered for the duration of administration of the antibody or antigen binding fragment thereof, such that the NPS of the subject is decreased (e.g., by about 10% to about 50%, by about 20% to about 40%, or by about 25% to about 30%) and one or more additional nasal polyposis-associated parameters of the subject are improved. in one embodiment, the antibody or antigen binding fragment thereof comprises heavy chain CDR sequences of SEQ ID NOs:3, 4 and 5, and light chain CDR sequences of SEQ ID NOs:6, 7 and 8. For example, in one embodiment, the antibody or antigen-binding fragment thereof comprises an HCVR having the amino acid sequence of SEQ ID NO:1 and an LCVR having the amino acid sequence of SEQ ID NO:2. The antibody can have, for example, a heavy chain sequence of SEQ ID NO:9, and a light chain sequence of SEQ ID NO:10. In one embodiment, the IL-4R antagonist is dupilumab or an antigen binding fragment thereof. In one embodiment, one or more additional nasal polyposis-associated parameters are selected from the group consisting of loss of smell, runny nose, post nasal drip, and NPIF.

In another aspect, the invention provides a method of treating CSwNP, in patients with or without asthma, by administering to the subject an therapeutically effective amount of an anti-IL-4R antibody, or antigen binding fragment thereof. The antibody can have, for example, a heavy chain sequence of SEQ ID NO:9, and a light chain sequence of SEQ ID NO:10. In some embodiments, the antibody or antigen binding fragment thereof comprises heavy chain and light chain CDR sequences from the HCVR and LCVR sequence pair of SEQ ID NOs:1 and 2. In some embodiments, the antibody or antigen binding fragment is administered as an initial loading dose of about 400 mg to about 600 mg followed by one or more maintenance doses of about 200 mg to about 300 mg each of the antibody or antigen binding fragment thereof, such that one or more symptoms of the CSwNP are decreased. In some embodiments, one of more of endoscopic, radiographic and clinical endpoints of CSwNP are improved. In other embodiments, lung function and disease control in patients with comorbid asthma are improved. In other embodiments, the NPS of the subject with CSwNP is decreased by about 10% to about 50%, by about 20% to about 40%, or by about 25% to about 30%).

Other embodiments will become apparent from the Figures, tables and detailed description provided herein.

BRIEF DESCRIPTION OF THE FIGURES

FIG. 22A graphically depicts that dupilumab was associated with a significant improvement in mean Forced Expiratory Volume in 1 second (FEV1) in liters and FEV1 percent predicted (%), as compared with placebo. FIG. 22B graphically depicts that dupilumab was associated with a significant improvement in mean Asthma Control Questionnaire score, 5-question version (ACQ-5), as compared with placebo. FIG. 22C graphically depicts that dupilumab was associated with a significant improvement in mean endoscopic Nasal Polyp Score (NPS), as compared with placebo.

FIGS. 23A-23D graphically depict pharmacodynamics biomarkers expressed in serum. FIG. 23A graphically depicts that least square mean percent change from baseline in total serum IgE is decreased in patients who received dupilumab but remained unchanged in patients who received placebo. FIG. 23B graphically depicts that least square mean percent change from baseline in total serum Thymus- and Activation-Regulated Chemokine (TARC) is decreased in patients who received dupilumab but remained unchanged in patients who received placebo. FIG. 23C graphically depicts that least square mean percent change from baseline in total serum Eotaxin-3 is decreased in patients who received dupilumab but remained unchanged in patients who received placebo. FIG. 23D graphically depicts that least square mean percent change from baseline in blood eosinophil counts remained unchanged in both patients who received dupilumab and patients who received placebo.

FIG. 24A graphically depicts that least square mean percent change from baseline of Eotaxin-3 in nasal secretions is significantly lower after dupilumab treatment. FIG. 24B graphically depicts least square mean percent change from baseline of IgE in nasal secretions is significantly lower after dupilumab treatment. FIG. 24C graphically depicts least square mean percent change from baseline of Eosinophil Cationic Protein (ECP) in nasal secretions is significantly lower after dupilumab treatment.

DETAILED DESCRIPTION

Figure 1:
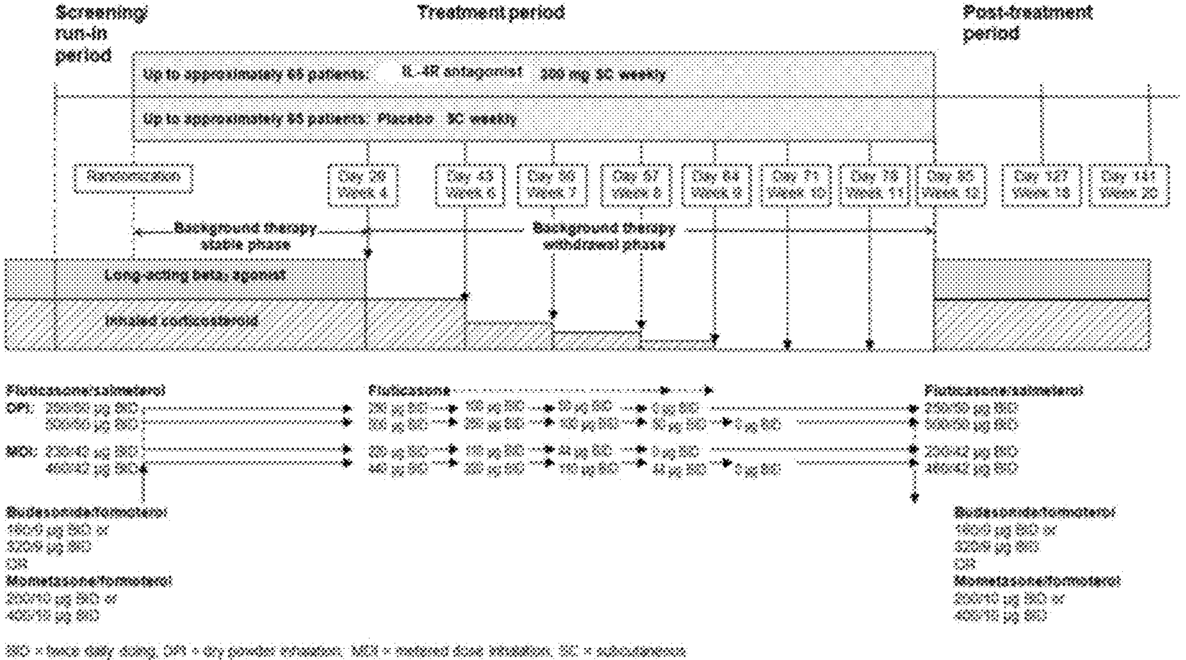
FIG. 1 schematically represents an example of background therapy withdrawal time period in the treatment of an asthma patient.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

All publications mentioned herein are incorporated herein by reference in their entirety for all purposes.

Methods for Treating Chronic Sinusitis with Nasal Polyps

In certain aspects, the present invention provides methods for treating Chronic Sinusitis with Nasal Polyps/Nasal Polyposis (CSwNP). In other aspects, the present invention provides methods for treating chronic sinusitis without nasal polyps/nasal polyposis.

As used herein, "chronic sinusitis" ("CS") refers to an inflammatory condition of the sinuses characterized by any combination of specific symptoms including, but not limited to, nasal congestion, decreased or lost sense of smell, anterior and/or posterior nasal discharge, facial pain, and/or headache and consequences thereof, often for a period of years. A formal diagnosis is made on the basis of sinus computed tomography (CT) scan and/or sinus endoscopy. Based on endoscopic evaluation, CS can be clinically divided as CS with nasal polyps/nasal polyposis (CSwNP) or CS without nasal polyps/nasal polyposis.

In certain embodiments, an IL-4R antagonist described herein is indicated for the long-term treatment of adults with chronic sinusitis with bilateral nasal polyposis, who have persistent signs and symptoms despite treatment with intranasal corticosteroids (INCS). In other embodiments, an IL-4R antagonist described herein is indicated for the long-term treatment of adults with bilateral nasal polyposis with associated chronic sinusitis who have persistent signs and symptoms despite treatment with INCS.

In certain aspects, the present invention provides methods for treating nasal polyps. As used herein, a "nasal polyp" is an overgrowth of tissue in one or more of the nasal cavities. The condition of having nasal polyps is called "nasal polyposis." About 80% of nasal polyps are highly edematous and filled with eosinophils. Nasal polyps can also present as fibrous, glandular or cystic. Nasal polyps are typically teardrop-shaped growths that form in the nose and/or sinuses, obstructing the sinuses and nasal passages.

In certain aspects, the present invention provides methods for treating Nasal Polyposis (NP). NP is a clinical condition characterized by the presence of multiple polyps in the upper nasal cavity, originating from the osteomeatal complex. NP is a T helper cell-2 (Th-2) driven inflammatory process affecting the mucosa of the nose and paranasal sinuses. Eosinophils and their products are thought to be a hallmark of nasal polyp-associated inflammation as elevated levels of interleukin-5 (IL-5; promotes eosinophil survival and differentiation), ECP, and eotaxin (eosinophil chemoattractant), factors that attract and activate eosinophils, are typically found in nasal polyps. Eosinophils are the predominant inflammatory cell found in the sinuses and nasal polyps, and nasal polyps are also associated with elevated levels of IgE.

NP is characterized by long-term symptoms of nasal obstruction and congestion, reduction in or loss of sense of smell, anterior and posterior rhinorrhea, and facial pain. The presence or absence of nasal polyps can be confirmed for example by performing endoscopy, and the presence and extent of sinus and polyp involvement can be confirmed by methods such as coronal computed tomography (CT) scans.

As used herein, "bilateral NP" refers to the presence of one or more NPs at each side of the nasal cavity.

An IL-4R antagonist can be used to treat nasal polyposis associated with a variety of conditions. For example, nasal polyposis is associated with sinusitis (e.g., allergic or non-allergic sinusitis), rhinitis (e.g., allergic and non-allergic rhinitis), rhinosinusitis (e.g., allergic or non-allergic rhinosinusitis), asthma (e.g., moderate-to-severe asthma), NSAID sensitivity (e.g., aspirin sensitivity), and infection, such as bacterial and fungal infection. A subject with nasal polyposis, such as a patient with chronic sinusitis with bilateral nasal polyposis, can have concomitant Samter's triad (defined by present of NP, asthma, and aspirin and NSAID sensitivity). A subject with nasal polyposis can also have concomitant asthma, and/or other Th2 concomitant systemic conditions. Bacterial infections include, for example, *Staphylococcus* infections. A subject with nasal polyposis can have a chronic infection, such as a chronic bacterial infection, e.g., a chronic *Staphylococcus aureus* infection. In some embodiments, the subject has recurring nasal polyposis, such as may be associated with recurring sinusitis. In other embodiments, the subject as cystic fibrosis or NARES (Non-Allergic Rhinitis with Eosinophilia Syndrome). In other embodiments, the subject has a relapse of nasal polyposis after receiving surgery to treat the polyps. Risk factors for nasal polyposis include genetic susceptibility, anatomic abnormality, mucociliary impairment, infection, and local immunologic imbalance.

An IL-4R antagonist can also be used to treat nasal polyposis in patients who have never previously received a treatment or surgery for NP. An IL-4R antagonist can also be used to treat nasal polyposis in patients who have previously undergone surgery, such as a nasal surgery, such as for treatment of nasal polyps. In certain embodiments, an IL-4R antagonist is administered to a subject whose nasal polyposis has relapsed after the subject received prior treatment for the polyps, such as a prior nasal surgery.

As used herein, the term "sinusitis" refers to any inflammatory condition characterized by inflammation of the paranasal sinuses, including inflammation of the maxillary, frontal, ethmoid and/or sphenoid paranasal sinuses. An IL-4R antagonist is suitable for treatment of nasal polyposis is associated with acute sinusitis, sub-acute sinusitis, chronic sinusitis and recurrent sinusitis. Acute sinusitis is characterized by a sudden onset of cold-like symptoms such as runny, stuffy nose and facial pain that does not go away after 10 to 14 days. Acute sinusitis typically lasts less than four weeks. Sub-acute sinusitis lasts four to eight weeks. Chronic sinusitis lasts eight weeks or longer, and recurrent sinusitis is characterized by sinusitis episodes that occur three or more times in one year. More than 80% of patients with CSwNP have eosinophilic upper airway inflammation.

Many patients with chronic sinusitis have "chronic hyperplastic eosinophilic sinusitis," which is characterized by marked inflammation of the sinuses, increased eosinophils and mixed mononuclear cells, and a relative paucity of neutrophils. Some of these patients have one or more of associated nasal polyps, asthma, and aspirin or NSAID sensitivity. In certain embodiments, an IL-4R antagonist can be used to treat nasal polyposis in a subject who has chronic hyperplastic eosinophilic sinusitis.

As used herein, "allergic sinusitis" refers to sinusitis that occurs when the body's immune system responds to specific, non-infectious irritants such as e.g., plant pollens, molds, dust mites, animal hair, industrial chemicals (including tobacco smoke), foods, medicines, and insect venom.

As used herein, "non-allergic sinusitis" refers to sinusitis that is not due to an allergic reaction, e.g., from colds, allergies, and tissue irritants (e.g., nasal sprays, cocaine, cigarette smoke and the like). Less commonly, sinuses can become obstructed by tumors or growths.

The term "rhinitis" refers to an allergic response, such as to a common allergen ("allergic rhinitis," e.g., perennial allergic rhinitis) or to an environmental irritant ("non-allergic rhinitis"). Symptoms of allergic rhinitis include sneezing; stuffy or runny nose; sinus pressure, and pain or throbbing in the cheeks or nose; and itching in the nose, throat, eyes and ears.

As used herein, "allergic rhinitis" refers to rhinitis that occurs when the body's immune responds to specific, non-infectious irritants.

As used herein, "non-allergic rhinitis" refers to rhinitis that is not due to an allergic reaction, that can be triggered by factors such as, e.g., cigarette smoke and other pollutants, strong odors, strong chemical environments, alcoholic beverages, cold, blockages in the nose, a deviated septum, infections and over-use of medications such as decongestants and/or nasal sprays. Symptoms of non-allergic rhinitis include constriction or inflammation in the nasal passages which leads to many of the same symptoms of allergic rhinitis.

As used herein, the term "rhinosinusitis" refers to a condition that has symptoms of both rhinitis and sinusitis. Rhinosinusitis includes acute rhinosinusitis and chronic rhinosinusitis. Acute rhinosinusitis can be caused by an infection, such as a bacterial, viral or fungal infection, or by a chemical irritation. Cigarette-smoke-induced acute rhinosinusitis and chlorine fume-induced chronic rhinosinusitis are examples of acute rhinosinusitis. NP is most commonly associated with chronic rhinosinusitis (CRS), which is characterized by mucosal inflammation of the nasal cavity and paranasal sinuses with symptoms lasting more than 8 weeks. Chronic eosinophilic rhinosinusitis with nasal polyps is a condition that lasts longer than 8 weeks.

Chronic sinusitis (CS) and chronic rhinosinusitis (CRS) are conditions that last longer than eight weeks. The underlying causes of acute sinusitis and acute rhinosinusitis may lead to chronic sinusitis or chronic rhinosinusitis if the resulting inflammation persists for more than 8 weeks.

Chronic rhinosinusitis includes for example, eosinophilic chronic hyperplastic rhinosinusitis.

Additional subcategories of chronic sinusitis (and chronic rhinosinusitis) include, e.g., superantigen-induced eosinophilic chronic sinusitis (e.g., sinusitis induced by exo- and endo-toxins produced by bacteria such as *Staphylococcus aureus*); allergic fungal sinusitis (e.g., sinusitis induced by fungi such as *Aspergillus* or *Alternaria*); non-allergic fungal eosinophilic chronic sinusitis; and aspirin-exacerbated eosinophilic chronic sinusitis. Rhinosinusitis is further classified as allergic rhinosinusitis and non-allergic rhinosinusitis.

As used herein, "allergic rhinosinusitis" refers to rhinosinusitis that occurs in response to exposure to one or more allergens.

As used herein, "non-allergic rhinosinusitis" refers to rhinosinusitis caused by factors including, but not limited to: pregnancy; thyroid disorders as a side effect of certain blood pressure and/or topical OTC decongestant medications; structural abnormalities in the nasal septum, structural abnormalities in the nasal filtering structures (turbinates), and/or structural abnormalities in the sinus drainage tracts; nasal polyps; and eosinophils.

An IL-4R antagonist can be used to treat nasal polyposis in subjects having any of the disorders described above.

Methods for Improving Nasal Polyp-Associated Parameters

The present invention includes methods for improving one or more nasal polyp-associated parameters in a subject in need thereof, wherein the methods include administering a pharmaceutical composition comprising an interleukin-4 receptor (IL-4R) antagonist to the subject. For example, an IL-4R receptor antagonist can reduce endoscopic Nasal Polyp Score (NPS) in a patient. A nasal polyp score of 0 indicates the presence of no polyps. An NPS of 1 indicates the presence of small polyps in the middle meatus not reaching below the inferior border of the middle turbinate. An NPS of 3 indicates large polyps reaching the lower border of the inferior turbinate or polyps medial to the middle turbinate. An NPS of 4 indicates large polyps causing complete obstruction of the inferior nasal cavity (see Table 15 below). The maximum score is 8 (4 points per nasal cavity). Treatment with an IL-4R antagonist can decrease NPS by about 1 to about 8 points. For example, treatment with an IL-4R antagonist can decrease NPS by about 1 point or more, by about 2 points or more, or by about 3 points or more. In some embodiments, treatment with an IL-4R antagonist can decrease NPS by about 1 point, or a fraction thereof; by 2 points, or a fraction thereof; by 3 points, or a fraction thereof; by 4 points, or a fraction thereof; by 5 points, or a fraction thereof; by 6 points, or a fraction thereof; by 7 points, or a fraction thereof; or by 8 points or a fraction thereof.

Treatment with an IL-4R antagonist can decrease NPS in a patient relative to NPS prior to treatment. In certain aspects, NPS is decreased after treatments with an IL-4R antagonist by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30, about 31%, about 32%, about 33%, about 34%, about 35%, about 40%, about 45%, about 50%, about 55%, about 60%, about 65%, about 70%, about 75%, about 80%, about 85%, about 90%, about 95%, about 96%, about 97%, about 98%, or about 99%, or any ranges between these numbers.

A reduction in NPS may correlate with an improvement in one or more other nasal polyp-associated parameters. Such a correlation, however, is not necessarily observed in all cases.

Other examples of "nasal polyp-associated parameters" include, but are not limited to: (a) 22-item Sino Nasal Outcome Test (SNOT-22) score; (b) subject-assessed nasal congestion/obstruction, anterior rhinorrhea (runny nose), posterior rhinorrhea (post nasal drip) and loss of sense of smell; (c) number of nocturnal awakenings; (d) Visual Analog Score (VAS) to assess patient-rated rhinosinusitis symptom severity; (e) five-item Asthma Control Questionnaire (ACQ5) score, such as in patients with asthma; (f) Nasal Peak Inspiratory Flow (NPIF); (g) smell test (University of Pennsylvania Smell Identification Test (UPSIT)); (h) physiological parameters, such as measured by nasal endoscopy and CT scan; (i) Lund-Mackay Score; and (j) Three Dimensional volumetric measurement of the maxillary sinus.

22-Item Sinonasal Outcome Test (SNOT-22) Score. According to certain embodiments, administration of an IL-4R antagonist to a patient results in a decrease from baseline of 22-item Sinonasal Outcome Test (SNOT-22). The SNOT-22 is a questionnaire to assess the impact of chronic rhinosinusitis (CRS) on quality of life. The questionnaire measures items related to sinonasal conditions and surgical treatments. The score ranges from 0 to 110, and higher scores imply greater impact of CRS on Health Related Quality of Life (HRQoL) (Hopkins et al 2009, Clin. Otolaryngol. 34: 447-454).

The present invention includes therapeutic methods that result in a decrease in SNOT-22 score from baseline of at least 1 point at week 4 to week 16 following administration of the IL-4R antagonist. For example, administration of an IL-4R antagonist will result in a decrease in SNOT-22 score at week 4, week 6, week 8, week 12, or week 16 following initiation of treatment. In some embodiments, administration of an IL-4R antagonist to a subject in need thereof causes a decrease in SNOT-22 score from baseline of about 1, 2, 3, 4, 5, 6, 7, 8, 9, 10, 11, 12, 13 points, or more at week 4, week 6, week 8 or week 12.

Individual and Total Nasal Symptom Score. Subject-assessed symptoms are assayed by responding to morning and evening individual rhinosinusitis symptom questions using a 0-3 categorical scale (where 0=no symptoms, 1=mild symptoms, 2=moderate symptoms and 3=severe symptoms), and including the symptoms of congestion and/or obstruction, anterior rhinorrhea, posterior rhinorrhea, and loss of sense of smell. Nasal symptoms can be assayed in the day (AM), at night (PM) or both AM and PM.

A loss of sense of smell can be tracked. Administration of an IL-4R antagonist can result, for example, in a decrease in loss of sense of smell (i.e., achieving a lower number on the scale) from baseline compared to week 4 to week 16 following initiation of treatment with a pharmaceutical composition comprising an anti-IL-4R antagonist. For example, a decrease in loss of sense of smell from baseline (e.g., from about 0.5, about 1.0, about 1.5, about 2.0, about 2.5 or about 3.0) can be detected at week 4, week 6, week 8, week 12, or week 16 following initiation of treatment. Administration of an IL-4R antagonist to a subject in need thereof can cause a decrease in loss of sense of smell symptom score from baseline by about 0.5, about 1.0, about 1.5, about 2.0, about 2.5 or about 3.0 or more at week 4, week 8, week 12, or week 16, for example.

A decrease in congestion and/or obstruction can be tracked. Administration of an IL-4R antagonist can result, for example, in a decrease in congestion and/or obstruction (i.e., achieving a lower number on the scale) from baseline compared to week 4 to week 16 following initiation of treatment with a pharmaceutical composition comprising an anti-IL-4R antagonist. For example, a decrease in congestion and/or obstruction from baseline (e.g., from about 0.5, about 1.0, about 1.5, about 2.0, about 2.5 or about 3.0) can be detected at week 4, week 6, week 8, week 12, or week 16 following initiation of treatment. Administration of an IL-4R antagonist to a subject in need thereof can cause a decrease in congestion and/or obstruction symptom score from baseline by about 0.5, about 1.0, about 1.5, about 2.0, about 2.5 or about 3.0 or more at week 4, week 8, week 12, or week 16, for example.

A decrease in runny nose can be tracked. Administration of an IL-4R antagonist can result, for example, in a decrease in c runny nose (i.e., achieving a lower number on the scale) from baseline compared to week 4 to week 16 following initiation of treatment with a pharmaceutical composition comprising an anti-IL-4R antagonist. For example, a decrease in runny nose from baseline (e.g., from about 0.5, about 1.0, about 1.5, about 2.0, about 2.5 or about 3.0) can be detected at week 4, week 6, week 8, week 12, or week 16 following initiation of treatment. Administration of an IL-4R antagonist to a subject in need thereof can cause a decrease in runny nose symptom score from baseline by about 0.5, about 1.0, about 1.5, about 2.0, about 2.5 or about 3.0 or more at week 4, week 8, week 12, or week 16, for example.

A decrease in post nasal drip can be tracked. Administration of an IL-4R antagonist can result, for example, in a decrease in runny nose (i.e., achieving a lower number on the scale) from baseline compared to week 4 to week 16 following initiation of treatment with a pharmaceutical composition comprising an anti-IL-4R antagonist. For example, a decrease in post nasal drip from baseline (e.g., from about 0.5, about 1.0, about 1.5, about 2.0, about 2.5 or about 3.0) can be detected at week 4, week 6, week 8, week 12, or week 16 following initiation of treatment. Administration of an IL-4R antagonist to a subject in need thereof can cause a decrease in post nasal drip symptom score from baseline by about 0.5, about 1.0, about 1.5, about 2.0, about 2.5 or about 3.0 or more at week 4, week 8, week 12, or week 16, for example.

A measure of night-time awakenings can also be tracked. For example, a measure of night-time awakenings can be assessed according to the following scores based on subject self-assessment: 0=no symptoms, slept through the night; 1=slept well, but some complaints in the morning; 2=woke up once because of rhinosinusitis symptoms (including early awakening); 3=woke up several times because of symptoms (including early awakening); 4=bad night, awake most of the night because of symptoms. Administration of an IL-4R antagonist can result, for example, in a decrease in average number of nighttime awakenings per night from baseline of at least about 0.10 times per night at week 4 to week 16 following initiation of treatment with a pharmaceutical composition comprising an anti-IL-4R antagonist. For example, a decrease in frequency of nighttime awakenings per night from baseline of at least about 0.10 times per night can be detected at week 4, week 6, week 8, week 12, or week 16 following initiation of treatment. Administration of an IL-4R antagonist to a subject in need thereof can cause a decrease in average number of nighttime awakenings per night from baseline by about 0.10 times per night, 0.15 times per night, 0.20 times per night, 0.25 times per night, 0.30 times per night, 0.35 times per night, 0.40 times per night, 0.45 times per night, 0.50 times per night, 0.55 times per night, 0.60 times per night, 0.65 times per night, 0.70 times per night, 0.75 times per night, 0.80 times per night, 0.85 times per night, 0.90 times per night, 0.95 times per night, 1.0 time per night, 2.0 times per night, or more at week 4, week 8, week 12, or week 16, for example.

Visual Analog Score (VAS). The VAS is a measure to assess patient-related rhinosinusitis symptom severity on a scale of 1 to 10. Mild symptoms are indicated by a score of 0 to 3, moderate symptoms are indicated by a VAS score of >3 to 7, and severe symptoms are indicated by a VAS score of >7 to 10. Administration of an IL-4R antagonist to a subject in need thereof causes a decrease in VAS score from baseline of about 0.5 point, 1 point, 1.5 points, 2 points, 2.5 points, 3 points, 3.5 points, 4 points, or more at week 4, week 6 or week 12. The decrease in VAS score can be detected as early as week 4, and as late as week 12 or later following administration of the IL-4R antagonist.

5-Item Asthma Control Questionnaire (ACQ) Score. The ACQ5 measures both the adequacy of asthma control and change in asthma control, which occurs either spontaneously or as a result of treatment. The five questions on the ACQ5 reflect the top-scoring five asthma symptoms: woken at night by symptoms, wake in the mornings with symptoms, limitation of daily activities, shortness of breath and wheeze. Patients respond to the symptom questions on a 7-point scale (0=no impairment, totally controlled; 6=maximum impairment, severely uncontrolled).

The present invention includes therapeutic methods which result in a decrease in ACQ5 score from baseline of at least 0.10 point at week 12 following initiation of treatment with a pharmaceutical composition comprising an anti-IL-4R antagonist. For example, according to the present invention, administration of an IL-4R antagonist to a subject in need thereof causes a decrease in ACQ score from baseline of about 0.10 points, 0.15 points, 0.20 points, 0.25 points, 0.30 points, 0.35 points, 0.40 points, 0.45 points, 0.50 points, 0.55 points, 0.60 points, 0.65 points, 0.70 points, 0.75 points, 0.80 points, 0.85 points, or more at week 4, week 6 or week 12. The decrease in ACQ score can be detected as early as week 4, and as late as week 12 or later following administration of the IL-4R antagonist.

Nasal Peak Inspiratory Flow (NPIF). The Nasal Peak Inspiratory Flow (NPIF) represents a physiologic measure of air flow through both nasal cavities during forced inspiration and/or expiration expressed in liters per minute. Nasal inspiration correlates most with the subjective feeling of obstruction and is used to monitor nasal flow. Administration of an IL-4R antagonist to a subject in need thereof causes an increase in NPIF from baseline by about 0.10 liters per minute, 0.15 liters per minute, 0.20 liters per minute, 0.25 liters per minute, 0.30 liters per minute, 0.35 liters per minute, 0.40 liters per minute, 0.45 liters per minute, 0.50 liters per minute, 0.55 liters per minute, 0.60 liters per minute, 0.65 liters per minute, 0.70 liters per minute, 0.75 liters per minute, 0.80 liters per minute, 0.85 liters per minute, or more at week 4, week 6 or week 12. The increase in NPIF score can be detected as early as week 4, and as late as week 12 or later following administration of the IL-4R antagonist.

University of Pennsylvania Smell Identification Test (UPSIT). The UPSIT is a method to quantitatively assess human olfactory function. The test consists of samples of odorants, and the subject has to describe the odor. The score is based on the number of correct answers. This test can distinguish patients with a normal sense of smell ("normosmia") from those with different levels of reduction ("mild, moderate and severe microsmia") or loss ("anosmia"). Administration of an IL-4R antagonist to a subject in need thereof causes an increase in UPSIT score from baseline by about 0.5 points, 1 point, 1.5 points, 2 points, 2.5 points, 3 points, 3.5 points or more at week 4, week 6 or week 12. The increase in UPSIT score can be detected as early as week 4, and as late as week 12 or later following administration of the IL-4R antagonist.

Physiological parameters. Efficacy of an IL-4R antagonist can be assayed by measuring the effect of physiological parameters, such as within the nasal cavities, such as by nasal endoscopy or computed tomography (CT) scan.

Lund-Mackay Score. The Lund-Mackay scoring system is based on localization with points given for degree of opacification: 0=normal, 1=partial opacification, 2=total opacification. These points are then applied to the maxillary, anterior ethmoid, posterior ethmoid, sphenoid, and frontal sinus on each side. The osteomeatal complex is graded as 0=not occluded, or 2=occluded deriving a maximum score of 12 per side. For patients in whom the osteomeatal complex (OC) is missing (because of a previous surgery) the location of the former OC is considered and a score is provided, as if the OC was there. Administration of an IL-4R antagonist to a subject in need thereof causes a decrease in Lund-Mackay score from baseline by about 0.10 points, 0.15 points, 0.20 points, 0.25 points, 0.30 points, 0.35 points, 0.40 points, 0.45 points, 0.50 points, 0.55 points, 0.60 points, 0.65 points, 0.70 points, 0.75 points, 0.80 points, 0.85 points, or more at week 4, week 6 or week 12. The decrease in Lund-Mackay score can be detected as early as week 4, and as late as week 12 or later following administration of the IL-4R antagonist.

Three-Dimensional volumetric measurement of maxillary sinus. This value is used to calculate the volume of air (mL); the volume of mucosa (mL); the percent sinus occupied by disease; and the thickness of lateral wall in the maxillary sinus. Administration of an IL-4R antagonist to a subject in need thereof causes an increase in the Three-Dimensional volumetric measurement.

Quality of Life (QoL) Questionnaires. Various QoL Questionnaires can be used to monitor efficacy of an IL-4R antagonist, including Short-Form-36 (SF-36) Questionnaire, the Euroqol-5D (EQ-5D), nasal polyp related resource use questionnaire, and the patient qualitative self-assessment.

The SF-36 is a 36 item questionnaire that measures eight multi-item dimensions of health: physical functioning (10 items) social functioning (2 items) role limitations due to physical problems (4 items), role limitations due to emotional problems (3 items), mental health (5 items), energy/vitality (4 items), pain (2 items), and general health perception (5 items). For each dimension, item scores are coded, summed, and transformed on a scale from 0 (worst possible health state measured by the questionnaire) to 100 (best possible health state). Two standardized summary scores can also be calculated from the SF-36; the physical component summary (PCS) and the mental health component summary (MCS).

The EQ-5D is a standardized health-related quality of life questionnaire developed by the EuroQol Group in order to provide a simple, generic measure of health for clinical and economic appraisal and inter-disease comparisons. EQ-5D, designed for self-completion by patients, consists of two parts, the EQ-5D descriptive system and the EQ VAS. The EQ-5D descriptive system comprises 5 dimensions: mobility, self-care, usual activities, pain/discomfort and anxiety/depression; and each dimension has 3 levels: no problem, some problems, severe problems. The EQ Visual Analogue Scale (VAS) records the respondent's self-rated health on a vertical visual analogue scale. The EQ VAS 'thermometer' has endpoints of 100 (Best imaginable health state) at the top and 0 (Worst imaginable health state) at the bottom.

The nasal polyp related resource use questionnaire is a questionnaire of health care resource utilization for nasal polyposis, including specialist visits, emergency care visits, sick leaves, days off etc.

Nasal Polyp-Associated Biomarkers. Examples of nasal polyp-associated biomarkers include, but are not limited to, one or any combination of IgE, TARC, eotaxin-3 and ECP. In certain embodiment of the invention, one or more nasal polyp-associated biomarkers may be detected from a biological sample derived from a subject. A biological sample includes, but is not limited to, one or any combination of materials taken from a patient including cultures, cells, tissues, blood, saliva, nasal secretions, cerebrospinal fluid, pleural fluid, milk, lymph, sputum, semen, needle aspirates, and the like. Biological samples may be obtained using any methods known in the art. For example, nasal secretion samples may be obtained from smears, blown secretions, imprints, lavage, swabs, brushes and the like.

A normal IgE level in healthy subjects is less than about 100 kU/L (e.g., as measured using the IMMUNOCAP® assay [Phadia, Inc. Portage, MI]). Thus, the invention includes methods decreasing an elevated serum IgE level, which is a serum IgE level greater than about 100 kU/L, greater than about 150 kU/L, greater than about 500 kU/L, greater than about 1000 kU/L, greater than about 1500 kU/L, greater than about 2000 kU/L, greater than about 2500 kU/L, greater than about 3000 kU/L, greater than about 3500 kU/L, greater than about 4000 kU/L, greater than about 4500 kU/L, or greater than about 5000 kU/L, by administering to the subject a pharmaceutical composition comprising a therapeutically effective amount of an IL-4R antagonist.

TARC levels in healthy subjects are in the range of 106 ng/L to 431 ng/L, with a mean of about 239 ng/L. (An exemplary assay system for measuring TARC level is the TARC quantitative ELISA kit offered as Cat. No. DDN00 by R&D Systems, Minneapolis, MN) Thus, the invention includes methods decreasing an elevated serum TARC level, which is a serum TARC (e.g., serum TARC) level greater than about 431 ng/L, greater than about 500 ng/L, greater than about 1000 ng/L, greater than about 1500 ng/L, greater than about 2000 ng/L, greater than about 2500 ng/L, greater than about 3000 ng/L, greater than about 3500 ng/L, greater than about 4000 ng/L, greater than about 4500 ng/L, or greater than about 5000 ng/L, by administering to the subject a pharmaceutical composition comprising a therapeutically effective amount of an IL-4R antagonist.

Improvement of a nasal polyp-associated parameter, such as a nasal polyp-associated parameter described above, can be expressed as a percentage. For example, a score can be improved by 30% or more, by 40% or more, by 50% or more, by 60% or more, by 70% or more, or by 80% or more.

Biomarker expression, as discussed above, can be assayed by detection of protein or RNA in serum. In some embodiments, RNA samples are used to determine RNA levels (non-genetic analysis), e.g., RNA levels of biomarkers; and in other embodiments, RNA samples are used for transcriptome sequencing (e.g., genetic analysis).

An "improvement in a nasal polyp-associated parameter" means an increase from baseline of one or more of NPIF, UPSIT, and/or a decrease from baseline of one or more of SNOT-22 score, subject-assessed nasal congestion/obstruction, anterior rhinorrhea (runny nose), posterior rhinorrhea (post nasal drip) and loss of sense of smell; number of nocturnal awakenings; VAS score; Lund-Mackay score; and 3D volumetric scores; and ACQ5 score in patients with asthma. As used herein, the term "baseline," with regard to a nasal polyp-associated parameter, means the numerical value of the nasal polyp-associated parameter for a patient prior to or at the time of administration of a pharmaceutical composition of the present invention.

To determine whether a nasal polyp-associated parameter has "improved," the parameter is quantified at baseline and at a time point after administration of the pharmaceutical composition of the present invention. For example, a nasal polyp-associated parameter may be measured at day 1, day 2, day 3, day 4, day 5, day 6, day 7, day 8, day 9, day 10, day 11, day 12, day 14, or at week 3, week 4, week 5, week 6, week 7, week 8, week 9, week 10, week 11, week 12, week 13, week 14, week 15, week 16, week 17, week 18, week 19, week 20, week 21, week 22, week 23, week 24, or longer, after the initial treatment with a pharmaceutical composition of the present invention. In some embodiments, the parameter is measured daily (e.g., once or twice per day), weekly, biweekly, or monthly. In other embodiments, the parameter is measured daily and the mean value determined over the course of a month is compared to baseline.

The difference between the value of the parameter at a particular time point following initiation of treatment and the value of the parameter at baseline is used to establish whether there has been an "improvement" in the nasal associated parameter (e.g., an increase or decrease, as the case may be, depending on the specific parameter being measured).

Interleukin-4 Receptor Antagonists

In one embodiment, a subject in need thereof is administered a therapeutic composition comprising an interleukin-4 receptor (IL-4R) antagonist. As used herein, an "IL-4R antagonist" is any agent that binds to or interacts with IL-4R and inhibits the normal biological signaling function of IL-4R when IL-4R is expressed on a cell in vitro or in vivo. Non-limiting examples of categories of IL-4R antagonists include small molecule IL-4R antagonists, peptide-based IL-4R antagonists (e.g., "peptibody" molecules), and antibodies or antigen-binding fragments of antibodies that specifically bind human IL-4R.

The term "human IL-4R" (hIL-4R), as used herein, is intended to refer to the IL-4Rα subunit, which is a component of the IL-4 receptors Type I and Type II, as well as the IL-13 receptor system. An IL-4R antagonist, such as an anti-IL-4Rα antibody or antigen-binding fragment thereof, blocks the function of both IL-4 and IL-13 signal transduction.

The term "antibody", as used herein, is intended to refer to immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In some embodiments, the FRs of the anti-IL-4R antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an anti-IL-4R antibody using routine techniques available in the art.

The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

The term "human antibody", as used herein, is intended to include antibodies having variable and constant regions derived from human germline immunoglobulin sequences. The human antibodies featured in the invention may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody." An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" IL-4R, as used herein, includes antibodies that bind IL-4R or portion thereof with a $K_D$ of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or less than about 0.5 nM, as measured in a surface plasmon resonance assay. An isolated antibody that specifically binds human IL-4R may, however, have cross-reactivity to other antigens, such as IL-4R molecules from other (non-human) species.

The anti-IL-4R antibodies useful for the methods featured herein may include one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes methods involving the use of antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s)

of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. The use of antibodies and antigen-binding fragments obtained in this general manner are encompassed within the present invention.

The present invention also includes methods involving the use of anti-IL-4R antibodies comprising variants of any of the HCVR, LCVR, and/or CDR amino acid sequences disclosed herein having one or more conservative substitutions. For example, the present invention includes the use of anti-IL-4R antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "surface plasmon resonance", as used herein, refers to an optical phenomenon that allows for the analysis of real-time interactions by detection of alterations in protein concentrations within a biosensor matrix, for example using the BIAcore™ system (Biacore Life Sciences division of GE Healthcare, Piscataway, NJ).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

According to certain exemplary embodiments of the present invention, the IL-4R antagonist is an anti-IL-4Rα antibody, or antigen-binding fragment thereof comprising a heavy chain variable region (HCVR), light chain variable region (LCVR), and/or complementarity determining regions (CDRs) comprising any of the amino acid sequences of the anti-IL-4R antibodies as set forth in U.S. Pat. Nos. 7,608,693 and 7,605,237. In certain exemplary embodiments, the anti-IL-4Rα antibody or antigen-binding fragment thereof that can be used in the context of the methods of the present invention comprises the heavy chain complementarity determining regions (HCDRs) of a heavy chain variable region (HCVR) comprising the amino acid sequence of SEQ ID NO:1 and the light chain complementarity determining regions (LCDRs) of a light chain variable region (LCVR) comprising the amino acid sequence of SEQ ID NO:2. According to certain embodiments, the anti-IL-4Rα antibody or antigen-binding fragment thereof comprises three HCDRs (HCDR1, HCDR2 and HCDR3) and three LCDRs (LCDR1, LCDR2 and LCDR3), wherein the HCDR1 comprises the amino acid sequence of SEQ ID NO:3; the HCDR2 comprises the amino acid sequence of SEQ ID NO:4; the HCDR3 comprises the amino acid sequence of SEQ ID NO:5; the LCDR1 comprises the amino acid sequence of SEQ ID NO:6; the LCDR2 comprises the amino acid sequence of SEQ ID NO:7; and the LCDR3 comprises the amino acid sequence of SEQ ID NO:8. In yet other embodiments, the anti-IL-4R antibody or antigen-binding fragment thereof comprises an HCVR comprising SEQ ID NO:1 and an LCVR comprising SEQ ID NO:2. In certain exemplary embodiments of the present invention, the IL-4R antagonist is an anti-IL-4Rα antibody, or antigen-binding fragment thereof comprising a heavy chain sequence of SEQ ID NO:9 and a light chain sequence of SEQ ID NO:10. According to certain exemplary embodiments, the methods of the present invention comprise the use of the anti-IL-4Rα antibody referred to and known in the art as dupilumab, or a bioequivalent thereof.

The term "bioequivalent" as used herein, refers to a molecule having similar bioavailability (rate and extent of availability) after administration at the same molar dose and under similar conditions (e.g., same route of administration), such that the effect, with respect to both efficacy and safety, can be expected to be essentially same as the comparator molecule. Two pharmaceutical compositions comprising an IL-4R antagonist are bioequivalent if they are pharmaceutically equivalent, meaning they contain the same amount of active ingredient (e.g., IL-4R antagonist), in the same dosage form, for the same route of administration and meeting the same or comparable standards. Bioequivalence can be determined, for example, by an in vivo study comparing a pharmacokinetic parameter for the two compositions. Parameters commonly used in bioequivalence studies include peak plasma concentration ($C_{max}$) and area under the plasma drug concentration time curve (AUC).

Other anti-IL-4Rα antibodies that can be used in the context of the methods of the present invention include, e.g., the antibody referred to and known in the art as AMG317 (Corren et al., 2010, *Am J Respir Crit Care Med.,* 181(8): 788-796), or any of the anti-IL-4Rα antibodies as set forth in U.S. Pat. No. 7,186,809, or U.S. Pat. No. 8,092,804.

The anti-IL-4Rα antibodies used in the context of the methods of the present invention may have pH-dependent binding characteristics. For example, an anti-IL-4Rα antibody for use in the methods of the present invention may exhibit reduced binding to IL-4Rα at acidic pH as compared to neutral pH. Alternatively, an anti-IL-4Rα antibody of the invention may exhibit enhanced binding to its antigen at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding to IL-4Rα at acidic pH as compared to neutral pH" is expressed in terms of a ratio of the $K_D$ value of the antibody binding to IL-4Rα at acidic pH to the $K_D$ value of the antibody binding to IL-4Rα at neutral pH (or vice versa). For example, an antibody or antigen-binding fragment thereof may be regarded as exhibiting "reduced binding to IL-4Rα at acidic pH as compared to neutral pH" for purposes of the present invention if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment of the present invention can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0. 25.0, 30.0, 40.0, 50.0, 60.0, 70.0, 100.0 or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained. As used herein, the expression "acidic pH" means a pH of 6.0 or less.

Pharmaceutical Compositions

The present invention includes methods which include administering an IL-4R antagonist to a patient, where the IL-4R antagonist is contained within a pharmaceutical composition. The pharmaceutical compositions featured in the invention are formulated with suitable carriers, excipients, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, PA These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient may vary depending upon the age and the size of the patient, symptoms, conditions, route of administration, and the like. The preferred dose is typically calculated according to body weight or body surface area. Depending on the severity of the condition, the frequency and the duration of the treatment can be adjusted. Effective dosages and schedules for administering pharmaceutical compositions comprising anti-IL-4R antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer a pharmaceutical composition containing an IL-4R antagonist, including encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of administration include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents.

A pharmaceutical composition can be delivered subcutaneously or intravenously with a standard needle and/or syringe (e.g., a prefilled needle and/or syringe or a needle and/or syringe filled from a vial). In addition, with respect to subcutaneous delivery, a pen delivery device readily has applications in delivering a pharmaceutical composition. Such a pen delivery device, including an auto-injection pen delivery device, can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition include, but are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN (Dey, L. P.), and the HUMIRA™ Pen (Abbott Labs, Abbott Park IL), to name only a few.

For direct administration to the sinuses, the pharmaceutical compositions containing IL-4R antagonists may be administered using, e.g., a microcatheter (e.g., an endoscope and microcatheter), an aerosolizer, a powder dispenser, a nebulizer or an inhaler.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Florida In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 20, polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is typically filled in an appropriate ampoule.

A pharmaceutical composition can be delivered intranasally. As used herein, "intranasal" administration refers to administration of a pharmaceutical compound to the nasal cavity. Intranasal delivery can be performed using any method known in the art, including, but not limited to, inhalation, spraying, liquid stream lavage, nebulizing, atomizing or nasal irrigation. A pharmaceutical composition can be delivered intranasally using a syringe, a dropper, a squeeze bottle or a spray (atomizer) device (e.g., a syringe-driven atomizer or a pump-driven atomizer). Suitable prefillable syringes that can be used for intranasal delivery include, but are not limited to, Carpuject™ (Hospira), Accuspray (BD Pharmaceutical Systems), Direct-Haler (Direct-Haler A/S), Go-Pump, mucosal atomization devices, Veridoser (Mystic Pharmaceuticals), OptiNose (OptiNose US), ViaNase™ (Kurve technology), Nebu-Laser and the like.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

Dosage

The amount of IL-4R antagonist (e.g., anti-IL-4R antibody, or antigen binding fragment thereof) administered to a subject according to the methods featured herein is generally a therapeutically effective amount. As used herein, the phrase "therapeutically effective amount" means a dose of IL-4R antagonist that results in a detectable improvement in one or more symptoms associated with nasal polyps, or a dose of IL-4R antagonist that inhibits, prevents, lessens, or delays the progression of nasal polyps or a condition associated with nasal polyps. In the case of an anti-IL-4R antibody, a therapeutically effective amount can be from about 0.05 mg to about 600 mg, e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the anti-IL-4R antibody or antigen binding fragment.

The amount of IL-4R antagonist contained within the individual doses may be expressed in terms of milligrams of antibody per kilogram of patient body weight (i.e., mg/kg). For example, the IL-4R antagonist may be administered to a patient at a dose of about 0.0001 to about 10 mg/kg of patient body weight.

Combination Therapies

The methods, according to certain embodiments, include administering to the subject one or more additional therapeutic agents in combination with the IL-4R antagonist. As used herein, the expression "in combination with" means that the additional therapeutic agents are administered before, after, or concurrent with the pharmaceutical composition comprising the IL-4R antagonist. For example, when administered "before" the pharmaceutical composition comprising the IL-4R antagonist, the additional therapeutic agent may be administered about 72 hours, about 60 hours, about 48 hours, about 36 hours, about 24 hours, about 12 hours, about 10 hours, about 8 hours, about 6 hours, about 4 hours, about 2 hours, about 1 hour, about 30 minutes, about 15 minutes or about 10 minutes prior to the administration of the pharmaceutical composition comprising the IL-4R antagonist. When administered "after" the pharmaceutical composition comprising the IL-4R antagonist, the additional therapeutic agent may be administered about 10 minutes, about 15 minutes, about 30 minutes, about 1 hour, about 2 hours, about 4 hours, about 6 hours, about 8 hours, about 10 hours, about 12 hours, about 24 hours, about 36 hours, about 48 hours, about 60 hours or about 72 hours after the administration of the pharmaceutical composition comprising the IL-4R antagonist. Administration "concurrent" with the pharmaceutical composition comprising the IL-4R antagonist means that the additional therapeutic agent is administered to the subject in a separate dosage form within less than 5 minutes (before, after, or at the same time) of administration of the pharmaceutical composition comprising the IL-4R antagonist, or administered to the subject as a single combined dosage formulation comprising both the additional therapeutic agent and the IL-4R antagonist.

The additional therapeutic agent may be, e.g., another IL-4R antagonist, an IL-1 antagonist (including, e.g., an IL-1 antagonist as set forth in U.S. Pat. No. 6,927,044), an IL-6 antagonist, an IL-6R antagonist (including, e.g., an anti-IL-6R antibody as set forth in U.S. Pat. No. 7,582,298), an IL-13 antagonist, a TNF antagonist, an IL-8 antagonist, an IL-9 antagonist, an IL-17 antagonist, an IL-5 antagonist, an IgE antagonist, a CD48 antagonist, an antibiotic (e.g., doxycycline), an anti-fungal agent, a leukotriene, an antihistamine, an α-adrenergic decongestant, a mucolytic, an NSAID, a long-acting $beta_2$ agonist (e.g., salmeterol or formoterol), a short-acting $beta_2$ agonist, a steroid (e.g., an oral steroid), a corticosteroid, such as an intranasal corticosteroid (e.g., mometasone furoate (MFNS; e.g., Nasonex®)), or an inhaled corticosteroid (e.g., fluticasone or budesonide), an allergen immunotherapy, or combinations thereof. For example, in certain embodiments, the pharmaceutical composition comprising an IL-4R antagonist is administered in combination with a combination comprising a long-acting $beta_2$ agonist and an inhaled corticosteroid (e.g., fluticasone+salmeterol [e.g., Advair® (GlaxoSmithKline)]; or budesonide+formoterol [e.g., Symbicort® (Astra Zeneca)]).

In some embodiments, the IL-4R antagonist is administered after a subject receives surgery to treat nasal polyposis.

Administration Regimens

According to certain embodiments, multiple doses of an IL-4R antagonist may be administered to a subject over a defined time course. The methods include, for example, sequentially administering to a subject multiple doses of an IL-4R antagonist. As used herein, "sequentially administering" means that each dose of IL-4R antagonist is administered to the subject at a different point in time, e.g., on different days separated by a predetermined interval (e.g., hours, days, weeks or months). The present invention includes methods which comprise sequentially administering to the patient a single initial dose of an IL-4R antagonist, followed by one or more secondary doses of the IL-4R antagonist, and optionally followed by one or more tertiary doses of the IL-4R antagonist.

The terms "initial dose," "secondary doses," and "tertiary doses," refer to the temporal sequence of administration of the IL-4R antagonist. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of IL-4R antagonist, but will generally differ from one another in terms of frequency of administration. In certain embodiments, however, the amount of IL-4R antagonist contained in the initial, secondary and/or tertiary doses will vary from one another (e.g., adjusted up or down as appropriate) during the course of treatment.

In one exemplary embodiment, each secondary and/or tertiary dose is administered 1 to 14 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, or more) weeks after the immediately preceding dose. The phrase "the immediately preceding dose," as used herein, means, in a sequence of multiple administrations, the dose of IL-4R antagonist which is administered to a patient prior to the administration of the very next dose in the sequence with no intervening doses.

These methods may include administering to a patient any number of secondary and/or tertiary doses of an IL-4R antagonist. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

In certain embodiments, the initial dose (e.g., a "loading dose") is higher than either or both of the secondary and tertiary doses. For example, the initial dose can be a loading dose, which is 1.5×, 2×, 2.5×, 3× or more greater than the secondary dose.

Treatment Populations

The methods featured in the present invention including administering to a subject in need thereof a therapeutic composition comprising an IL-4R antagonist. As used herein, the expression "a subject in need thereof" means a human or non-human animal that exhibits one or more symptoms or indications of (i) nasal polyposis, (ii) chronic sinusitis with nasal polyps, (iii) allergic or non-allergic rhinitis, or (iv) allergic or non-allergic rhinosinusitis, or a subject who has been diagnosed with one of these conditions. For example, in one embodiment, a subject in need thereof has bilateral nasal polyps, and a nasal polyp score of at least 4 out of a maximum of 8 for both nostrils, with at least a score of 2 for each nostril. In certain embodiments, the polyps are in the middle meatus. In certain embodiments, the presence of nasal polyps is confirmed by endoscopy. In some embodiments, the subject also has bilateral mucosal disease, which is confirmed by a method such as CT scan. As used herein "bilateral mucosal disease" is an infection of the mucous lining of the sinus cavities, e.g., the maxillary sinus cavities. In some embodiments, bilateral nasal polyposis (e.g., a nasal polyp score of at least 4 out of a maximum of 8 for both nostrils, with at least a score of 2 for each nostril) persists even after a treatment regimen of inhaled corticosteroids (INCS), such as where the INCS was administered for at least 6 weeks, at least 7 weeks, at least 8 weeks, or longer.

In certain embodiments, a subject in need thereof has anterior and/or posterior mucopurulent drainage, nasal obstruction, and a decreased sense of smell. In certain embodiments, a subject in need thereof has had symptoms of chronic sinusitis with nasal polyps for 6 weeks, 7 weeks, 8 weeks, 9 weeks, 10 weeks, 11 weeks, 12 weeks or more. In yet other embodiments, the subject has received a previous treatment, such as with an intranasal corticosteroid (e.g., MFNS), for at least 4 weeks, at least 5 weeks, at least 6 weeks, at least 7 weeks, at least 8 weeks, at least 9 weeks, at least 10 weeks or longer, prior to receiving treatment with an IL-4R antagonist. In some embodiments the subject will continue to receive the INCS while receiving treatment with the IL-4R antagonist. In other embodiments, the subject stops receiving the INCS before receiving treatment with the IL-4R antagonist, or the subject stops receiving treatment with the INCS if administration with the IL-4R antagonist is effective to treat the chronic sinusitis with nasal polyps. In some embodiments, the subject tapers the dose of the INCS before stopping treatment completely.

A subject in need thereof may further have been diagnosed with nasal polyposis or a condition associated with nasal polyposis, such as chronic sinusitis with nasal polyps, allergic or non-allergic rhinitis, or allergic or non-allergic rhinosinusitis. The diagnosis may be on the basis of one or more of the following: (a) 22-item Sino Nasal Outcome Test (SNOT-22) score; (b) subject-assessed nasal congestion/obstruction, anterior rhinorrhea, posterior rhinorrhea and loss of sense of smell; (c) number of nocturnal awakenings; (d) Visual Analog Score (VAS) to assess patient-rated rhinosinusitis symptom severity; (e) five-item Asthma Control Questionnaire (ACQ5) score in patients with asthma; (f) Nasal Polyp Score (NPS); (g) Nasal Peak Inspiratory Flow (NPIF); (h) smell test (University of Pennsylvania Smell Identification Test (UPSIT); (i) physiological parameters, such as measured by nasal endoscopy and CT scan; (j) Lund-Mackay Score; and (k) Three Dimensional volumetric measurement of the maxillary sinus.

For example, in certain embodiments, a "subject in need thereof" is a human patient with chronic symptoms of sinusitis, which are the presence of at least two of the following symptoms: nasal blockade/obstruction/congestion or nasal discharge (anterior/posterior nasal drip); facial pain/pressure; and reduction or loss of smell.

In certain embodiments, a "subject in need thereof" is a human patient with a SNOT-22 score of greater than about 7, greater than about 10, greater than about 15, greater than about 20, greater than about 25, greater than about 30, greater than about 35, greater than about 40, greater than about 45, or greater than about 50. A "subject in need thereof" may also be a human patient who exhibits a Lund-Mackay score of greater than about 4, greater than about 5, greater than about 6, greater than about 7, greater than about 8, greater than about 9, greater than about 10, greater than about 11, greater than about 12, or greater than about 13.

In a related embodiment, a "subject in need thereof" may be a subject who, prior to receiving an IL-4R antagonist, has been prescribed or is currently taking another medication, "a background therapy." The background therapy can be, for example, an intranasal corticosteroid (INCS, or ICS), such as Mometasone furoate nasal spray (MFNS; Nasonex®). In some embodiments, a "subject in need thereof" is an asthma patient who prior to receiving an IL-4R antagonist, has been prescribed or is currently taking an INCS in combination with a long-acting beta$_2$-adronergic antagonist (LABA). Examples of INCS/LABA therapies include fluticasone/salmeterol combination therapy and budesonide/formoterol combination therapy. In some embodiments, the background therapy is a nasal saline, a topical decongestant, a topical anesthetic, a leukotriene antagonist or a systemic antihistamine. In some embodiments, the "subject in need thereof" continues the background therapy after the subject receives the IL-4R antagonist, and in other embodiments, the subject in need thereof stops receiving the background therapy (e.g., at once or gradually) before receiving the IL-4R antagonist.

EXAMPLES

The following examples are put forth so as to provide those of ordinary skill in the art with a complete disclosure and description of how to make and use the methods and compositions featured in the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Clinical Trial of Subcutaneously Administered Anti-IL-4R Antibody (mAb1) in Patients with Persistent Moderate-to-Severe Eosinophilic Asthma, Including Asthma Patients with Chronic Hyperplastic Eosinophilic Sinusitis A. Study Objectives and Overview A randomized, placebo-controlled, double-blind, parallel group study was conducted with once-a-week subcutaneous administration of either 300 mg dupilumab ("mAb1") or placebo for 12 weeks to patients with persistent moderate-to-severe eosinophilic asthma who were partially controlled/uncontrolled by inhaled corticosteroid (ICS) and long-acting beta2 agonist (LABA) therapy. Dupilumab is an anti-IL-4R antibody having a heavy chain variable region of SEQ ID NO:1, and a light chain variable region of SEQ ID NO:2. In certain exemplary embodiments, Dupilumab comprises a heavy chain sequence of SEQ ID NO:9 and a light chain sequence of SEQ ID NO:10. Dupilumab is described in U.S. Pat. No. 7,608,693.

The primary objective of the study was to investigate the effects of mAb1 administered subcutaneously once weekly for 12 weeks as compared to placebo on reducing the incidence of asthma exacerbations in patients with persistent moderate-to-severe eosinophilic asthma. The secondary objectives of the study were to assess the safety and tolerability of mAb1 administered subcutaneously once weekly for 12 weeks in patients with persistent moderate to severe eosinophilic asthma, and to assess mAb1 serum concentrations following once weekly subcutaneous dosing for 12 weeks in patients with persistent moderate to severe eosinophilic asthma.

Prior to screening, patients were required to be on a stable dose of any of the following doses and formulations of ICS/LABA combination therapy (also called "background therapy") for at least 1 month:

- Fluticasone/salmeterol combination therapy
  - Advair® Diskus—dry powder inhaler (DPI): 250/50 μg BID or 500/50 μg BID; or
  - Advair® HFA—metered dose inhaler (MDI): 230/42 μg BID or 460/42 μg BID; or
- Budesonide/formoterol combination therapy (Symbicort® 160/9 μg BID or 320/9 μg BID); or
- Mometasone/formoterol combination therapy (Dulera® 200/10 μg BID or 400/10 μg BID)

Patients who were on budesonide/formoterol or mometasone/formoterol were switched to an equivalent dose of fluticasone/salmeterol at randomization (Day 1) and patients who had been on fluticasone/salmeterol remained on the same as background therapy.

Patients who satisfied the inclusion and exclusion criteria (see below) were randomized to one of the following treatments: 300 mg of mAb1 administered subcutaneously once weekly for 12 weeks; or placebo administered subcutaneously once weekly for 12 weeks.

The study comprised a 2-week screening period, a 12-week treatment period comprising a 4-week background therapy stable phase and an 8-week background therapy withdrawal phase post-randomization, followed by an 8-week post-treatment follow-up period.

Algorithm for Background Therapy (ICS/LABA) Withdrawal:

Patients remained on BID fluticasone/salmeterol background therapy for 4 weeks after starting add-on therapy or treatment of 300 mg mAb1 (or placebo). At 4 weeks post-randomization, patients were switched from the BID fluticasone/salmeterol combination therapy to an equivalent ICS dose of fluticasone monotherapy (comprising either FLOVENT® Diskus—DPI formulation of 250 ug or 500 μg BID; or FLOVENT® HFA—MDI formulation of 220 μg or 440 μg BID). The LABA component (i.e., salmeterol) was discontinued. At subsequent visits, beginning with week 6, the fluticasone dose was reduced by approximately 50%, provided the patient did not meet any of the criteria for an asthma exacerbation (as defined below). If no asthma exacerbations occurred, the ICS withdrawal proceeded according to the dosing schedule set forth in Table 1.

TABLE 1

Dosing schedule.

| Background therapy | Background therapy withdrawal phase | | | | |
|---|---|---|---|---|---|
| stable phase | Week 4 | Week 6 | Week 7 | Week 8 | Week 9 |
| Fluticasone/salmeterol (DPI): 250/50 μg BID | Fluticasone (DPI): 250 μg BID | 100 μg BID | 50 μg BID | 0 μg BID | 0 μg BID |
| Fluticasone/salmeterol (DPI): 500/50 μg BID | Fluticasone (DPI): 500 μg BID | 250 μg BID | 100 μg BID | 50 μg BID | 0 μg BID |
| Fluticasone/salmeterol (MDI): 230/42 μg BID | Fluticasone (MDI): 220 μg BID | 110 μg BID | 44 μg BID | 0 μg BID | 0 μg BID |
| Fluticasone/salmeterol (MDI): 460/42 μg BID | Fluticasone (MDI): 440 μg BID | 220 μg BID | 110 μg BID | 44 μg BID | 0 μg BID |

Upon completing 12 weeks of treatment with investigational product (or after early discontinuation), patients were placed on their original dose of fluticasone/salmeterol, budesonide/formoterol, or mometasone/formoterol (dose at study entry) and albuterol or levalbuterol as-needed to control their symptoms for an additional 8 weeks off study medication before a final safety evaluation.

A schematic of the study protocol is provided in FIG. 1.

Adult patients were included in the study based on the following criteria: (1) physician's diagnosis of persistent asthma for at least ≥12 months based on the Global Initiative for Asthma (GINA) 2009 Guidelines, whose airway inflammation is likely to be eosinophilic; and (2) whose asthma is partially controlled or uncontrolled in inhaled corticosteroids/long acting beta-agonists combination therapy according to the following criteria: (i) stable dose of either fluticasone/salmeterol combination therapy (DPI formulation: 250/50 μg BID or 500/50 μg BID or MDI formulation: 230/42 μg BID or 460/42 μg BID), or budesonide/formoterol combination therapy (160/9 μg BID or 320/9 μg BID), or mometasone/formoterol combination therapy (200/10 μg BID or 400/10 μg BID) for at least 1 month prior to screening; (ii) blood eosinophils ≥300 cells/μL or sputum eosinophils ≥3% during the screening phase; (iii) Juniper asthma control questionnaire (5-question version, ACQ) score of ≥1.5 and ≤3.0 at screening; (iv) FEV1≥50% predicted normal during the screening phase (3 attempts maximum) and on the randomization day prior to the first dose (3 attempts maximum); (v) has had within the 2 years prior to screening either treatment with one or more systemic (oral and/or parenteral) steroid bursts for worsening asthma or in-patient hospitalization or an emergency care visit for worsening asthma; and (vi) documented history of reversibility within 12 months of screening that meets the criterion—at least 12% and 200 mL in FEV1 after 200 μg to 400 μg (2 to 4 inhalations) of albuterol during the screening phase (3 attempts maximum), or documented history of a positive methacholine challenge (PD20 methacholine ≤8 mg) within 12 months prior to screening. Patients with moderate-to-severe asthma that is partially controlled or uncontrolled with moderate to high doses of combination therapy with inhaled corticosteroids and long-acting beta agonists (ADVAIR®, SYMBICORT® or DULERA®) and with blood eosinophils greater than or equal to 300 cells per microliter, or sputum eosinophils greater than or equal to 3% during the screening phase, were included in the study.

Patients who met all the inclusion criteria were screened for the following exclusion criteria: (1) patients less than 18 years of age or greater than 65 years of age; (2) clinically relevant abnormal laboratory values suggesting an unknown disease and requiring further evaluation; (3) chronic obstructive pulmonary disease (COPD) and/or other lung diseases impairing pulmonary function tests; (4) patients requiring beta-adrenergic receptor blockers for any reason; (5) current smoker or cessation of smoking within the 6 months prior to screening; (6) previous smoking with a smoking history >10 cigarette pack-years; (7) in-patient hospitalization or emergency care visit due to asthma exacerbation in the 2 months prior to screening; (8) plans to begin allergen immunotherapy within the study period; (9) exposure to another investigative antibody within a time period prior to screening that is less than 5 half-lives of the antibody but not less than 30 days, or if the half-life of the antibody is not known, then a time period prior to screening that is at least 6 months; (10) previous enrollment into the current study; (11) patient was the investigator, his/her family member or an employee at the investigational site; (12) known or suspected non-compliance, alcohol or drug abuse; (13) inability to follow the procedures of the study (e.g., due to language problems or psychological disorders); (14) reversal of sleep pattern (e.g., night shift worker); (15) treatment with drugs known to prolong QTc interval; (16) concomitant severe disease(s) for which the use of ICS (e.g., active or inactive pulmonary tuberculosis) or LABA (e.g., diabetes, cardiovascular diseases, hypertension, hyperthyroidism, thyrotoxicosis, etc.) are contra-indicated; (17) use of injectable glucocorticosteroids or oral systemic glucocorticosteroids within 2 months prior to screening or more than 3 courses within the 6 months prior to screening; (18) pre-treatment with variable doses of ICS, either alone or in combination with a non-steroidal controller (other than fluticasone/salmeterol combination therapy, budesonide/formoterol combination therapy, or mometasone/formoterol combination therapy); (19) patients receiving prohibited concomitant medications (listed below); (20) known allergy to doxycycline or related compounds; (21) pregnancy or intention to become pregnant during the course of the study, breast feeding or unwillingness to use an effective method of contraception; and (22) recent history of a parasitic infection or travel to a parasitic endemic area within 6 months prior to screening.

Patients remained on a constant dose of the background asthma therapy for the first four weeks of the study after which the dose of background therapy was reduced gradually. First, the long-acting beta agonist component of the background therapy was withdrawn at week 4, and then the inhaled corticosteroid dose was reduced by half every 2 weeks until week 12. Patients continued on study treatment until the end of the study or until they were withdrawn due to an asthma exacerbation or for any other reason.

B. Study Treatments

Investigational medicinal product(s): Dupilumab or Matching Placebo. Formulation: Sterile dupilumab 150 mg/mL solution for SC injection, provided in 5 mL glass vials. Each vial contains a withdrawable volume of 2 mL. Sterile placebo provided in identically matched glass 5 mL vials. Route(s) of administration: Subcutaneous (SC) injection. Dose regimen: Dupilumab 600 mg SC (loading dose) on D1 followed by weekly 300 mg SC injection for 15 weeks. Placebo SC loading dose on D1 followed by weekly SC injection for 15 weeks.

Non-investigational medicinal product(s) (if applicable): Formulation: Mometasone furoate (NASONEX®) 50 micrograms/actuation nasal spray contained in a bottle, that contained 18 g (140 actuations) of product formulation. Route of administration: Nasal spray. Dose regimen: After the screening visit (V1), all patients received mometasone furoate (NASONEX®) 50 μg/actuation nasal spray 2 actuations (50 μg/actuation) in each nostril twice daily (total daily dose of 400 μg), or once daily (total daily dose of 200 μg) until end of post-treatment observation period.

The following concomitant medications were not allowed during the duration of the study: any other inhaled steroid other than fluticasone/salmeterol combination therapy or fluticasone administered per the protocol (or budesonide/formoterol or mometasone/formoterol during the screening period); systemic or ocular steroids; LABAs other than the salmeterol component of the fluticasone/salmeterol combination therapy administered per the protocol; any other ICS/LABA combination products other than those given above; any inhaled anti-cholinergic agents (e.g., Ipratropium bromide or tiotropium); methylxanthines (theophylline, aminophyllines); cromones; anti-IgE therapy; lipoxygenase inhibitors; and leukotriene receptor antagonists or leukotriene synthesis inhibitors.

C. Efficacy of Treatment

The primary endpoint of this study was the occurrence of an exacerbation of asthma as defined by any of the following: (1) a 30% or greater reduction from baseline in morning peak expiratory flow (PEF) on two consecutive days; or (2) six or more additional reliever puffs of albuterol or levalbuterol in a 24 hour period (compared to baseline) on 2 consecutive days; or (3) deterioration of asthma, as determined by the Investigator, requiring: (a) systemic (oral and/or parenteral) steroid treatment, or (b) an increase in ICS times the last dose received prior to discontinuation from the study, or (c) hospitalization.

Secondary endpoints of the study included mean changes from baseline of the following parameters: (1) Forced expiratory volume in 1 second (FEV1) in liters measured at every visit; (2) Morning and evening peak expiratory flow rate (AM PEF and PM PEF) in liters/minute measured daily; (3) Daily Albuterol/Levalbuterol use in inhalations/day; (4) Five-item Asthma Control Questionnaire (ACQ5) score at every visit; and (5) Nighttime awakenings (no. of times per night) measured daily and (6) a 22-item Sino-Nasal Outcome Test (SNOT-22), evaluated at baseline and end of treatment (at Week 12), to assess upper airway symptoms. Secondary endpoints also included proportion of patients with a composite asthma event defined by a 30% or greater reduction from baseline in morning PEF on two consecutive days together with ≥6 additional reliever puffs of albuterol or levalbuterol in a 24-hour period (compared to baseline) on 2 consecutive days. PEF, ACQ5, asthma symptoms scores, nocturnal awakenings, and reliever medication use were captured in an electronic daily diary. Mean daily nocturnal awakenings, ranging from 0-10, were averaged from the previous 7 days. Morning and evening asthma symptom scores consisted of a non-validated patient-reported outcome assessed on a 5-point Likert-type scale, with higher scores indicating worse outcomes (Table 2). Patients recorded overall symptom scores twice a day prior to measuring PEF. Data were described as the average for the 7 days prior to the specified time point.

TABLE 2

| Asthma Symptom Score Assessment |
|---|
| A) Morning symptom score: |
| 0 = No asthma symptoms, slept through the night |
| 1 = Slept well, but some complaints in the morning. No nighttime awakenings |
| 2 = Woke up once because of asthma (including early awakening) |
| 3 = Woke up several times because of asthma (including early awakening) |
| 4 = Bad night, awake most of the night because of asthma |
| B) Evening symptom score: |
| 0 = Very well, no asthma symptoms |
| 1 = One episode of wheezing, cough, or breathlessness |
| 2 = More than one episode of wheezing, cough, or breathlessness without interference of normal activities |
| 3 = Wheezing, cough, or breathlessness most of the day, which interfered to some extent with normal activities |
| 4 = Asthma very bad. Unable to carry out daily activities as usual |

D. Adverse Events Monitoring

Safety was assessed throughout the study by monitoring Adverse Events and Serious Adverse Events.

An Adverse Event (AE) is any untoward medical occurrence in a subject or clinical investigation subject administered a pharmaceutical product. An AE can, therefore, be any unfavorable and unintended sign (including abnormal laboratory finding), symptom, or disease temporally associated with the use of a medicinal product, whether or not considered related to the medicinal (investigational) product. AEs also include: any worsening (i.e., any clinically significant change in frequency and/or intensity) of a pre-existing condition that is temporally associated with the use of the study drug; abnormal laboratory findings considered by the Investigator to be clinically significant; and any untoward medical occurrence.

A Serious Adverse Event (SAE) is any untoward medical occurrence that at any dose results in death; is life-threatening; requires in-patient hospitalization or prolongation of existing hospitalization; results in persistent or significant disability/incapacity; is a congenital anomaly/birth defect; or is an important medical event.

E. Statistical Methods

For the primary analysis of proportion of patients experiencing an asthma exacerbation, a logistic regression model was used to compare SAR group with placebo. The model included terms for treatment and stratification factor (prior ICS/LABA combination therapy dose). The primary analysis was performed based on modified intent-to-treat (mITT) population which included all randomized patients who received at least one dose of mAb1. A stratified chi-square test was also used to corroborate the primary analysis.

For secondary efficacy endpoints except SNOT-22, the change from baseline was analyzed using a mixed-effect model with repeated measures (MMRM) approach. The model included change from baseline values up to week 12 as response variables, and factors (fixed effects) for treatment, stratification factor, visit, treatment-by-visit interaction, baseline value, and baseline-by-visit interaction. Statistical inferences on treatment comparisons for the change from baseline at week 12 were derived from the mixed-effect model. Change from baseline in SNOT-22 was analyzed using an analysis of covariance (ANCOVA), with end of treatment measurements used to impute missing data. Pharmacodynamic effects were evaluated using MMRM models in a post hoc fashion. No adjustments were made for multiplicity, since there was only one primary endpoint and analysis. Safety variables including AEs, laboratory parameter, vital signs, ECG, clinical laboratory observations and physical examinations were summarized using descriptive statistics.

Demographic and clinical characteristics were summarized using descriptive characteristics. Plots of secondary and pharmacodynamic variables are presented as mean change from baseline over time with standard error. Comparison of treatment effects from the MMRM analyses are based on least square mean change (95% confidence intervals [CI]) from baseline at Week 12.

F. Results

The results observed with all 104 randomized patients (from 491 screened) who either completed or discontinued the treatment phase of the study are summarized below. All randomized patients were exposed to study treatment and included in the mITT population. Baseline characteristics were similar between groups. The demographic and clinical characteristics were also similar between the two groups (Table 3). As noted above, patients were treated either with 300 mg subcutaneous mAb1 once a week, or with placebo. The study treatment period was completed by 86.5% and 67.3% of the mAb1 and placebo patients, respectively. The most common cause of discontinuation was lack of efficacy, which was more frequent with placebo (21.2%) than mAb1 (1.9%).

TABLE 3

Baseline Demographic and Clinical Characteristics of Treatment Groups.*

| Variable | Placebo (N = 52) | mAb1 300 mg (N = 52) |
|---|---|---|
| Age (yr) | 41.6 ± 13.1 | 37.8 ± 13.2 |
| Male sex, no. (%) | 26 (50.0) | 26 (50.0) |
| Race or ethnic group, no. (%) | | |
| White | 38 (73.1) | 45 (86.5) |
| Black or African American | 9 (17.3) | 5 (9.6) |
| Asian | 3 (5.8) | 1 (1.9) |
| Other | 2 (3.8) | 1 (1.9) |
| Body mass index | | |
| Mean (kg/m$^2$) | 31.6 ± 7.0 | 31.3 ± 8.0 |
| ≥30, no. (%) | 25 (48.1) | 24 (46.2) |
| Duration of asthma (yr) | 26.9 ± 14.8 | 24.2 ± 12.6 |
| Number of asthma exacerbations in prior 2 years | 1.4 ± 1.3 | 1.4 ± 1.0 |
| Prior ICS/LABA combination therapy dose, no. (%) | | |
| High Dose | 41 (78.8) | 42 (80.8) |
| Low Dose | 11 (21.2) | 10 (19.2) |
| Blood eosinophils (× $10^{-1}$/l) | 0.47 ± 0.21 | 0.55 ± 0.19 |
| $FEV_1$ (l) | 2.54 ± 0.66 | 2.47 ± 0.65 |
| $FEV_1$ (% of predicted value) | 72.0 ± 12.7 | 72.0 ± 12.6 |
| PEF (l/min) | | |
| Morning | 406.9 ± 110.7 | 393.0 ± 101.1 |
| Evening | 416.6 ± 116.8 | 414.6 ± 102.3 |
| ACQ5 score | 2.1 ± 0.5 | 2.1 ± 0.5 |
| Asthma symptom score | | |
| Morning | 0.73 ± 0.63 | 0.75 ± 0.81 |
| Evening | 1.12 ± 0.73 | 0.92 ± 0.71 |
| Nocturnal awakenings per day | 0.21 ± 0.50 | 0.44 ± 0.80 |
| SNOT-22 | 26.2 ± 15.6 | 30.9 ± 14.8 |
| Inhalations of albuterol or levalbuterol/24-hour period | 2.0 ± 1.8 | 2.2 ± 2.4 |
| FeNO (ppb) | 35.0 ± 27.1 | 37.6 ± 28.1 |
| TARC (pg/ml) | 470.5 ± 204.7 | 496.1 ± 342.4 |
| Eotaxin-3 (pg/ml) | 117.3 ± 349.2 | 75.4 ± 44.0 |
| IgE (IU/ml) | 694.7 ± 1837.8 | 657.7 ± 1482.3 |

*Plus-minus values are means ± SD, except as otherwise noted. ACQ5 denotes the Asthma Control Questionnaire (5 question version), FeNO fraction of exhaled nitric oxide, $FEV_1$ forced expiratory volume in 1 second, IgE immunoglobulin E, PEF peak expiratory volume, SNOT-22 the 22-item Sinonasal Outcome Test, and TARC thymus and activation regulated chemokine.

(i) Primary Efficacy Endpoint

The incidence of asthma exacerbations in the placebo and mAb1 treatment groups is presented in Table 4.

TABLE 4

Incidence of Asthma Exacerbations in mITT population

| | Placebo (N = 52) | mAb1 (N = 52) |
|---|---|---|
| Patients With No Asthma Exacerbations | 29 (55.8%) | 49 (94.2%) |
| Patients With Asthma Exacerbations | 23 (44.2%) | 3 (5.8%) |
| Odds Ratio vs Placebo (95% Cl) | — | 0.077 (0.021, 0.279) |

There were a total of 26 asthma exacerbations during the treatment period, and no patients were hospitalized for asthma exacerbations. There were 23 patients (44.2%) who experienced an asthma exacerbation in the placebo group, whereas only 3 patients (5.8%) experienced an asthma exacerbation in the mAb1 treatment group. The odds ratio is 0.077 ($p<0.0001$) and the relative risk reduction is approximately 87%.

Out of the 26 asthma exacerbations experienced during this study, 9 were considered severe as demonstrated by a need for immediate intervention in the form of treatment with either systemic corticosteroids or with inhaled corticosteroids at 4 or more times the dose taken prior to the event. A summary of the incidence of severe asthma exacerbations is presented in Table 5.

TABLE 5

| Incidence of Severe Asthma Exacerbations in mITT population | | |
|---|---|---|
| | Placebo (N = 52) | mAb1 (N = 52) |
| Patients With No Asthma Exacerbations | 29 (55.8%) | 49 (94.2%) |
| Patients With Severe Asthma Exacerbations | 8 (15.4%) | 1 (1.9%) |
| Patients With Non-Severe Asthma Exacerbations | 15 (28.8%) | 2 (3.8%) |

As shown in Table 5, eight severe asthma exacerbations were observed in the placebo group, and only 1 severe asthma exacerbation was observed in the mAb1 treatment group. The remaining 15 asthma exacerbations in the placebo group and 2 in the mAb1 group met the protocol definition of exacerbation based on decreased morning PEF and/or increased albuterol/levalbuterol use. Within the active treatment group, a sustained improvement versus baseline was observed during the course of the study for all parameters, despite steroid withdrawal.

TABLE 6

| Exacerbation Events | | |
|---|---|---|
| Outcome | Placebo (N = 52) | mAb1 ( N = 52) |
| ≥30% reduction from baseline in morning PEF in a 24-hr period on 2 consecutive days | 10* (19.2) | 1 (1.9) |
| ≥6 additional inhalations of albuterol/levalbuterol in a 24-hr period on 2 consecutive days | 10 (19.2) | 1 (1.9) |
| Systemic steroid treatment | 5 (9.6) | 1 (1.9) |
| ≥4-fold increase in ICS from the previous dose | 3 (5.8) | 0 |
| Hospitalization | 0 | 0 |

*4 Placebo patients met both PEF and systemic steroid treatment criteria, and 1 placebo patient met both PEF and additional albuterol/levalbuterol use.

With mAb1, the time to exacerbation was longer, and the risk of exacerbation was reduced relative to placebo (hazard ration 0, 10; 95% CI 0.03, 0.34; P<0.001). An analysis of the time to asthma exacerbation by Kaplan-Meier Plot revealed that the effect of treatment with mAb1 is sustained over time, including after 8 weeks when patients are at higher risk of developing exacerbations due to steroid withdrawal.

Only 1 patient from the placebo group had a composite asthma event. A composite asthma event is defined as a 30% or greater reduction from baseline in morning PEF on 2 consecutive days together with ≥6 additional reliever puffs of albuterol or levalbuterol in a 24-hour period (compared to baseline) on 2 consecutive days.

(ii) Other Efficacy Endpoints

Lung function parameters (FEV1, AM PEF and PM PEF), asthma symptom-based endpoints (ACQ score, nighttime awakenings) and albuterol use were assessed for each patient at each visit. In addition, the SNOT-22 score was assessed at baseline and at the end of treatment. For all parameters, the baseline and Week 12 (LOCF) mean values along with the mean difference between treatment groups (ANOVA model for SNOT-22) are summarized in Table 7. In Table 7, the column labeled "Difference vs. Placebo" reflects the placebo-corrected value from baseline which takes into account changes that are observed in the value of the parameter as compared to the changes that were observed for that parameter in the placebo-treated group.

TABLE 7

| Secondary Parameters of Lung Function and Symptom Scores | | | | | |
|---|---|---|---|---|---|
| | N | Baseline Mean (SD) | Least-Squared Mean Change (SD) | Difference vs. Placebo | p value |
| FEV1 (L) | | | | | |
| Placebo | 52 | 2.54 (0.66) | −0.22 (0.06) | — | |
| mAb1 | 52 | 2.47 (0.65) | 0.05 (0.06) | 0.27 (0.11, 0.42) | 0.0009 |
| AM PEF (L/min) | | | | | |
| Placebo | 52 | 406.9 (110.7) | −20.7 (9.1) | — | |
| mAb1 | 51 | 393.0 (101.1) | 13.9 (8.8)† | 34.6 (10.6, 58.5) | 0.0051 |
| PM PEF (L/min) | | | | | |
| Placebo | 51 | 416.6 (116.8) | −18.4 (8.9)† | — | |
| mAb1 | 52 | 414.6 (102.3) | 4.3 (8.5) | 22.7 (−0.7, 46.0) | 0.0567 |
| Albuterol Use (Puffs/Day) | | | | | |
| Placebo | 52 | 2.0 (1.8) | 0.7 (0.3) | — | |
| mAb1 | 50 | 2.2 (2.4) | −1.3 (0.3)‡ | −2.0 (−2.9, −1.2) | <0.0001 |
| ACQ Score | | | | | |
| Placebo | 52 | 2.08 (0.52) | −0.27 (0.16) | — | |
| mAb1 | 52 | 2.09 (0.46) | −1.00 (0.16) | −0.73 (−1.15, −0.30) | 0.0011 |
| Night-time Awakenings (No. of times/night) | | | | | |
| Placebo | 52 | 0.2 (0.5) | 0.1 (0.1) | — | |
| mAb1 | 52 | 0.4 (0.8) | −0.2 (0.1) | −0.2 (−0.5, −0.0) | 0.0518 |

TABLE 7-continued

| Secondary Parameters of Lung Function and Symptom Scores | | | | | |
|---|---|---|---|---|---|
| | N | Baseline Mean (SD) | Least-Squared Mean Change (SD) | Difference vs. Placebo | p value |
| SOT22 Average Score | | | | | |
| Placebo | 51 | 26.24 (15.62) | 0.23 (2.15)† | — | |
| mAb1 | 50 | 30.92 (14.77) | −8.26 (2.20)‡ | −8.49 (−13.96, −3.03) | 0.0027 |

†51 patients with at least 1 post-baseline assessment.
‡50 patients with at least 1 post-baseline assessment.

Treatment with mAb1 resulted in a significant change from baseline in FEV1 at Week 1, which was maintained through Week 12 despite LABA and ICS withdrawal, with a small decrease in FEV1 at Week 5 coinciding with LABA withdrawal. Similar improvements were observed in morning PEF, but less so in evening PEF. The least-squared (LS) mean change from baseline to week 12 in FEV1 was −0.22 L for placebo and 0.05 L for the mAb1 group. (p=0.0009).

ACQ5 score improved in both treatment groups at Week 1. However, while ACQ5 improved further with mAb1 between Weeks 1 and 4, the placebo effect stabilized, maintaining the difference through Week 12.

Morning symptom scores increased from baseline to Week 12 with placebo. With mAb1, there was an initial decrease which remained below baseline through Week 12. A similar pattern (with greater variability) was observed for evening asthma symptom scores.

Nocturnal awakenings were stable from the placebo group through Week 6, then increased from Weeks 6 to 12. In contrast, nocturnal awakenings decreased in the mAb1 group by Week 1 and remained improved versus baseline through Week 12.

Changes in albuterol/levalbuterol use were similar to other secondary endpoints: an initial decrease followed by a return towards baseline with placebo. With mAb1, the initial decrease was maintained over time.

There was a non-significant difference at baseline between the SNOT-22 values with the mean placebo score at 26.24 and the mean mAb1 score at 39.02. At week 12, the LS mean change was a slight increase of 0.23 points for the placebo group and a mean decrease (improvement) of 8.26 points for the mAb1 group. This represented a magnitude of improvement of 8.49 points for the mAb1 group (p=0.0027).

TABLE 8

| Secondary Endpoints | | | | |
|---|---|---|---|---|
| Outcome | Placebo (N = 52) | mAb1 ( N = 52) | Difference vs Placebo (95% Cl)** | P Value |
| Kaplan-Meier estimate at 12 weeks | 46.0 (31.8, 60.2) | 5.8 (0.0, 2.1) | 0.10 (0.03 to 0.34) | <0.001 |
| Change in morning asthma symptom scores, baseline to week 12 | 0.3 ± 0.1 | −0.4 ± 0.1 | −0.7 (−0.9 to −0.4) | <0.001 |
| Change in evening asthma symptom scores, baseline to week 12 | 0.1 ± 0.1 | −0.6 ± 0.1 | −0.7 (−0.9 to −0.4) | <0.001 |

TABLE 9

| Change From Baseline at Week 12 in SNOT−22 Items Relevant to Upper Airway Disease. | | | | |
|---|---|---|---|---|
| | Least-Squares Mean Change ± Standard Error | | Difference vs | |
| SNOT-22 Subscale | Placebo ( N = 52) | mAb1 (N = 52) | Placebo (95% Cl) | P Value |
| Need to blow nose | −0.25 ± 0.17* | 0.95 ± 0.17† | −0.70 (−1.13, −0.26) | 0.002 |
| Nasal blockage | −0.20 ± 0.19* | −0.94 ± 0.19† | 0.75 (−1.22, −0.28) | 0.002 |
| Decreased sense of smell/taste | 0.04 ± 0.18* | −1.13 ± 0.18† | −1.16 (−1.62, −0.71) | <0.001 |

*51and †50 patients with at least 1 post-baseline assessment respectively

For all secondary endpoints, Week 12 measurements favored mAb1 treatment and were significant except for evening PEF and nocturnal awakenings (Table 7 and 8). Significant improvements with mAb1 were also observed for the three SNOT-22 items relevant to upper airway disease (Table 9)

(iii) Safety mAb1 was generally safe and well tolerated. Treatment-emergent adverse events (TEAEs) were reported similarly by 40 (76.9%) of placebo-treated patients and by 42 (80.8%) of mAb1-treated patients (Table 10). TEAEs were non-specific, generally mild to moderate in intensity and the majority recovered by the end of the study. An increased reporting of the following TEAEs was observed for mAb1 in comparison with placebo: injection site reactions were reported by 15 (28.8%) mAb1 patients and by 5 (9.6%) placebo patients; nasopharyngitis was reported by 7 (13.5%) mAb1 patients and 2 (3.8%) placebo patients; headache was reported by 6 (11.5%) mAb1 patients and 3 (5.85) placebo patients and nausea was reported by 4 (7.7%) mAb1 patients and 1 (1.9%) placebo patients.

TABLE 10

| Adverse Events. | | |
|---|---|---|
| Adverse event | Placebo (N = 52) | mAb1 300 mg (N = 52) |
| | no. of patients (%) | |
| Any adverse event | 40 (76.9) | 42 (80.8) |
| Any serious adverse event | 3 (5.8) | 1 (1.9) |
| Study discontinuation owing to adverse event | 3 (5.8) | 3 (5.8) |
| Death | 0 | 0 |
| Most common AEs* | | |
| Injection site reactions† | 5 (9.6) | 15 (28.8) |
| Nasopharyngitis | 2 (3.8) | 7 (13.5) |

TABLE 10-continued

Adverse Events.

| Adverse event | Placebo (N = 52) | mAb1 300 mg (N = 52) |
|---|---|---|
| Upper respiratory tract infection | 9 (17.3) | 7 (13.5) |
| Headache | 3 (5.8) | 6 (11.5) |
| Nausea | 1 (1.9) | 4 (7.7) |
| Arthropod bite | 0 | 3 (5.8) |
| Muscle spasms | 0 | 3 (5.8) |
| Nasal congestion | 1 (1.9) | 3 (5.8) |
| Rash | 1 (1.9) | 3 (5.8) |
| Urticaria | 0 | 3 (5.8) |
| Viral upper respiratory tract infection | 0 | 3 (5.8) |

*≥3 patients in any treatment group by Preferred Term

†Injection site reaction includes events reported as: injection site pain, injection site reaction, injection site erythema, injection site rash, injection site hematoma, injection site urticaria, injection site dermatitis, injection sites inflammation, injection site nodule, injection site pruritus and injection site swelling.

There were no deaths reported during the study period. Of the 4 treatment emergent serious adverse events (SAEs) reported: 1 mAb1 patient experienced bipolar disorder and 3 placebo patients experienced SAEs of asthma with pneumonia, gunshot wound with left pneumothorax, and right ankle fracture. None of these SAEs were considered as related to the mAb1 and all but the recent ankle fracture were recovered by the end of the study. There were no deaths.

A total of 6 patients discontinued the study due to a TEAE: 3 patients in the mAb1 group (bipolar disorder, asthma with wheezing, and angioedema) and 3 patients in the placebo group (upper respiratory tract infection, psoriasis and asthma). The TEAE of angioedema occurred in a 42-year old African-American female after the ninth study treatment dose as a pruritic, popular rash observed at, and distant to, the injection site. It persisted for one week, resolved after study treatment discontinuation, and prednisone and diphenhydramine treatment. It was deemed treatment-related. This AE was subsequent to milder rashes at the injection site after the first and sixth study treatment doses.

Among the most common AEs occurring in patients in any treatment group (Table 10), injection site reactions, nasopharyngitis, nausea, and headache occurred more frequently with mAb1 than placebo. No clinically significant changes in vital signs, physical examination, clinical laboratory or ECG findings were reported in either group.

G. Conclusion

Significant improvements were observed for lung function and other asthma control parameters. Efficacy was observed early and sustained despite background therapy withdrawal. A relative reduction of approximately 87% (p<0.0001) in the primary endpoint of the incidence of asthma exacerbations in persistent, moderate-to-severe asthma patients with eosinophilia was observed after 12-week treatment with 300 mg of mAb1 once weekly (5.8%) compared with placebo (44.2%). As shown in Table 7, clinically meaningful and statistically significant (without multiplicity adjustment) improvements with treatment compared with placebo were observed in lung function parameters (FEV1, PEF AM), asthma symptom scores (ACQ) and albuterol use. Positive trends were observed for PEF PM (p=0.0567) and nocturnal awakenings (p=0.0518). A statistically significant (without multiplicity adjustment) improvement was also observed for the SNOT-22 score. Within the active treatment group, a sustained improvement versus baseline was observed during the course of study for all parameters, despite LABA and ICS withdrawal. mAb1 was generally safe and well tolerated.

Example 2

Biomarker Studies

Biomarker analysis was conducted on samples taken from subjects who participated in clinical trials of mAb1 (see Example 1 above). In particular, serum/plasma biomarkers associated with TH2 inflammation such as thymus and activation chemokine (TARC; CCL17), Immunoglobulin E (IgE), eotaxin-3, periostin, carcinoembryonic antigen (CEA), YKL-40 and blood eosinophils were measured in samples from patients at baseline and at different time points following initiation of study treatment(s). Baseline levels of these biomarkers were assessed for potential predictive value for treatment response. In addition, the fraction of exhaled NO (FeNO) and induced sputum eosinophils and neutrophils were measured as biomarkers of bronchial inflammation. Exhaled nitric oxide assessment was conducted prior to spirometry and following a fast of at least 1 hour using a NIOX instrument (Aerocrine AB, Solna, Sweden). Biomarkers were analyzed using a mixed model and the least square mean derived from the model are reported below.

Asthma subjects (N=104) were administered either mAb1 (300 mg) or placebo subcutaneously, on days 1, 8, 15, 22, 29, 36, 43, 50, 57, 64, 71 and 78 of the study (i.e., 12 weekly doses) (see Example 1, above). Samples for biomarker analysis were collected from the antibody- and placebo-treated subjects at week 0, 1, 4, 8 and 12. Antigen-specific IgE was detected using the Phadiatop® test.

TARC, eotaxin-3 and IgE remained unchanged in response to placebo. In contrast, a rapid reduction in TARC (mean % change −22.7% vs +0.3%; p=0.0003) and eotaxin-3 (mean % change −39.62% vs 12.69%; p<0.0001) was observed within one week in patients treated with mAb1 and persisted until week 12: TARC: −26.0% vs +7.6% placebo (p=0.0005); Eotaxin-3: −45.67% vs +5.13% placebo (p<0.0001).

TARC levels responded within a week following exposure to mAb1 at 300 mg administered subcutaneously. TARC levels plateau at approximately 50% of the baseline level in mAb1-treated subjects, regardless of ICS withdrawal. The data suggest that TARC expression is more directly linked to IL-4R signaling, than FEV1 changes (which drop in parallel to ICS withdrawal [after Week 4]) and that IL-4R blockage induces a shift towards a TH1 signature, as observed with, for example, IFNγ administration. It might be possible to titrate the mAb1 dose using TARC (and for example CXCL10) in particular in patients requiring long term treatment and at risk for TH1 type immune diseases.

Total serum IgE also decreased following mAb1 treatment. Total serum IgE response was more heterogeneous and delayed compared to TARC response. Mean (SD) baseline IgE levels were 694.68 IU/L (1837.82) for the placebo group (n=52) and 657.66 (1482.25) for the mAb1 group (n=52), whereas median was 169.95 for the placebo group and 206.15 for the mAb1 group. Despite this heterogeneity, a trend towards IgE decrease in mAb1-exposed patients compared with placebo was observed—however, starting at week 4 only. Serum IgE was significantly reduced in the mAb1 group compared with placebo (mean % change, −10.1% vs +13.5%; p=0.0325) starting from week 4 and continued to decrease until week 12 (mean % change, −36.8% for mAb1 vs −5.5% for placebo; p<0.0001).

Changes from baseline and placebo at Week 12 for FeNO, TARC, eotaxin-3, and IgE all favored mAb1 (all P<0.001) (Table 11). No differences from baseline or between treatments were observed in YKL-40 or CEA.

TABLE 11

Percent Change From Baseline at Week 12 in Pharmacodynamic Endpoints.

| Outcome | Least-Squares Change ± Standard Placebo (N = 52) | Mean Percent Error mAb1 (N = 52) | P Value |
|---|---|---|---|
| FeNO | 35.0 ± 10.8 | 28.7 ± 11.2 | <0.001 |
| TARC | 7.6 ± 6.9 | −26.0 ± 6.9 | <0.001 |
| Eotaxin-3 | 5.1 ± 4.7 | −45.7 ± 4.7 | <0.001 |
| IgE | 5.5 ± 3.6 | −36.8 ± 3.6 | <0.001 |
| Blood eosinophils | 2.7 ± 15.8 | 41.6 ± 15.7 | 0.078 |

There was a transient decrease in periostin levels, followed by an increase with LABA/ICS withdrawal. Administration of mAb1 delayed the increase, but did not prevent the increase above baseline. No consistent treatment effect was observed with CEA and YKL-40. The number of blood eosinophils remained unchanged through Week 6, but then increased at Weeks 8 and 12. Peripheral blood eosinophil numbers were unchanged on placebo throughout treatment. The difference between the treatments was not significant, with the borderline increase driven by larger blood eosinophil elevations in only a few patients treated with mAb1. Little or no increases were observed in the majority of patients.

TABLE 12

Proportions of Patients Achieving Thresholds of Change in Blood Eosinophil Levels.

| Change in eosinophils | Number (%) of patients: Placebo (n = 52) | mAb1 (n = 52) |
|---|---|---|
| >15% Decrease | 13 (30.2) | 21 (47.7) |
| 15% Decrease-0% change | 7 (16.3) | 6 (13.6) |
| 0%-15% Increase | 8 (18.6) | 4 (9.1) |
| 15%-100% Increase | 13 (30.2) | 6 (13.6) |
| 100%-200% increase | 2 (4.7) | 3 (6.8) |
| >200% increase | 0 | 4 (9.1) |

Since only 3 mAb1 patients experienced asthma exacerbation during the study, no conclusion could be drawn regarding the association between baseline biomarker levels and asthma exacerbations.

mAb1 treatment was also associated with a significant decrease from baseline in FeNO at week 4, and FeNO remained below baseline through Week 12, regardless of ICS withdrawal (mean % change at week 12: −28.7 for mAb1 vs 35.0 for placebo; p<0.0001). In contrast, placebo FeNO values remained stable through week 8, followed by an increase at week 12 coincident with ICS withdrawal.

Forced expiratory volume in 1 second ($FEV_1$) improvement significantly correlated with FeNO reduction (r=−0.408, p=0.009) at week 12. Similarly, improvements in AM-PEF and PM-PEF correlated with FeNO reduction. Other correlations with FeNO were not significant. See Table 13.

TABLE 13

Correlation between $FEV_1$ and PD Endpoints.

| Outcome | Correlation | P Value |
|---|---|---|
| FeNO | −0.408 | <0.009 |
| TARC | −0.248 | 0.10 |
| Eotaxin-3 | −0.146 | 0.34 |
| IgE | −0.279 | 0.06 |
| Blood eosinophils | 0.165 | 0.28 |

Scatter plot analysis of baseline eosinophils versus change from baseline in FEV1 at week 12 did not seem to suggest association of baseline eosinophils and treatment effect, as measured by change from baseline in FEV1 at week 12 in the study population (baseline eosinophils ≥0.3 Giga/L). Baseline eosinophils correlated with decreased ACQ and decreased albuterol/levalbuterol use. Periostin and YKL-40 at baseline correlated with decreased ACQ.

The FEV1 change from baseline at week 12 was compounded by the withdrawal of ICS (starting at week 4). Similar analyses did not suggest association between baseline TARC or IgE and change from baseline in FEV1 at week 12 in the study population (baseline eosinophils ≥0.3 Giga/L).

SUMMARY

These results show that mAb1 significantly reduced serum biomarkers associated with Th2 inflammation (TARC, eotaxin-3 and IgE) and bronchial inflammation (FeNO) in adult asthma patients. The correlation between FeNO reduction and $FEV_1$ improvement suggests a relationship between IL-4/IL-13 mediated anti-inflammatory activity and improvement in pulmonary function in moderate-to-severe, uncontrolled asthma.

Example 3

Clinical Trial of Subcutaneously Administered Anti-IL-4R Antibody (mAb1) in Patients with Bilateral Nasal Polyposis and Chronic Symptoms of Sinusitis A. Study Objectives and Overview The positive effect of mAb1 on the SNOT-22 test described in Example 1 suggested that the anti-IL-4R antibody might also be effective for treating chronic sinusitis with nasal polyps. Further, nasal polyps are most commonly eosinophilic/TH2 driven, and mAb1 significantly reduced biomarkers associated with Th2 inflammation (see Example 2). A clinical trial was therefore designed to test the therapeutic effect of mAb1 on chronic sinusitis with nasal polyps.

A randomized, double-blind, phase 2, placebo controlled, 2 arm study was performed to evaluate mAb1 administered once a week (QW) subcutaneously (SC) for 16 weeks in patients having chronic sinusitis with nasal polyps (bilateral nasal polyposis and chronic symptoms of sinusitis).

The primary efficacy evaluation was the change from baseline at week 16 in bilateral endoscopic Nasal Polyp Score (NPS) in an intent to treat (ITT) population using an MMRM analysis. The main secondary efficacy analyses included the SNOT-22 score, loss of sense of smell (daily AM/PM daily evaluations), smell test (UPSIT), subject-assessed symptoms of rhinitis (daily AM/PM evaluations), Lund-Mackay sinus CT scan score (central reading), nasal peak inspiratory flow (daily AM/PM evaluations) and a responder analysis (defined as 1 or 2-point improvement in total NPS at week 16 compared to baseline).

mAb1 was administered concomitantly with Mometasone Furoate Nasal Spray (MFNS) (2 actuations of NASONEX® 50 micrograms/actuation per nostril twice daily). There is high co-morbidity of NP with asthma, aspirin/nonsteroidal anti-inflammatory drug (NSAID) hypersensitivity and previous surgeries, and therefore patients were allowed to enter the study unless they presented any of the exclusion criteria described below. 60 patients were randomized into 2 treatment groups of 30 patients per group. To ensure at least 30 patients with co-morbid asthma were included in the study, recruitment of NP patients without co-morbid asthma stopped when approximately 30 patients without asthma were randomized. Ultimately, there were 35 patients with asthma who participated in the study, and 25 patients without asthma who participated. Both the patient and the investigator were blinded to the assigned treatment group.

The study consisted of three periods: 1) a four week screening run in period on MFNS (Visit 1); (2) a 16 week randomized mAb1 or placebo treatment period (visits 2-18); and (3) a 16 week post-treatment period to assay pharmacokinetics, immunogenicity, safety and efficacy (visits 19-22). The total duration of the study is up to 36 weeks.

The primary endpoint was the change from baseline at week 16 in bilateral NPS.

Numerous secondary efficacy endpoints were measured to more comprehensively evaluate the efficacy of mAb1. The study explored improvements in SNOT-22 score, loss of sense of smell (daily AM/PM daily evaluations), smell test (UPSIT), subject-assessed symptoms of rhinitis (daily AM/PM evaluations), Lund-Mackay sinus CT scan score (central reading), nasal peak inspiratory flow (daily AM/PM evaluations) and a responder analysis (defined as 1 or 2-point improvement in total NPS at week 16 compared to baseline).

These endpoints, together with exploratory sub-group analysis and biomarkers provided the information on the therapeutic value of mAb1 to reduce nasal polyp score and to improve symptoms in NP and its subsets. The sustainability of the effect was also explored through the 4-month post-treatment evaluation period.

The 300 mg QW dose regimen saturated apparent target mediated clearance level (10-15 mg/L). This regimen was tested and provided statistically significant and clinically relevant response in two previous proof of concept studies performed with mAb1 in asthma and atopic dermatitis (see, e.g., Example 1 above, U.S. Ser. Nos. 61/805,797 and 61/816,191). The first dose employed a loading dose of 600 mg in order to achieve faster steady-state concentration. This loading dose range is supported by the acceptable safety profile of the highest loading dose (600 mg) demonstrated in a prior study conducted in Japanese healthy subjects.

In addition, given that the Cmax after 600 mg loading dose is around 70 mg/L and that the steady state Ctrough of 300 mg QW is around 150 mg/L, the Cmax after the proposed dosing regimen (i.e., 600 mg loading dose followed by 300 mg QW) was below the mean Cmax of 12 mg/kg IV dose (421 mg/L), the highest single dose tested in healthy subjects that was well tolerated, providing additional confidence that this dose regimen should have an acceptable safety profile.

Patient inclusion criteria included (i) a physician endoscopic diagnosis of bilateral nasal polyposis (i.e., a minimum bilateral nasal polyp score of 5 out of a maximum score of 8 for both nostrils, with at least a score of 2 for each nostril, despite completion of a prior Intranasal Corticosteroid (INCS) treatment) for at least 8 weeks before screening, and (ii) chronic symptoms of sinusitis, which are the presence of at least two of the following symptoms prior to screening: nasal blockade/obstruction/congestion or nasal discharge (anterior/posterior nasal drip); facial pain/pressure; and reduction or loss of smell.

Patients met these criteria were screened for the following exclusion criteria: age <18 or >65 years; any technical/administrative reason that made it impossible to randomize the patient in the study; previous participation in any clinical trial of mAb1; a SNOT22 score <7; receipt of any other investigational drug or prohibited therapy for this study within 2 months before screening or 5 half-lives, whichever was longer; receipt of oral corticosteroids (OCS) or intranasal corticosteroid drops within 2 months or 1 month before screening or scheduled to receive OCS during the study period for another condition; treatment with mAb or immunosuppressive therapy; treatment with an anti-immunoglobulin E (IgE) therapy (e.g., omalizumab) within 130 days of visit 1; treatment with a leukotriene antagonist/modifier for patients who were not on a continuous treatment for ≥30 days prior to visit 1; initiation of allergen immunotherapy within 3 months prior to visit 1 or a plan to begin therapy during the screening period or the randomized treatment period; any nasal surgery within six months before screening or have had more than five sinonasal surgeries in the past of which maximal two were surgeries changing the lateral wall structure of the nose; or a condition/concomitant disease that makes a patient non-evaluable for the primary efficacy endpoint (e.g., antrochoanal polyps; nasal septal deviation that would occlude at least one nostril; acute sinusitis, nasal infection or upper respiratory infection at screening or in the two weeks before screening; ongoing rhinitis medicamentosa; Churg-Strauss syndrome, Young's syndrome, Kartagener's syndrome or dyskinetic ciliary syndromes, Cystic fibrosis; signs or a CT scan suggestive of allergic fungal rhinosinusitis). Patients with co-morbid asthma were excluded if: the patient had a forced expiratory volume (FEV1) of 60% or less; an exacerbation requiring systemic (oral and/or parenteral) steroid treatment or hospitalization (>24 h) for treatment of asthma, had occurred within 3 months prior screening; or the patient was receiving a dose higher than 1000 μg fluticasone or the equivalent of inhaled corticosteroids. Other exclusion criteria included patients with short life expectancy (less than 6 months); patients receiving concomitant treatment prohibited in the study; women who were pregnant or intend to become pregnant during the study, or breast-feeding women. Other exclusion criteria included concomitant severe diseases (e.g., active and inactive pulmonary tuberculosis, Diabetes mellitus etc.); diagnosed active parasitic infection; suspected or high risk of parasitic infection; history of human immunodeficiency virus (HIV) infection or positive HIV screen at visit 1; evidence of acute or chronic infection; known or suspected immunosuppression, including history of invasive opportunistic infections (e.g., tuberculosis, histoplasmosis, listeriosis, coccidioidomycosis, pneumocystosis, aspergillosis), despite infection resolution; live vaccinations within 12 weeks prior to visit 1 or planned vaccinations during the study; patients with active autoimmune disease or patients using immunosuppressive therapy for autoimmune disease (e.g., Hashimoto's thyroiditis, Graves' disease, inflammatory bowel disease, primary biliary cirrhosis, systemic lupus erythematous, multiple sclerosis, psoriasis vulgaris, rheumatoid arthritis); patients with positive or indeterminate hepatitis B surface antigen (HBsAg), hepatitis B core antibody (HBcAb), or hepatitis C antibody at visit 1; and patients with liver injury related criteria (e.g., underlying hepatobiliary disease, or ALT>3 ULN).

B. Study Treatments

Investigational Product: Sterile mAb1 of various concentrations were provided in 5 mL glass vials. Each vial contained a withdrawable volume of 2 mL: 150 mg/mL solution (300 mg dose/2 mL). Sterile placebo was provided in identically matched glass 5 mL vials, where each vial contained a deliverable volume of 2 mL.

mAb1 was administered every 7±2 days (QW). The doses of mAb1 were separated by ≥5 days to avoid an overdose. At Visit 2 (V2), 2 injections were performed. After V2, one injection of mAb1 was performed weekly at the investigational site throughout the randomized treatment period. The mAb1 was administered following clinic procedures and blood collection. Patients were monitored for at least 1 hour after each administration for any signs or symptoms of a local site injection or hypersensitivity reaction. Subcutaneous injection sites were alternated among the 4 quadrants of the abdomen (avoiding navel and waist areas) or upper thighs so that the same site was not injected for two consecutive times/weeks.

On a daily basis throughout the study, the subject used an electronic diary to record daily use of Mometasone Furoate (MFNS). MFNS (NASONEX®) 50 micrograms/actuation nasal spray, was contained in a bottle, that contained 18 g (140 actuations) of product formulation.

Screening Period: Prior to screening, subjects were on a stable dose of intranasal corticosteroids (INCS) for ≥2 month prior to Visit 1 (V1). If the patient was using an alternative INCS product other than MFNS prior to the screening visit, at V1, the patient was switched to MFNS. After V1, all patients entered a run-in period of 4 weeks where they received MFNS: 2 actuations (50 μg/actuation) in each nostril twice daily (BID) (total daily dose of 400 μg), unless they were intolerant to BID INCS in which case, they stayed on the lower dose (QD) regimen. To be accepted for the study, patients also had the presence of at least two of the following symptoms prior to screening: nasal blockade/obstruction/congestion or nasal discharge (anterior/posterior nasal drip); +/−facial pain/pressure or +/−reduction or loss of smell Treatment Period: The treatment period proceeded as indicated in the study flow-chart at Table 14.

TABLE 14

| | Screen-ing | Randomized treatment period | | | | | | | | | | | | | | | | Post-treatment period | | | |
|---|---|---|---|---|---|---|---|---|---|---|---|---|---|---|---|---|---|---|---|---|---|
| | period | RDN | | | | | | | | | | | | | | | EOT[a] | | | | EOS |
| VISIT | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
| Week (DAY) | W-4 (D-28) | W0 (D1) | 1 | 2 | 3 | 4 | 5 | 6 | 7 | 8 | 9 | 10 | 11 | 12 | 13 | 14 | 15 | 16 | 20 | 24 | 28 | 32 |
| Inclusion Criteria including Informed Consent (s) | X | X | | | | | | | | | | | | | | | | | | | | |
| Exclusion Criteria | X | X | | | | | | | | | | | | | | | | | | | | |
| Patient Demography | X | | | | | | | | | | | | | | | | | | | | | |
| Medical/Surgical History | X | | | | | | | | | | | | | | | | | | | | | |
| Prior Medication History[b] | X | | | | | | | | | | | | | | | | | | | | | |
| Physical Examination | X | | | | | | | | | | | | | | | | | X | | | | X |
| Spirometry[c] | | X | | | | X | | | | X | | | | X | | | | X | | | | |
| Randomization | | X | | | | | | | | | | | | | | | | | | | | |
| Treatment: | | | | | | | | | | | | | | | | | | | | | | |
| mAb1 weekly SC administration[d] | X | X (loading) | X | X | X | X | X | X | X | X | X | X | X | X | X | X | | | | | | |
| Call IVRS | X | X | X | X | X | X | X | X | X | X | X | X | X | X | X | X | X | X | X | | | |
| Dispense or download electronic diary/NPIF[e] | X | X | | | | X | | | | X | | | | X | | | | X | X | X | X | X |
| NIMP (MFNS) | ------ | ------ | ------ | ------ | ------ | ------ | ------ | ------ | ------ | ------ | ------ | ------ | ------ | ------ | ------ | ------ | ------ | ------ | ------ | ------ | ------ | ------ |
| Record concomitant medication | ------ | ------ | ------ | ------ | ------ | ------ | ------ | ------ | ------ | ------ | ------ | ------ | ------ | ------ | ------ | ------ | ------ | ------ | ------ | ------ | ------ | ------ |
| Efficacy | | | | | | | | | | | | | | | | | | | | | | |
| Nasal endoscopy | X | X | | | | X | | | | X | | | | X | | | | X | | | | X |
| CT scan[g] | | X | | | | | | | | | | | | | | | | X | | | | |
| Smell test (UPSIT) | | X | | | | | | | | X | | | | | | | | X | | | | |
| SNOT-22 | X | X | | | | X | | | | X | | | | X | | | | X | | | | X |
| Visual analogue scale (VAS) | | X | | | | X | | | | X | | | | X | | | | X | | | | X |
| QoL (SF-36, EQ-5D) | | X | | | | X | | | | X | | | | X | | | | X | | | | X |
| Nasal polyp related resource use questionnaire | | X | | | | X | | | | X | | | | X | | | | X | | | | X |
| ACQ-5[h] | | X | | | | X | | | | X | | | | X | | | | X | | | | X |
| Safety | | | | | | | | | | | | | | | | | | | | | | |
| AE/SAE recording (if any) | ------ | ------ | ------ | ------ | ------ | ------ | ------ | ------ | ------ | ------ | ------ | ------ | ------ | ------ | ------ | ------ | ------ | ------ | ------ | ------ | ------ | ------ |
| Vital Signs | X | X | | | | X | | | | X | | | | X | | | | X | X | X | X | X |
| ECG | X | | | | | | | | | X | | | | X | | | | X | | | | X |

TABLE 14-continued

| | Screening | Randomized treatment period | | | | | | | | | | | | | | | | | Post-treatment period | | | |
|---|---|---|---|---|---|---|---|---|---|---|---|---|---|---|---|---|---|---|---|---|---|---|
| | period 1 | RDN 2 | | | | | | | | | | | | | | | | EO T[a] | | | | EO S |
| VISIT | W-4 | W0 | 3 | 4 | 5 | 6 | 7 | 8 | 9 | 10 | 11 | 12 | 13 | 14 | 15 | 16 | 17 | 18 | 19 | 20 | 21 | 22 |
| Week (DAY) | (D-28) | (D1) | 1 | 2 | 3 | 4 | 5 | 6 | 7 | 8 | 9 | 10 | 11 | 12 | 13 | 14 | 15 | 16 | 20 | 24 | 28 | 32 |
| Laboratory Testing | | | | | | | | | | | | | | | | | | | | | | |
| Clinical laboratory X testing[i] | X | | | | X | | | | X | | | | X | | | | X | | X | | X | |
| Urinalysis (dipstick) X | | | | | | | | | X | | | | | | | | X | | | | X | |
| Pregnancy test (for X WOCBP)[j] | X | | | | X | | | | X | | | | X | | | | X | | | | X | |
| PK/Anti-drug antibody sampling PK[k] | | X | | X | | X | | | | X | | | | X | | | | X | X | X | X | X |
| Serum Biomarker sampling | | X | | X | | X | | | | X | | | | X | | | | X | X | | | X |
| Archival nasal secretion sampling[m] | | X | | | | X | | | | X | | | | X | | | | X | X | | | |
| Polyp biopsy[n] | | X | | | | | | | | | | | | | | | | X | | | | |
| Stored DNA sampling | | X | | | | | | | | | | | | | | | | | | | | |
| Stored whole blood RNA sampling[o] | | X | | X | | | | | | | | | | | | | | X | | | | X |

The Screening Period is 28 days in duration to run in any patient on MFNS, and to collect baseline data. V2 will take place 28 days +/−2 day window after V1

[a]No mAb1 administration during this visit. Patients who discontinue treatment early will be assessed as soon as possible using the procedures normally planned for the End-of-treatment Visit and the 4 Post-treatment Period Visits.

[b]Prior to screening, patients must be on a stable dose of INCS for more than 8 weeks

[c]Spirometry: all patients should have FEV1 anytime during Screening Period (before V2) and at the other scheduled visits during the Randomized treatment period

[d]Weekly mAb1 administrations starting from V2 at the site investigational site must be separated by at least 5 days.

[e]Electronic diary/NPIF meter is used for daily recording of MFNS use, nocturnal awakenings, morning and evening NPIF and rhinosinusitis symptom scores 1) nasal congestion/obstruction 2) anterior rhinorrhea (runny nose), 3) posterior rhinorrhea (post nasal drip), and 4) loss of sense of smell, scored using a 0-3 categorical scale where 0 = no symptoms, 1 = mild symptoms, 2 = moderate symptoms and 3 = severe symptoms); This device is dispensed at Visit 1 and information is downloaded from this device on the other indicated days. The average of the last 7 days before V2 is needed to determine the baseline value

[f]Nasal endoscopy: endoscopy (including use of decongestants before the procedure) will be performed after all other efficacy assessments have been completed for each visit; Standard video sequences will be downloaded by the investigator to the central readers secured Internet site. For eligibility central reading of V1 will be used. At V2 investigator review V1 results from central reader to confirm entry criteria and reconfirm eligibility based on review of Inclusion/Exclusion Criteria and the V2 endoscopy local reading

[g]CT scan should be performed anytime during Screening Period before a first administration of mAb1 and at EOT. Central reading will be used for comparison baseline (BL) to EOT

[h]Only for patients with co-morbid asthma, ACQ-5 is completed in the patient's electronic diary during clinic visits.

[i]Hematology: hemoglobin, hematocrit, platelet count, total white blood cell count with five-part differential count, differential count, and total red blood cell count. Serum chemistry (Obtain fasting at planned visits but V2): creatinine, blood urea nitrogen, glucose, uric acid, total cholesterol, total protein, albumin, total bilirubin, alanine aminotransferase, aspartate aminotransferase, alkaline phosphatase, electrolytes (sodium, potassium, chloride), bicarbonate, and creatine phosphokinase. Clinical laboratory testing at Visit 1 includes hepatitis screen (hepatitis B surface antigen (HBsAg), Hepatitis B IgM core antibody (HBcAb-IgM), hepatitis C antibodies (HC Ab), HIV screen (Anti-HIV-1 and HIV-2 antibodies), anti-nuclear antibody (ANA). Clinical laboratory testing at Visit 2 is limited to hematology and a separate hematology sample obtained for local analysis. Note: Anti-ds DNA antibody will be tested if ANA is positive (>1:160 titer). Clinical lab testing at Visit 2 consists of hematology only

[j]Serum pregnancy test at Visit 1 and urine pregnancy tests at other visits. A negative result must be obtained at Visits 1 and 2 prior to randomization visits

[k]Serum pharmacokinetic samples, immune response assessment (ADA) samples and optional whole blood RNA samples will be collected prior to administration of investigational product during the Randomized Treatment Period. During the post-treatment period PK samples will be collected at all visits and ADA samples only at EOS visit. Patients with titers >1000 of the ADA at last visit may be followed after the study. Blood samples for PK and ADA assessment will be collected at any time in case an SAE occurs.

[m]Nasal secretion samples will be collected and stored for potential future discovery efforts to identify predictors of treatment response

[n]Optional polyp biopsies will be collected in selected clinical centers

[o]Samples will be collected prior to administration of investigational product during the Randomized Treatment Period During the treatment period, patients continued the stable dose of mometasone furoate: two actuations of MFNS in each nostril BID or QD (in case patient cannot tolerate the high dose). At Visit 2, patients were administered the SNOT-22 test, VAS and QoL questionnaires (SF-36, EQ-5D, Nasal polyp related resource use questionnaire), the smell test, and the ACQ-5 in patients with asthma.

Clinical laboratory testing at Visit 2 was limited to hematology, pharmacokinetics, anti-drug antibodies, biomarkers in serum and plasma, allergen-specific IgE panel sampling. Blood samples were taken prior to administration of mAb1. Nasal secretion sampling for biomarkers. For those patients who had signed a specific informed consent form, a blood sample was collected for DNA and RNA sampling (prior to administration of investigational product during the randomized treatment period).

Temporary treatment discontinuation was considered by the investigator because of suspected Adverse Events (AEs). Re-initiation of treatment with mAb1 was done under close and appropriate clinical/and or laboratory monitoring once the investigator had considered according to his/her best medical judgment that the responsibility of mAb1 in the occurrence of the concerned event was unlikely and if the selection criteria for the study were still met.

An AE was any untoward medical occurrence in a patient or clinical investigation patient administered a pharmaceutical product and which did not necessarily have to have a causal relationship with the treatment.

A serious adverse event (SAE) was any untoward medical occurrence that at any dose: resulted in death, or was life-threatening, (the term "life-threatening" in the definition of "serious" referred to an event in which the patient was at risk of death at the time of the event; it did not refer to an event which hypothetically might have caused death if it were more severe); required inpatient hospitalization or prolongation of existing hospitalization, or resulted in persistent or significant disability/incapacity, or was a congenital anomaly/birth defect; was a medically important event. Medical and scientific judgment was exercised in deciding whether expedited reporting was appropriate in other situations, such as important medical events that were not immediately life-threatening or resulted in death or hospitalization but could have jeopardized the patient or could have required intervention (i.e., specific measures or corrective treatment) to prevent one of the other outcomes listed in the definition above (the following list of medically important events was intended to serve as a guideline for determining which condition had to be considered as a medically important event. The list was not intended to be exhaustive: intensive treatment in an emergency room or at home for: allergic bronchospasm, anaphylaxis, blood dyscrasias (i.e., agranulocytosis, aplastic anemia, bone marrow aplasia, myelodysplasia, pancytopenia, etc.), convulsions (seizures, epilepsy, epileptic fit, absence, etc.), development of drug dependency or drug abuse); ALT>3×ULN+ total bilirubin>2×ULN or asymptomatic ALT increase>10× ULN; Suicide attempt or any event suggestive of suicidality; syncope, loss of consciousness (except if documented as a consequence of blood sampling); bullous cutaneous eruptions; cancers diagnosed during the study or aggravated during the study; chronic neurodegenerative diseases (newly diagnosed) or aggravated during the study (only if judged unusual/significant by the Investigators in studies assessing specifically the effect of a study drug on these diseases).

Post-treatment Period: Upon completing the randomized treatment period (or following early discontinuation of mAb1), patients continued treatment with the stable dose of MFNS maintained over the randomized treatment period, or modified treatment based on medical judgment.

The following concomitant treatments were not permitted during the screening period and the randomized treatment period: use of intranasal medication that would interfere with the symptoms of diseases (antihistamines, nasal atropine, ipratropium bromide, nasal cromolyn), except nasal saline; INCS drops; systemic corticosteroid; decongestion (topical or systemic), except before endoscopy; long term use of systemic antibiotics (for 2 weeks or more); lipoxygenase inhibitors; any immunosuppressive treatment including but not limited to methotrexate, cyclosporine, mycophenolate, tacrilomus, gold, penicillamine, sulfasalazine, hydroxychloroquine, azathioprine, cyclophosphamide; anti-immunoglobulin E (IgE) therapy (omalizumab); and aspirin or NSAID in patients with hypersensitivity to aspirin.

The following concomitant treatments were allowed: MFNS during the screening and throughout the whole study; nasal normal saline; topical decongestants (e.g., oxymetazoline hydrochloride to reduce the swelling and widen the path for the endoscope), as well as a topical anesthetic, e.g., lidocaine was allowed before endoscopy; short term use of antibiotics (<2 weeks); and for patients with asthma, SABA, LABA, and methylxanthines (e.g., theophylline, aminophyllines). The following inhaled corticosteroids were allowed for patients on a stable dose ≤1000 μg Fluticasone (or the equivalent dose of another inhaled CS; see Table 16) and only for patients that were on a stable dose ≥30 days prior to visit 1: Leukotriene antagonists/modifiers were permitted during the study, only for patients that were on a continuous treatment for ≥30 days prior to visit 1; systemic antihistamines; and initiation of allergen immunotherapy (allergen immunotherapy in place for ≥3 months prior to visit 1 was permitted).

C. Efficacy of Treatment

The primary endpoint of this study was the change from baseline at week 16 in bilateral endoscopic Nasal Polyp Score. (See Table 15.)

TABLE 15

| Polyp score | Polyp size |
|---|---|
| 0 | No polyps |
| 1 | Small polyps in the middle meatus not reaching below the inferior border of the middle turbinate |
| 2 | Polyps reaching below the lower border of the middle turbinate |
| 3 | Large polyps reaching the lower border of the inferior turbinate or polyps medial to the middle turbinate |
| 4 | Large polyps causing complete obstruction of the inferior nasal cavity |

Nasal endoscopy was performed at the end of the scheduled visits and preceded by local administration of anesthetic drugs in combination with a decongestant. Standard video sequences were downloaded or sent to a centralized reader. Centralized imaging data assessments and scoring by an independent physician reviewer for the imaging data was performed for all endoscopies. To confirm eligibility at V2, only the V1 central reading was made available to the site. The final results of central reading were made available after the study.

For the analysis of the primary endpoint, central reading of V2 was used for comparison with End Of Treatment (EOT) reading. The sites removed subject-identifying information from the imaging data header prior to sending the imaging data to the central reader.

Secondary endpoints of the study included change from baseline at week 16 in: patient reported symptoms (including SNOT-22); subject-assessed nasal congestion/obstruction, anterior rhinorrhea (runny nose), posterior rhinorrhea (post nasal drip), and loss of sense of smell, (daily AM and PM e-diary) month average; number of nocturnal awakenings; patient-rated rhinosinusitis symptoms severity using a visual analog scale (VAS); 5-item Asthma Control Questionnaire (ACQ-5) in asthma sub-group); Nasal Peak Inspiratory Flow (NPIF); smell test (UPSIT); NPS in patients with co-morbid asthma; CT scan assessments; spirometry (overall and in sub-group with asthma); time to first response (≥1 point improvement) in NPS; time to study treatment discontinuation; and incidence of treatment discontinuation due to need for OCS or nasal surgery.

Quality of life (QoL) end points included change from baseline at week 16 in: 36-item Short Form health survey (SF36); European Quality of life scale (EQ-5D); and nasal polyp related resource use questionnaire.

Disease-specific efficacy measures included Computed Tomography (CT). CT of the sinuses was performed before V2 and at EOT. For both Lund-Mackay scores and 3D volumetric measurement of the maxillary sinus, the same acquisitions (sequences) were used for centralized imaging data assessments and scoring by an independent physician reviewer for the imaging data. Central reading of V2 was used for comparison with EOT. The final results of central reading were made available after the study.

For three-dimensional volumetric measurement of the maxillary sinus, central reading before V2 was used for comparison with EOT reading. The sites removed subject-identifying information from the imaging data header prior to sending the imaging data to the central reader. The % change in opacification from BL to EOT was calculated.

At screening (visit 1), patients were issued an NPIF meter for recording morning (AM) and evening (PM) NPIF. The patients were instructed to record the following variables in the e-diary on a daily basis: AM NPIF performed within 15 minutes after arising (between 6 am and 10 am) prior to taking MFNS; and PM NPIF performed in the evening (between 6 pm and 10 pm) prior to taking MFNS.

Three NPIF efforts were performed by the patient; all three values were recorded by the patient in the e-diary, and the highest value was used for evaluation. The baseline AM NPIF was the mean AM measurement recorded for the 28 days prior to the first dose of investigational product, and baseline PM NPIF was the mean PM measurement recorded for the 28 days prior to the first dose of investigational product.

To assess disease-specific, daily symptoms, the patient used an electronic diary to: respond to the morning and evening individual rhinosinusitis symptom questions using a 0-3 categorical scale (where 0=no symptoms, 1=mild symptoms, 2=moderate symptoms and 3=severe symptoms), and including the symptoms of congestion and/or obstruction, anterior rhinorrhea (runny nose), posterior rhinorrhea (post-nasal drip), and loss of sense of smell. The number of nocturnal awakenings was also recorded.

The same safety assessments were applied across all arms. Adverse events, including SAEs and Adverse Events of Special Interest (AESI), were collected at every visit.

Pre-dose blood samples were collected for determination of serum functional mAb1 and anti-mAb1 antibodies as designated in Table 14.

Optional sampling for exploratory analysis of DNA and RNA, required separate pharmacogenetics informed consent.

Pharmacokinetics. Functional mAb1 and anti-mAb1 antibodies in serum were assayed by ELISA. Pre-dose functional mAb1 concentrations in serum at visit 2 (day 1), mAb1 trough concentrations at week 2, week 4, week 8, week 12, week 16, and follow-up serum mAb1 at week 20, week 24, week 28 and week 32 were provided. Anti-mAb1 antibody status (negative or titer value) at visit 2 (day 1), week 2, week 4, week 8, week 12, week 16, and week 32 were also provided. Patients with ADA titers ≥1000 at the end of study visit were scheduled to return approximately 6 months later for an additional assessment of ADA titer. Further follow-up was considered based on the overall assessment of antibody titers and clinical presentation.

Pharmacodynamics. Since the secretion of certain proteins is dependent, at least in part, on Th2 cytokines and is associated with chronic inflammation of the airway mucosa, including sinus tissue, expression of certain biomarkers were assayed to monitor a therapeutic effect of mAb1. These biomarkers were also assessed for their value in predicting toxicity and/or in documenting the time course of drug response. The values to be used as baselines were those collected on day 1 (pre-dose assessments).

Nasal secretions were obtained by inserting nasal swabs bilaterally into the nasal cavity for five minutes. The nasal secretions were preserved for possible analysis of additional biomarkers related to nasal polyposis and responses to mAb1 treatment.

At selected clinical site(s) and with specific informed consent, nasal polyp tissue was optionally obtained by biopsy. A baseline biopsy was obtained at V2 of the study. After randomization, another biopsy of nasal polyp tissue was obtained at the end of treatment visit (week 16).

The biopsied nasal polyp tissue was assessed for various biomarkers of inflammation and disease process or response. For example, RNA was extracted and used for expression profiling (e.g., microarray, transcriptome sequencing, quantitative RT-PCR or the like).

DNA and RNA samples were used to determine a possible relationship between genes and response to treatment with mAb1 and possible side effects to mAb1.

Analysis of proportion of patients with binary events. The proportion of patients with binary events was assessed for: ≥1 point improvement (reduction) in NPS at week 16 (as read centrally); 10% or more improvement in CT opacification from baseline at week 16; drop-out due to oral CS or surgery; or INCS increase after 8 weeks were analyzed using a logistic model with the above responses, respectively, as the response variable, and treatment group, pooled countries/regions and the stratification factor(s) prior to the study as covariates.

Analysis of time to event variables. Time to event (e.g., the first response with ≥1 point improvement (reduction) in NPS, study treatment discontinuation, etc.) was analyzed suing a Cox regression model with time to event as the dependent variable, and treatment, pooled countries/regions, asthma comorbidity prior to the study as covariates. The Kaplan-Meier method was used to derive the proportion of patients with an event at week 4, 8, 12 and 16 specific to each treatment group. For analysis during the treatment period, if a patient had no event before treatment discontinuation/completion, then the patient was considered as free of event until the end of treatment period (last dose date+7 days).

Analysis of change from baseline for continuous variables. The change from baseline at week 16 in: NPS for patients with co-morbid asthma; Lund Mackay score; SNOT-22; subject-assessed congestion and/or obstruction score; NPIF; ACQ-5 in patients with co-morbid asthma; QoL measures (SF36, EQ-5D), and VAS was analyzed using MMRM the same as the primary endpoints. Descriptive statistics including number of patients, mean, standard error and LS means was provided. In addition, differences in LS means, the corresponding 95% CI and the p-value was provided for comparisons of each dose against placebo.

Analysis of efficacy in baseline biomarker of characteristics defined subsets. To examine baseline biomarkers for their potential value to predict treatment response, analyses of change in NPS were also performed for the following subsets and the entire ITT population by each dose group and selected pooled dose group.

Subgroup analysis. To assess the consistency of treatment effects across the subgroup levels and to examine baseline biomarkers for their potential value to predict treatment response, exploratory subgroup analyses were conducted for the change from baseline in NPS with respect to age group, gender, region, race, INCS dose level, baseline NPS, baseline CT scan score, asthma comorbidity, and selected biomarkers prior to the study.

Listings of anti-mAb1 antibody results (negative or titer value) were presented by patient, time point and treatment groups. ADA titer levels were classified into categories: low, moderate and high. Low levels of ADA titers were defined as titers below 1000; moderate levels of ADA titers were defined as titers between 1000 and 10,000; high levels of ADA titers were defined as titers >10,000.

Anti-mAb1 antibody assay results were described categorically. The following summary was provided for patients with any positive ADA assay response during the TEAE period, and patients with treatment-induced positive ADA assay response during the TEAE period. Patients with treatment-induced positive ADA assay response during the TEAE period were further described as patients with transient positive response and patients with persistent positive response. Patients with any positive ADA assay response during the TEAE period were defined as those having at least one sample positive in the ADA assay.

The treatment-induced positive ADA assay response was defined as: patients with no positive assay response at baseline but with a positive assay response during the TEAE period or patients with a positive ADA assay response at baseline that also had at least a 4-fold increase in titer during the TEAE period.

A persistent positive was a treatment-induced positive ADA assay response in which at least two consecutive post-baseline samples from a patient were positive in the ADA assay or the last post-baseline sample collected was positive in the ADA assay. A transient positive response was defined as any treatment-induced positive ADA assay response that was not considered persistent.

performed using logistic regression analysis, including terms for treatment and stratification variables. Two categories of response were defined a priori; reductions of NPS of ≥1.0 or ≥2.0 units versus baseline at week 16.

Descriptive statistics were used for demographics, baseline characteristics, and safety variables, including adverse events, vital signs, physical examination, clinical laboratory and ECG findings. Plots of secondary and pharmacodynamic variables were presented as mean change or percent change from baseline over time with standard error. Comparison of treatment effects from the MMRM analyses were based on least squares mean change (95% confidence intervals [CI] and P value) from baseline to Week 16.

D. Data

Demographic and baseline clinical characteristics were similar in the two groups (Table 51). The 16 week treatment period was completed by 23 of 30 placebo patients and 28 of 30 dupilumab patients, respectively. In the placebo group, 5 of 7 patients prematurely discontinued the study due to 1 or more adverse events, and 2 of 7 due to lack of efficacy. In the dupilumab group, 2 of 30 patients did not complete the treatment period, both due to adverse events.

TABLE 16

Allowable Inhaled Glucocorticosteroid/Long-Acting Beta2 Adonist Combination Products and Acceptable Dosage Form, Strength and Dosage Schedule

| Generic Name | Brand Name | Acceptable Product | Acceptable Dosage Form, Strength and Dosage Schedule |
|---|---|---|---|
| Fluticasone propionate and salmeterol | Adyair ®/ Seretide ® | DPI (250/50 or 500/50) | DPI: 1 puff twice daily (500/50)<br>DPI: 1 puffs twice daily (250/50) |
| | | MDI (115/21 or 230/21) | MDI: 2 puffs twice daily (115/21)<br>MDI: 2 puffs twice daily (230/21) |
| Budesonide and formoterol | Symbicort ® | DPI (200/6 or 400/12 | DPI: 1 puff twice daily (400/12)<br>DPI: 2 puffs twice daily (200/6) |
| | | MDI (160/4.5) | MDI: 2 puffs twice daily (160/4.5) |
| Mometasone furoate and formoterol | Dulera ® | MDI (100/5 or 200/5) | MDI: 2 puffs twice daily (200/5)<br>MDI: 2 puffs twice daily (100/5) |

Statistical Analysis

The pre-specified primary analysis was conducted at the end of the 16-week treatment period. Efficacy analyses were performed using the intent-to-treat (ITT) population, which was predefined as all patients randomized regardless of receipt of study treatment. Safety analyses were performed using the safety population, predefined as all randomized patients exposed to study medication, regardless of the amount of treatment administered.

The primary efficacy variable, change in endoscopic NPS over the intervention period, was analyzed using a mixed-effect model with repeated measures (MMRM) approach. The model included change from baseline values up to week 16 as response variables, and incorporated factors for the stratification variables, as well as treatment, visit, treatment-by-visit interaction, baseline NPS value and baseline-by-visit interaction as covariates. Statistical inference on treatment comparison for change from baseline in NPS at week 16 was derived from this model. For all continuous secondary endpoints, with the exception of CT scan data, a similar analytical approach was employed.

CT scan data were collected both at baseline and at week 16. The change from baseline to week 16 in the Lund-Mackay total score (sum of left and right sinuses) was analyzed using an ANCOVA model. The factors in the model included treatment, stratification factors, and baseline value as covariate. To further evaluate the treatment effect of dupilumab on nasal polyp disease, a responder analysis was Primary Endpoint. The primary analysis compared the dupilumab treatment group to the placebo group. The primary efficacy evaluation was the change from baseline at week 16 in bilateral endoscopic NPS in an ITT population using a mixed-effect model with repeated measures (MMRM) analysis.

Figure 2A:
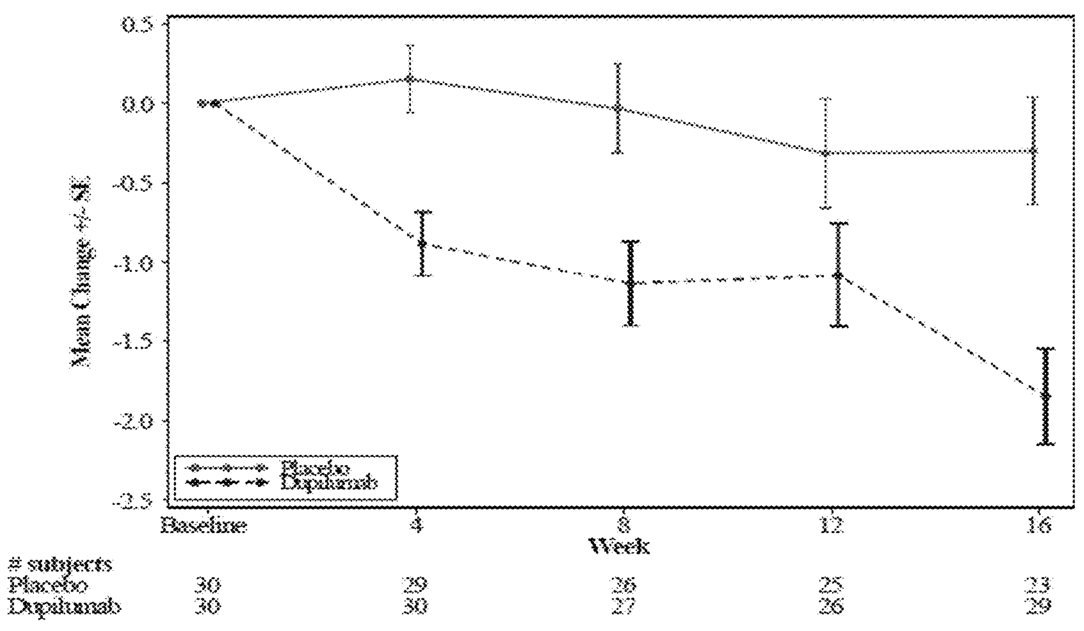
FIG. 2A graphically depicts least square mean change from baseline in bilateral endoscopic nasal polyp score (NPS) by visit in an Intent To Treat (ITT) population.
Figure 2B:
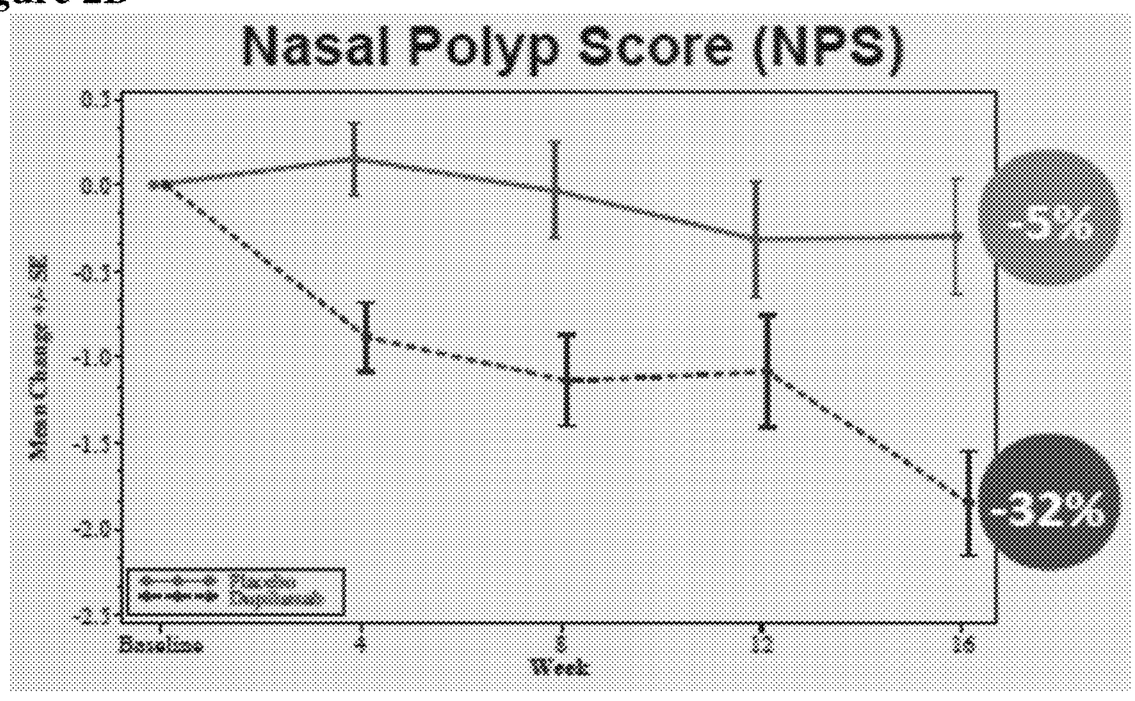
FIG. 2B graphically depicts least square mean change from baseline in bilateral endoscopic NPS by visit in an ITT population.
Figure 2C:
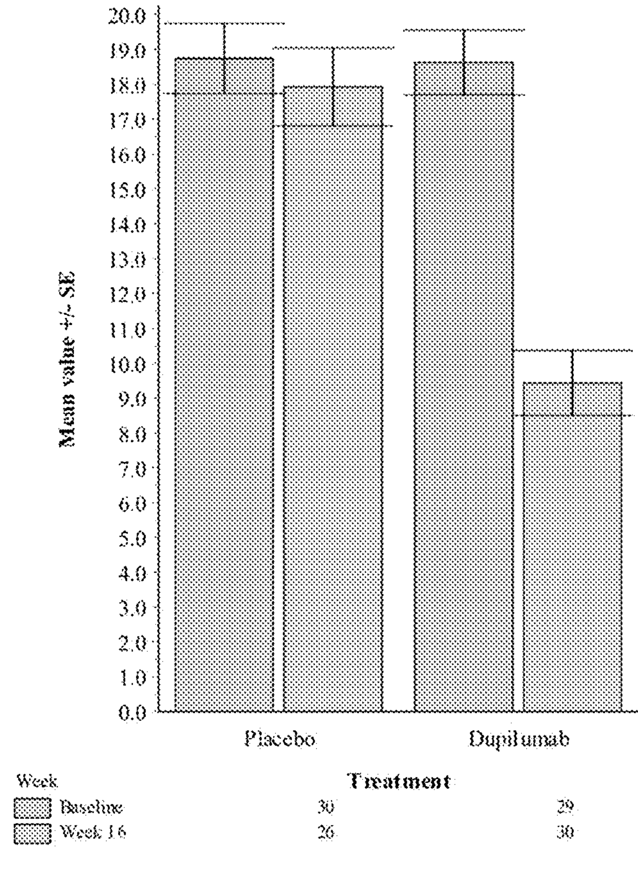
FIG. 2C graphically depicts least square mean change from baseline at week 16 in bilateral NPS by visit in an ITT population.
Figure 2D:
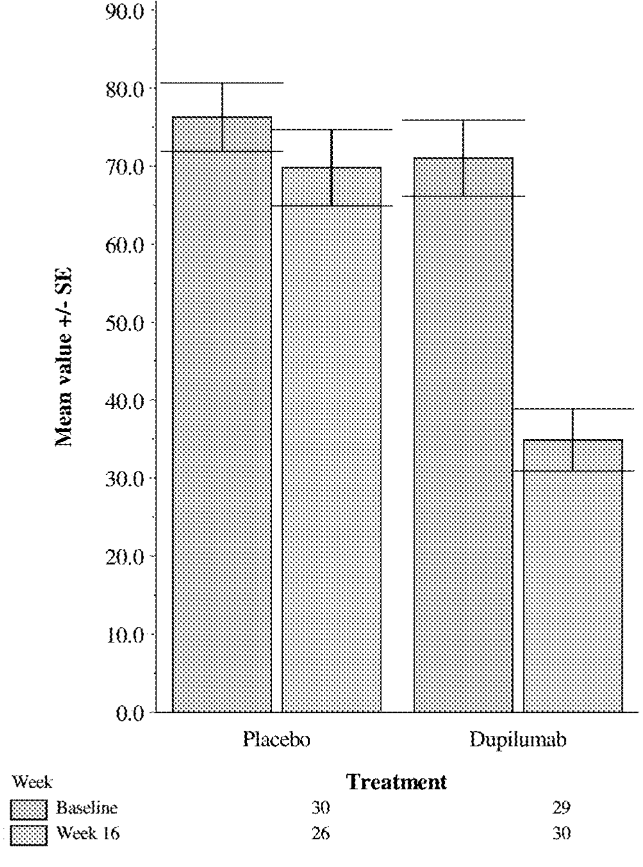
FIG. 2D graphically depicts least square mean change at week 16 in bilateral NPS reduction by visit in an ITT population.

The least squares (LS) mean (SE) change from baseline at week 16 was −0.30 (0.34) in the placebo group, and −1.85 (0.30) in the dupilumab group, resulting in a LS mean difference of −1.55 (95% CI, −2.43 to −0.67, p=0.0009), favoring dupilumab (Table 17, Table 52 and FIG. 2A). A pre-specified responder analysis indicated that a ≥1 point change in the NPS (NPS1 score) was observed in 20% of patients who received placebo versus 70% of those who received dupilumab, with an odds ratio (OR) of 9.5 (95% CI, 2.8 to 31.8, p=0.0003). A ≥2 point change (NPS 2 score) was observed in 10% of patients who received placebo and 53.3% of those who received dupilumab, yielding an OR=10.6 (2.6 to 43.6, p=0.001) (Table 19). Changes in NPS were sustained at the end of the 16-week follow-up period, during which patients received only MFNS (Table 53).

TABLE 17

Mean change from baseline at week 16 in bilateral endoscopic nasal polyp score in an ITT population (MMRM).

| NPS | Placebo (N = 30) | Dupilumab 300 mg qw (N = 30) |
|---|---|---|
| Baseline | | |
| Number | 30 | 30 |
| Mean (SD) | 5.67 (0.88) | 5.87 (1.01) |
| Medium | 6.00 | 6.00 |
| Min:Max | 4.0:8.0 | 3.0:8.0 |
| Week 16 | | |
| Number | 23 | 29 |
| Mean (SD) | 5.39 (1.47) | 3.97 (1.90) |
| Medium | 6.00 | 6.00 |
| Min:Max | 4.0:8.0 | 3.0:8.0 |
| Change from baseline | | |
| Number | 23 | 29 |
| Mean (SD) | −0.26 (1.32) | −1.90 (1.76) |
| Medium | 0.00 | −2.00 |
| Min:Max | −3.0:2.0 | −6.0:1.0 |
| LS Mean (SE)[a] | −0.30 (0.34) | −1.85 (0.30) |
| LS Mean Diff, 95% CI[a] | | −1.55 (−2.43, −0.67) |
| P-value vs placebo[a] | | 0.0009 |

[a]Analysis of a mixed model repeated measures (MMRM) model with treatment groups, stratification factor (asthma, biopsy), visit, treatment-by-visit interaction, baseline-by-visit interaction and baseline as covariates. Baseline for NPS was the central reading at V2, in the event that there was missing data due to image quality, the central reading at V1 was used.

The dupilumab effect on bilateral NPS was observed from week 4 (LS mean difference of −1.03; 95% CI [−1.58, −1.03]; p=0.004) through week 16. At week 12, however, statistical significance was not demonstrated in the difference in NPS (LS mean [SE] −0.30 [0.34]; −1.08 [0.33] placebo vs dupilumab; p=0.1011 (FIG. 2).

The mean change from baseline at week 16 in bilateral NPS was evaluated by the following subgroups: gender, race, age, weight, prior nasal polyp surgery, baseline NPS, co-morbid asthma and region (Europe and US) (Table 18). Mean decreases in NPS, in the general range of 1 in favor of dupilumab, were demonstrated across most subgroup analyses, with the exception of the subgroup of patients without co-morbid asthma.

Figure 3:
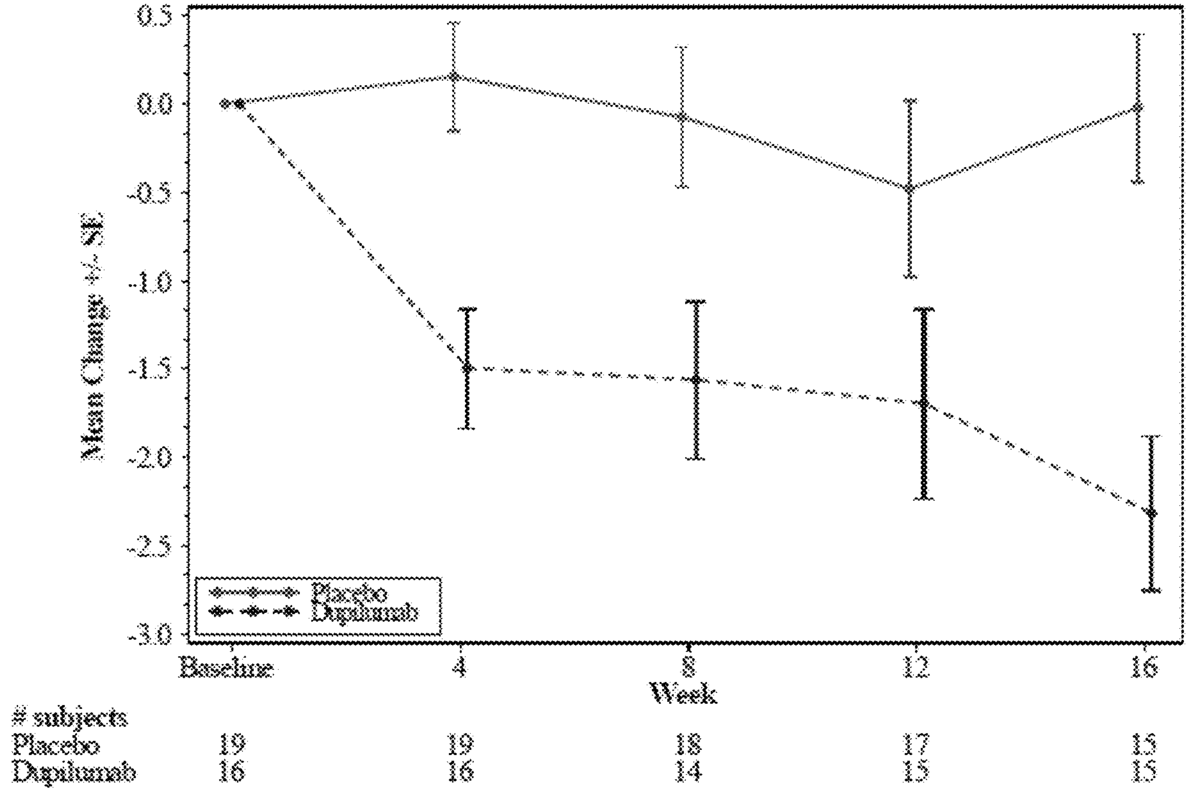
FIG. 3 graphically depicts LS mean change from baseline in bilateral endoscopic nasal polyps score by visit for subgroup of patients with co-morbid asthma in an ITT population.
Figure 4:
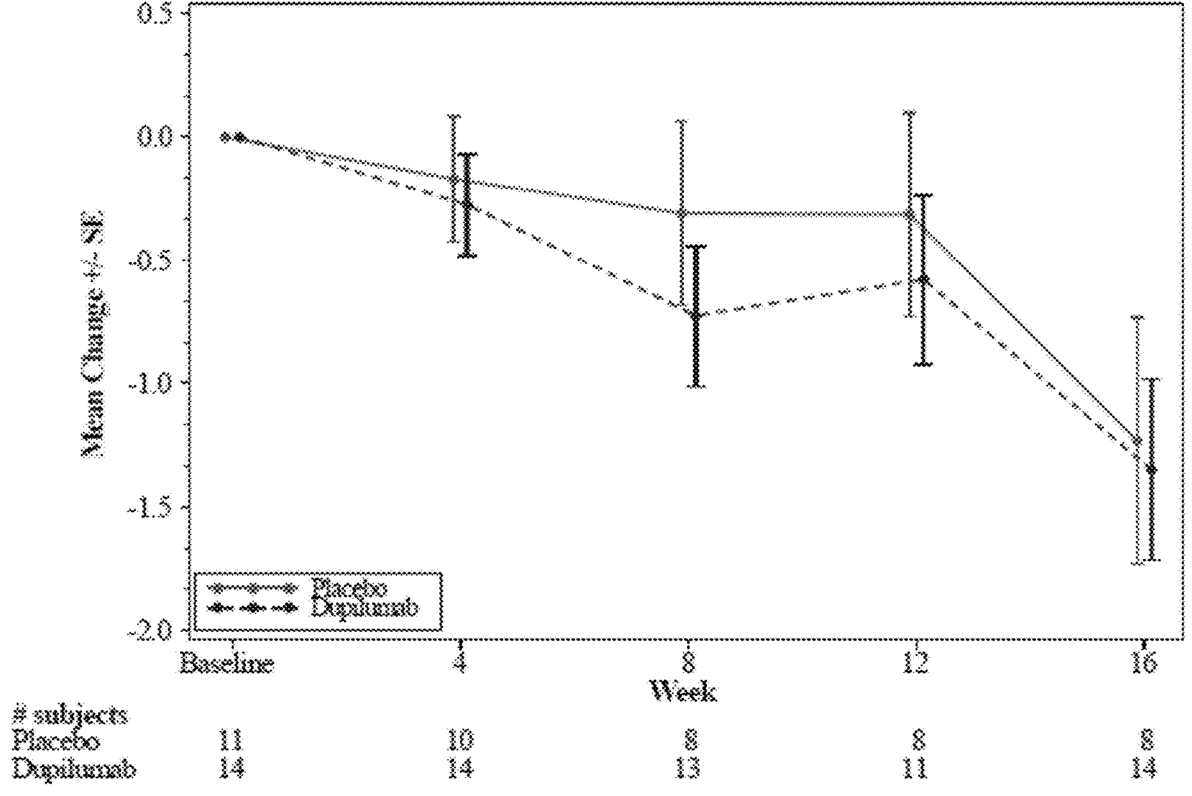
FIG. 4 graphically depicts LS mean change from baseline in bilateral endoscopic nasal polyps score by visits for subgroup of patients without co-morbid asthma in an ITT population.

In patients with comorbid asthma, the mean (SD) difference in NPS at week 16 was 0.27 (0.88) vs −2.40 (2.03), respectively, for the placebo and dupilumab treatment groups (Table 18 and FIG. 3). In the patients without comorbid asthma, the mean (SD) difference in NPS was −1.25 (1.49) vs −1.36 (1.28), respectively, for the placebo and dupilumab treatment groups (Table 18 and FIG. 4).

Baseline weight<90 kg≥90 kg did not affect the treatment benefit of dupilumab (Table 18).

TABLE 18

Descriptive statistics of change from baseline at week 16 in bilateral endoscopic nasal polyp score by subgroups in an ITT population.

| | Placebo (N = 30) | Dupilumab 300 mg qw (N = 30) |
|---|---|---|
| Gender | | |
| Male | | |
| Number | 12 | 18 |
| Mean (SD) | −0.83 (1.34) | −1.72 (1.90) |
| Medium | 0.00 | −2.00 |
| Min:Max | −3.0:0.0 | −6.0:1.0 |

TABLE 18-continued

Descriptive statistics of change from baseline at week 16 in bilateral endoscopic nasal polyp score by subgroups in an ITT population.

| | Placebo (N = 30) | Dupilumab 300 mg qw (N = 30) |
|---|---|---|
| Female | | |
| Number | 11 | 11 |
| Mean (SD) | 0.36 (1.03) | −2.18 (1.54) |
| Medium | 0.00 | −2.00 |
| Min:Max | −1.0:2.0 | −4.0:0.0 |
| Race | | |
| Caucasion/White | | |
| Number | 23 | 28 |
| Mean (SD) | −0.26 (1.32) | −1.82 (1.74) |
| Medium | 0.00 | −2.00 |
| Min:Max | −3.0:2.0 | −6.0:1.0 |
| All other races | | |
| Number | 0 | 1 |
| Mean (SD) | | −4.00 (NC) |
| Medium | | −4.00 |
| Min:Max | | −4.0:−4.0 |
| Age group (year) | | |
| >= 18 and <45 | | |
| Number | 6 | 10 |
| Mean (SD) | 0.00 (1.10) | −1.60 (1.90) |
| Medium | 0.00 | −0.50 |
| Min:Max | −1.0:2.0 | −4.0:0.0 |
| >= 45 | | |
| Number | 17 | 19 |
| Mean (SD) | −0.35 (1.41) | −2.05 (1.72) |
| Medium | 0.00 | −2.00 |
| Min:Max | −3.0:2.0 | −6.0:1.0 |
| Baseline weight (kg) | | |
| <90 | | |
| Number | 15 | 21 |
| Mean (SD) | −0.33 (1.29) | −1.71 (1.68) |
| Medium | 0.00 | −1.00 |
| Min:Max | −3.0:2.0 | −4.0:1.0 |
| >= 90 | | |
| Number | 8 | 8 |
| Mean (SD) | −0.13 (1.29) | −2.38 (2.00) |
| Medium | 0.00 | −2.00 |
| Min:Max | −3.0:2.0 | −6.0:0.0 |
| Previous surgery for nasal polyposis (yes or no) | | |
| Yes | | |
| Number | 14 | 16 |
| Mean (SD) | −0.29 (1.33) | −2.56 (1.75) |
| Medium | 0.00 | −2.00 |
| Min:Max | −3.0:2.0 | −6.0:0.0 |
| No | | |
| Number | 9 | 13 |
| Mean (SD) | −0.22 (1.39) | −1.08 (1.44) |
| Medium | 0.00 | −1.00 |
| Min:Max | −3.0:2.0 | −4.0:1.0 |
| Baseline NPS | | |
| <5 | | |
| Number | 3 | 3 |
| Mean (SD) | 1.33 (1.15) | −2.33 (0.58) |
| Medium | 0.00 | −2.00 |
| Min:Max | 0.0:2.0 | −3.0:−2.0 |
| 5 to 6 | | |
| Number | 18 | 22 |
| Mean (SD) | −0.56 (1.25) | −1.59 (1.71) |
| Medium | 0.00 | −1.00 |
| Min:Max | −3.0:1.0 | −4.0:1.0 |

TABLE 18-continued

Descriptive statistics of change from baseline at week 16 in bilateral endoscopic nasal polyp score by subgroups in an ITT population.

| | Placebo (N = 30) | Dupilumab 300 mg qw (N = 30) |
|---|---|---|
| 7 to 8 | | |
| Number | 2 | 4 |
| Mean (SD) | 0.00 (0.00) | −3.25 (2.22) |
| Medium | 0.00 | −3.00 |
| Min:Max | 0.0:0.0 | −6.0:1.0 |
| Co-morbid asthma | | |
| Yes | | |
| Number | 15 | 15 |
| Mean (SD) | 0.27 (0.88) | −2.40 (2.03) |
| Medium | 0.00 | −2.00 |
| Min:Max | −1.0:2.0 | −6.0:1.0 |
| No | | |
| Number | 8 | 14 |
| Mean (SD) | −1.25 (1.49) | −1.36 (1.28) |
| Medium | −0.50 | −1.50 |
| Min:Max | −3.0:0.0 | −4.0:0.0 |
| Region | | |
| Europe | | |
| Number | 19 | 19 |
| Mean (SD) | −0.32 (1.42) | −1.58 (1.64) |
| Medium | 0.00 | −2.00 |
| Min:Max | −3.0:2.0 | −4.0:1.0 |
| US | | |
| Number | 4 | 10 |
| Mean (SD) | 0.00 (0.82) | −2.50 (1.90) |
| Medium | 0.00 | −2.00 |
| Min:Max | −1.0:1.0 | −6.0:0.0 |

To further evaluate the treatment effect of dupilumab on nasal polyp disease, a responder analysis was performed. Two categories of response were defined a priori; NPS reduction of ≥1.0 from baseline at week 16 (NPS 1 response) and NPS reduction of ≥2.0 from baseline at week 16 (NPS 2 response).

TABLE 19

Responder (reduction in NPS score from baseline at week 16) analysis in an ITT population.

| | Placebo (N = 30) | Dupilumab 300 mg qw (N = 30) |
|---|---|---|
| NPS reduction >= 1.0 from baseline at Week 16 | | |
| Responders | 6 (20.0%) | 21 (70.0%) |
| Non-responders | 24 (80.0%) | 9 (30.0%) |
| OR 95% CI vs placebo[a] | | 9.48 (2.83, 31.77) |
| P-value vs placebo[a] | | 0.0003 |
| NPS reduction >= 2.0 from baseline at Week 16 | | |
| Responders | 3 (10.0%) | 16 (53.3%) |
| Non-responders | 27 (90.0%) | 14 (46.7%) |
| OR 95% CI vs placebo[a] | | 10.56 (2.56, 43.58) |
| P-value vs placebo[a] | | 0.0011 |

OR: Odds ratio.

Note:

Patients are considered non-responders if the central NPS are missing at week 16. Percentages were calculated using the number of ITT patients in the corresponding treatment group as denominator.

[a]Analysis of a logistic model with treatment groups, stratification factor (asthma, biopsy) and baseline as covariates.

In patients with comorbid asthma, the responder analysis results demonstrated statistically significant NPS 1 response (75%) at week 16 in the dupilumab treatment group, compared to placebo (10.5%), p=0.0009. The NPS 2 response also numerically favored dupilumab (56.3%) compared to placebo (0) (Table 20).

TABLE 20

Responder (reduction in NPS score from baseline at week 16) analysis for subgroup of patients with co-morbid asthma in an ITT population.

| | Placebo (N = 19) | Dupilumab 300 mg qw (N = 16) |
|---|---|---|
| NPS reduction >= 1.0 from baseline at Week 16 | | |
| Responders | 2 (10.5%) | 12 (75.0%) |
| Non-responders | 17 (89.5%) | 4 (25.0%) |

TABLE 20-continued

Responder (reduction in NPS score from baseline at week 16) analysis for subgroup of patients with co-morbid asthma in an ITT population.

| | Placebo (N = 19) | Dupilumab 300 mg qw (N = 16) |
|---|---|---|
| OR 95% CI vs placebo[a] | | 26.05 (3.78, 179.31) |
| P-value vs placebo[a] | | 0.0009 |
| NPS reduction >= 2.0 from baseline at Week 16 | | |
| Responders | 0 | 9 (56.3%) |
| Non-responders | 19 (100%) | 7 (43.8%) |
| OR 95% CI vs placebo[a] | | NA |
| P-value vs placebo[a] | | NA |

OR: Odds ratio.

Note:

Patients are considered non-responders if the central NPS are missing at week 16. Percentages were calculated using the number of ITT patients in the corresponding treatment group as denominator.

[a]Analysis of a logistic model with treatment groups, stratification factor (asthma, biopsy) and baseline as covariates.

In patients without comorbid asthma, the responder analysis similarly numerically favored dupilumab for both NPS 1 and NPS 2 responses (64.3% and 50%, respectively), however, the placebo group showed responder rates of 36.4% and 27.3%, respectively (Table 21), thus the numerical differences between the 2 treatment groups for NPS 1 and NPS 2 responses were less in patients without comorbid asthma, compared to patients with comorbid asthma.

TABLE 21

Responder (reduction in NPS score from baseline at week 16) analysis for subgroup of patients without co-morbid asthma in an ITT population.

| | Placebo (N = 11) | Dupilumab 300 mg qw (N = 14) |
|---|---|---|
| NPS reduction >= 1.0 from baseline at Week 16 | | |
| Responders | 4 (36.4%) | 9 (64.3%) |
| Non-responders | 7 (63.6%) | 5 (35.7%) |
| OR 95% CI vs placebo[a] | | 3.17 (0.57, 17.56) |
| P-value vs placebo[a] | | 0.1869 |
| NPS reduction >= 2.0 from baseline at Week 16 | | |
| Responders | 3 (27.3%) | 7 (50.0%) |
| Non-responders | 8 (72.7%) | 7 (50.0%) |
| OR 95% CI vs placebo[a] | | 2.49 (0.44, 14.08) |
| P-value vs placebo[a] | | 0.3025 |

OR: Odds ratio.

Note:

Patients are considered non-responders if the central NPS are missing at week 16. Percentages were calculated using the number of ITT patients in the corresponding treatment group as denominator.

[a]Analysis of a logistic model with treatment groups, stratification factor (asthma, biopsy) and baseline as covariates.

Sino Nasal Outcome Test (SNOT-22)

Figure 5:
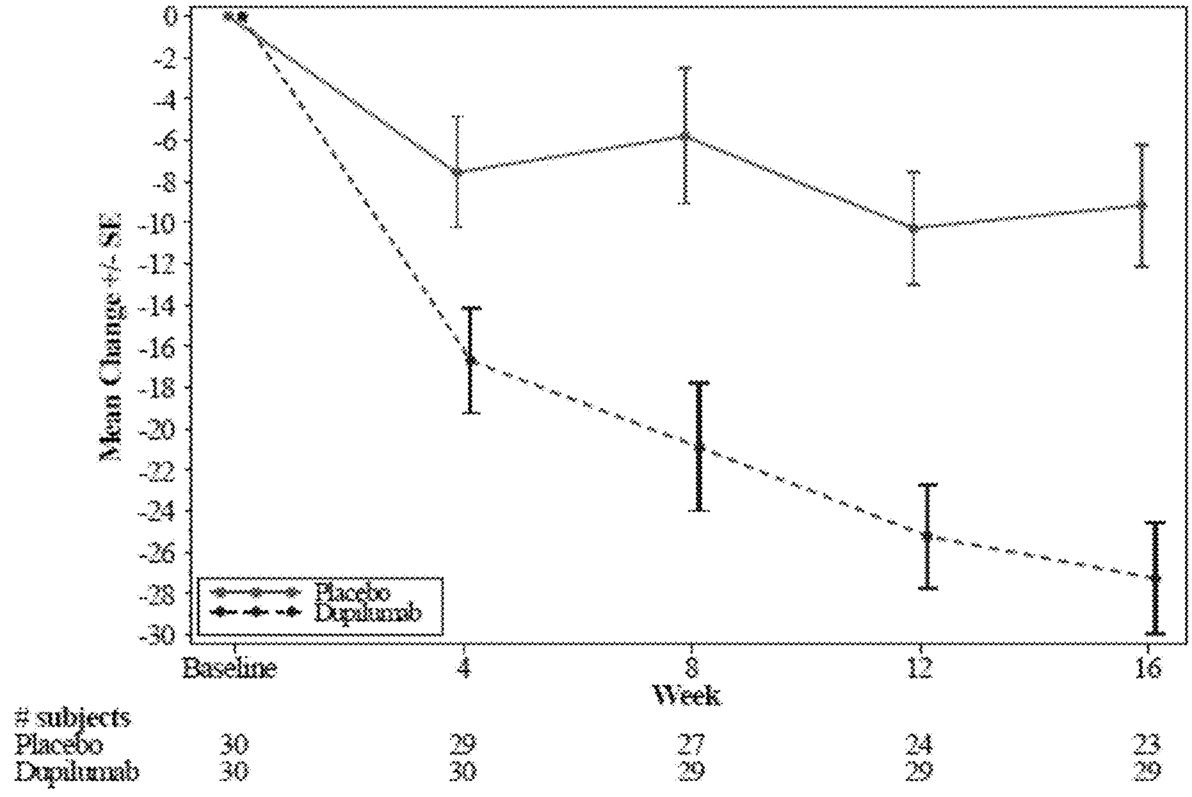
FIG. 5 graphically depicts LS mean change from baseline in 22-item Sinonasal Outcome Test (SNOT-22) total score in an ITT population.

SNOT-22 was used by patients in the study to evaluate the impact of rhinosinusitis on quality of life. Higher scores indicated worse disease; the total maximum score being 110. The results demonstrated statistical significance at week 16 in favor of dupilumab; the LS mean (SE) change from baseline at week 16 was −9.17 (2.96) in the placebo group, and −27.28 (2.71) in the dupilumab group, resulting in a LS mean difference of −18.11 (95% CI, −25.62 to −10.60, p<0.0001) (Table 22). The effect of dupilumab on SNOT-22 score was observed from week 4 through week 16 (FIG. 5).

TABLE 22

Mean change from baseline at week 16 in SNOT-22 total score in an ITT population (MMRM).

| SNOT-22 Total Score | Placebo (N = 30) | Dupilumab 300 mg qw (N = 30) |
|---|---|---|
| Baseline | | |
| Number | 30 | 30 |
| Mean (SD) | 40.57 (19.91) | 41.43 (18.20) |
| Medium | 40.50 | 40.50 |
| Min:Max | 8.0:81.0 | 12.0:91.0 |

TABLE 22-continued

Mean change from baseline at week 16 in SNOT-22 total score in an ITT population (MMRM).

| SNOT-22 Total Score | Placebo (N = 30) | Dupilumab 300 mg qw (N = 30) |
|---|---|---|
| Week 16 | | |
| Number | 23 | 29 |
| Mean (SD) | 30.17 (19.59) | 12.76 (10.99) |
| Medium | 26.00 | 11.00 |
| Min:Max | 1.0:79.0 | 0.0:42.0 |
| Change from baseline | | |
| Number | 23 | 29 |
| Mean (SD) | −8.26 (17.63) | −1.90 (1.76) |
| Medium | −4.00 | −27.00 |
| Min:Max | −51.0:13.0 | −85.0:10.0 |
| LS Mean (SE)[a] | −9.17 (2.96) | −27.28 (2.71) |
| LS Mean Diff, 95% CI[a] | | −18.11 (−25.62, −10.60) |
| P-value vs placebo[a] | | <.0001 |

[a]Analysis of a mixed model repeated measures (MMRM) model with treatment groups, stratification factor (asthma, biopsy), visit, treatment-by-visit interaction, baseline-by-visit interaction and baseline as covariates.

Additional patient reported outcomes included the visual analog scale (1-10 cm) that patients used to rate rhinosinusitis symptom severity, daily (AM/PM) loss of sense of smell ratings (0-3 point scale), the smell test (UPSIT), and typical symptoms of rhinitis ratings (nasal obstruction/congestion, runny nose and post-nasal drip) (0-3 point scale).

Figure 6:
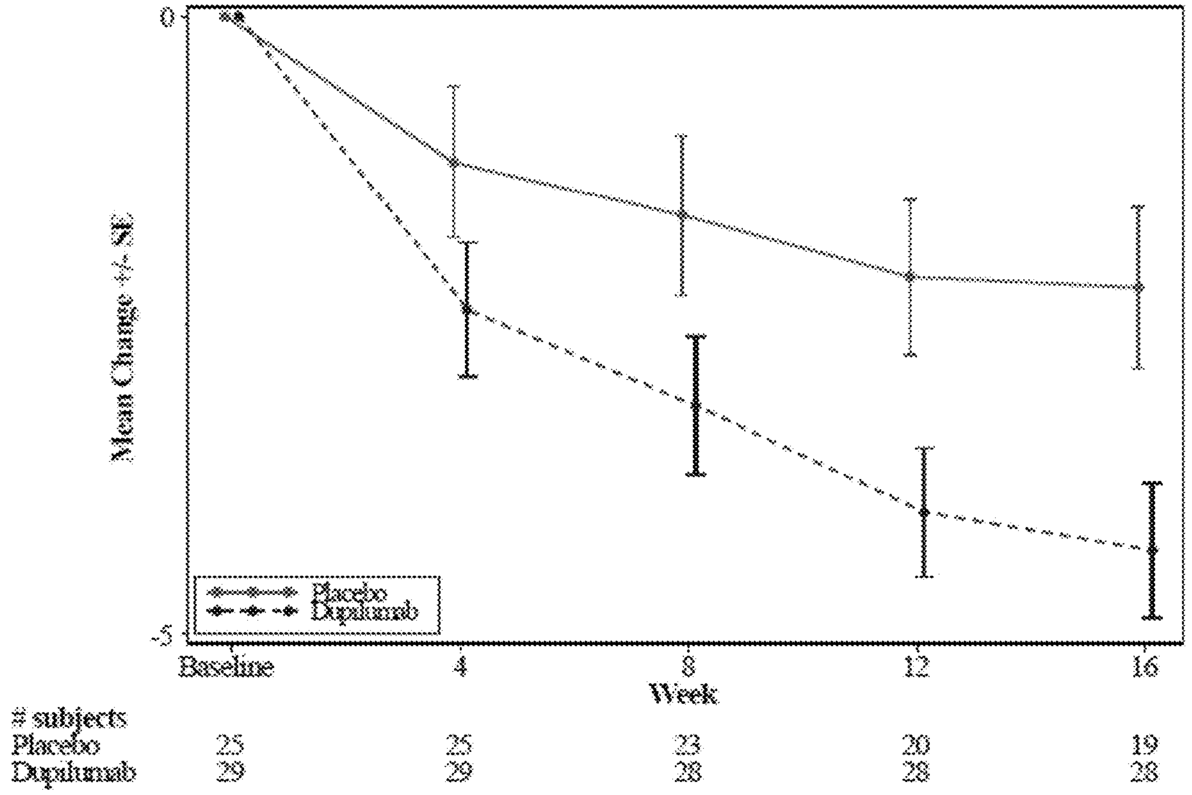
FIG. 6 graphically depicts LS mean change from baseline in Visual Analogue Scale (VAS) for rhinosinusitis symptoms severity in an ITT population.

The Visual Analogue Scale (VAS) for rhinosinusitis symptoms severity results demonstrated statistical significance at week 16; the LS mean (SE) change from baseline at week 16 was −2.19 (0.65) in the placebo group, and −4.32 (0.55) in the dupilumab group, resulting in a LS mean difference of −2.13 (95% CI, −3.68 to −0.58, p=0.0082) (Table 23). The effect of dupilumab on VAS score was observed from week 4 through week 16 (FIG. 6).

TABLE 23

Mean change from baseline at week 16 in VAS for rhinosinusitis symptoms severity-ITT population (MMRM).

| VAS for rhinosinusitis symptoms severity | Placebo (N = 30) | Dupilumab 300 mg qw (N = 30) |
|---|---|---|
| Baseline | | |
| Number | 25 | 29 |
| Mean (SD) | 6.42 (2.73) | 6.43 (2.74) |
| Medium | 7.30 | 7.50 |
| Min:Max | 1.0:10.0 | 0.0:9.9 |
| Week 16 | | |
| Number | 23 | 29 |
| Mean (SD) | 4.34 (3.08) | 2.16 (2.74) |
| Medium | 4.80 | 0.80 |
| Min:Max | 0.0:9.3 | 0.0:10.0 |
| Change from baseline | | |
| Number | 19 | 28 |
| Mean (SD) | −1.84 (3.60) | −4.32 (2.75) |
| Medium | −0.60 | −4.35 |
| Min:Max | −7.6:3.6 | −8.7:0.1 |
| LS Mean (SE)[a] | −2.19 (0.65) | −4.32 (0.55) |
| LS Mean Diff, 95% CI[a] | | −2.13 (−3.68, −0.58) |
| P-value vs placebo[a] | | 0.0082 |

[a]Analysis of a mixed model repeated measures (MMRM) model with treatment groups, stratification factor (asthma, biopsy), visit, treatment-by-visit interaction, baseline-by-visit interaction and baseline as covariates.

Figure 7:
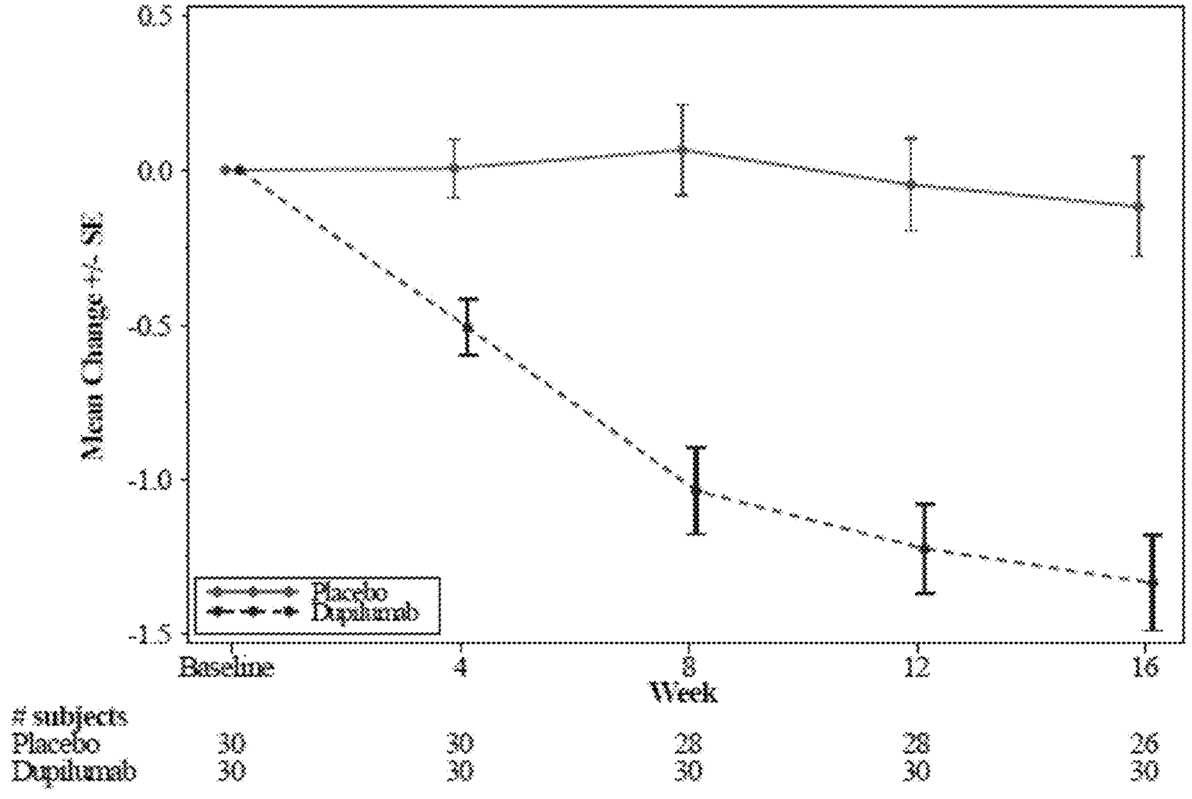
FIG. 7 graphically depicts LS mean change from baseline in day (AM) symptom score for loss of smell in an ITT population.
Figure 8:
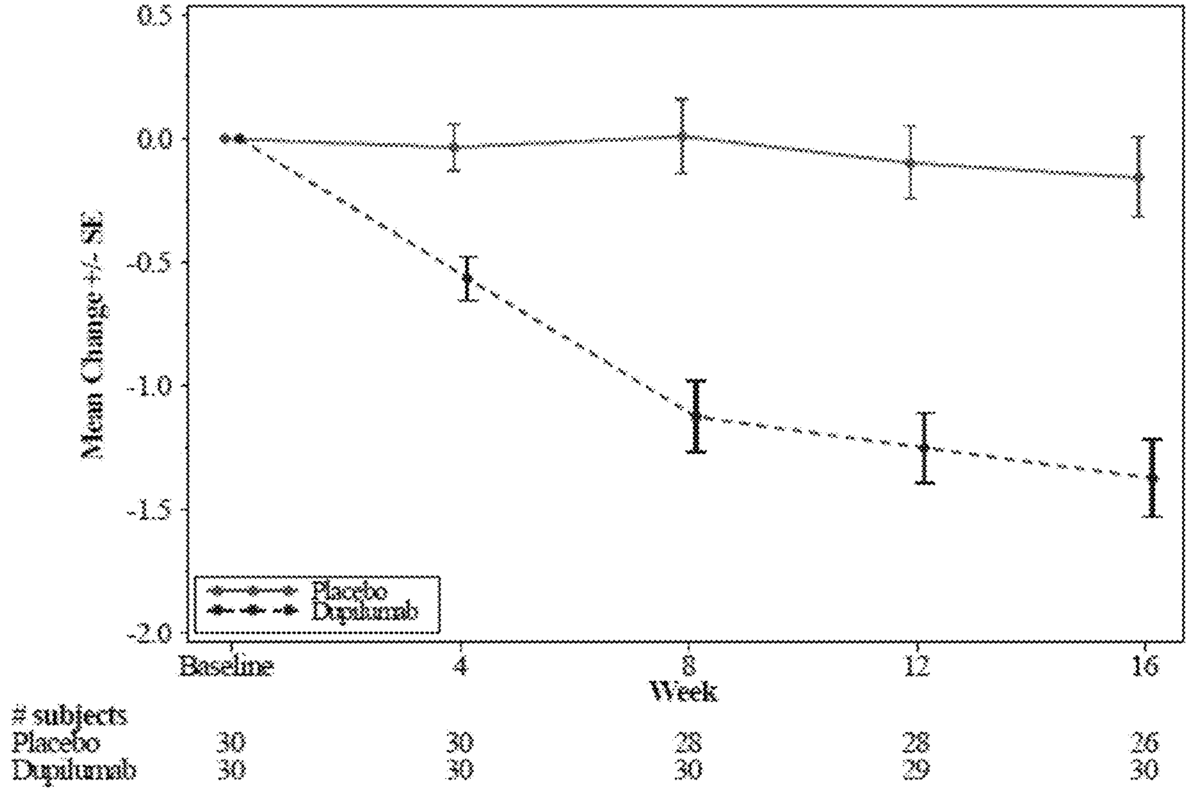
FIG. 8 graphically depicts LS mean change from baseline in night (PM) symptom score for loss of smell in an ITT population.
Figure 9:
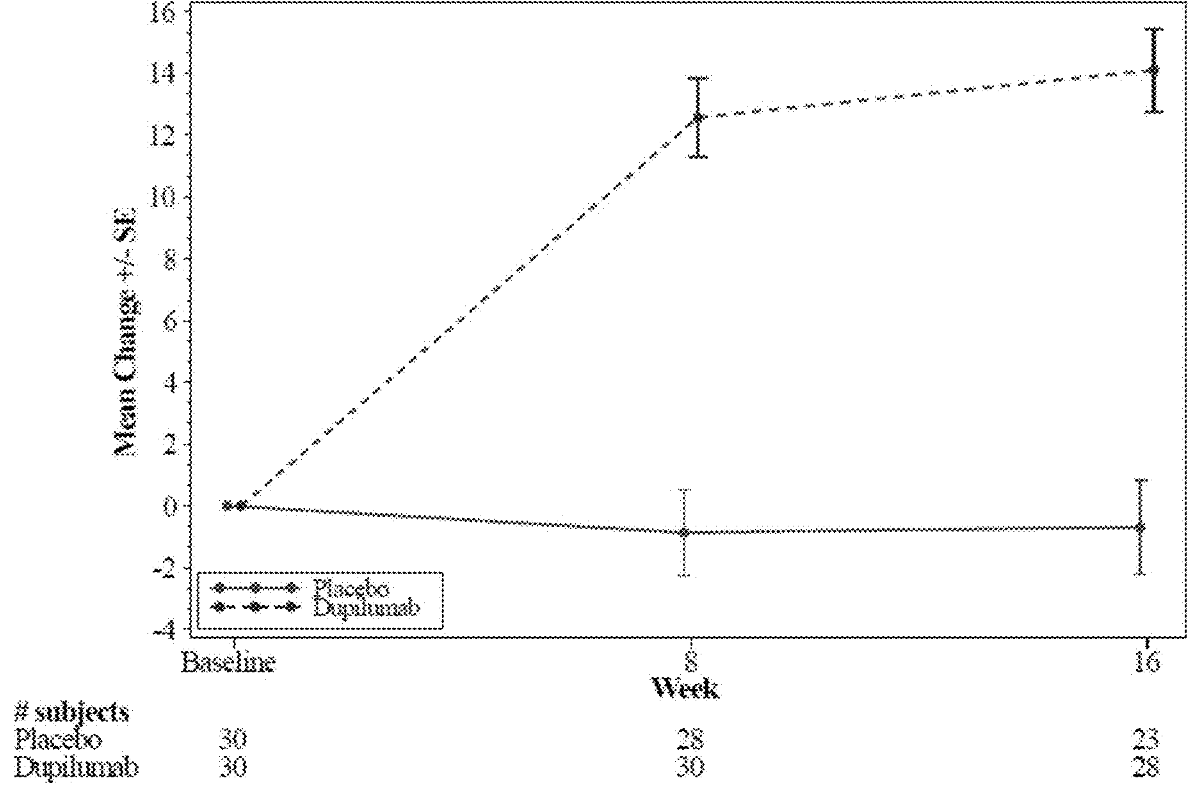
FIG. 9 graphically depicts LS mean change from baseline in smell test in an ITT population.
Figure 10:
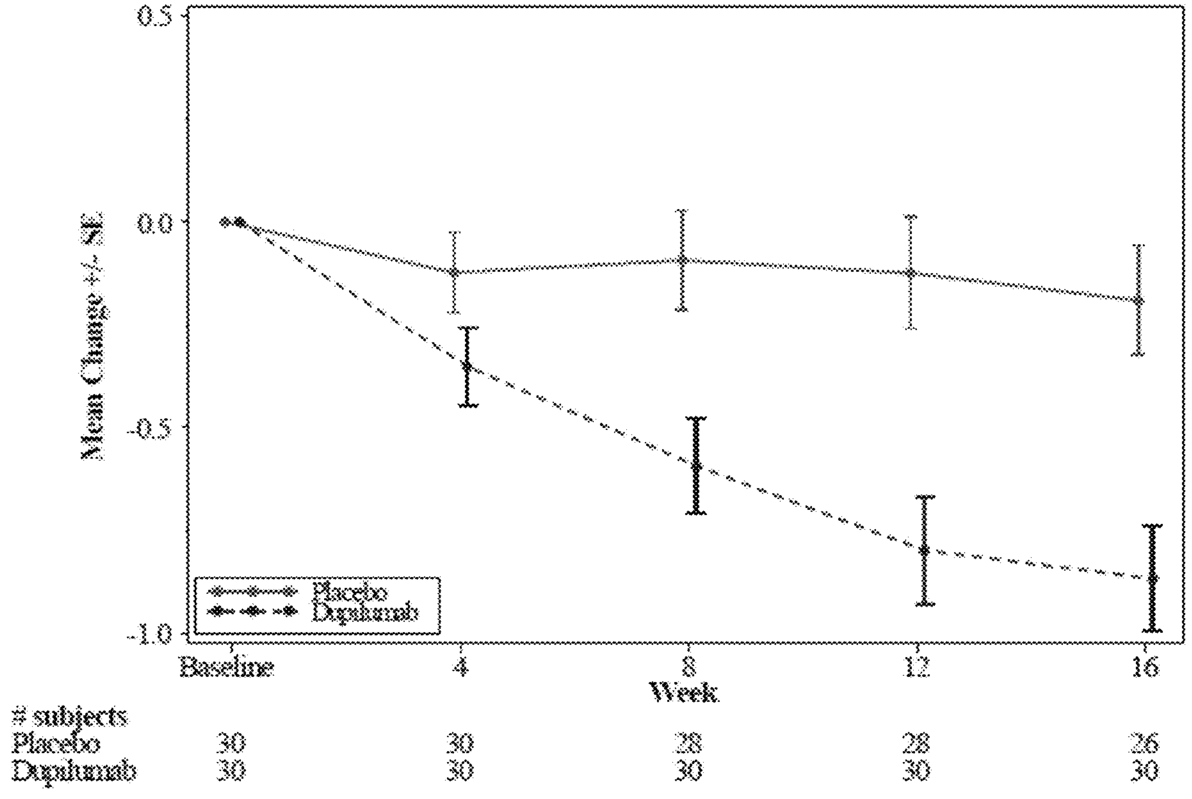
FIG. 10 graphically depicts LS mean change from baseline in AM symptom score for congestion/obstruction in an ITT population.
Figure 11:
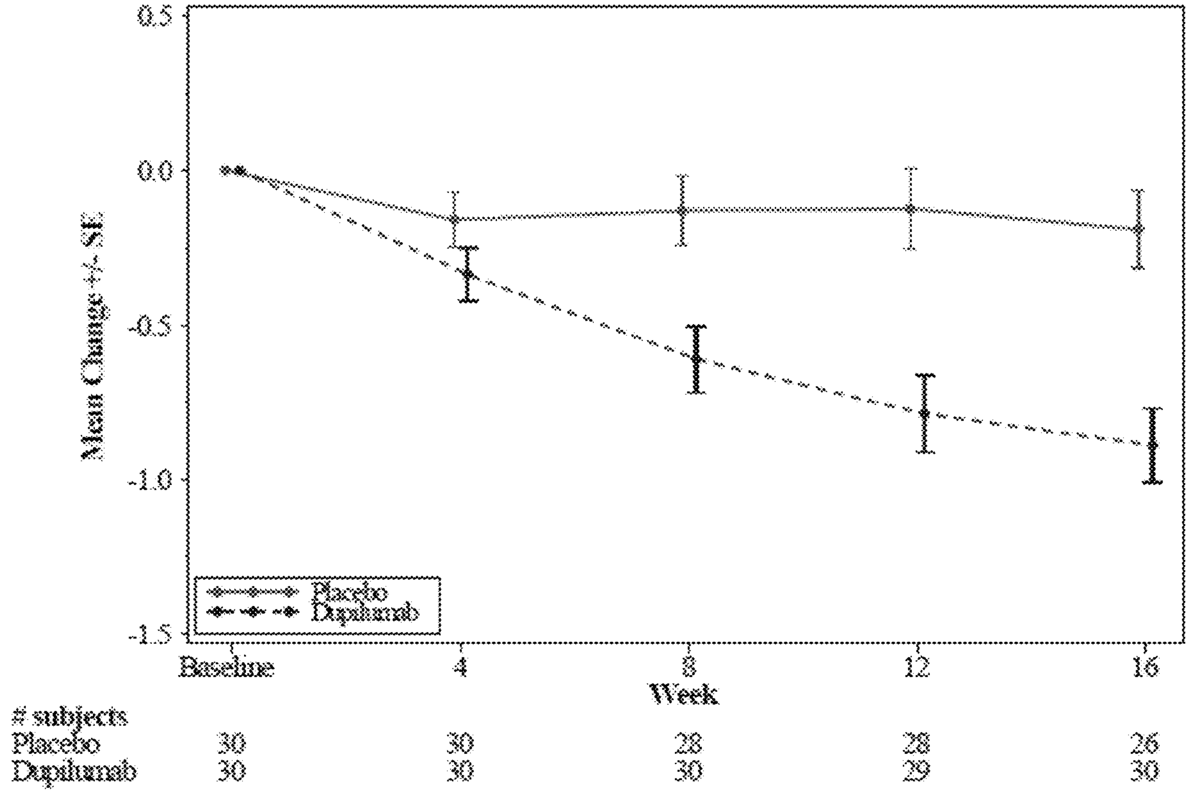
FIG. 11 graphically depicts LS mean change from baseline in PM symptom score for congestion/obstruction in an ITT population.
Figure 12:
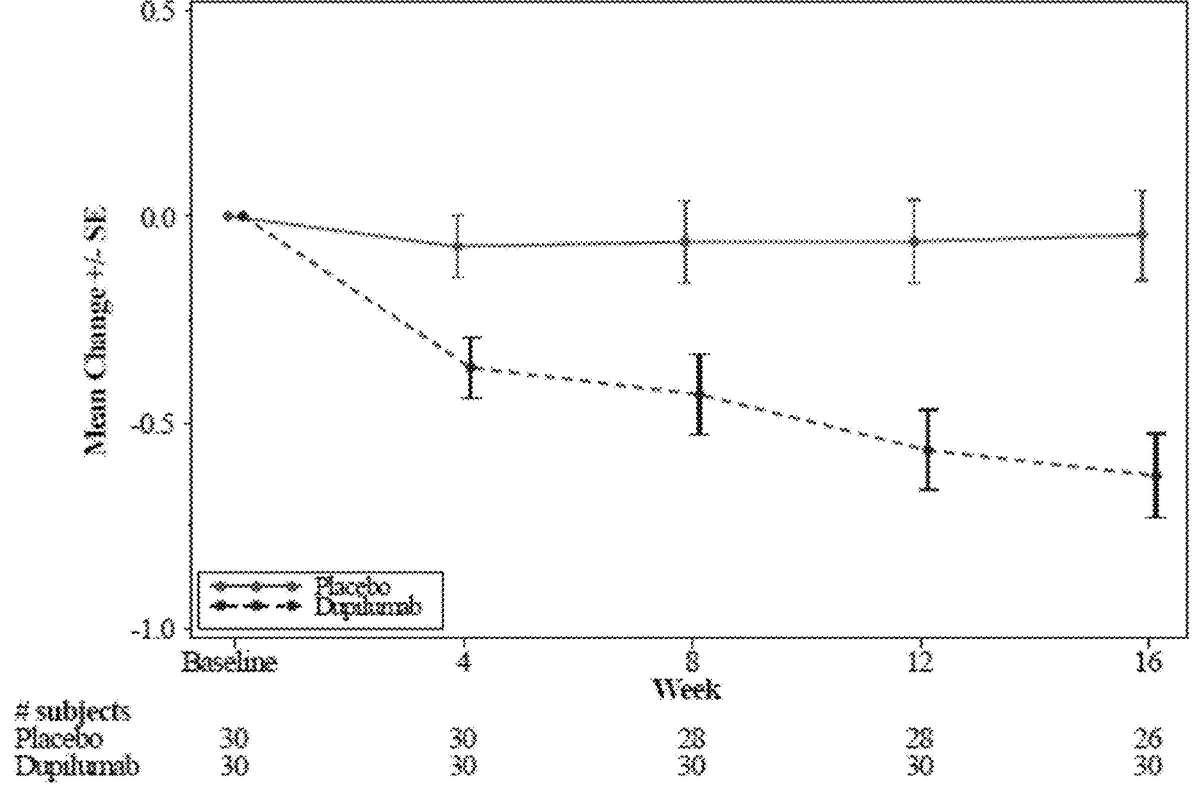
FIG. 12 graphically depicts LS mean change from baseline in AM symptom score for runny nose in an ITT population.
Figure 13:
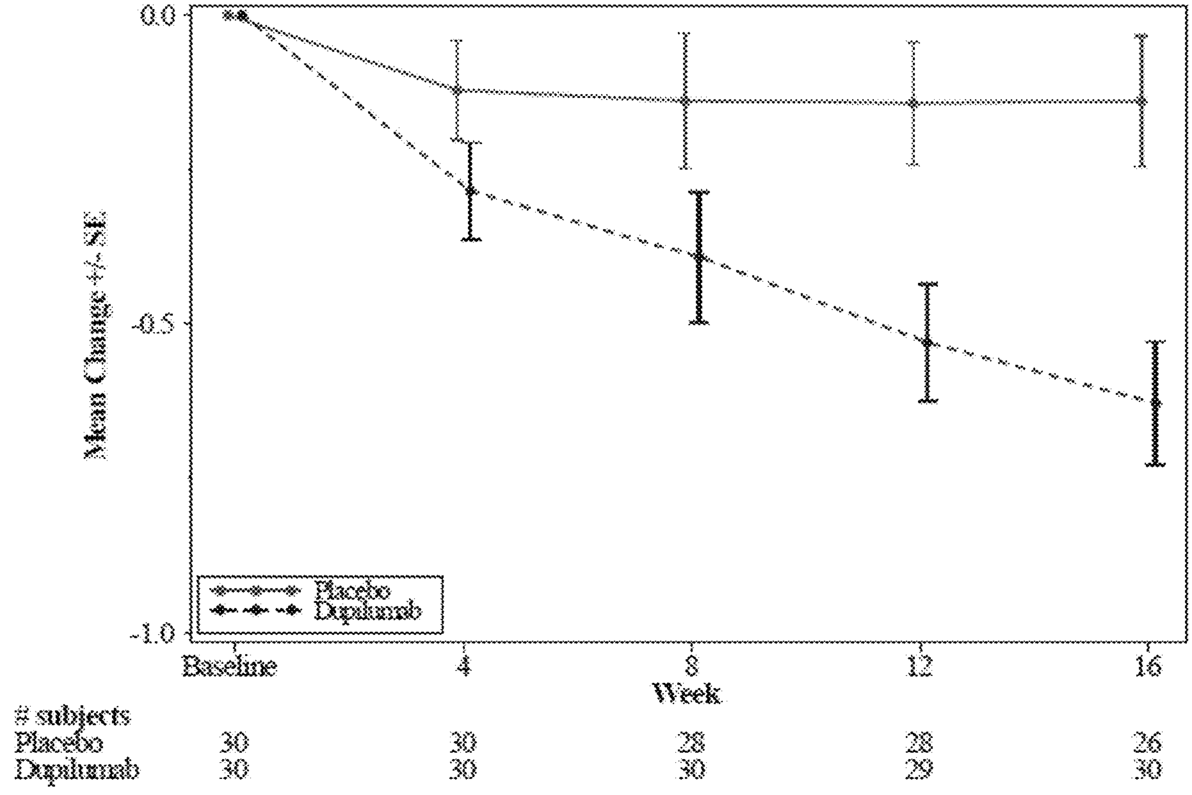
FIG. 13 graphically depicts LS mean change from baseline in PM symptom score for runny nose in an ITT population.
Figure 14:
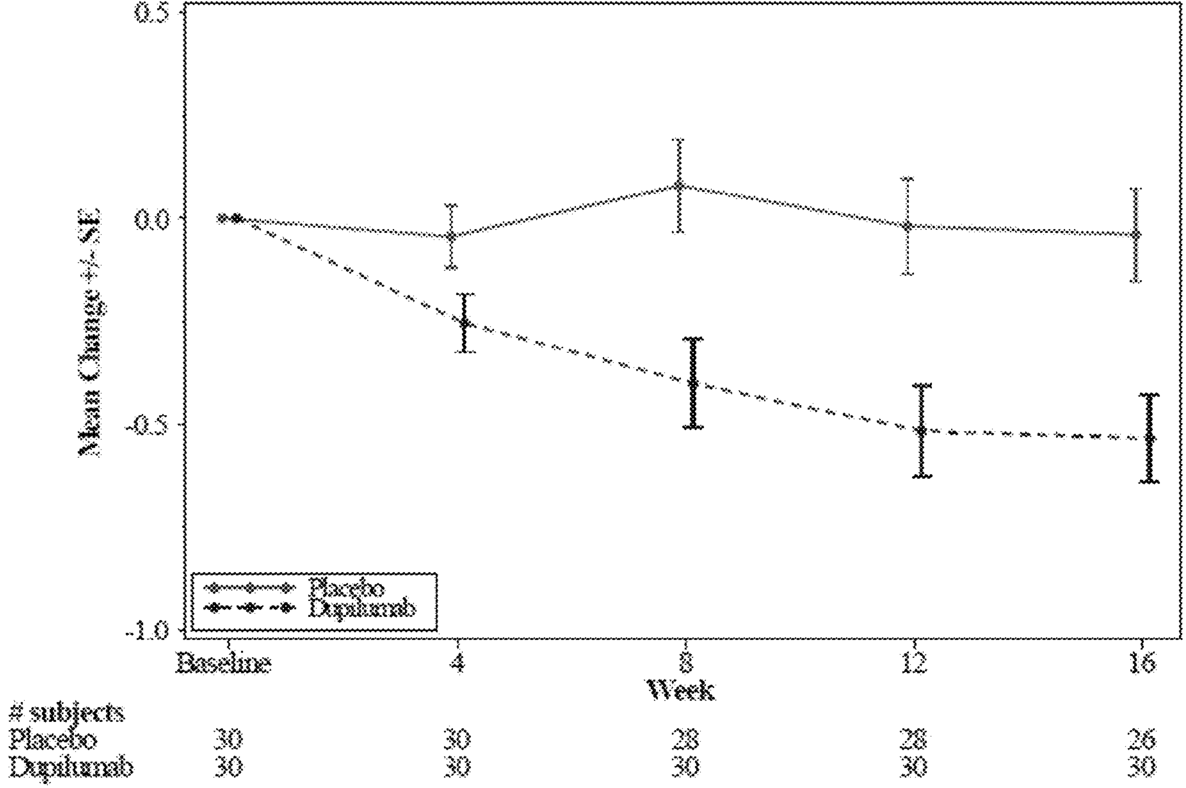
FIG. 14 graphically depicts LS mean change from baseline in AM symptom score for post nasal drip in an ITT population.
Figure 15:
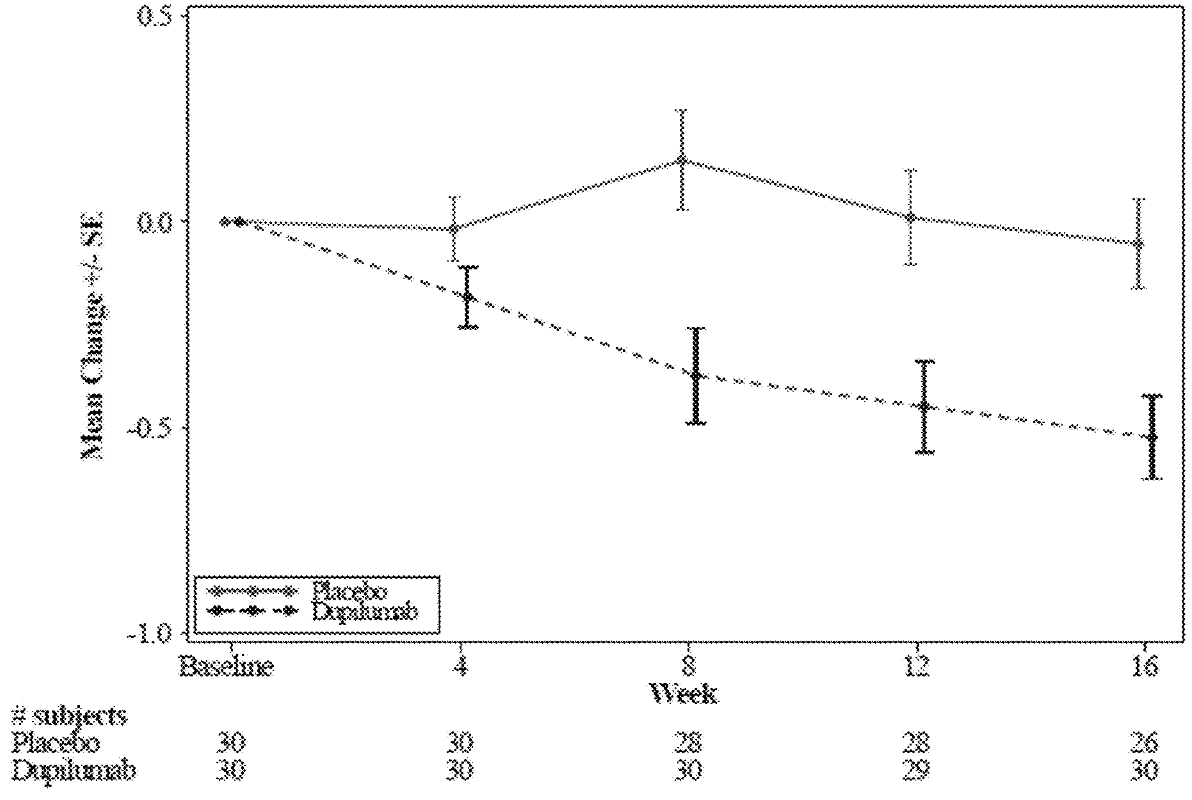
FIG. 15 graphically depicts LS mean change from baseline in PM symptom score for post nasal drip in an ITT population.

The results of the patient-reported evaluations for loss of smell (daily AM/PM e-diary records and the smell test score using University of Pennsylvania's Smell Identification Test (UPSIT) smell test) demonstrated statistical significance in favor of dupilumab at week 16 (Tables 24-26). Better ability to smell was demonstrated in the dupilumab treatment arm at the earliest evaluation time point in the study for each of these patient-reported outcomes (FIGS. 7-9). Significant improvements were also observed for the secondary endpoints of morning anterior rhinorrhea, subjective sense of smell, evening symptoms, and nocturnal awakenings (Table 54). Changes in symptom-based endpoints were sustained at the end of the 16-week follow-up period (Table 53).

TABLE 24

Mean change from baseline at week 16 in AM symptom score for loss of smell in an ITT population (MMRM).

| AM loss of smell | Placebo (N = 30) | Dupilumab 300 mg qw (N = 30) |
|---|---|---|
| Baseline | | |
| Number | 30 | 30 |
| Mean (SD) | 2.82 (0.49) | 2.41 (0.91) |
| Medium | 3.00 | 3.00 |
| Min:Max | 0.8:3.0 | 0.2:3.0 |
| Week 16 | | |
| Number | 26 | 30 |
| Mean (SD) | 2.53 (0.78) | 1.11 (1.07) |
| Medium | 2.92 | 1.00 |
| Min:Max | 0.0:3.0 | 0.0:3.0 |
| Change from baseline | | |
| Number | 26 | 30 |
| Mean (SD) | −0.26 (0.56) | −1.31 (1.08) |
| Medium | 0.00 | −1.00 |
| Min:Max | −1.9:0.2 | −3.0:0.5 |
| LS Mean (SE)[a] | −0.12 (0.16) | −1.34 (0.16) |
| LS Mean Diff, 95% CI[a] | | −1.22 (−1.66, −0.77) |
| P-value vs placebo[a] | | <.0001 |

[a]Analysis of a mixed model repeated measures (MMRM) model with treatment groups, stratification factor (asthma, biopsy), visit, treatment-by-visit interaction, baseline-by-visit interaction and baseline as covariates.

TABLE 25

Mean change from baseline at week 16 in PM symptom score for loss of smell in an ITT population (MMRM).

| PM loss of smell | Placebo (N = 30) | Dupilumab 300 mg qw (N = 30) |
|---|---|---|
| Baseline | | |
| Number | 30 | 30 |
| Mean (SD) | 2.81 (0.49) | 2.40 (0.88) |
| Medium | 3.00 | 3.00 |
| Min:Max | 0.8:3.0 | 0.1:3.0 |
| Week 16 | | |
| Number | 26 | 30 |
| Mean (SD) | 2.51 (0.80) | 1.07 (1.07) |
| Medium | 3.00 | 0.95 |
| Min:Max | 0.0:3.0 | 0.0:3.0 |
| Change from baseline | | |
| Number | 26 | 30 |
| Mean (SD) | −0.27 (0.58) | −1.32 (1.08) |
| Medium | 0.00 | −1.00 |
| Min:Max | −2.0:0.3 | −3.0:0.3 |
| LS Mean (SE)[a] | −0.16 (0.16) | −1.38 (0.16) |

TABLE 25-continued

Mean change from baseline at week 16 in PM symptom score for loss of smell in an ITT population (MMRM).

| PM loss of smell | Placebo (N = 30) | Dupilumab 300 mg qw (N = 30) |
|---|---|---|
| LS Mean Diff, 95% CI[a] | | −1.22 (−1.67, −0.77) |
| P-value vs placebo[a] | | <.0001 |

[a]Analysis of a mixed model repeated measures (MMRM) model with treatment groups, stratification factor (asthma, biopsy), visit, treatment-by-visit interaction, baseline-by-visit interaction and baseline as covariates.

TABLE 26

Mean change from baseline at week 16 in smell test score (UPSIT) in an ITT population (MMRM).

| Smell test (UPSIT) | Placebo (N = 30) | Dupilumab 300 mg qw (N = 30) |
|---|---|---|
| Baseline | | |
| Number | 30 | 30 |
| Mean (SD) | 15.63 (7.92) | 12.77 (8.28) |
| Medium | 12.00 | 10.00 |
| Min:Max | 9.0:35.0 | 3.0:33.0 |
| Week 16 | | |
| Number | 23 | 28 |
| Mean (SD) | 16.17 (8.68) | 28.71 (8.20) |
| Medium | 12.00 | 30.00 |
| Min:Max | 7.0:38.0 | 6.0:39.0 |
| Change from baseline | | |
| Number | 23 | 28 |
| Mean (SD) | −0.17 (5.10) | 15.36 (9.61) |
| Medium | 0.00 | 16.50 |
| Min:Max | −12.0:14.0 | −5.0:29.0 |
| LS Mean (SE)[a] | −0.69 (1.53) | 14.09 (1.35) |
| LS Mean Diff, 95% CI[a] | | 14.78 (10.90, 18.65) |
| P-value vs placebo[a] | | <.0001 |

[a]Analysis of a mixed model repeated measures (MMRM) model with treatment groups, stratification factor (asthma, biopsy), visit, treatment-by-visit interaction, baseline-by-visit interaction and baseline as covariates.

The typical symptoms of rhinitis (nasal obstruction/congestion, runny nose and post-nasal drip) were evaluated daily (AM/PM e-diary records) by the patients. The results demonstrated statistical significance in favor of dupilumab at week 16 across all these evaluations (Tables 27-32). Improvement in rhinosinusitis symptoms was observed from week 4 through week 16 in the dupilumab treatment arm for each of these patient-reported outcomes (FIGS. 10-15).

TABLE 27

Mean change from baseline at week 16 in AM symptom score for congestion/obstruction in an ITT population (MMRM).

| AM congestion/obstruction | Placebo (N = 30) | Dupilumab 300 mg qw (N = 30) |
|---|---|---|
| Baseline | | |
| Number | 30 | 30 |
| Mead (SD) | 1.69 (0.69) | 1.66 (0.73) |
| Median | 1.71 | 1.57 |
| Min:Max | 0.6:3.0 | 0.6:3.0 |
| Week 16 | | |
| Number | 26 | 30 |
| Mead (SD) | 1.37 (0.67) | 0.75 (0.70) |
| Median | 1.21 | 0.68 |
| Min:Max | 0.0:3.0 | 0.0:2.3 |

TABLE 27-continued

Mean change from baseline at week 16 in AM symptom score for congestion/obstruction in an ITT population (MMRM).

| AM congestion/obstruction | Placebo (N = 30) | Dupilumab 300 mg qw (N = 30) |
|---|---|---|
| Change from baseline | | |
| Number | 26 | 30 |
| Mead (SD) | −0.22 (0.67) | −0.91 (0.86) |
| Median | −0.09 | −0.82 |
| Min:Max | −1.6:1.0 | −3.0:0.3 |
| LS Mean (SE)[a] | −0.19 (0.13) | −0.87 (0.13) |
| LS Mean Diff, 95% CI[a] | | −0.68 (−1.03, −0.32) |
| P-value vs placebo[a] | | 0.0004 |

[a]Analysis of a mixed model repeated measures (MMRM) model with treatment groups, stratification factor (asthma, biopsy), visit, treatment-by-visit interaction, baseline-by-visit interaction and baseline as covariates.

TABLE 28

Mean change from baseline at week 16 in PM symptom score for congestion/obstruction in an ITT population (MMRM).

| PM congestion/obstruction | Placebo (N = 30) | Dupilumab 300 mg qw (N = 30) |
|---|---|---|
| Baseline | | |
| Number | 30 | 30 |
| Mead (SD) | 1.62 (0.69) | 1.59 (0.08) |
| Median | 1.39 | 1.71 |
| Min:Max | 0.8:3.0 | 0.0:3.0 |
| Week 16 | | |
| Number | 26 | 30 |
| Mead (SD) | 1.32 (0.67) | 0.65 (0.63) |
| Median | 1.12 | 0.56 |
| Min:Max | 0.1:3.0 | 0.0:2.2 |
| Change from baseline | | |
| Number | 26 | 30 |
| Mead (SD) | −0.22 (0.65) | −0.94 (0.86) |
| Median | −0.05 | −0.83 |
| Min:Max | −2.0:1.0 | −3.0:0.2 |
| LS Mean (SE)[a] | −0.19 (0.13) | −0.89 (0.12) |
| LS Mean Diff, 95% CI[a] | | −0.70 (−1.04, −0.36) |
| P-value vs placebo[a] | | 0.0001 |

[a]Analysis of a mixed model repeated measures (MMRM) model with treatment groups, stratification factor (asthma, biopsy), visit, treatment-by-visit interaction, baseline-by-visit interaction and baseline as covariates.

TABLE 29

Mean change from baseline at week 16 in AM symptom score for runny nose in an ITT population (MMRM).

| AM runny nose | Placebo (N = 30) | Dupilumab 300 mg qw (N = 30) |
|---|---|---|
| Baseline | | |
| Number | 30 | 30 |
| Mead (SD) | 1.14 (0.77) | 1.02 (0.91) |
| Median | 1.07 | 0.90 |
| Min:Max | 0.0:3.0 | 0.0:2.8 |
| Week 16 | | |
| Number | 26 | 30 |
| Mead (SD) | 1.03 (0.78) | 0.42 (0.53) |
| Median | 1.00 | 0.18 |
| Min:Max | 0.0:3.0 | 0.0:2.0 |

TABLE 29-continued

Mean change from baseline at week 16 in AM symptom score for runny nose in an ITT population (MMRM).

| AM runny nose | Placebo (N = 30) | Dupilumab 300 mg qw (N = 30) |
|---|---|---|
| Change from baseline | | |
| Number | 26 | 30 |
| Mead (SD) | −0.09 (0.56) | −0.60 (0.88) |
| Median | −0.14 | −0.25 |
| Min:Max | −1.8:1.0 | −2.5:0.9 |
| LS Mean (SE)[a] | −0.05 (0.11) | −0.63 (0.10) |
| LS Mean Diff, 95% CI[a] | | −0.58 (−0.88, −0.29) |
| P-value vs placebo[a] | | 0.0002 |

[a]Analysis of a mixed model repeated measures (MMRM) model with treatment groups, stratification factor (asthma, biopsy), visit, treatment-by-visit interaction, baseline-by-visit interaction and baseline as covariates.

TABLE 30

Mean change from baseline at week 16 in PM symptom score for runny nose in an ITT population (MMRM).

| PM runny nose | Placebo (N = 30) | Dupilumab 300 mg qw (N = 30) |
|---|---|---|
| Baseline | | |
| Number | 30 | 30 |
| Mead (SD) | 1.23 (0.71) | 0.99 (0.87) |
| Median | 1.14 | 1.00 |
| Min:Max | 0.0:3.0 | 0.0:2.9 |
| Week 16 | | |
| Number | 26 | 30 |
| Mead (SD) | 0.99 (0.70) | 0.42 (0.48) |
| Median | 1.00 | 0.22 |
| Min:Max | 0.0:2.2 | 0.0:1.9 |
| Change from baseline | | |
| Number | 26 | 30 |
| Mead (SD) | −0.25 (0.63) | −0.57 (0.82) |
| Median | −0.15 | −0.18 |
| Min:Max | −1.8:1.0 | −2.8:0.4 |
| LS Mean (SE)[a] | −0.14 (0.11) | −0.63 (0.10) |
| LS Mean Diff, 95% CI[a] | | −0.49 (−0.07, −0.21) |
| P-value vs placebo[a] | | 0.0009 |

[a]Analysis of a mixed model repeated measures (MMRM) model with treatment groups, stratification factor (asthma, biopsy), visit, treatment-by-visit interaction, baseline-by-visit interaction and baseline as covariates.

TABLE 31

Mean change from baseline at week 16 in AM symptom score for post nasal drip in an ITT population (MMRM).

| AM post nasal drip | Placebo (N = 30) | Dupilumab 300 mg qw (N = 30) |
|---|---|---|
| Baseline | | |
| Number | 30 | 30 |
| Mead (SD) | 1.40 (0.80) | 1.05 (0.91) |
| Median | 1.29 | 1.00 |
| Min:Max | 0.0:3.0 | 0.0:3.0 |
| Week 16 | | |
| Number | 26 | 30 |
| Mead (SD) | 1.24 (0.85) | 0.58 (0.58) |
| Median | 1.29 | 0.60 |
| Min:Max | 0.0:3.0 | 0.0:2.0 |

TABLE 31-continued

Mean change from baseline at week 16 in AM symptom score for post nasal drip in an ITT population (MMRM).

| AM post nasal drip | Placebo (N = 30) | Dupilumab 300 mg qw (N = 30) |
|---|---|---|
| Change from baseline | | |
| Number | 26 | 30 |
| Mead (SD) | −0.15 (0.59) | −0.48 (0.77) |
| Median | −0.00 | −0.20 |
| Min:Max | −1.7:1.0 | −2.6:0.6 |
| LS Mean (SE)[a] | −0.04 (0.11) | −0.54 (0.11) |
| LS Mean Diff, 95% CI[a] | | −0.50 (−0.80, −0.19) |
| P-value vs placebo[a] | | 0.0020 |

[a]Analysis of a mixed model repeated measures (MMRM) model with treatment groups, stratification factor (asthma, biopsy), visit, treatment-by-visit interaction, baseline-by-visit interaction and baseline as covariates.

TABLE 32

Mean change from baseline at week 16 in PM symptom score for post nasal drip in an ITT population (MMRM).

| PM post nasal drip | Placebo (N = 30) | Dupilumab 300 mg qw (N = 30) |
|---|---|---|
| Baseline | | |
| Number | 30 | 30 |
| Mead (SD) | 1.41 (0.79) | 1.03 (0.90) |
| Median | 1.24 | 1.00 |
| Min:Max | 0.0:3.0 | 0.0:3.0 |
| Week 16 | | |
| Number | 26 | 30 |
| Mead (SD) | 1.15 (0.76) | 0.54 (0.55) |
| Median | 1.10 | 0.41 |
| Min:Max | 0.0:2.4 | 0.0:2.0 |
| Change from baseline | | |
| Number | 26 | 30 |
| Mead (SD) | −0.23 (0.60) | −0.49 (0.80) |
| Median | −0.07 | −0.16 |
| Min:Max | −1.5:1.0 | −3.0:0.6 |
| LS Mean (SE)[a] | −0.05 (0.11) | −0.53 (0.10) |
| LS Mean Diff, 95% CI[a] | | −0.47 (−0.76, −0.18) |
| P-value vs placebo[a] | | 0.0018 |

[a]Analysis of a mixed model repeated measures (MMRM) model with treatment groups, stratification factor (asthma, biopsy), visit, treatment-by-visit interaction, baseline-by-visit interaction and baseline as covariates.

Figure 16:
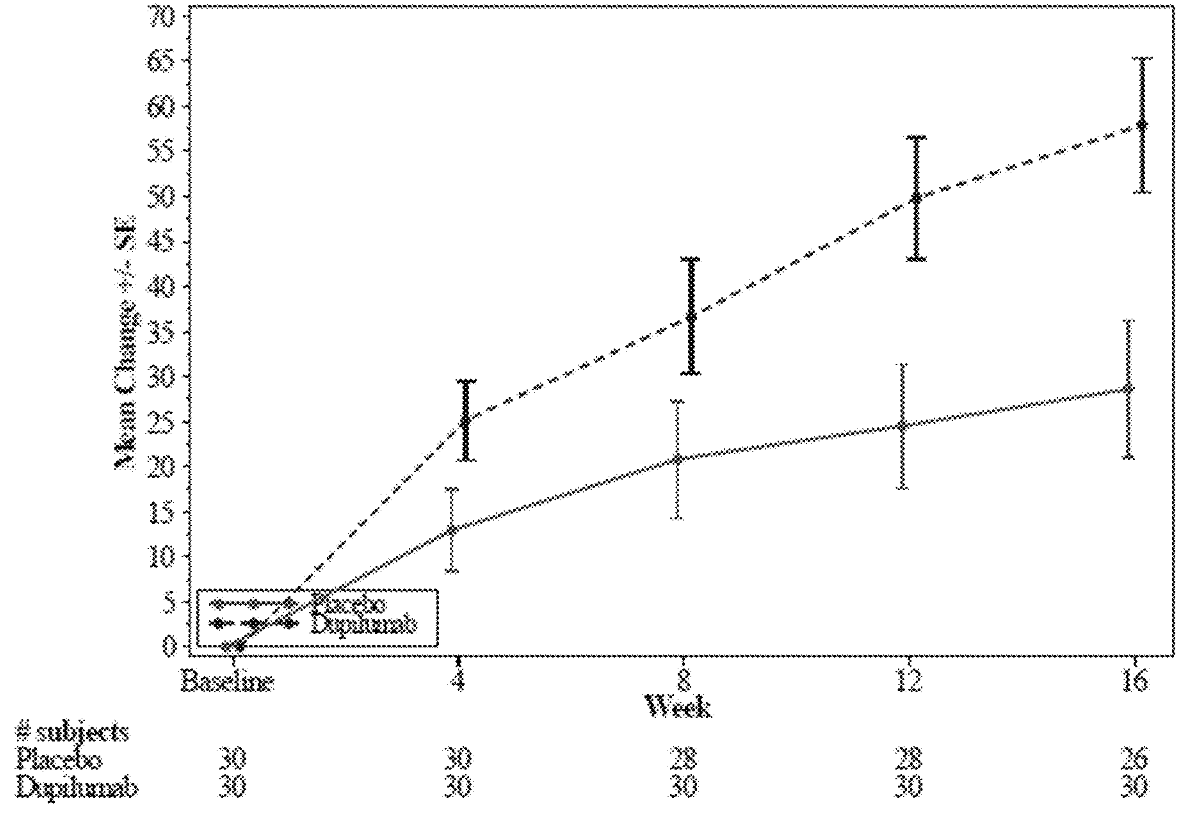
FIG. 16 graphically depicts LS mean change from baseline in AM Nasal Peak Inspiratory Flow (NPIF) in an ITT population.
Figure 17:
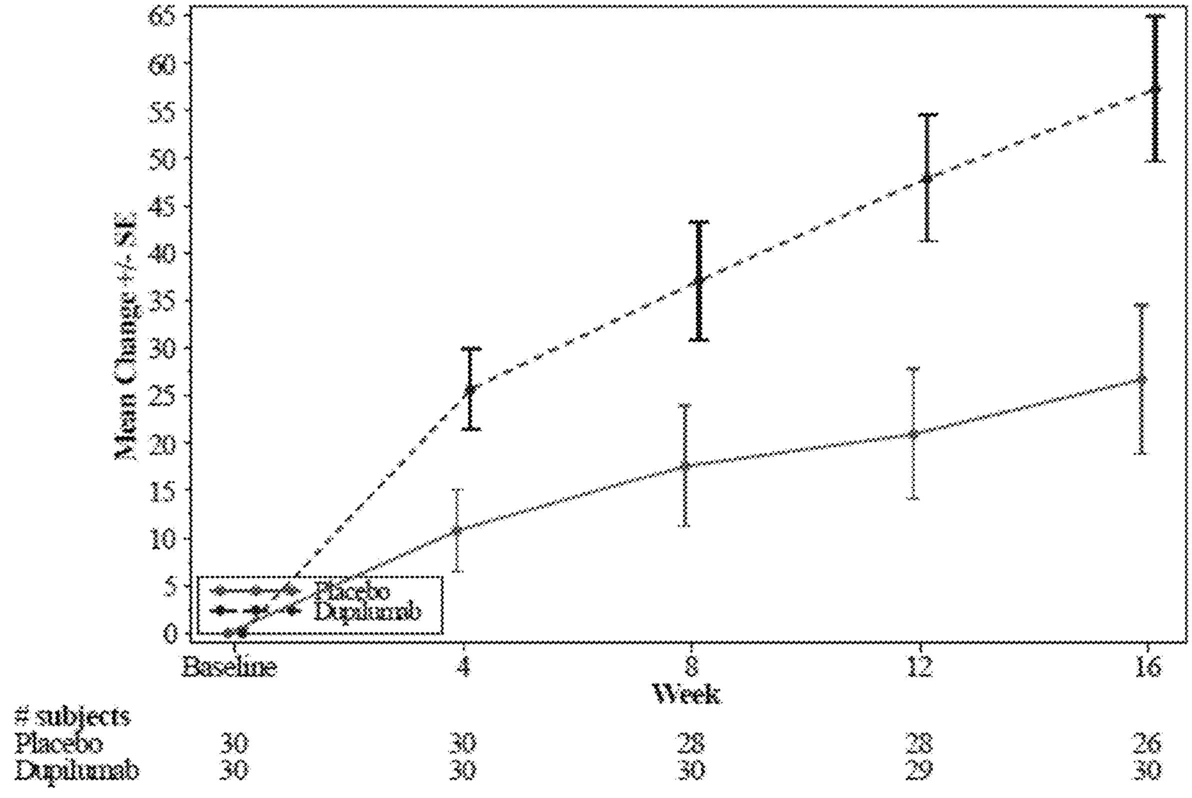
FIG. 17 graphically depicts LS mean change from baseline in PM NPIF in an ITT population.

The nasal peak inspiratory flow (NPIF) was assessed with NPIF meters to evaluate the impact of nasal polyposis disease on forced AM/PM inspiration and expiration through the nasal cavity (L/min). Normal NPIF rates are approximately 140 L/min and above, whereas, severely limited flow rates are in the range of 110-120 L/min. The results of AM/PM NPIF rates demonstrated statistical significance at week 16 in favor of dupilumab (p=0.0073 and p=0.0064, respectively) (Table 33 and Table 34). The effect of dupilumab on AM/PM NPIF was observed from week 4 through week 16 (FIG. 16 and FIG. 17). Changes in AM NPIF were sustained at the end of the 16 week follow-up period (Table 53).

TABLE 33

Mean change from baseline at week 16 in AM NPIF in an ITT population (MMRM).

| AM NPIF | Placebo (N = 30) | Dupilumab 300 mg qw (N = 30) |
|---|---|---|
| Baseline | | |
| Number | 30 | 30 |
| Mead (SD) | 109.22 (46.77) | 98.44 (48.45) |
| Median | 100.54 | 101.79 |
| Min:Max | 44.3:232.9 | 0.0:186.7 |
| Week 16 | | |
| Number | 26 | 30 |
| Mead (SD) | 141.92 (59.27) | 157.38 (55.75) |
| Median | 142.36 | 156.63 |
| Min:Max | 43.3:251.3 | 36.9:305.8 |
| Change from baseline | | |
| Number | 26 | 30 |
| Mead (SD) | 30.01 (34.94) | 58.94 (44.56) |
| Median | 19.57 | 54.53 |
| Min:Max | −18.9:114.3 | −14.6:148.5 |
| LS Mean (SE)[a] | 28.64 (7.66) | −57.90 (7.49) |
| LS Mean Diff, 95% CI[a] | | 29.25 (8.23, 50.28) |
| P-value vs placebo[a] | | 0.0073 |

[a]Analysis of a mixed model repeated measures (MMRM) model with treatment groups, stratification factor (asthma, biopsy), visit, treatment-by-visit interaction, baseline-by-visit interaction and baseline as covariates.

TABLE 34

Mean change from baseline at week 16 in PM NPIF in an ITT population (MMRM).

| PM NPIF | Placebo (N = 30) | Dupilumab 300 mg qw (N = 30) |
|---|---|---|
| Baseline | | |
| Number | 30 | 30 |
| Mead (SD) | 121.29 (51.77) | 105.23 (52.46) |
| Median | 115.95 | 101.00 |
| Min:Max | 44.3:241.4 | 0.0:218.8 |
| Week 16 | | |
| Number | 26 | 30 |
| Mead (SD) | 149.62 (63.80) | 164.19 (57.62) |
| Median | 148.51 | 167.82 |
| Min:Max | 51.2:275.5 | 48.7:322.7 |
| Change from baseline | | |
| Number | 26 | 30 |
| Mead (SD) | 27.37 (33.60) | 58.96 (46.56) |
| Median | 24.82 | 51.51 |
| Min:Max | −26.0:102.9 | −3.4:155.1 |
| LS Mean (SE)[a] | 26.69 (7.84) | 57.28 (7.65) |
| LS Mean Diff, 95% CI[a] | | 30.59 (8.95, 52.23) |
| P-value vs placebo[a] | | 0.0064 |

[a]Analysis of a mixed model repeated measures (MMRM) model with treatment groups, stratification factor (asthma, biopsy), visit, treatment-by-visit interaction, baseline-by-visit interaction and baseline as covariates.

CT scans of the sinuses were used to evaluate nasal polyposis and associated sinus inflammation. The Lund-Mackay total score evaluates the patency of each sinus using a 0-2 scale (0=complete lucency and 2=complete opacity; 0-24 point range). The CT results demonstrated statistical significance at week 16 in favor of dupilumab; the LS mean (SE) change from baseline at week 16 was −0.23 (0.95) in the placebo group, and −9.07 (0.81) in the dupilumab group, resulting in a LS difference of −8.84 (95% CI, −11.07 to −6.61, p<0.0001) (Table 24).

TABLE 35

Mean change from baseline at week 16 in Lund-Mackay score in an ITT population.

| Lund-Mackay score | Placebo (N = 30) | Dupilumab 300 mg qw (N = 30) |
|---|---|---|
| Baseline | | |
| Number | 30 | 30 |
| Mead (SD) | 18.73 (5.52) | 18.62 (5.00) |
| Median | 20.50 | 20.00 |
| Min:Max | 1.0:24.0 | 7.0:24.0 |
| Week 16 | | |
| Number | 26 | 30 |
| Mead (SD) | 17.92 (5.69) | 9.43 (5.10) |
| Median | 21.00 | 9.50 |
| Min:Max | 1.0:24.0 | 0.0:24.0 |
| Change from baseline | | |
| Number | 26 | 29 |
| Mead (SD) | −0.23 (3.74) | −0.24 (4.58) |
| Median | 0.00 | −9.00 |
| Min:Max | −16.0:6.0 | −18.0:0.0 |
| LS Mean (SE)[a] | −0.23 (0.95) | −9.07 (0.81) |
| LS Mean Diff, 95% CI[a] | | −8.84 (−11.07, −6.61) |
| P-value vs placebo[a] | | <.0001 |

[a]Analysis of covariance (ANCOVA) model with treatment groups, stratification factor (asthma, biopsy), as fixed effects and baseline as a covariate.

Pharmacodynamic measurements included serum total immunoglobulin E (IgE), thymus and activation regulated chemokine (TARC), plasma eotaxin-3 and blood eosinophils. Safety and tolerability assessments were based on the incidence of adverse events (AEs) and serious AEs (SAEs), as well as vital signs, physical examination, clinical laboratory evaluation and 12-lead electrocardiogram (ECG) findings.

Levels of serum total IgE, TARC and eotaxin-3 (FIGS. 23A-23D) decreased in patients who received dupilumab plus mometasone but remained unchanged in patients who received placebo plus mometasone. The observed reductions in IgE progressed over the course of the 16-week treatment period, whereas TARC and eotaxin-3 levels decreased significantly by week 2 and remained reduced throughout the treatment period. Mean peripheral-blood eosinophil levels remained unchanged with both placebo and dupilumab throughout the treatment period (FIG. 23D).

Figure 18:
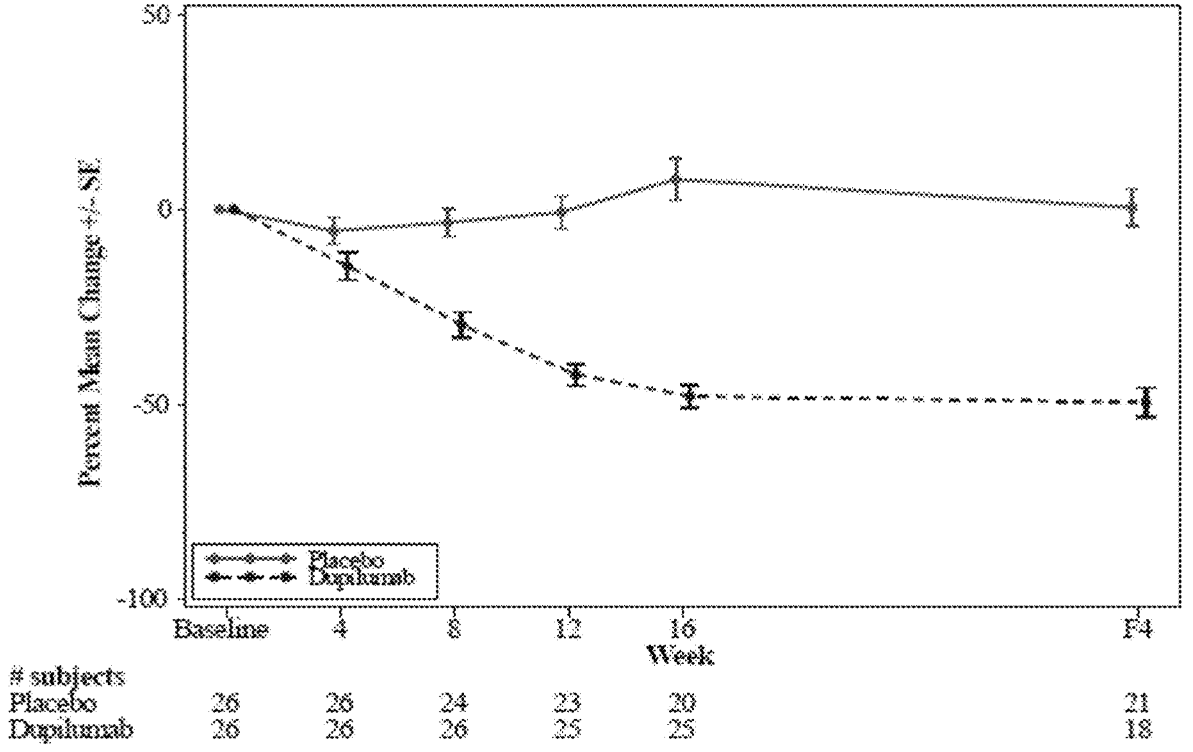
FIG. 18 graphically depicts serum total Immunoglobulin E (IgE) mean percent change from baseline by treatment in an ITT population.

Serum total IgE at baseline was overall normal or modestly elevated in the study population (mean 140 IU/mL for dupilumab group vs 195 IU/mL for the placebo group). Total IgE progressively declined during treatment with dupilumab (mean percent change from baseline at week 16: −48.0% dupilumab vs +7.6% placebo) (FIG. 18).

Figure 19:
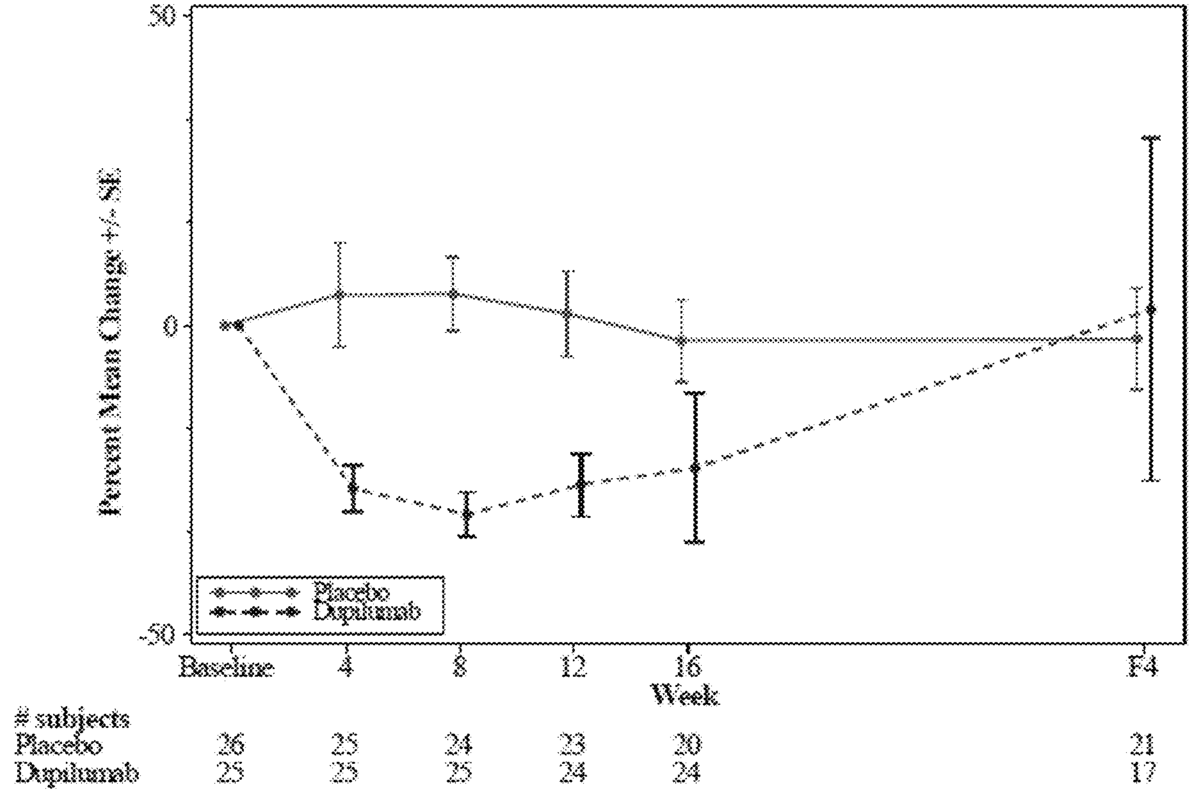
FIG. 19 graphically depicts serum Thymus and Activation-Regulated Chemokine (TARC) mean percent change from baseline by treatment in an ITT population.

Baseline mean (SD) Thymus and Activation-Regulated Chemokine (TARC) levels for placebo and dupilumab, respectively, were 449.31 (376.77) pg/mL and 469.65 (298) pg/mL. During dupilumab treatment, serum TARC concentration declined by week 4 and remained suppressed through week 16 (mean percent change from baseline at week 4: −26.5% dupilumab vs +5.0% placebo and at week 16: −23.0% dupilumab vs −2.5% placebo) (FIG. 19).

In nasal secretions (saline eluates), Th2 biomarkers were significantly (or borderline significantly) lower after dupilumab (DPL) vs placebo (PBO) (mean % change from baseline) treatment: eotaxin-3 from week 8 (−32.4 DPL vs +74.4 PBO p=0.017) through week 16 (−38.5 DPL vs +183.0 PBO p=0.040), ECP at week 12 (−2.5 DPL vs +102.6 PBO p=0.055) and week 16 (+7.2 DPL vs +120.2 PBO p=0.072), and total IgE from week 8 (−15.7 DPL vs +60.1

Figure 24A:
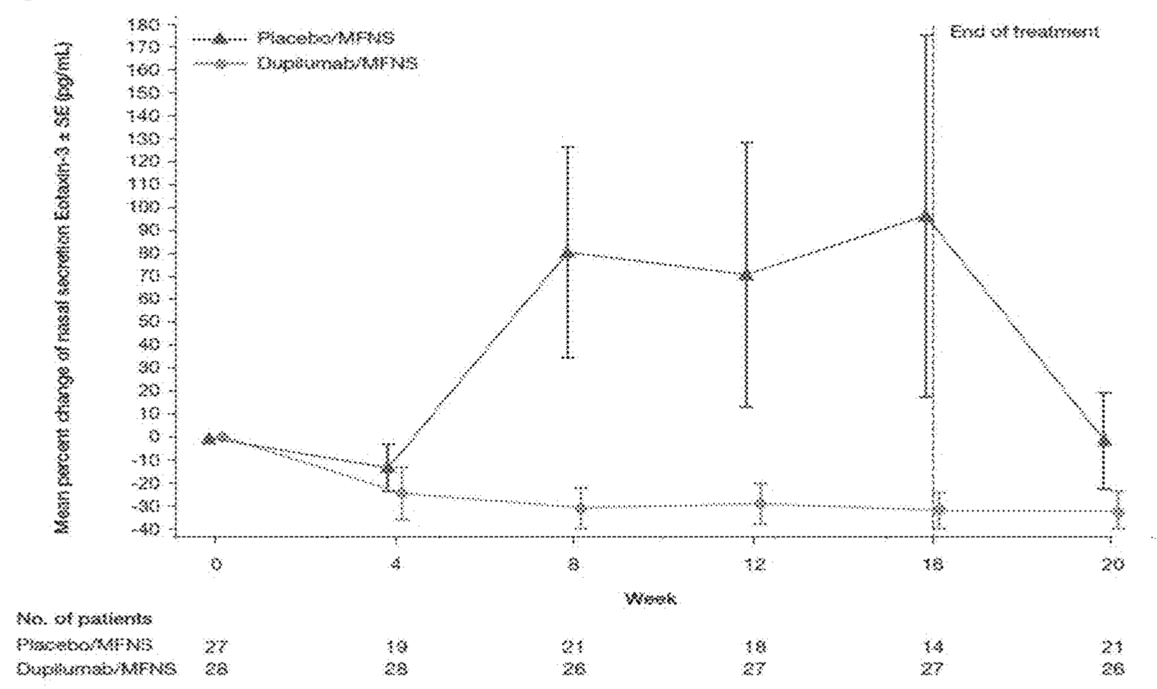
FIGS. 24A-24C graphically depict pharmacodynamics biomarkers expressed in nasal secretions.
Figure 24B:
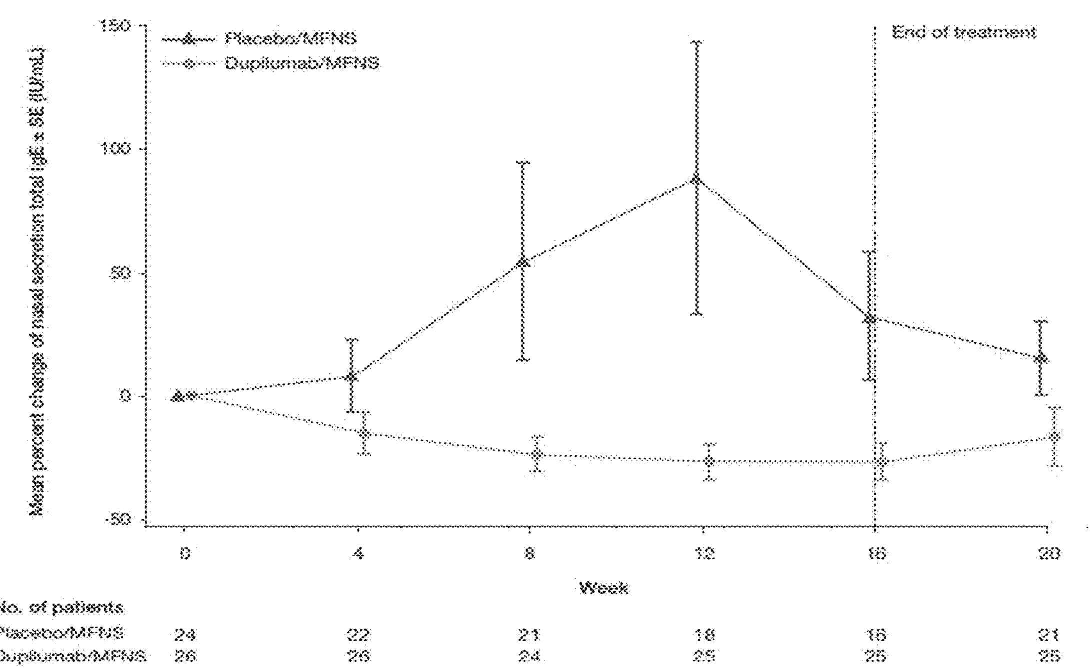
Figure 24C:
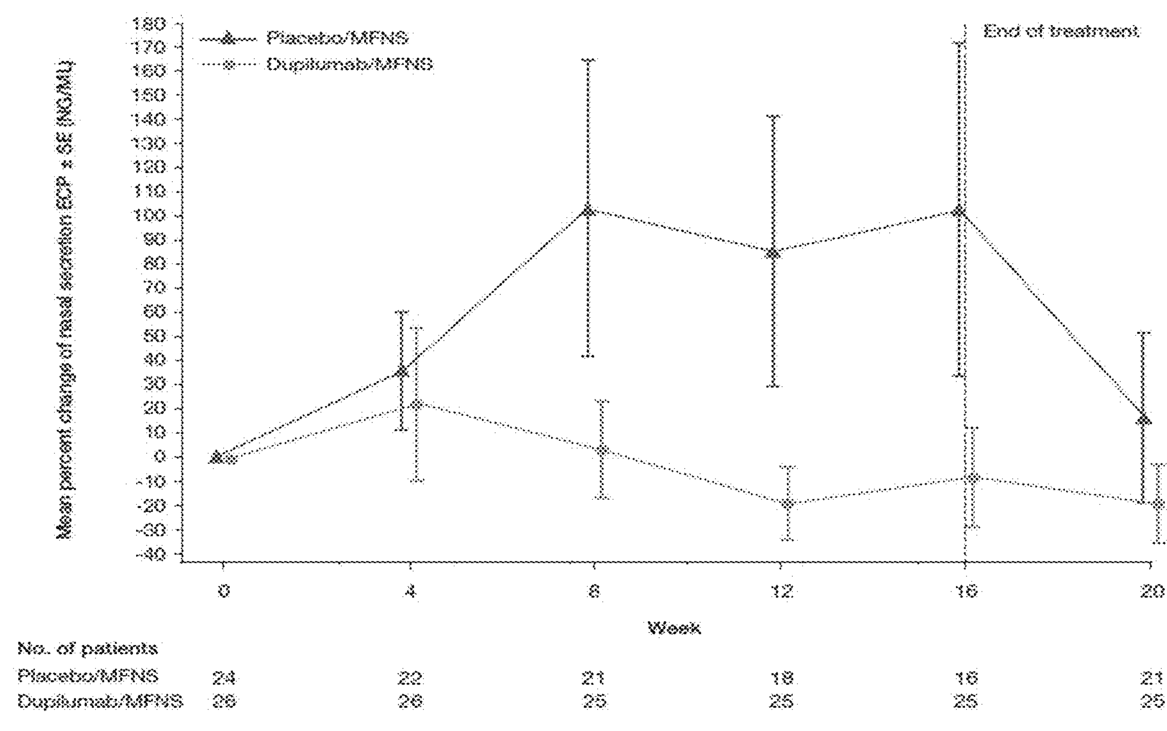

PBO p=0.043) through week 16 (−15.9 DPL vs +43.8 PBO p=0.025) (FIGS. 24A, 24B, and 24C, respectively). The mean serum ECP, unlike the mean NS ECP, did not show a decrease during dupilumab treatment. After dupilumab, there were transient increases in blood eosinophil count (Eos) (mean percent change from baseline) (W4: +49 DPL vs +0.2 PBO) that resolved during treatment (W16: −5.8 DPL vs +3.8 PBO) (FIG. 23C). The mean absolute changes from baseline in nasal secretion biomarkers at Week 16 are shown below in Table 56.

Trial endpoints are summarized in Table 52.

Safety was assessed by the evaluation of AE reporting, physical examination findings, ECGs and laboratory test results.

In the dupilumab treatment group 29 of 30 patients reported a Treatment-Emergent Adverse Event (TEAE) compared to 25 of 30 patients in the placebo group with 2 dupilumab and 4 placebo patients reporting serious TEAEs, respectively. No patient died during the treatment period. One patient in the dupilumab and 5 patients in the placebo group discontinued from treatment due to a TEAE (Table 36).

TABLE 36

Overview of adverse event profile: TEAEs in a safety population.

| n (%) | Placebo (N = 30) | Dupilumab 300 mg qw (N = 30) |
|---|---|---|
| Patients with any TEAE | 25 (83.3%) | 29 (96.7%) |
| Patients with any treatment emergent SAE | 4 (13.3%) | 2 (6.7%) |
| Patients with any TEAE leading to death | 0 | 0 |
| Patients with any TEAE leading to permanent treatment discontinuation | 5 (16.7%) | 1 (3.3%) |

SAE: Serious Adverse Event. n (%) = number and percentage of patients with at least one TEAE.

The most frequently affected system organ classes (SOC) were: infections and infestations (56.7% in placebo and 70.0% in dupilumab); general disorders and administration site conditions (6.7% in placebo and 43.3% in dupilumab); respiratory, thoracic and mediastinal disorders (33.3% in placebo and 43.3 in dupilumab); nervous system disorders (20.0% in placebo and 36.7% in dupilumab); gastrointestinal disorders (20.0% each in placebo and dupilumab); and musculoskeletal and connective tissue disorders (3.3% in placebo and 26.7% in dupilumab) (Table 37).

TABLE 37

Number (%) of patients with TEAE(s) by primary SOC and PT in a safety population.

| Primary System Organ Class Preferred Term n (%) | Placebo (N = 30) | Dupilumab 300 mg qw (N = 30) |
|---|---|---|
| Any Class | 25 (83.3%) | 29 (96.7%) |
| Infections and infestations | 17 (56.7%) | 21 (70.0%) |
| Nasopharyngitis | 10 (33.3%) | 11 (36.7%) |
| Upper respiratory tract infection | 0 | 3 (10.0%) |
| Sinusitis | 0 | 2 (6.7%) |
| Acute sinusitis | 0 | 1 (3.3%) |
| Bronchitis | 4 (13.3%) | 1 (3.3%) |
| Bronchopneumonia | 0 | 1 (3.3%) |
| Ear infection | 1 (3.3%) | 1 (3.3%) |
| Fungal skin infection | 0 | 1 (3.3%) |
| Furuncle | 0 | 1 (3.3%) |
| Gastroenteritis viral | 0 | 1 (3.3%) |
| Gastroeneritis infection | 0 | 1 (3.3%) |
| Herpes zoster | 0 | 1 (3.3%) |
| Influenza | 0 | 1 (3.3%) |
| Laryngitis fungal | 0 | 1 (3.3%) |
| Oral herpes | 0 | 1 (3.3%) |
| Pharyngitis | 0 | 1 (3.3%) |
| Rhinitis | 0 | 1 (3.3%) |
| Skin infection | 0 | 1 (3.3%) |
| Urinary tract infection | 0 | 1 (3.3%) |
| Viral upper respiratory tract infection | 0 | 1 (3.3%) |
| Conjuctivitis | 1 (3.3%) | 0 |
| Laryngitis | 1 (3.3%) | 0 |
| Otitus media | 1 (3.3%) | 0 |
| Respiratory tract infection | 1 (3.3%) | 0 |
| Neoplasms benign, malignant and unspecified (incl cysts and polyps) | 1 (3.3%) | 0 |
| Uterine cancer | 1 (3.3%) | 0 |
| Uterine leiomyoma | 1 (3.3%) | 0 |
| Blood and lymphatic system disorders | 2 (6.7%) | 0 |
| Anaemia | 1 (3.3%) | 0 |
| Neutropenia | 1 (3.3%) | 0 |
| Immune system disorders | 1 (3.3%) | 1 (3.3%) |
| Drug hypersensitivity | 0 | 1 (3.3%) |
| Hypersensitivity | 1 (3.3%) | 0 |
| Psychiatric disorders | 1 (3.3%) | 1 (3.3%) |
| Insomnia | 0 | 1 (3.3%) |
| Sleep disorder | 1 (3.3%) | 0 |
| Nervous system disorders | 6 (20.0%) | 11 (36.7%) |
| Headache | 5 (16.7%) | 6 (20.0%) |
| Dizziness | 1 (3.3%) | 3 (10.0%) |
| Hypoaesthesia | 0 | 1 (3.3%) |
| Migraine | 0 | 1 (3.3%) |

TABLE 37-continued

Number (%) of patients with TEAE(s) by primary SOC and PT in a safety population.

| Primary System Organ Class Preferred Term n (%) | Placebo (N = 30) | Dupilumab 300 mg qw (N = 30) |
|---|---|---|
| Mononeuropathy | 0 | 1 (3.3%) |
| Paraesthesia | 0 | 1 (3.3%) |
| Sinus headache | 1 (3.3%) | 1 (3.3%) |
| Tension headache | 1 (3.3%) | 1 (3.3%) |
| Transient ischaemic attack | 1 (3.3%) | 0 |
| Ear and labyrinth disorders | 1 (3.3%) | 2 (6.7%) |
| Ear discomfort | 1 (3.3%) | 1 (3.3%) |
| Vertigo | 0 | 1 (3.3%) |
| Cardiac disorders | 1 (3.3%) | 4 (13.3%) |
| Arrhythmia | 0 | 1 (3.3%) |
| Atrioventricular block first degree | 0 | 1 (3.3%) |
| Palpitations | 0 | 1 (3.3%) |
| Ventricular extrasystoles | 0 | 1 (3.3%) |
| Bundle branch block left | 1 (3.3%) | 0 |
| Vascular disorders | 2 (6.7%) | 0 |
| Hypertension | 2 (6.7%) | 0 |
| Respiratory, thoracic and mediastinal disorders | 10 (33.3%) | 13 (43.3%) |
| Oropharyngeal pain | 2 (6.7%) | 7 (23.3%) |
| Epistaxis | 2 (6.7%) | 6 (20.0%) |
| Cough | 1 (3.3%) | 2 (6.7%) |
| Rhinalgia | 0 | 2 (6.7%) |
| Rhinitus allergic | 0 | 2 (6.7%) |
| Asthma | 3 (10.0%) | 1 (3.3%) |
| Haemoptysis | 0 | 1 (3.3%) |
| Nasal discomfort | 0 | 1 (3.3%) |
| Nasal obstruction | 0 | 1 (3.3%) |
| Nasal polyps | 3 (10.0%) | 1 (3.3%) |
| Rhinorrhoea | 1 (3.3%) | 1 (3.3%) |
| Wheezing | 0 | 1 (3.3%) |
| Bronchial secretion retention | 1 (3.3%) | 0 |
| Nasal congestion | 1 (3.3%) | 0 |
| Upper-airway cough syndrome | 3 (10.0%) | 0 |
| Gastrointestinal disorders | 6 (20.0%) | 6 (20.0%) |
| Abdominal pain upper | 0 | 1 (3.3%) |
| Constpation | 0 | 1 (3.3%) |
| Diarrhoea | 1 (3.3%) | 1 (3.3%) |
| Gastritis | 0 | 1 (3.3%) |
| Gastrointestinal hypermotility | 0 | 1 (3.3%) |
| Odynophagia | 0 | 1 (3.3%) |
| Abdominal pain | 2 (6.7%) | 0 |
| Faeces soft | 1 (3.3%) | 0 |
| Gastrooesophageal reflux disease | 1 (3.3%) | 0 |
| Haematochezia | 1 (3.3%) | 0 |
| Vomiting | 1 (3.3%) | 0 |
| Skin and subcutaneous tissue disorders | 0 | 1 (3.3%) |
| Pruritis | 0 | 1 (3.3%) |
| Musculoskeletal and connective tissue disorders | 1 (3.3%) | 8 (26.7%) |
| Back pain | 0 | 3 (10.0%) |
| Arthralgia | 1 (3.3%) | 2 (6.7%) |
| Bursitis | 0 | 1 (3.3%) |
| Muscle spasms | 0 | 1 (3.3%) |
| Musculoskeletal chest pain | 0 | 1 (3.3%) |
| Osteoarthritis | 0 | 1 (3.3%) |
| Pain in extremity | 0 | 1 (3.3%) |
| Temporomandibular joint syndrome | 0 | 1 (3.3%) |
| Tendon disorders | 0 | 1 (3.3%) |
| Reproductive system and breast disorders | 1 (3.3%) | 1 (3.3%) |
| Menorrhagia | 0 | 1 (3.3%) |
| Premenstrual headache | 0 | 1 (3.3%) |
| Vaginal haemorrhage | 1 (3.3%) | 0 |
| Congenital, familial and genetic disorders | 1 (3.3%) | 0 |
| Gilbert's syndrome | 1 (3.3%) | 0 |
| General disorders and administration site conditions | 2 (6.7%) | 13 (43.3%) |
| Injection site reaction | 2 (6.7%) | 12 (40.0%) |
| Injection site pain | 0 | 1 (3.3%) |
| Puncture site pain | 0 | 1 (3.3%) |
| Pyrexia | 0 | 1 (3.3%) |
| Fatigue | 1 (3.3%) | 0 |
| Investigations | 1 (3.3%) | 0 |
| Blood creatine phosphokinase increased | 1 (3.3%) | 0 |
| Injury, poisoning and procedural complications | 3 (10.0%) | 2 (6.7%) |

TABLE 37-continued

Number (%) of patients with TEAE(s) by primary SOC and PT in a safety population.

| Primary System Organ Class<br>Preferred Term n (%) | Placebo<br>(N = 30) | Dupilumab<br>300 mg qw<br>(N = 30) |
|---|---|---|
| Joint injury | 1 (3.3%) | 1 (3.3%) |
| Tendon rupture | 1 (3.3%) | 1 (3.3%) |
| Limb injury | 1 (3.3%) | 0 |
| Upper limb fracture | 1 (3.3%) | 0 |
| Surgical and medical procedures | 1 (3.3%) | 1 (3.3%) |
| Endodontic procedure | 0 | 1 (3.3%) |
| Inguinal hernia repair | 1 (3.3%) | 0 |

TEAE: Treatment emergent adverse event, SOC: System organ class, PT: Preferred term. MEDDRA 17.0. n (%) = number and percentage of patients with at least one TEAE.
Note:
Table sorted by SOC internationally agreed order and decreasing percentage of PT in dupilumab 300 mg group.

The most frequently reported TEAEs were nasopharyngitis (10 (33.3%) in placebo and 11 (36.7%) in dupilumab) and headache (5 (16.7%) in placebo and 6 (20.0%) in dupilumab), which were both balanced between the two treatment groups, while injection site reaction, was predominantly reported for the dupilumab group (2 (6.7%) in placebo and 12 (40.0%) in dupilumab). In addition, two patients each reported injection and puncture site pain, respectively (6.7% overall). Other frequently reported TEAEs that were also reported at a higher percentage in the dupilumab than in the placebo group were oropharyngeal pain (2 (6.7%) in placebo and 7 (23.3%) in dupilumab), epistaxis (2 (6.7%) in placebo and 6 (20.0%) in dupilumab), and upper respiratory infection and back pain (both 0 in placebo and 3 (10.0%) in dupilumab, respectively). There were only a few events that were reported more frequently by patients in the placebo group or by 2 or 3 patients overall. The majority of TEAEs were reported only by single patients in both the placebo and the dupilumab groups.

Four patients in the placebo and two patients in the dupilumab group reported serious TEAEs. There was no pattern of TEAEs. No patient died during the treatment period. One patient died during screening due to the rupture of an aneurysm of the aorta without having received study medication (non-TEAE) (Table 38).

TABLE 38

Number (%) of patients with treatment emergent SAEs by primary SOC, HLGT, HLT AND PT in a safety population.

| PRIMARY SYSTEM ORGAN CLASS<br>HLGT: High Levet Group Term<br>HLT: High Level Term<br>Preferred Term n (%) | Placebo<br>(N = 30) | Dupilumab<br>300 mg qw<br>(N = 30) |
|---|---|---|
| Any Class | 4 (13.3%) | 2 (6.7%) |
| INFECTIONS AND INFESTATIONS | 0 | 1 (3.3%) |
| HLGT: Viral infectious disorders | 0 | 1 (3.3%) |
| HLT: Herpes viral infections | 0 | 1 (3.3%) |
| Herpes zoster | 0 | 1 (3.3%) |
| NEOPLASMS BENIGN, MALIGNANT AND UNSPECIFIED (INCL CYSTS AND POLYPS) | 1 (3.3%) | 0 |
| HLGT: Reproductive neoplasms female malignant and unspecified | 1 (3.3%) | 0 |
| HLT: Uterine neoplasms malignant NEC | 1 (3.3%) | 0 |
| Uterine cancer | 1 (3.3%) | 0 |
| NERVOUS SYSTEM DISORDERS | 1 (3.3%) | 1 (3.3%) |
| HLGT: Central nervous system vascular disorders | 1 (3.3%) | 0 |
| HLT: Transient cerebrovascular events | 1 (3.3%) | 0 |
| Transient ischeaemic attack | 1 (3.3%) | 0 |
| HLGT: Neurological disorders NEC | 0 | 1 (3.3%) |
| HLT: Paraesthesias and dysaesthesias | 0 | 1 (3.3%) |
| Hypoaesthesia | 0 | 1 (3.3%) |
| HLGT: Peripheral neuropathies | 0 | 1 (3.3%) |
| HLT: Mononeuropathies | 0 | 1 (3.3%) |
| Mononeuropathy | 0 | 1 (3.3%) |
| CARDIAC DISORDERS | 0 | 1 (3.3%) |
| HLGT: Cardiac arrhythmias | 0 | 1 (3.3%) |
| HLT: Rate and rhythm disorders NEC | 0 | 1 (3.3%) |
| Arrhythmia | 0 | 1 (3.3%) |
| RESPIRATORY, THORACIC AND MEDIASTINAL DISORDERS | 2 (6.7%) | 0 |
| HLGT: Bronchial disorders (excl neoplasms) | 1 (3.3%) | 0 |
| HLT: Bronchospasms and obstruction | 1 (3.3%) | 0 |
| Asthma | 1 (3.3%) | 0 |
| HLGT: Upper respiratory tract disorders (excl infections) | 1 (3.3%) | 0 |
| HLT: Nasal disorders NEC | 1 (3.3%) | 0 |

TABLE 38-continued

Number (%) of patients with treatment emergent SAEs by primary SOC, HLGT, HLT AND PT in a safety population.

| PRIMARY SYSTEM ORGAN CLASS<br>HLGT: High Levet Group Term<br>HLT: High Level Term<br>Preferred Term n (%) | Placebo<br>(N = 30) | Dupilumab<br>300 mg qw<br>(N = 30) |
|---|---|---|
| Nasal polyps | 1 (3.3%) | 0 |
| MUSCULOSKELETAL AND CONNECTIVE TISSUE DISORDERS | 0 | 1 (3.3%) |
| HLGT: Musculoskeletal and connective tissue disorders NEC | 0 | 1 (3.3%) |
| HLT: Musculoskeletal and connective tissue pain and discomfort | 0 | 1 (3.3%) |
| Pain in extremity | 0 | 1 (3.3%) |

SAE: Serious adverse event, SOC: System organ class, HLGT: High level group term, HLT: High level term, PT: Preferred term. MEDDRA 17.0. n (%) = number and percentage of patients with at least one treatment emergent SAE.
Note:
Table sorted by SOC internationally agreed order and HLGT, HLT, PT by alphabetic order.

A total of 6 patients discontinued the study due to TEAEs, 5 in the placebo group and 1 in the dupilumab group. With the exception of asthma, which was reported by 2 placebo patients, all other terms were only reported once (Table 39).

TABLE 39

Number (%) of patients with TEAE(s) leading to permanent treatment discontinuation by primary SOC, HLGT, HLT and PT in a safety population.

| PRIMARY SYSTEM ORGAN CLASS<br>HLGT: High Levet Group Term<br>HLT: High Level Term<br>Preferred Term n (%) | Placebo<br>(N = 30) | Dupilumab<br>300 mg qw<br>(N = 30) |
|---|---|---|
| Any Class | 5 (16.7%) | 1 (3.5%) |
| INFECTIONS AND INFESTATIONS | 2 (6.7%) | 0 |
| HLGT: Infections-pathogen unspecified | 2 (6.7%) | 0 |
| HLT: Ear infections | 1 (3.3%) | 0 |
| Otitus media | 1 (3.3%) | 0 |
| HLT: Lower respiratory tract and lung infections | 1 (3.3%) | 0 |
| Bronchitis | 1 (3.3%) | 0 |
| IMMUNE SYSTEM DISORDERS | 1 (3.3%) | 0 |
| HLGT: Allergic conditions | 1 (3.3%) | 0 |
| HLT: Allergic conditions NEC | 1 (3.3%) | 0 |
| Hypersensitivity | 1 (3.3%) | 0 |
| NERVOUS SYSTEM DISORDERS | 1 (3.3%) | 0 |
| HLGT: Headaches | 1 (3.3%) | 0 |
| HLT: Headaches NEC | 1 (3.3%) | 0 |
| Headache | 1 (3.3%) | 0 |
| VACULAR DISORDERS | 1 (3.3%) | 0 |
| HLGT: Vascular hypertensive disorders | 1 (3.3%) | 0 |
| HLT: Vascular hypertensive disorders NEC | 1 (3.3%) | 0 |
| Hypertension | 1 (3.3%) | 0 |
| RESPIRATORY, THORACIC AND MEDIASTINAL DISORDERS | 2 (6.7%) | 0 |
| HLGT: Bronchial disorders (excl neoplasms) | 2 (6.7%) | 0 |
| HLT: Bronchospasms and obstruction | 2 (6.7%) | 0 |
| Asthma | 2 (6.7%) | 0 |
| GASTROINTESTINAL DISORDERS | 1 (3.3%) | 1 (3.3%) |
| HLGT: Gastrointestinal motility and defaecation conditions | 0 | 1 (3.3%) |
| HLT: Gastrointestinal atonic and hypomotility disorders NEC | 0 | 1 (3.3%) |
| Constipation | 0 | 1 (3.3%) |
| HLGT: Gastrointestinal signs and symptoms | 1 (3.3%) | 0 |
| HLT: Gastrointestinal and abdominal pains (excl oral and throat) | 1 (3.3%) | 0 |
| Abdominal pain | 1 (3.3%) | 0 |

MEDDRA 17.0. n (%) = number and percentage of patients with at least one TEAE leading to permanent treatment discontinuation.
Note:
Table sorted by SOC internationally agreed order and HLGT, HLT, PT by alphabetic order.

Adverse Events of Special Interest (AESIs) were defined as: ALT increase; anaphylactic reactions or acute allergic reactions that require immediate treatment; severe injection site reactions that last longer than 24 hours; severe infections including parasitic infections; pregnancy; and overdose (Table 40).

TABLE 40

Number (%) of patients with adverse event of special interest reported by investigators in a safety population.

| Primary System Organ Class<br>Preferred Term n (%) | Placebo<br>(N = 30) | Dupilumab<br>300 mg qw<br>(N = 30) |
|---|---|---|
| Any Class | 0 | 1 (3.3%) |
| Infections and infestations | 0 | 1 (3.3%) |
| Herpes zoster | 0 | 1 (3.3%) |

n (%) = number and percentage of patients with at least one AESI.
Note:
Table sorted by SOC internationally agreed order and PT sorted by decreasing frequency in dupilumab 300 mg group.

There were only few laboratory values which met the criteria of potentially clinically significantly abnormal. Higher numbers of patients, although balanced between the two treatment groups, were recorded for elevated basophil and eosinophil counts (Tables 41-46).

TABLE 41

Red blood cells, platelets and coagulation panel showing the number of patients with Potentially Clinically Significant Abnormalities (PCSA) during the TEAE period in a safety population.

| Laboratory parameter<br>PCSA criteria n/N1 (%) | Placebo<br>(N = 30) | Dupilumab<br>300 mg qw<br>(N = 30) |
|---|---|---|
| Hemoglobulin | | |
| <= 115 g/L (Male); <= 95 g/L (Female) | 1/29 (3.4%) | 1/30 (3.3%) |
| <= 185 g/L (Male); <= 165 g/L (Female) | 1/29 (3.4%) | 0/30 |
| Decrease from baseline >= 20 g/L | 1/29 (3.4%) | 1/30 (3.3%) |
| Hematocrit | | |
| <= 0.37 v/v (Male); <= 0.32 v/v (Female) | 1/29 (3.4%) | 2/30 (6.7%) |
| <= 0.55 v/v (Male); <= 0.5 v/v (Female) | 1/29 (3.4%) | 0/30 |
| Erythrocytes | | |
| >= 6 Tera/L | 1/29 (3.4%) | 0/30 |
| Platelets | | |
| <100 Giga/L | 0/29 | 0/30 |
| >= 700 Giga/L | 0/29 | 0/30 |

Note:
The number (n) represents the subset of the total number of patients who met the criterion in question at least once during treatment. The denominator (/N1) for each parameter within a treatment group is the number of patients for the treatment group who had that parameter assessed post-baseline. For PCSA including condition based only on change from baseline, the denominator is restricted on patients having a baseline and a post-baseline values.

TABLE 42

White blood cells panel showing the number of patients with abnormalities (PCSA) during the TEAE period in a safety population.

| Laboratory parameter<br>PCSA criteria n/N1 (%) | Placebo<br>(N = 30) | Dupilumab<br>300 mg qw<br>(N = 30) |
|---|---|---|
| Leukocytes | | |
| <3.0 Giga/L (Non-Black); <2.0 Giga/L (Black) | 2/29 (6.9%) | 0/30 |
| >=16.0 Giga/L | 0/29 | 0/30 |
| Neutrophils | | |
| <1.5 Giga/L (Non-Black); <1.0 Giga/L (Black) | 2/29 (6.9%) | 0/30 |
| Lymphocytes | | |
| >= 0.5 Giga/L - LLN | 1/29 (3.4%) | 1/30 (3.3%) |
| <0.5 Giga/L | 0/29 | 0.30 |
| >4.0 Giga/L | 0/29 | 1/30 (3.3%) |
| Monocytes | | |
| >0.7 Giga/L | 3/29 (10.3%) | 0/30 |
| Basophils | | |
| >0.1 Giga/L | 7/29 (24.1%) | 11/30 (36.7%) |
| Eosinophils | | |
| >0.5 Giga/L or >ULN (if ULN >=0.5 Giga/L) | 10/29 (34.5%) | 13/30 (43.3%) |

Note:
The number (n) represents the subset of the total number of patients who met the criterion in question at least once during treatment. The denominator (/N1) for each parameter within a treatment group is the number of patients for the treatment group who had that parameter assessed post-baseline.

TABLE 43

Metabolic function panel showing the number of patients with abnormalities (PCSA) during the TEAE period in a safety population.

| Laboratory parameter<br>PCSA criteria n/N1 (%) | Placebo<br>(N = 30) | Dupilumab<br>300 mg qw<br>(N = 30) |
|---|---|---|
| Glucose | | |
| <=3.9 mmol/L and <LLN | 2/29 (6.9%) | 2/30 (6.7%) |
| >=11.1 mmol/L (unfasted); >=7 mmol/L (fasted) | 0/29 | 3/30 (10.0%) |
| Cholesterol | | |
| >=7.74 mmol/L | 0/30 | 0/30 |
| Triglycerides (mmol/L) | | |
| >=4.6 mmol/L | 0/1 | 0/0 |
| Creatine Kinase | | |
| >3 ULN | 2/29 (6.9%) | 1/30 (3.3%) |
| >10 ULN | 1/29 (3.4%) | 0/30 |
| Albumin | | |
| <=25 g/L | 0/29 | 0/30 |

Note:
The number (n) represents the subset of the total number of patients who met the criterion in question at least once during treatment. The denominator (/N1) for each parameter within a treatment group is the number of patients for the treatment group who had that parameter assessed post-baseline.

TABLE 44

Electrolyte panel showing the number of patients with abnormalities (PCSA) during the TEAE period in a safety population.

| Laboratory parameter<br>PCSA criteria n/N1 (%) | Placebo<br>(N = 30) | Dupilumab<br>300 mg qw<br>(N = 30) |
|---|---|---|
| Sodium | | |
| <=129 mmol/L | 0/30 | 0/30 |
| >=160 mmol/L | 0/30 | 0/30 |
| Potassium | | |
| <3 mmol/L | 0/30 | 0/30 |
| >=5.5 mmol/L | 0/30 | 0/30 |
| Chloride | | |
| <80 mmol/L | 0/30 | 0/30 |
| >115 mmol/L | 0/30 | 0/30 |

Note:
The number (n) represents the subset of the total number of patients who met the criterion in question at least once during treatment. The denominator (/N1) for each parameter within a treatment group is the number of patients for the treatment group who had that parameter assessed post-baseline.

TABLE 45

Renal function panel showing the number of patients with abnormalities (PCSA) during the TEAE period in a safety population.

| Laboratory parameter<br>PCSA criteria n/N1 (%) | Placebo<br>(N = 30) | Dupilumab<br>300 mg qw<br>(N = 30) |
|---|---|---|
| Creatinine | | |
| >=150 umol/L (Adults) | 0/30 | 0/30 |
| >=30% change from baseline | 2/30 (6.7%) | 1/29 (3.4%) |
| >=100% change from baseline | 0/30 | 0/29 |
| Creatinine Clearance (Cockcrofts Formula) (mL/min) | | |
| >=50 - <=80 ml/min (mild renal impairment) | 6/30 (20.0%) | 5/30 (16.7%) |
| >30-<50 ml/min (moderate renal impairment) | 0/30 | 0/30 |
| <30 ml/min (severe renal impairment) | 0/30 | 0/30 |
| Blood Urea Nitrogen | | |
| >=17 mmol/L | 0/30 | 0/30 |

TABLE 45-continued

Renal function panel showing the number of patients with abnormalities (PCSA) during the TEAE period in a safety population.

| Laboratory parameter PCSA criteria n/N1 (%) | Placebo (N = 30) | Dupilumab 300 mg qw (N = 30) |
|---|---|---|
| Urate | | |
| <120 umol/L | 0/30 | 0/30 |
| >408 umol/L | 5/30 (16.7%) | 5/30 (16.7%) |

Note:
The number (n) represents the subset of the total number of patients who met the criterion in question at least once during treatment. The denominator (/N1) for each parameter within a treatment group is the number of patients for the treatment group who had that parameter assessed post-baseline. For PCSA including condition based only on change from baseline, the denominator is restricted on patients having a baseline and a post-baseline values. For PCSA clearance categories, a patient who experienced one PCSA in several categories is counted only in the worst category.

TABLE 46

Liver function panel showing the number of patients with abnormalities (PCSA) during the TEAE period in a safety population.

| Laboratory parameter PCSA criteria n/N1 (%) | Placebo (N = 30) | Dupilumab 300 mg qw (N = 30) |
|---|---|---|
| Alanine Aminotransferase | | |
| >3 ULN | 0/29 | 0/30 |
| Aspartate Aminotransferase | | |
| >3 ULN | 1/29 (3.4%) | 0/30 |
| >5 ULN | 1/29 (3.4%) | 0/30 |
| >10 ULN | 0/29 | 0/30 |
| Alkaline Phosphatase | | |
| >1.5 ULN | 0/30 | 0/30 |
| Bilirubin | | |
| >1.5 ULN | 0/29 | 0/30 |
| ALT and total bilirubin | | |
| ALT >3 ULN and TBILI >2 ULN | 0/29 | 0/30 |

Note:
The number (n) represents the subset of the total number of patients who met the criterion in question at least once during treatment. The denominator (/N1) for each parameter within a treatment group is the number of patients for the treatment group who had that parameter assessed post-baseline. AST or ALT >5 ULN and over are presented only if incidence >0. There was one AESI of severe infection, herpes zoster, reported for a patient in the dupilumab group.

Figure 20:
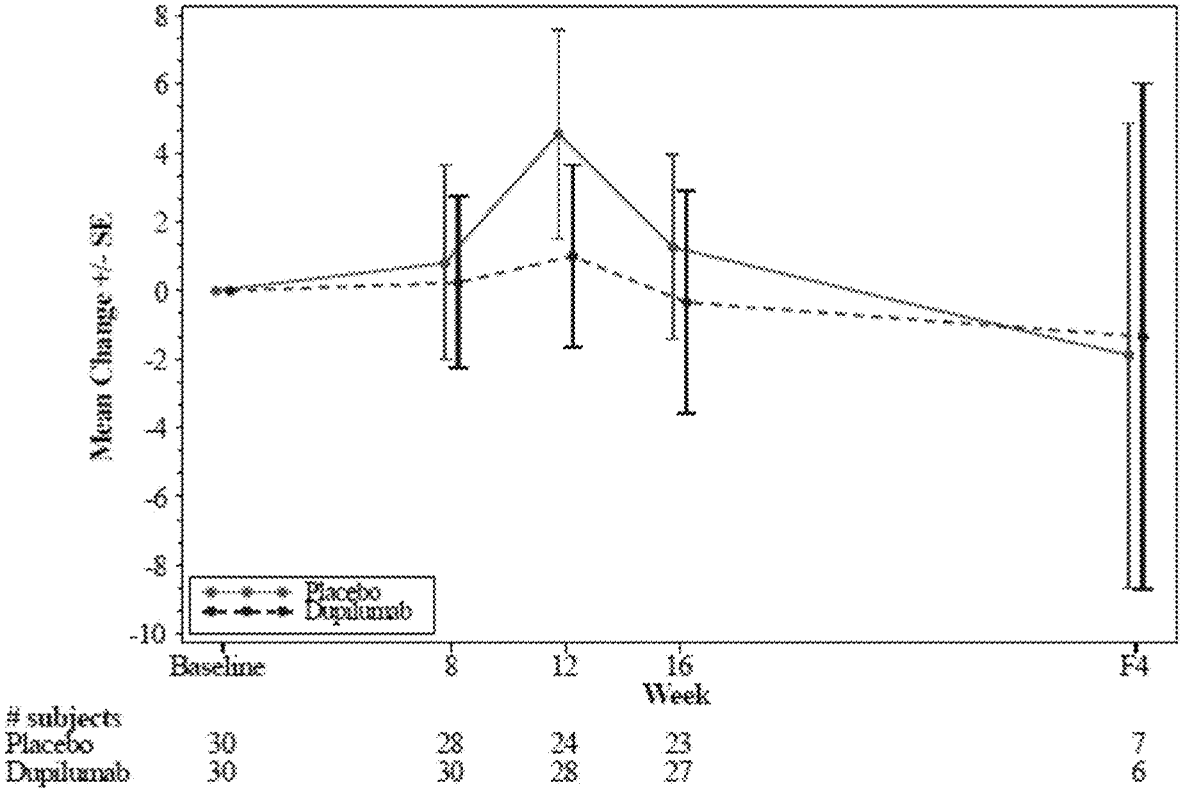
FIG. 20 graphically depicts Fridericia correction (QTc) (MS) mean change from baseline by visit in safety population.
Figure 21A:
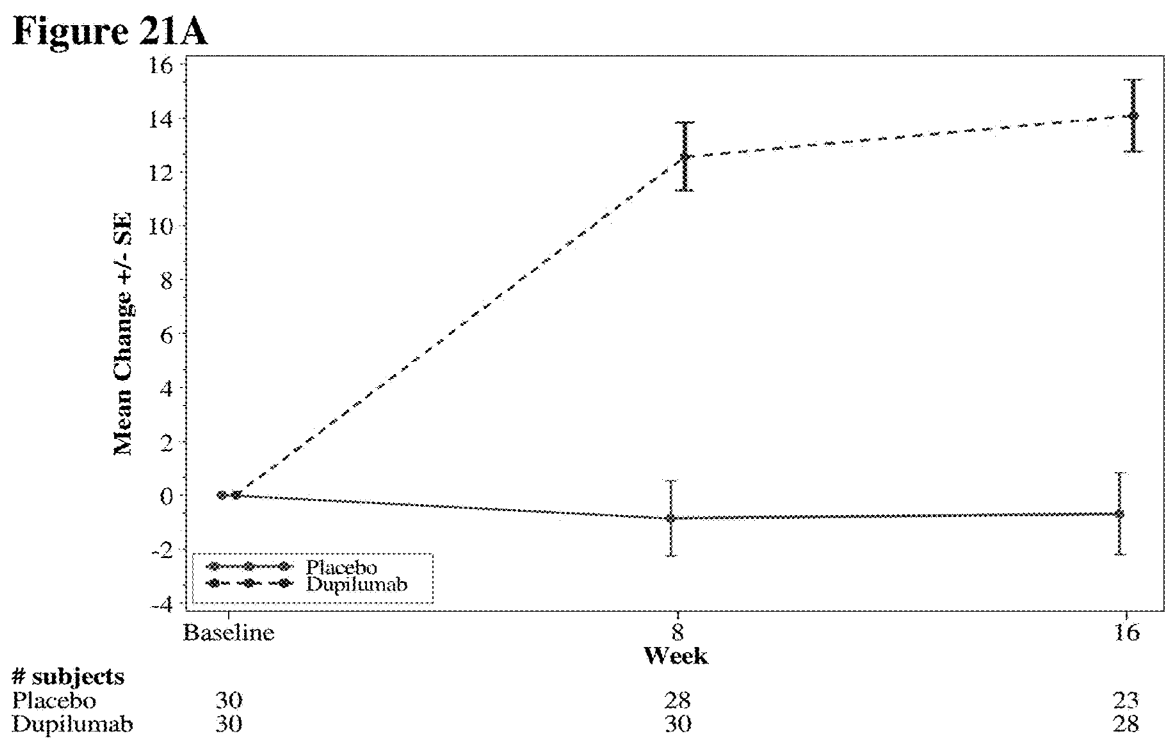
FIG. 21A graphically depicts the results from subjective secondary endpoints including smell, as assessed by the University of Pennsylvania Smell Identification Test (UPSIT).
Figure 21B:
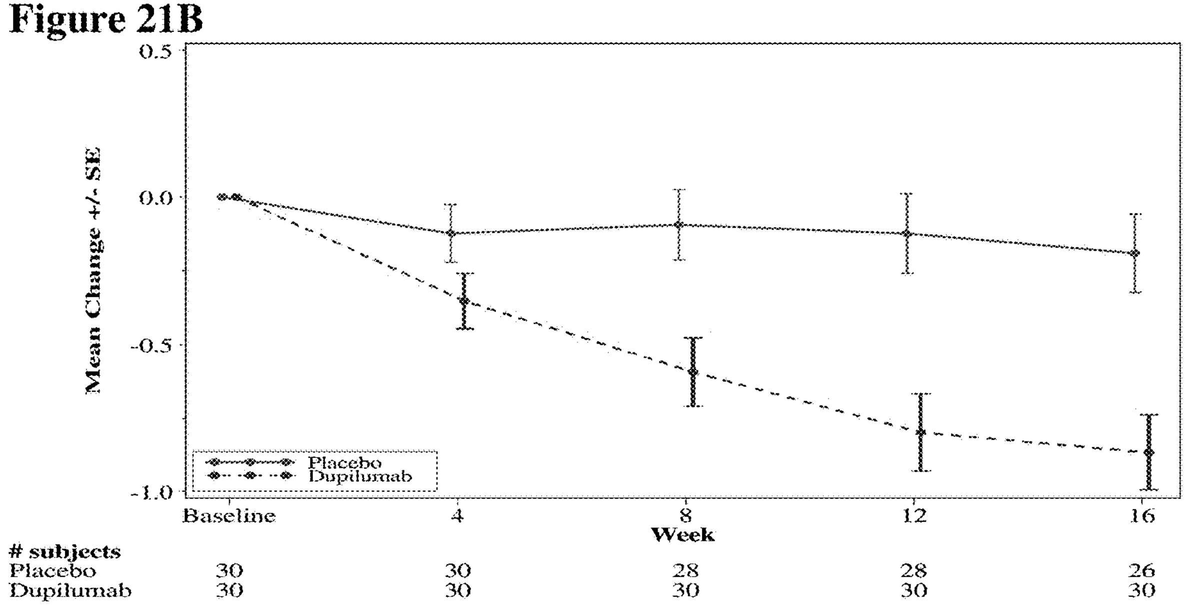
FIG. 21B graphically depicts the results from subjective secondary endpoints including smell, as assessed by self-reported morning nasal congestion/obstruction.
Figure 21C:
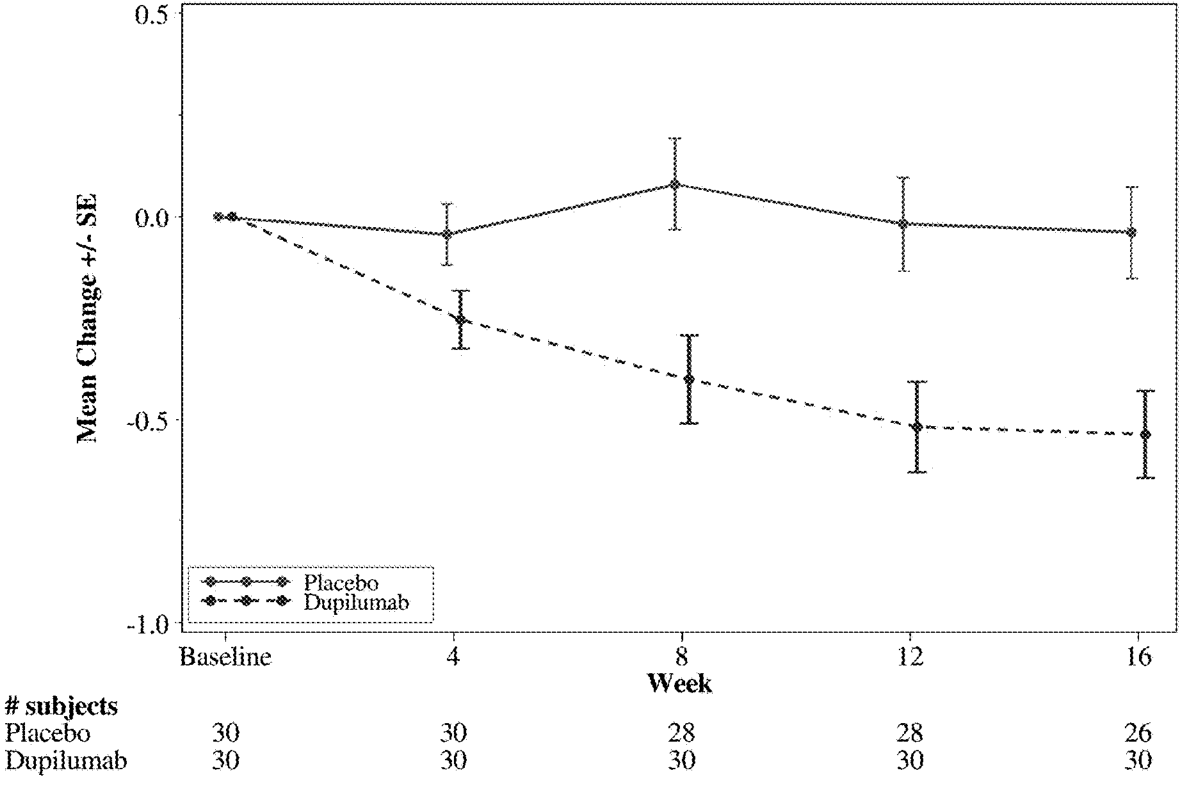
FIG. 21C graphically depicts the results from subjective secondary endpoints including smell, as assessed by self-reported morning posterior rhinorrhea.

There were no clinically meaningful differences between the treatment groups regarding any of the vital signs, ECG and physical findings (Table 47, Table 48 and FIG. 20).

TABLE 47

Vital signs panel showing the number of patients with abnormalities (PCSA) during the TEAE period in a safety population.

| Vital Signs by PCSA criteria n/N1 (%) | Placebo (N = 30) | Dupilumab 300 mg qw (N = 30) |
|---|---|---|
| Supine Systolic Blood Pressure (Mmhg) | | |
| ≤95 mmHg and decrease from baseline ≥20 mmHg | 0/30 | 0/30 |
| ≥160 mmHg and increase from baseline ≥20 mmHg | 1/30 (3.3%) | 0/30 |
| Supine Diastolic Blood Pressure (Mmhg) | | |
| ≤45 mmHg and decrease from baseline ≥10 mmHg | 0/30 | 0/30 |
| ≥110 mmHg and increase from baseline ≥10 mmHg | 0/30 | 0/30 |
| Supine Heart Rate (Beats/Min) | | |
| ≤50 bpm and decrease from baseline ≥20 bpm | 0/30 | 0/30 |
| ≥120 bpm and increase from baseline ≥20 bpm | 0/30 | 0/30 |
| Weight (Kg) | | |
| ≥5% decrease from baseline | 4/30 (13.3%) | 4/30 (13.3%) |
| ≥5% increase from baseline | 4/30 (13.3%) | 3/30 (10.0%) |

Orthostatic = standing - supine.

Note:
The number (n) represents the subset of the total number of patients who met the criterion in question at least once during treatment. The denominator (/N1) for each parameter within a treatment group is the number of patients for the treatment group who had that parameter assessed post-baseline. For PCSA including condition based only on change from baseline, the denominator is restricted on patients having a baseline and a post-baseline values.

TABLE 48

ECG panel showing the number of patients with abnormalities (PCSA) during the TEAE period in a safety population.

| ECG parameter<br>PCSA criteria n/N1 (%) | Placebo<br>(N = 30) | Dupilumab<br>300 mg qw<br>(N = 30) |
|---|---|---|
| Heart Rate | | |
| ≤50 bpm and decrease from baseline ≥20 bpm | 0/30 | 0/30 |
| ≥120 bpm and increase from baseline ≥20 bpm | 0/30 | 0/30 |
| PR | | |
| ≥220 ms and increase from baseline ≥20 ms | 1/30 (3.3%) | 1/30 (3.3%) |
| QRS | | |
| ≥120 ms | 3/30 (10.0%) | 3/30 (10.0%) |
| QTc Bazett | | |
| Borderline: 431-450 ms (Male); 451-470 ms (Female) | 5/30 (16.7%) | 3/30 (10.0%) |
| Prolonged: >450 ms (Male; >470 ms (Female) | 1/30 (3.3%) | 3/30 (10.0%) |
| ≥500 ms | 0/30 | 0/30 |
| QTc Bazett - Change from baseline | | |
| Borderline: Increase versus baseline ≥30 and ≤60 ms | 2/30 (6.7%) | 3/30 (10.0%) |
| Prolonged: Increase versus baseline >60 ms | 0/30 | 0/30 |
| QTc Fridericia | | |
| Borderline: 431-450 ms (Male); 451-470 ms (Female) | 3/30 (10.0%) | 4/30 (13.3%) |
| Prolonged: >450 ms (Male; >470 ms (Female) | 0/30 | 1/30 (3.3%) |
| ≥500 ms | 0/30 | 0/30 |
| QTc Fridericia - Change from baseline | | |
| Borderline: Increase versus baseline ≥30 and ≤60 ms | 2/30 (6.7%) | 3/30 (10.0%) |
| Prolonged: Increase versus baseline >60 ms | 0/30 | 0/30 |

Note:
The number (n) represents the subset of the total number of patients who met the criterion in question at least once during treatment. The denominator (/N1) for each parameter within a treatment group is the number of patients for the treatment group who had that parameter assessed post-baseline. For PCSA including condition based only on change from baseline, the denominator is restricted on patients having a baseline and a post-baseline values. For QTc Bazett and Fridericia, a patient who experienced at least one value greater than 500 ms is counted also in the prolonged category. For other categories of PCSA related to QTc, a patient who experienced one PCSA in several categories is counted only in the worst category.

Of the patients with available Anti-Drug Antibodies (ADA) results at baseline, 7/28 and 7/30, respectively, in the placebo and dupilumab treatments groups had pre-existing ADA titers. With the exception of 1 patient in the dupilumab group, the pre-existing ADA titers were not boosted during the treatment period (Table 49).

During the study treatment period, 3 patients on placebo, and 2 patients on dupilumab, respectively, had positive treatment-emergent ADA titers. One dupilumab-treated patient was transiently ADA positive, and after week 8, had a negative ADA titer. The placebo patients had low titers in

TABLE 49

PK panel summarizing pre-existing ADA in a randomized population.

| | | Dupilumab | |
|---|---|---|---|
| | Placebo<br>(N = 30) | 300 mg qw<br>(N = 30) | All<br>(N = 60) |
| Patients with positive response at baseline [a] | 7/28 (25.00%) | 7/30 (23.33%) | 14/58 (24.14%) |
| Titer for positive samples | | | |
| Number | 7 | 7 | 14 |
| Mean (SD) | 1534.29 (2788.89) | 784.29 (1390.98) | 1159.29 (2152.73) |
| SEM | 1054.103 | 525.741 | 575.342 |
| CV | 181.771 | 177.356 | 185.695 |
| Geometric Mean | 323.02 | 178.32 | 240.00 |
| Median | 480.00 | 120.00 | 300.00 |
| Q1:Q3 | 30.00:1920.00 | 30.00:960.00 | 30.00:960.00 |
| Min:Max | 30.0:7680.0 | 30.0:3840.0 | 30.0:7680.0 |
| Patients with negative response at baseline [a] | 21/28 (75.00%) | 23/30 (76.67%) | 44/58 (75.86%) |

[a] The denominator is the number of patients with evaluable ADA samples at baseline.

the range of 30 to 60, whereas, the dupilumab-treated patients titers ranged from 480 to 1920 (Table 50).

TABLE 50

PK panel summarizing ADA incidence in an ADA population.

| | Placebo (N = 30) | Dupilumab 300 mg qw (N = 30) |
|---|---|---|
| ADA negative patients[a] | 27/30 (90.00%) | 28/30 (93.33%) |
| Treatment-unaffected ADA positive patients[a] | 7/30 (23.33%) | 6/30 (20.00%) |
| ADA positive patients[a] | 3/30 (10.00%) | 2/30 (6.67%) |
| Treatment-induced ADA patients[b] | 3/23 (13.04%) | 1/23 (4.35%) |
| Transient treatment-induced ADA patients[b] | 0/23 (0.00%) | 1/23 (4.35%) |
| Persistent treatment-induced ADA patients[b] | 0/23 (0.00%) | 0/23 (0.00%) |
| Indeterminate[b] | 3/23 (13.04%) | 0/23 (0.00%) |
| Peak titer for treatment-induced ADA patients | | |
| Number | 3 | 1 |
| Mean (SD) | 40.00 (17.32) | 480.00 (NC) |
| SEM | 10.000 | NC |
| CV | 43.301 | NC |
| Geometric Mean | 37.80 | 480.00 |
| Median | 30.00 | 480.00 |
| Q1:Q3 | 30.00:60.00 | 480.00:480.00 |
| Min:Max | 30.0:60.0 | 480.0:480.0 |
| Treatment-boosted ADA patients[c] | 0/7 (0.00%) | 1/7 (14.29%) |
| Peak titer for treatment-boosted ADA patients | | |
| Number | 0 | 1 |
| Mean (SD) | | 1920.00 (NC) |
| SEM | | NC |
| CV | | NC |
| Geometric Mean | | 1920.00 |
| Median | | 1920.00 |
| Q1:Q3 | | 1920.00:1920.00 |
| Min:Max | | 1920.0:1920.0 |
| Ratio of peak post-baseline titer to baseline tier for treatment-boosted ADA patients | | |
| Number | 0 | 1 |
| Mean (SD) | | 4.00 (NC) |
| Median | | 4.00 |
| Q1:Q3 | | 4.00:4.00 |
| Min:Max | | 4.0:4.0 |

[a]The denominator is the number of evaluable patients defined as patients with at least 1 evaluable post-baseline ADA sample.

[b]The denominator is the number of evaluable patients that were ADA negative or non-evaluable at baseline.

[c]The denominator is the number of evaluable patients that were ADA positive at baseline.

No definitive conclusions could be made with respect to ADA response since the study was ongoing at the time of interim analysis, and the final assessment of ADA response will be made at the conclusion of the study.

D. Summary of Results

Baseline characteristics were similar between groups. Least squares (LS) mean change in NPS was −0.30 in the placebo/mometasone group, and −1.85 in the dupilumab/mometasone group (LS mean difference (95% CI) of −1.55; p=0.0009). Significant changes favoring dupilumab were also observed for the Lund-Mackay CT score (difference of −8.84; p<0.0001), percent of the maxillary sinus volume with disease (difference of −32.24%; p<0.0001), SNOT-22 (difference of −18.1; p<0.0001), sense of smell, and all other secondary end points. In patients with asthma (n=16), dupilumab improved FEV1% predicted (7.2% increase, p=0.04) and asthma control (1.1 unit reduction in ACQ5; p<0.0001). Injection site reactions, headache, and nasopharyngitis were the most frequently reported adverse events with dupilumab.

In patients refractory to nasal corticosteroids, the addition of dupilumab improved endoscopic, radiographic and clinical endpoints of Chronic Sinusitis with Nasal Polyps (CSwNP), while improving lung function and disease control in patients with comorbid asthma.

Dupilumab delivered positive results in a proof of concept study in patients with nasal polyposis and chronic symptoms of sinusitis. With respect to CSwNP, strong efficacy of dupilumab 300 mg QW was observed vs. placebo, when added to NASONEX®. Rapid, clinically and significant reduction size of nasal polyposis was observed. Consistent improvement in measures of sinusitis by CT scan, nasal air flow and patient-reported symptoms were observed.

The most frequently reported TEAEs were nasopharyngitis, headache and injection site reaction, with injection site reaction being more frequently reported in the dupilumab treatment group. Other frequently reported TEAEs that were also reported at a higher percentage in the dupilumab treatment group, compared to the placebo group, were oropharyngeal pain, epistaxis, upper respiratory infection and back pain. There were no other clinically meaningful safety findings or differences in safety parameters between the treatment groups.

A low incidence of treatment emergent anti-drug antibody response was observed in both dupilumab and placebo treatment groups. No definitive conclusions were made with respect to ADA response since the study was ongoing at the time of interim analysis and the final assessment of ADA response will be made at the conclusion of the study.

The present invention is not to be limited in scope by the specific embodiments described herein. Indeed, various modifications in addition to those described herein will become apparent to those skilled in the art from the foregoing description and the accompanying figure. Such modifications are intended to fall within the scope of the appended claims.

TABLE 51

Baseline demographic and clinical characteristics of the patients.

| | Placebo + Mometasone (N = 30) | Dupilumab + Mometasone (N = 30) |
|---|---|---|
| Age (yr) | 49.3 ± 9.1 | 47.4 ± 9.8 |
| Male, n (%) | 16 (53.3) | 18 (60.0) |
| Body mass index (BMI) | | |
| Mean (kg/m$^2$) | 26.8 ± 3.9 | 28.1 ± 4.2 |
| <30, n (%) | 24 (80.0) | 22 (73.3) |
| Bilateral endoscopic nasal polyp score (NPS) | 5.7 ± 0.9 | 5.9 ± 1.0 |
| CT: Lund McKay Score (total) | 18.7 ± 5.5 | 18.6 ± 5.0 |
| CT: % maxillary sinus volume occupied by disease | 76.3 ± 23.9 | 71.0 ± 26.2 |
| AM Nasal peak inspiratory flow (NPIF) | 109.2 ± 46.8 | 98.4 ± 48.5 |
| SNOT-22 total score | 40.6 ± 19.9 | 41.4 ± 18.2 |
| VAS rhinosinusitis | 6.4 ± 2.7 | 6.4 ± 2.7 |
| Smell test (UPSIT) | 15.6 ± 7.9 | 12.8 ± 8.3 |
| Congestion/obstruction, AM | 1.7 ± 0.7 | 1.7 ± 0.7 |
| Loss of smell, AM | 2.8 ± 0.5 | 2.4 ± 0.9 |
| Anterior rhinorrhea, AM | 1.1 ± +00.8 | 1.0 ± 0.9 |
| Posterior rhinorrhea, AM | 1.4 ± 0.8 | 1.1 ± 0.9 |
| ≥1 prior surgery, n (%) | 19 (63.3) | 16 (53.3) |
| Duration of nasal polyposis (yr) | 11.5 ± 8.7 | 7.6 ± 6.1 |
| Aspirin sensitivity, n (%) | 9 (30) | 6 (20) |
| Comorbid Asthma, n (%) | 19 (63) | 16 (53) |
| Duration of asthma (yr) | 20.2 ± 17.4 | 15.5 ± 12.1 |
| FEV1 (L) - total population | 3.0 ± 0.9 | 3.2 ± 0.9 |
| FEV1 (% predicted) - total population | 86.5 ± 18.4 | 87.9 ± 18.9 |
| FEV1 (L) - asthma | 2.7 ± 0.9 | 2.7 ± 0.7 |
| FEV1 (% predicted) - asthma | 79.8 ± 14.6 | 82.2 ± 17.7 |
| ACQ - 5 in participants with asthma | 1.5 ± 0.9 | 1.6 ± 1.1 |
| Total IgE (IU/ml) | 195.3 ± 251.5 | 139.7 ± 136.2 |
| TARC (pg/ml) | 449.3 ± 376.8 | 469.7 ± 298.0 |
| Eotaxin-3 (pg/ml) | 61.6 ± 48.4 | 64.0 ± 29.8 |
| Blood eosinophils (10^9/L) | 0.45 ± 0.67 | 0.41 ± 0.24 |

TABLE 52

Trial endpoints.

| | Placebo + Mometasone (N = 30) | Dupilumab + Mometasone (N = 30) | Difference vs Placebo + Mometasone (95% CI) | P value |
|---|---|---|---|---|
| Primary end point | | | | |
| Bilateral endoscopic NPS score | −0.3 (0.3) | −1.9 (0.3) | −1.6 (−2.4 to −0.7) | 0.0009 |
| Secondary end points | | | | |
| CT: Lund McKay Score (total) | −0.2 (1.0) | −9.1 (0.8) | −8.8 (−11.1 to −6.6) | <.0001 |
| CT: % maxillary sinus volume occupied by disease | −4.2 (4.7) | −36.4 (4.0) | −32.2 (−43.1 to −21.4) | <.0001 |
| NPIF (AM) | +28.6 (7.7) | +57.9 (7.5) | +29.3 (8.2 to 50.3) | 0.0073 |
| SNOT-22 | −9.2 (3.0) | −27.3 (2.7) | −18.1 (−25.6 to −10.6) | <.0001 |
| VAS rhinosinusitis | −2.2 (0.7) | −4.3 (0.6) | −2.1 (−3.7 to −0.6) | 0.0082 |
| UPSIT | −0.7(1.5) | +14.1 (1.4) | +14.8 (10.9 to 18.7) | <.0001 |
| Congestion/ obstruction (AM) | −0.2 (0.1) | −0.9 (0.1) | −0.7 (−1.0 to −0.3) | 0.0004 |
| Loss of smell (AM) | −0.1 (0.2) | −1.4 (0.2) | −1.3 (−1.7 to −0.8) | <0.0001 |
| Anterior rhinorrhea (AM) | −0.0 (0.1) | −0.7 (0.1) | −0.6 (−0.9, −0.3) | 0.0001 |
| Posterior rhinorrhea (AM) | −0.0 (0.1) | −0.5 (0.1) | −0.5 (−0.8 to −0.2) | 0.0019 |
| FEV1 (L), in patients with asthma | 0.08 (0.09) | 0.31 (0.10) | 0.22 (−0.02 to 0.47) | 0.0739 |
| FEV1 ( % predicted), in patients with asthma | 1.9 (2.8) | 9.0 (3.0) | 7.2 (0.4 to 13.9) | 0.0397 |
| ACQ - 5, in patients with asthma | −0.3 (0.3) | −1.4 (0.4) | −1.1 (−1.5 to −0.6) | <.0001 |
| Total IgE (IU/mL), % change | 7.9 (4.5) | −48.4 (4.2) | −56.3 (−68.2 to −44.4) | <.0001 |
| TARC (pg/mL), % change | 0.7 (10.3) | −20.5 (9.4) | −21.1 (−48.6 to 6.3) | .1276 |

TABLE 52-continued

| Trial endpoints. | | | | |
|---|---|---|---|---|
| | Placebo + Mometasone (N = 30) | Dupilumab + Mometasone (N = 30) | Difference vs Placebo + Mometasone (95% CI) | P value |
| Eotaxin-3 (pg/mL), % change | 10.0 (4.8) | −35.5 (4.4) | −45.5 (−57.6 to −33.3) | <.0001 |
| Blood eosinophils ($\times 10^9$/L), % change | −2.9 (13.2) | −7.3 (10.9) | −4.5 (−36.2 to 27.3) | .7792 |
| Safety end points | | | | |
| TEAE, n (%) | 25 (83.3) | 30 (100) | — | — |
| TESAE, n (%) | 4(13.3) | 2 (6.7) | — | — |
| TEAE leading to discontinuation, n (%) | 5 (16.7) | 1 (3.3) | — | — |

TABLE 53

Treatment differences from baseline to 32 weeks, after 16 weeks of dupilumab/MFNS or placebo/MFNS plus 16 weeks of MFNS-only follow-up

| | Placebo/MFNS (n = 30) | Dupilumab/MFNS (n = 30) |
|---|---|---|
| Bilateral endoscopic NPS | −0.7 (1.4) | −1.7 (1.7) |
| NPIF (AM) | +33.0 (33.4) | +60.6 (52.0) |
| SNOT-22 | −9.6 (18.8) | −19.6 (20.4) |
| Nasal congestion/obstruction (AM) | −0.2 (0.6) | −0.8 (0.9) |
| Anterior rhinorrhea (AM) | −0.1 (0.5) | −0.4 (0.8) |
| Posterior rhinorrhea (AM) | −0.2 (0.7) | −0.3 (0.9) |
| Loss of smell (AM) | −0.3 (0.5) | −1.1 (1.1) |
| Nocturnal awakenings | −0.2 (1.0) | −0.6 (0.7) |

All values are mean (SD).

Abbreviations:

MFNS, mometasone furoate nasal spray;

NPS, nasal polyp score;

PNIF, peak nasal inspiratory flow;

SNOT-22, 22-item Sinonasal Outcome Test.

TABLE 54

| Additional secondary endpoints | | | | |
|---|---|---|---|---|
| | Placebo/MFNS (n = 30) | Dupilumab/MFNS (n = 30) | Difference (95% CI) | P-value |
| NPIF (PM) | +25.8 (7.8) | +59.2 (7.5) | +33.4 (12.0, 54.8) | .0028 |
| Loss of smell (AM) | −0.1 (0.2) | −1.4 (0.2) | −1.3 (−1.7, −0.8) | <.0001 |
| Loss of smell (PM) | −0.2 (0.2) | −1.4 (0.2) | −1.3 (−1.7, −0.8) | <.0001 |
| Anterior rhinorrhea (AM) | 0 (0.1) | −0.7 (0.1) | −0.6 (−0.9, −0.3) | <1.0001 |
| Anterior rhinorrhea (PM) | −0.2 (0.1) | −0.7 (0.1) | −0.5 (−0.8, −0.3) | .0008 |
| Posterior rhinorrhea (PM) | −0.1 (0.1) | −0.5 (0.1) | −0.5 (−0.8, −0.2) | .003 |
| Nocturnal awakenings | −0.2 (0.1) | −0.6 (0.1) | −0.4 (−0.7, −0.1) | .0076 |

II values are LS mean (SE).

Abbreviations:

LS, least square;

MFNS, mometasone furoate nasal spray;

PNIF, peak nasal inspiratory flow.

End Points in Patients with and without Comorbid Asthma

Figure 22A:
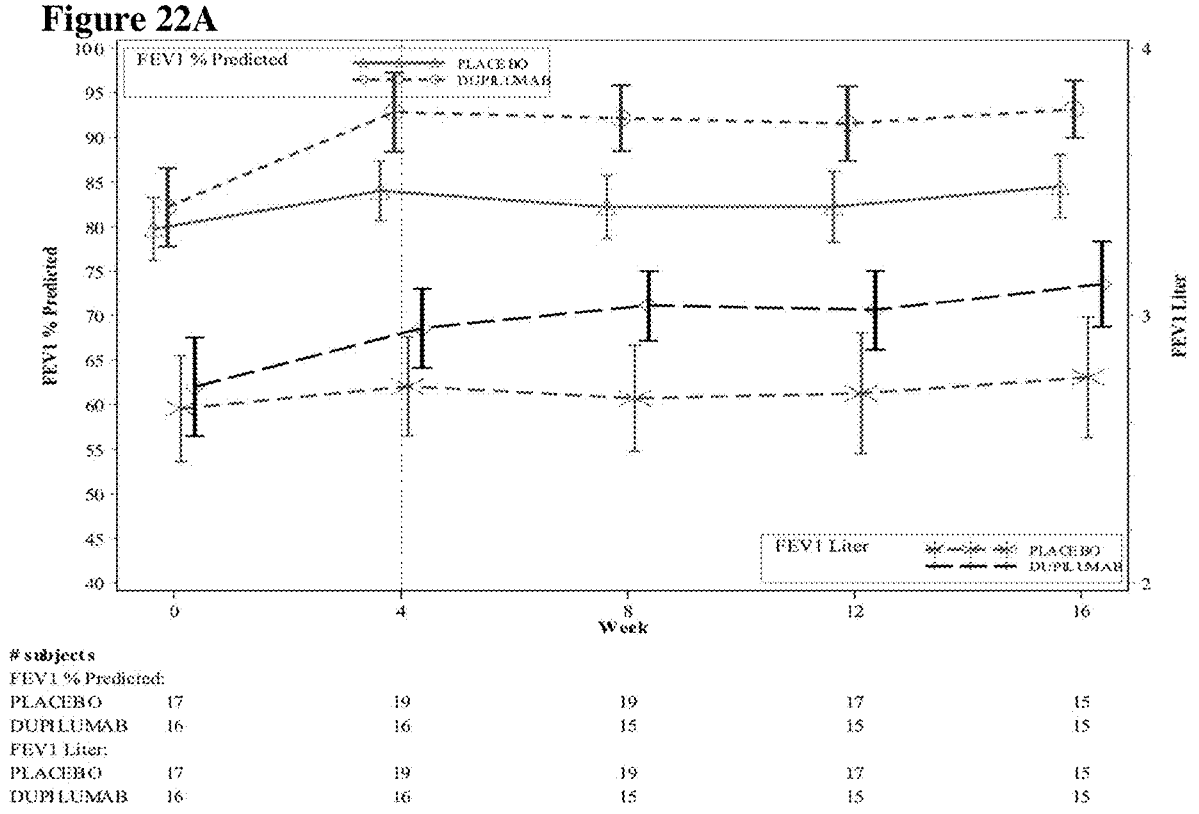
FIGS. 22A-22C graphically depict end points in patients with asthma.
Figure 22B:
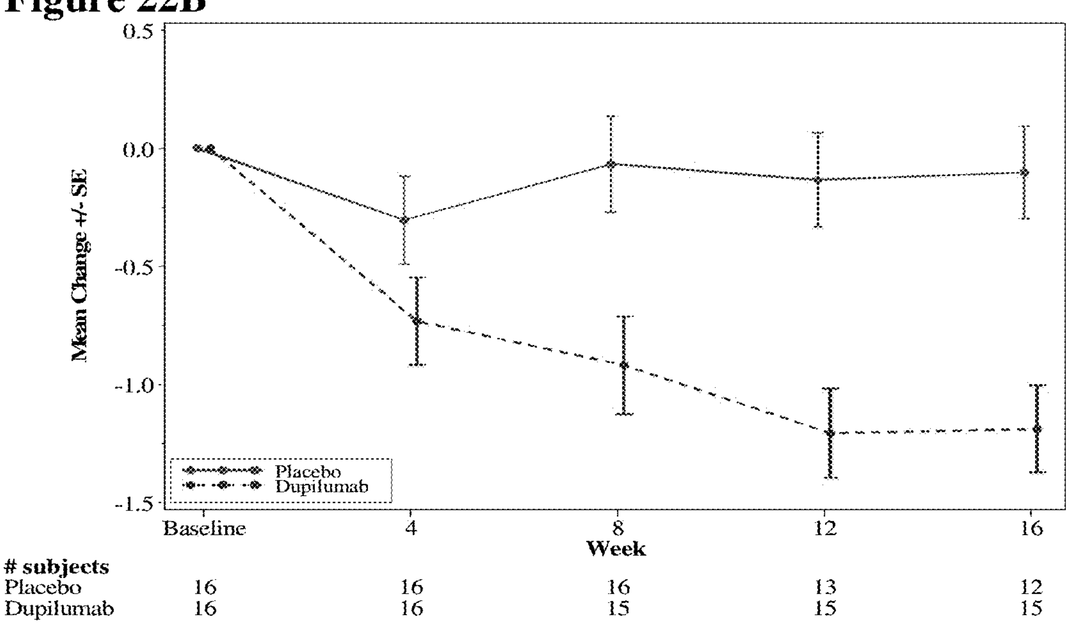
Figure 22C:
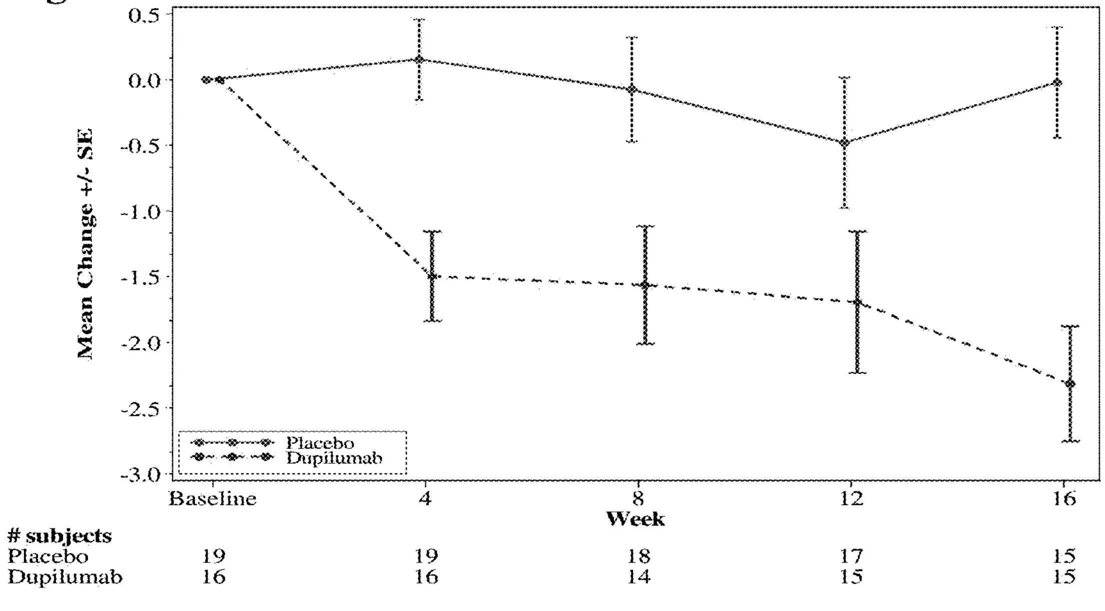

In the subset of patients with comorbid asthma, treatment with dupilumab was associated with improvements in lung function (FIG. 22A) and asthma control (FIG. 22B), with a between-treatment group LS mean difference in FEV1(%) of 7.2% (95% CI, 0.4 to 13.9, p=0.04) and a reduction of the ACQ-5 of 0.3 (0.3) units in the placebo group and 1.4 (0.4) units in the dupilumab group, resulting in a LS mean difference in ACQ score of −1.1 units (95% CI, −1.5 to −0.6, p<0.0001). Additionally, in this subgroup the mean change in bilateral endoscopic nasal polyp score between baseline and week 16 was 0.3 (0.9) in the placebo group, and −2.4 (2.0) in the dupilumab group, resulting in a LS mean difference of −2.3 (95% CI, −3.4 to −1.2, p=0.0002) favoring dupilumab. Patients with asthma also experienced improvements in UPSIT, SNOT-22, and symptoms of congestion with dupilumab/MFNS (Table 55).

A ≥1 point change in the NPS was observed in 10.5% of patients who received placebo versus 75% of those who received dupilumab, with an odds ratio (OR) of 26.1 (95% CI 3.8 to 179.3, p=0.0009). A ≥2 point change was observed in none of the patients who received placebo and 56.3% of those who received dupilumab.

Analysis of the effect of dupilumab/MFNS in patients without asthma did not demonstrate a significant effect of dupilumab versus placebo with regard to endoscopic NPS. However, an effect of dupilumab on UPSIT, SNOT-22, symptoms of congestion, and other clinical and radiographic endpoints was observed in this subgroup (Table 55).

TABLE 55

Efficacy endpoints in patients with and without comorbid asthma

| Endpoints | Comorbid asthma | | No comorbid asthma | |
|---|---|---|---|---|
| | Placebo/MFNS (n = 19) | Dupilumab/MFNS (n = 16) | Placebo/MFNS (n = 11) | Dupilumab/MFNS (n = 14) |
| Primary endpoint | | | | |
| Bilateral endoscopic NPS | | | | |
| Mean (SD) | 0.3 (0.9) | −2.4 (2.0) | −1.3 (1.5) | −1.4 (1.3) |
| Median | 0.0 | −2.0 | −0.5 | −1.5 |
| Secondary endpoints | | | | |
| NPS reduction ≥1.0, No. (%) | 2 (10.5) | 12 (75.0) | 4(36.4) | 9 (64.3) |
| NPS reduction ≥2.0, No. (%) | 0 | 9 (56.3) | 3 (27.3) | 7 (50.0) |
| CT: Lund-Mackay score (total), mean (SD) | −0.9 (4.2) | −8.5 (4.8) | 1.1 (2.4) | −10.0 (4.4) |
| NPIF (AM), mean (SD), L/min | 21.6 (32.7) | 56.8 (37.8) | 41.9 (35.5) | 67.4 (49.5) |
| SNOT-22 total score, mean (SD) | −8.1 (18.6) | −29.3 (16.9) | −8.5 (16.8) | −28.9 (23.4) |
| Sinusitis symptom severity (VAS), mean (SD), cm | −1.6 (3.6) | −4.7 (2.5) | −2.4 (4.0) | −3.9 (3.1) |
| Smell test (UPSIT), mean (SD) | 0.8 (5.0) | 18.5 (9.7) | −2.4 (5.0) | 11.8 (8.5) |
| Nasal congestion/obstruction (AM), mean (SD) | −0.1 (0.6) | −0.8 (0.7) | −0.5 (0.8) | −1.1 (1.0) |
| Loss of smell (AM), mean (SD) | −0.3 (0.6) | −1.4 (1.2) | −0.4 (0.6) | −1.4 (1.0) |
| Anterior rhinorrhea (AM), mean (SD) | −0.0 (0.4) | −0.3 (0.8) | −0.2 (0.8) | −1.0 (0.9) |
| Posterior rhinorrhea (AM), mean (SD) | −0.1 (0.5) | −0.5 (0.8) | −0.3 (0.8) | −0.5 (0.8) |
| $FEV_1$, mean (SD), L | 0.10 (0.30) | 0.31 (0.37) | 0.14 (0.45) | −0.07 (0.31) |
| $FEV_1$ (% predicted), mean (SD) | 3.4 (9.7) | 9.6 (13.1) | −3.4 (12.2) | −1.5 (9.0) |

Abbreviations:
CT, computed tomography;
$FEV_1$, forced expiratory volume in 1 second;
MFNS, mometasone furoate nasal spray;
NPS, nasal polyp score;
PNIF, peak nasal inspiratory flow;
SNOT-22, 22-item Sinonasal Outcome Test;
UPSIT, University of Pennsylvania Smell Identification Test;
VAS, visual analogue scale.

TABLE 56

Mean absolute changes from baseline in nasal secretion biomarkers at Week 16.

| | Eotaxin-3 (pg/mL) | Total IgE (IU/mL) | ECP (ng/mL) |
|---|---|---|---|
| Dupilumab/MFNS | −38.9 | −18.8 | −17.4 |
| Placebo/MFNS | +18.9 | +4.50 | +7.75 |

Safety

Adverse events were reported by 25 of 30 patients in the placebo group and 29 of 30 in the dupilumab group (Table 37). Injection site reactions (ISR), headache, and nasopharyngitis were the most frequent adverse events across the entire study population, with ISR seen more frequently with dupilumab treatment. The events were generally nonspecific and of mild-to-moderate intensity.

Six patients had a serious adverse event: four in the placebo group (uterine cancer, transient ischemic attack, asthma and nasal polyps) and two in the dupilumab group (herpes zoster in one patient and arrhythmia and upper extremity pain/numbness in the other); no serious adverse events were considered by the investigator to be related to the study drug. Five patients in the placebo group experienced adverse events that led to discontinuation of study drug (otitis media, bronchitis, hypersensitivity, headache, hypertension, asthma, and abdominal pain), as did one patient in the dupilumab group (constipation). No clinically significant changes in vital signs or findings on physical examination, clinical laboratory testing, or ECG were reported in either group.

There were no deaths during the active treatment period; one patient died of a ruptured aortic aneurysm during the screening period, prior to having been randomized to study treatment.

Administration of dupilumab to patients with chronic sinusitis with nasal polyposis, rapid and significant improvements were observed in endoscopic, clinical, radiographic and pharmacodynamic end points, indicating an important role for IL-4 and IL-13 in the pathogenesis and clinical manifestations of this disorder. Significant efficacy of dupilumab on CSwNP-related outcomes was also observed in analyses restricted to the subset of patients with co-morbid asthma; these patients additionally experienced improvements in lung function and asthma control, important asthma outcomes. These data indicate that attenuation of IL-4 and IL-13-mediated signaling pathways can have broad therapeutic effects in patients with multiple concurrent Th-2 mediated diseases.

In comparison to other approaches, dupilumab treatment resulted in sustained clinical improvements which, over time, exceeded the clinical improvement observed with systemic glucocorticoids. Furthermore, in this trial dupilumab or placebo were added to the current standard of care for CSwNP and asthma.[3] When added to the current standard of care, dupilumab treatment was associated with broad and significant improvement in multiple clinically-relevant CSwNP and asthma parameters.

Levels of biomarkers of Th2 inflammation, including serum IgE, eotaxin-3, and TARC decreased with dupilumab, correlating with clinical improvements and confirming the biologic activity of the drug on many of these pathways. In this trial, patients with CSwNP who also reported a diagnosis of asthma on average manifested impaired lung function, suboptimal disease control, and had disease that was of adult onset. The clinical benefit observed in patients with both CSwNP and asthma illustrates that, in at least a subset of patients, a common set of Th2-related inflammatory pathways appear to be shared between asthma and CSwNP and demonstrates that targeting these pathways can lead to clinical improvement in both diseases.

In summary, this example shows that in patients with CSwNP refractory to nasal corticosteroids, treatment with dupilumab was associated with improvements in endoscopic, radiographic and clinical measures of disease. The efficacy of dupilumab was increased in patients with comorbid asthma, who also experienced concurrent improvements in lung function and disease control. Additional studies will be performed to fully elucidate the impact of targeting IL-4 and IL-13 in patients with multiple concurrent atopic diseases.

What is claimed:

1. A method of treating inadequately controlled chronic rhinosinusitis with nasal polyps (CRSwNP) in a subject in need thereof, the method comprising:

administering dupilumab subcutaneously to the subject at a dose of 300 mg;

wherein the dupilumab is administered as an add-on maintenance treatment;

wherein prior to the treatment the subject had a bilateral endoscopic nasal polyp score (NPS) of at least 5 points; and wherein the subject achieves a decrease in NPS.

2. The method of claim 1, wherein the dose of 300 mg of the dupilumab is administered once a week or once every two weeks.

3. The method of claim 2, wherein the dose of 300 mg of the dupilumab is administered once every two weeks.

4. The method of claim 3, wherein the subject achieves a decrease in NPS of 1 point.

5. The method of claim 4, wherein the subject is on a background therapy comprising an intranasal corticosteroid (INCS).

6. The method of claim 3, wherein the subject achieves a decrease in NPS of 2 points.

7. The method of claim 6, wherein prior to the treatment the subject had at least 1 nasal surgery.

8. A method of treating chronic rhinosinusitis with nasal polyps (CRSwNP) in a subject in need thereof, the method comprising administering dupilumab subcutaneously to the subject at a dose of 300 mg once every two weeks.

9. The method of claim 8, wherein the subject is on a background therapy comprising an INCS.

10. The method of claim 9, wherein prior to the treatment the subject had loss of smell as measured by morning (AM) loss of smell score.

11. The method of claim 10, wherein the subject achieves a decrease in AM loss of smell score.

12. The method of claim 11, wherein prior to the treatment the subject had an AM loss of smell score of at least 2.

13. The method of claim 12, wherein the subject achieves a decrease in AM loss of smell score of at least 1 point.

14. The method of claim 11, wherein prior to the treatment the subject had at least 1 nasal surgery.

15. The method of claim 11, wherein the subject achieves a decrease in NPS.

16. A method of treating inadequately controlled chronic rhinosinusitis with nasal polyps (CRSwNP) in a subject in need thereof, the method comprising:

administering dupilumab subcutaneously to the subject at a dose of 300 mg;

wherein the dupilumab is administered as an add-on maintenance treatment;

wherein prior to the treatment the subject had a nasal congestion/obstruction (NC) score of at least 1 at baseline; and wherein the subject achieves a decrease in NC score.

17. The method of claim 16, wherein the dose of 300 mg of dupilumab is administered once a week or once every 2 weeks.

18. The method of claim 17, wherein the dose of 300 mg of dupilumab is administered once every 2 weeks.

19. The method of claim 18, wherein the subject achieves an NC score of less than 1 point.

20. The method of claim 19, wherein prior to the treatment the subject had at least 1 nasal surgery.

21. The method of claim 19, wherein the subject achieves a decrease in NPS.

22. The method of claim 18, wherein the NC score is a morning (AM) NC score.

23. The method of claim 18, wherein the subject is on a background therapy comprising an INCS.

24. A method of treating inadequately controlled chronic rhinosinusitis with nasal polyps (CRSwNP) in a subject in need thereof, the method comprising:

administering dupilumab subcutaneously to the subject at a dose of 300 mg;

wherein the dupilumab is administered as an add-on maintenance treatment;

wherein prior to the treatment the subject had sinus opacification as measured by Lund-Mackay (LMK) sinus computed tomography (CT) scan total score; and wherein the subject achieves a decrease in LMK sinus CT scan total score.

25. The method of claim 24, wherein the dose of 300 mg of dupilumab is administered once a week or once every 2 weeks.

26. The method of claim 25, wherein the dose of 300 mg of dupilumab is administered once every 2 weeks.

27. The method of claim 26, wherein prior to the treatment the subject had a LMK sinus CT scan total score of at least 18 points.

28. The method of claim 27, wherein the subject achieves a decrease in LMK sinus CT scan total score of at least 8 points.

29. The method of claim 27, wherein prior to the treatment the subject had at least 1 nasal surgery.

30. The method of claim 27, wherein the subject is on a background therapy comprising an INCS.

* * * * *

```
                              SEQUENCE LISTING


<160> NUMBER OF SEQ ID NOS: 10

<210> SEQ ID NO 1
<211> LENGTH: 124
<212> TYPE: PRT
<213> ORGANISM: Artificial Sequence
<220> FEATURE:
<223> OTHER INFORMATION: Description of Artificial Sequence: Synthetic
      HCVR polypeptide

<400> SEQUENCE: 1

Glu Val Gln Leu Val Glu Ser Gly Gly Gly Leu Glu Gln Pro Gly Gly
1               5                   10                  15

Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

Ser Ser Ile Ser Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser
        115                 120


<210> SEQ ID NO 2
<211> LENGTH: 112
<212> TYPE: PRT
<213> ORGANISM: Artificial Sequence
<220> FEATURE:
<223> OTHER INFORMATION: Description of Artificial Sequence: Synthetic
      LCVR polypeptide

<400> SEQUENCE: 2

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Ile Gly Tyr Asn Tyr Leu Asp Trp Tyr Leu Gln Lys Ser Gly Gln Ser
        35                  40                  45

Pro Gln Leu Leu Ile Tyr Leu Gly Ser Asn Arg Ala Ser Gly Val Pro
    50                  55                  60
```

```
Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Thr Pro Tyr Thr Phe Gly Gln Gly Thr Lys Leu Glu Ile Lys
            100                 105                 110


<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      HCDR1 peptide

<400> SEQUENCE: 3

Gly Phe Thr Phe Arg Asp Tyr Ala
1               5


<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      HCDR2 peptide

<400> SEQUENCE: 4

Ile Ser Gly Ser Gly Gly Asn Thr
1               5


<210> SEQ ID NO 5
<211> LENGTH: 18
<212> TYPE: PRT
<213> ORGANISM: Artificial Sequence
<220> FEATURE:
<223> OTHER INFORMATION: Description of Artificial Sequence: Synthetic
      HCDR3 peptide

<400> SEQUENCE: 5

Ala Lys Asp Arg Leu Ser Ile Thr Ile Arg Pro Arg Tyr Tyr Gly Leu
1               5                   10                  15

Asp Val


<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      LCDR1 peptide

<400> SEQUENCE: 6

Gln Ser Leu Leu Tyr Ser Ile Gly Tyr Asn Tyr
1               5                   10


<210> SEQ ID NO 7
<211> LENGTH: 3
<212> TYPE: PRT
<213> ORGANISM: Artificial Sequence
<220> FEATURE:
<223> OTHER INFORMATION: Description of Artificial Sequence: Synthetic
      LCDR2 peptide

<400> SEQUENCE: 7
```

```
Leu Gly Ser
1


<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      LCDR3 peptide

<400> SEQUENCE: 8

Met Gln Ala Leu Gln Thr Pro Tyr Thr
1               5


<210> SEQ ID NO 9
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HC
      aa 1-124: HCVR
      aa 125-451: HC constant

<400> SEQUENCE: 9

Glu Val Gln Leu Val Glu Ser Gly Gly Gly Leu Glu Gln Pro Gly Gly
1               5                   10                  15

Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

Ser Ser Ile Ser Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255
```

```
Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly
    450


<210> SEQ ID NO 10
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: LC
      aa 1-112: LCVR
      aa 112-219: LC constant

<400> SEQUENCE: 10

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Ile Gly Tyr Asn Tyr Leu Asp Trp Tyr Leu Gln Lys Ser Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Thr Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125
```

-continued

```
Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```